(12) United States Patent
Milella et al.

(10) Patent No.: US 12,186,205 B2
(45) Date of Patent: *Jan. 7, 2025

(54) BONE GRAFT DELIVERY SYSTEMS AND METHODS FOR USING SAME

(71) Applicant: Spinal Surgical Strategies, Inc., Incline Village, NV (US)

(72) Inventors: Michael J. Milella, Escondido, CA (US); Jeffrey Kleiner, Denver, CO (US); Edward J. Grimberg, Golden, CO (US); Gregory Causey, Erie, CO (US); Alan Burkholder, Denver, CO (US)

(73) Assignee: Spinal Surgical Strategies, Inc., Incline Village, NV (US)

( * ) Notice: Subject to any disclaimer, the term of this patent is extended or adjusted under 35 U.S.C. 154(b) by 85 days.

This patent is subject to a terminal disclaimer.

(21) Appl. No.: 17/970,481

(22) Filed: Oct. 20, 2022

(65) Prior Publication Data

US 2023/0059830 A1 Feb. 23, 2023

Related U.S. Application Data

(63) Continuation of application No. 17/021,789, filed on Sep. 15, 2020, now Pat. No. 11,504,249.

(Continued)

(51) Int. Cl.
*A61F 2/46* (2006.01)
(52) U.S. Cl.
CPC .......... *A61F 2/4601* (2013.01); *A61F 2/4611* (2013.01); *A61F 2002/4687* (2013.01)

(58) Field of Classification Search
CPC ............ A61B 17/8802; A61B 17/8816; A61B 17/8822; A61B 17/8825; A61B 17/8827;
(Continued)

(56) References Cited

U.S. PATENT DOCUMENTS 5,431,654 A * 7/1995 Nic ...................... G01F 11/026
606/92
5,683,394 A 11/1997 Rinner
(Continued)

FOREIGN PATENT DOCUMENTS

WO WO-2010081068 A1 * 7/2010 ......... A61B 17/8833

*Primary Examiner* — Anu Ramana
(74) *Attorney, Agent, or Firm* — Corner Counsel

(57) ABSTRACT

The present invention relates to an apparatus and method for near-simultaneous and integrated delivery of bone graft material during the placement of surgical cages or other medical implants in a patient's spine, and methods for using same. The integrated fusion cage and graft delivery device according to various embodiments delivers and disperses biologic material through a fusion cage to a disc space and, without withdrawal from the surgical site, may selectively detach the fusion cage for deposit to the same disc space. The integrated fusion cage and graft delivery device is formed such that a hollow tube and plunger selectively and controllably place bone graft material and a fusion cage in or adjacent to the bone graft receiving area. In one embodiment, the integrated fusion cage is an expandable integrated fusion cage. In another embodiment, the bone graft material is loaded into a breech area in the hollow tube.

18 Claims, 80 Drawing Sheets

Related U.S. Application Data

(60) Provisional application No. 62/900,960, filed on Sep. 16, 2019.

(58) Field of Classification Search
CPC .. A61B 17/8833; A61F 2/4601; A61F 2/4611; A61F 2002/4687
See application file for complete search history.

(56) References Cited

U.S. PATENT DOCUMENTS

| | | | |
|---|---|---|---|
| 7,371,241 B2 * | 5/2008 | Evans | A61B 17/8822 606/92 |
| 8,343,224 B2 * | 1/2013 | Lynn | A61F 2/4611 623/17.16 |
| 8,366,669 B2 * | 2/2013 | Timothy Donald | A61M 5/2033 604/136 |
| 8,696,678 B2 * | 4/2014 | Foster | A61M 35/003 606/92 |
| 8,920,374 B2 | 12/2014 | Bokelman et al. | |
| 9,033,994 B2 | 5/2015 | Fingerhut | |
| 9,320,556 B2 | 4/2016 | Agard et al. | |
| 10,046,115 B2 | 8/2018 | Bokelman et al. | |
| 10,376,648 B1 * | 8/2019 | Hensler | A61B 17/8811 |
| 11,253,391 B2 * | 2/2022 | Grover | A61F 6/005 |
| 11,660,208 B2 * | 5/2023 | Kleiner | A61F 2/447 623/17.11 |
| 2001/0016703 A1 * | 8/2001 | Wironen | A61L 27/3604 604/82 |
| 2002/0161444 A1 | 10/2002 | Choi | |
| 2002/0169507 A1 | 11/2002 | Malone | |
| 2004/0204715 A1 * | 10/2004 | Evans | A61B 17/8819 606/92 |
| 2010/0198261 A1 | 8/2010 | Trieu et al. | |
| 2012/0065613 A1 * | 3/2012 | Pepper | A61B 17/8833 604/60 |
| 2012/0078371 A1 | 3/2012 | Gamache et al. | |
| 2014/0074170 A1 | 3/2014 | Mertens et al. | |
| 2015/0216577 A1 * | 8/2015 | Vogt | B01F 35/754251 366/76.7 |
| 2017/0238984 A1 | 8/2017 | Kleiner | |
| 2019/0269521 A1 | 9/2019 | Shostaev | |

\* cited by examiner

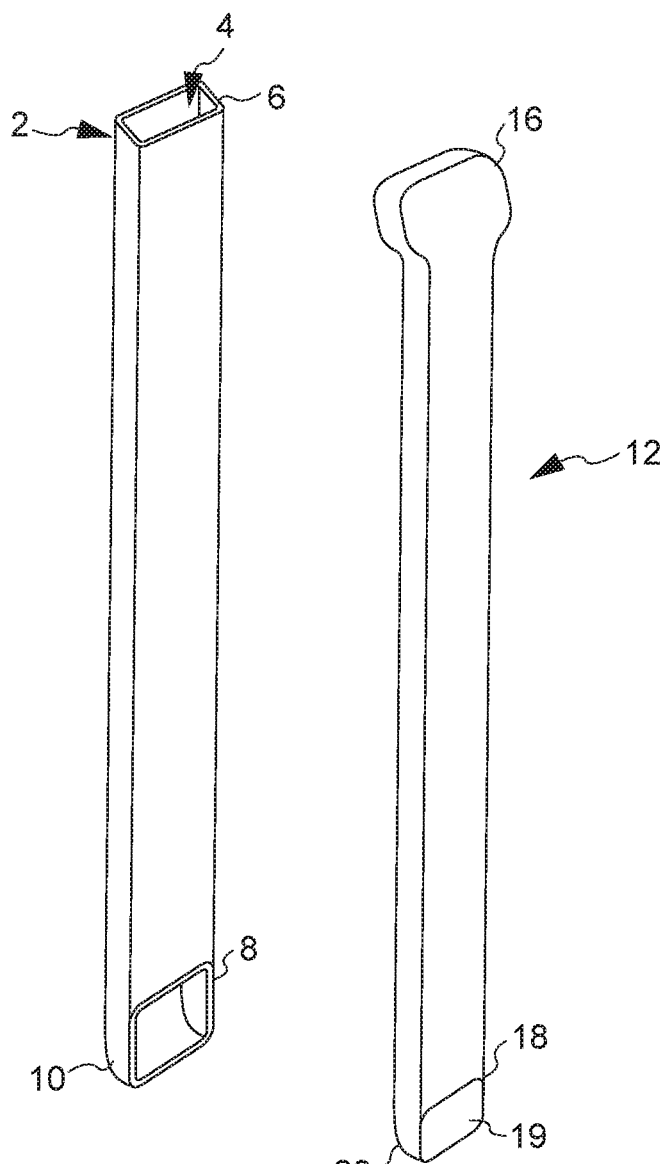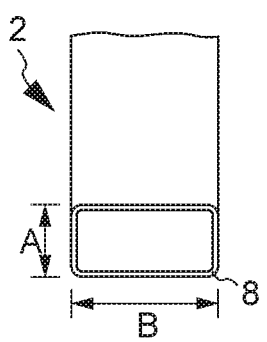
FIG. 1A
FIG. 1B
FIG. 1C

SECTION A-A

SECTION A-A

SECTION A-A

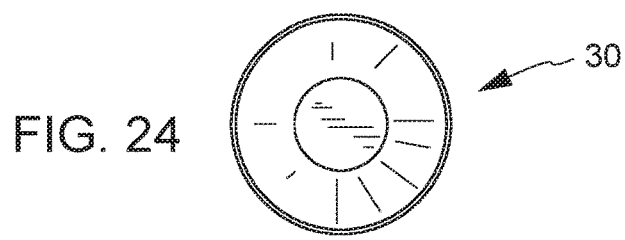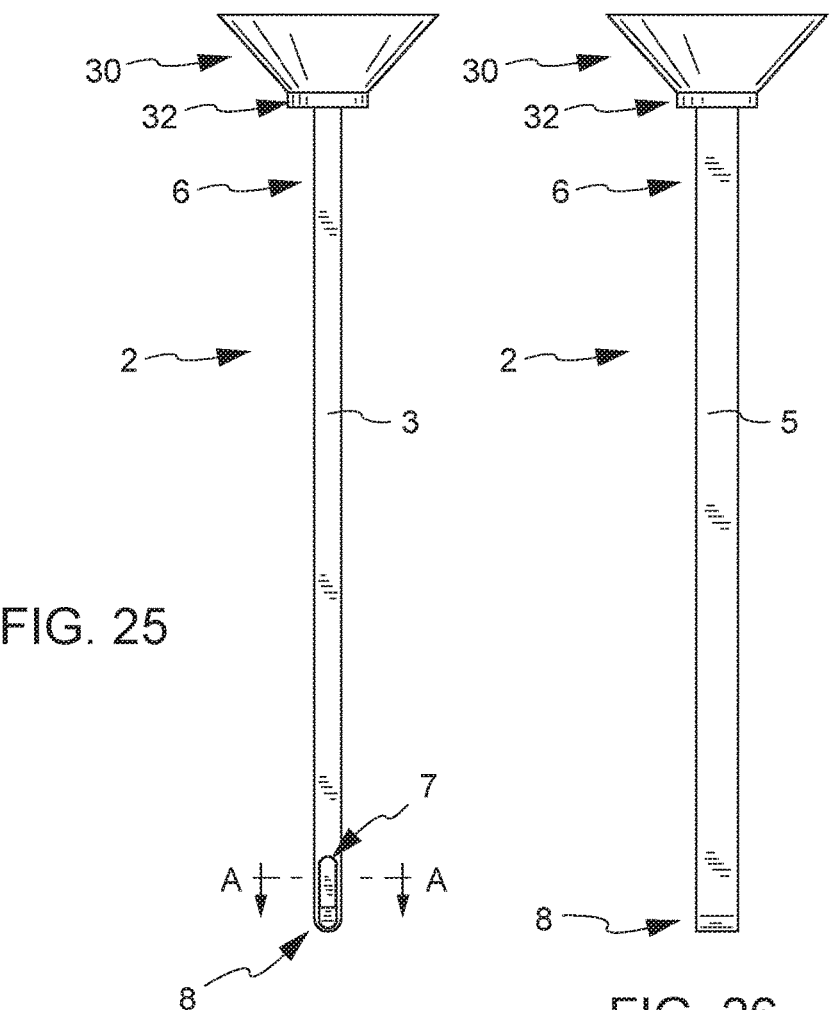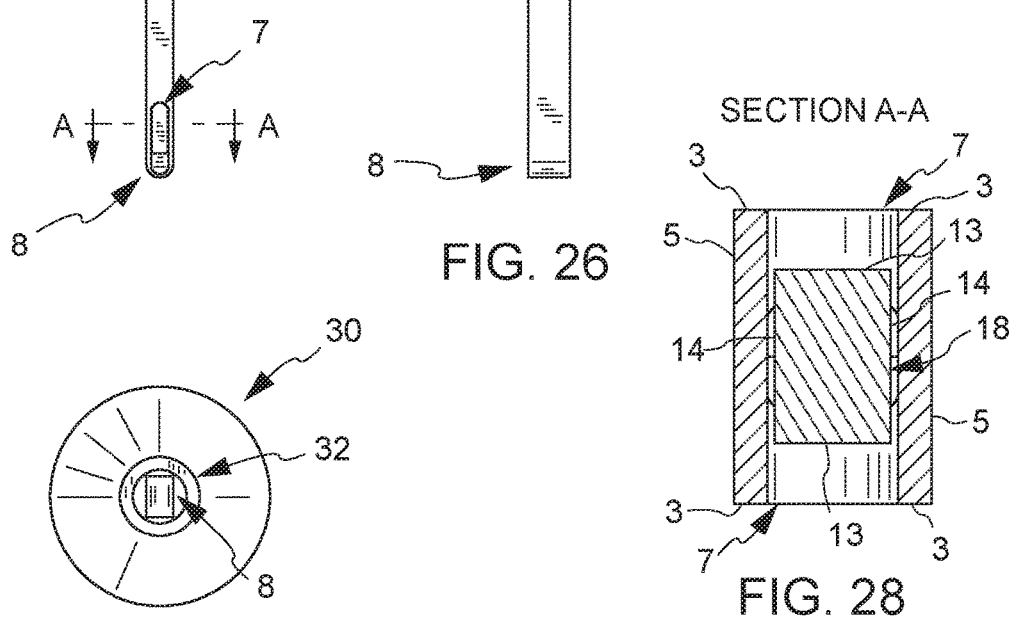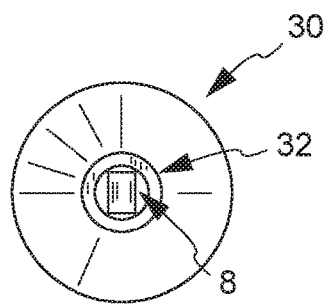

- 1ml DISK REMOVAL = 6.6+/-0.9ml
- 2ml DISK REMOVAL = 8.4+/-2.8ml
- 3ml DISK REMOVAL = 8.8+/-2.0ml
- 4ml DISK REMOVAL = 10.2+/-3.5ml
- 5ml DISK REMOVAL = 12.1+/-1.9ml
- 6ml DISK REMOVAL = 11.6+/-2.4ml
- 7ml DISK REMOVAL = 11.1+/-3.1ml
- 8ml DISK REMOVAL = 12.3+/-2.3ml

SECTION D-D

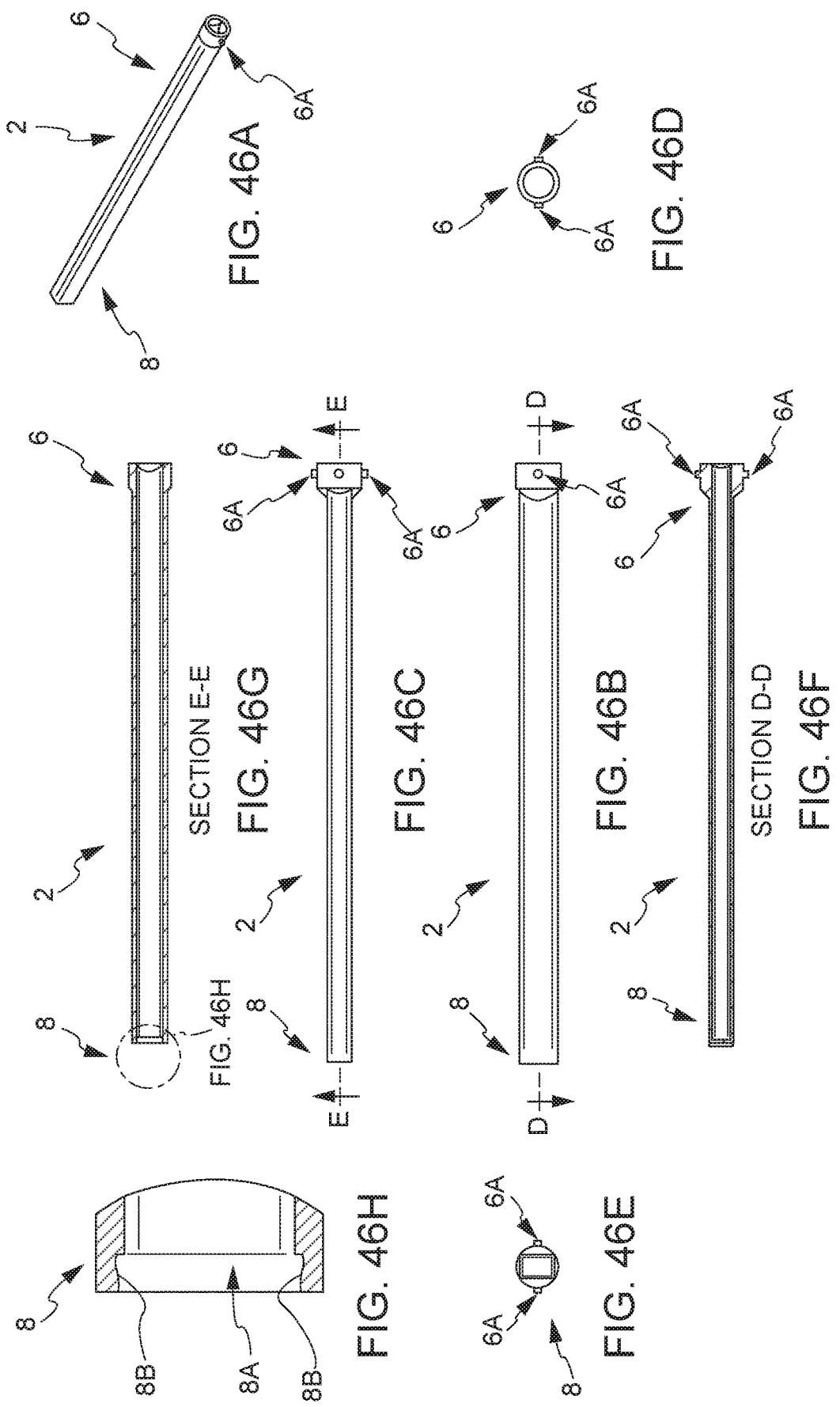

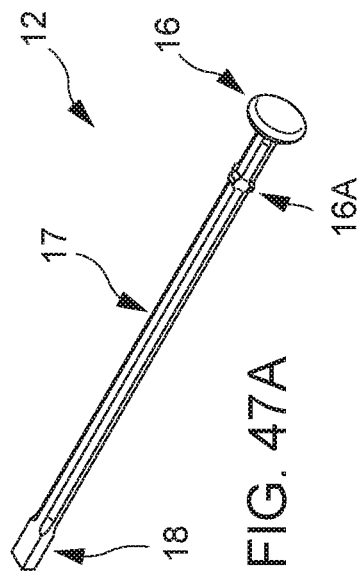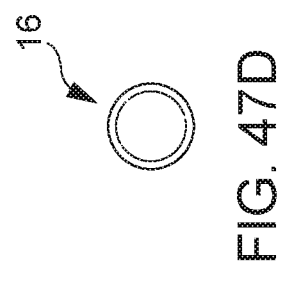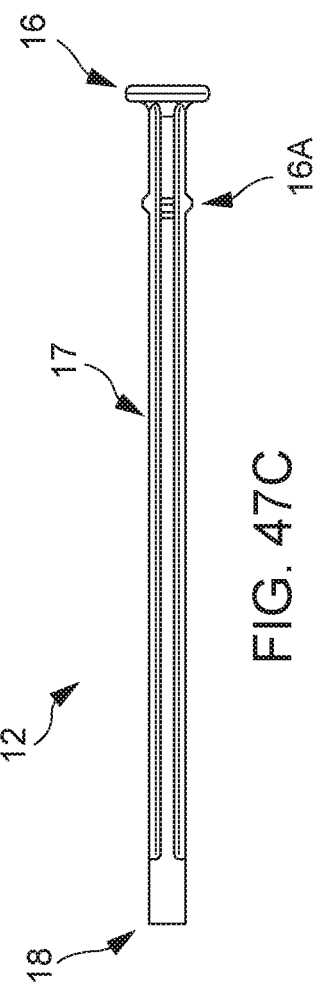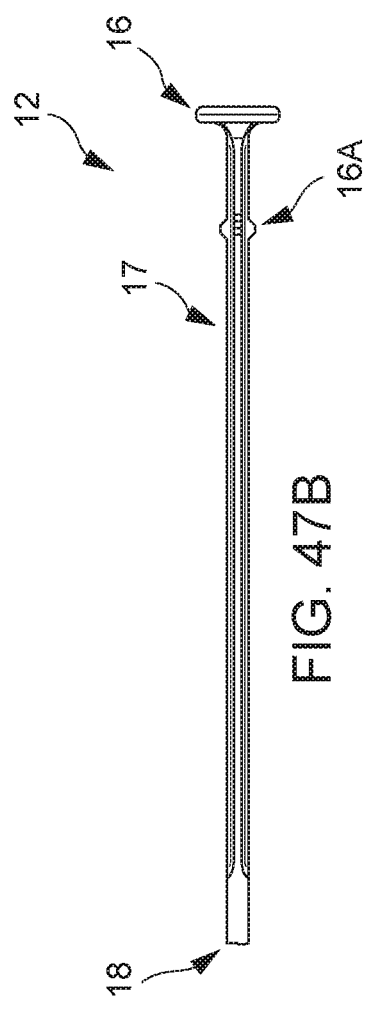

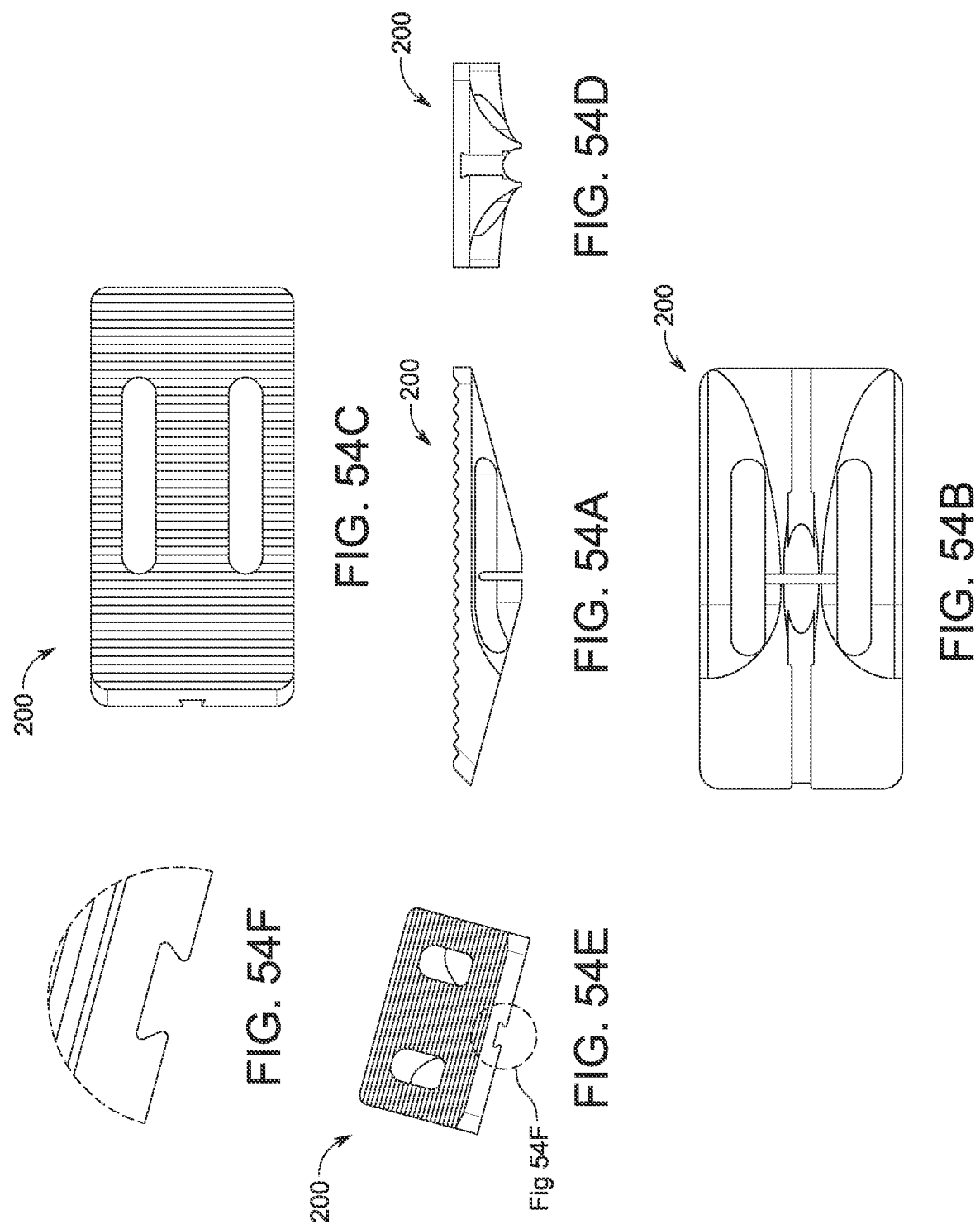

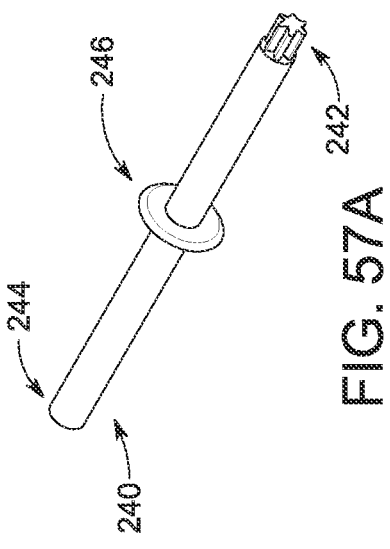
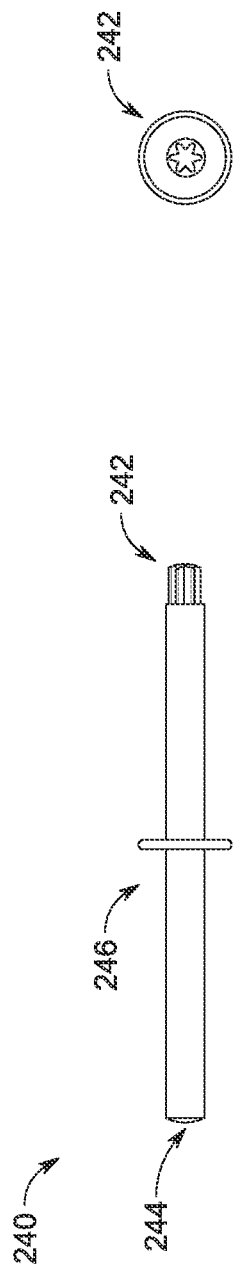

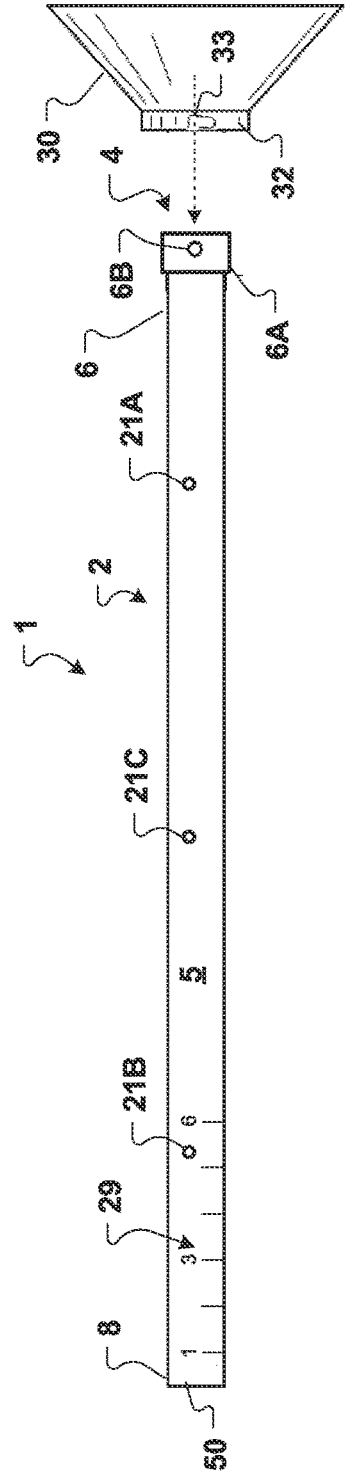
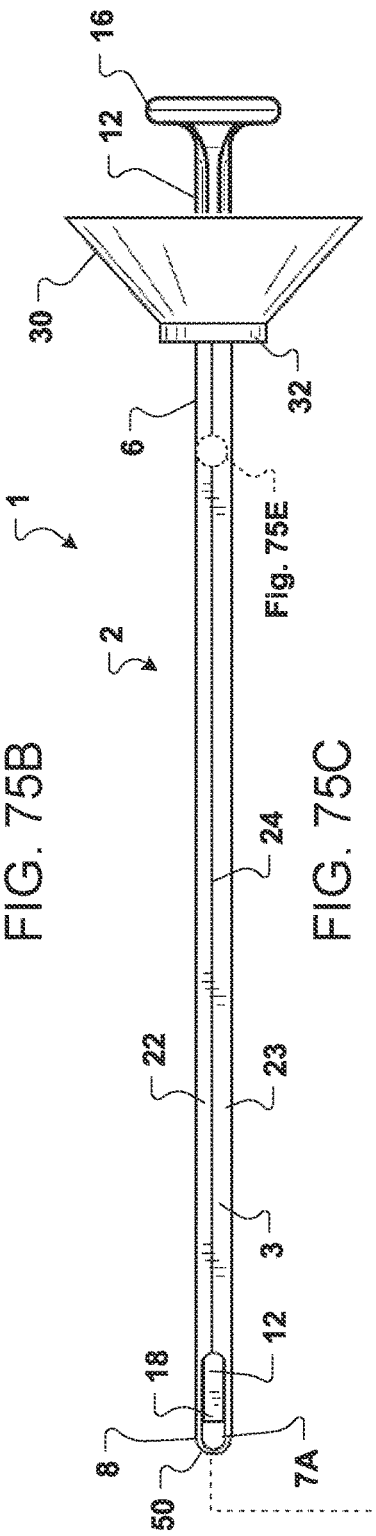
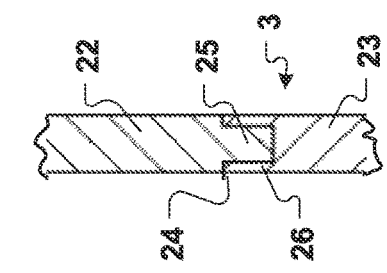
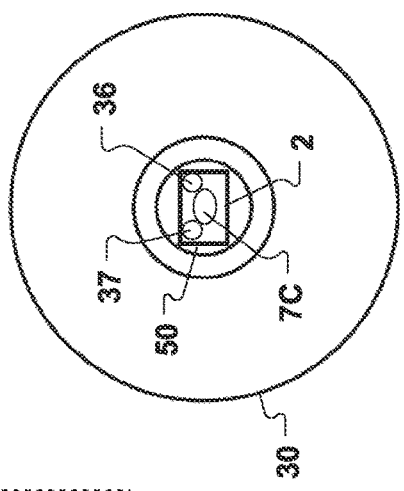
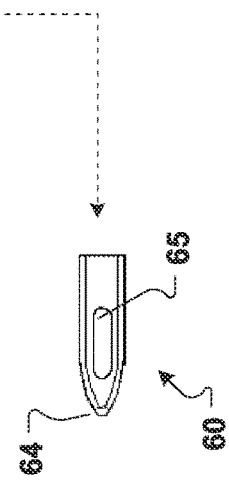

BONE GRAFT DELIVERY SYSTEMS AND METHODS FOR USING SAME

RELATED APPLICATIONS

This application is a continuation of and claims priority to U.S. patent application Ser. No. 17/021,789 filed Sep. 15, 2020, and claims priority to U.S. Provisional Patent Application Ser. No. 62/900,960, filed Sep. 16, 2019, the entire disclosures of both of which are hereby incorporated by reference in their entireties.

FIELD OF THE INVENTION

This disclosure relates to orthopedic surgery, and more specifically to an apparatus and method for near-simultaneous and integrated delivery of bone graft material during the placement of surgical cages or other medical implants in a patient's spine.

BACKGROUND OF THE INVENTION

Individuals who suffer degenerative disc disease, natural spine deformations, a herniated disc, spine injuries or other spine disorders may require surgery on the affected region to relieve the individual from pain and prevent further injury to the spine and nerves. Spinal surgery may involve removal of damaged joint tissue, insertion of a tissue implant and/or fixation of two or more adjacent vertebral bodies. In some instances, a medical implant is also inserted, such as a fusion cage. The surgical procedure will vary depending on the nature and extent of the injury. Generally, there are five main types of lumbar fusion, including: posterior lumbar fusion ("PLF"), posterior lumbar interbody fusion ("PLIF"), anterior lumbar interbody fusion ("ALIF"), circumferential 360 fusion, and transforaminal lumbar interbody fusion ("TLIF"). More recently, direct lateral interbody fusion ("D-LIF") has become available. A posterior approach is one that accesses the surgical site from the patient's back, an anterior approach is one that accesses the surgical site from the patient's front or chest, and a direct lateral approach is one that accesses the surgical site from the patient's side. There are similar approaches for fusion in the interbody or cervical spine regions. For a general background on some of these procedures and the tools and apparatus used in certain procedures, see U.S. Prov. Pat. Appl. No. 61/120,260 filed on Dec. 5, 2008, the entire disclosure of which is incorporated by reference in its entirety. In addition, further background on procedures and tools and apparatus used in spinal procedures is found in U.S. patent application Ser. No. 12/632,720 filed on Dec. 7, 2009, now U.S. Pat. No. 8,366,748, the entire disclosure of which is incorporated by reference in its entirety.

Vertebrectomy, or the removal or excision of a vertebra, is another type of spinal surgery that may be necessary to alleviate pain and/or correct spinal defects, such as when disk material above and below a particular vertebra protrudes from the spine and contacts the spinal cord. Once the problematic vertebra is removed, a specialized fusion cage (also called a vertebrectomy cage) may be inserted into its place to restore structural continuity to the spine.

Some disadvantages of traditional methods of spinal surgery include, for example, the pain associated with the procedure, the length of the procedure, the complexity of implements used to carry out the procedure, the prolonged hospitalization required to manage pain, the risk of infection due to the invasive nature of the procedure, and the possible requirement of a second procedure to harvest autograft bone from the iliac crest or other suitable site on the patient for generating the required quantity of cancellous and/or cortical bone.

A variety of semisolid bone graft materials are available on the market which ostensibly increase spinal fusion rates without the morbidity of autograft bone harvest. Each of the manufacturers espouses their product as the most advantageous for healing. These products all have similar handling characteristics and the literature reveals that they have similar healing prospects. They come in a syringe and it is up to the surgeon to apply the selected material to the target site. The most common site for application is to the disk space after it has been prepared to a bleeding bed and ready to accept a cage and/or the grafting material. This represents a long and narrow channel even in open procedures. The surgeon is left to his own devices as to how to get the graft from its container to the active site. The devices which have been used have included a "caulking gun" construct and a variety of barrel shaft with a plunger design.

Bone graft typically includes crushed bone (cancellous and cortical), or a combination of these (and/or other natural materials), and may further comprise synthetic biocompatible materials. Bone graft of this type is intended to stimulate growth of healthy bone. As used herein, "bone graft" shall mean materials made up entirely of natural materials, entirely of synthetic biocompatible materials, or any combination of these materials. Bone graft often is provided by the supplier in a gel or slurry form, as opposed to a dry or granule form. Many companies provide various forms of bone graft in varying degrees of liquidity and viscosity, which may cause problems in certain prior art delivery devices in both prepackaged or packaged by the surgeon embodiments. In addition, the method of delivery of bone graft to a particular location varies depending on the form of the bone graft utilized.

Autogenous bone (bone from the patient) or allograft bone (bone from another individual) are the most commonly used materials to induce bone formation. Generally, small pieces of bone are placed into the space between the vertebrae to be fused. Sometimes larger solid pieces of bone are used to provide immediate structural support. Autogenous bone is generally considered superior at promoting fusion. However, this procedure requires extra surgery to remove bone from another area of the patient's body such as the pelvis or fibula. Thus, it has been reported that about 30 percent of patients have significant pain and tenderness at the graft harvest site, which may be prolonged, and in some cases outlast the back pain the procedure intended to correct. Similarly, allograft bone and other bone graft substitutes, although eliminating the need for a second surgery, have drawbacks in that they have yet to be proven as cost effective and efficacious substitutes for autogenous bone fusion.

An alternative to autogenous or allograft bone is the use of growth factors that promote bone formation. For example, studies have shown that the use of bone morphogenic proteins ("BMPs") results in better overall fusion, less time in the operating room and, more importantly, fewer complications for patients because it eliminates the need for the second surgery. However, use of BMPs, although efficacious in promoting bone growth, can be prohibitively expensive.

Another alternative is the use of a genetically engineered version of a naturally occurring bone growth factor. This approach also has limitations. Specifically, surgeons have expressed concerns that genetically engineered BMPs can dramatically speed the growth of cancerous cells or cause non-cancerous cells to become more sinister. Another concern is unwanted bone creation. There is a chance that bone generated by genetically engineered BMPs could form over the delicate nerve endings in the spine or, worse, somewhere else in the body.

Many different methods and approaches have been attempted to induce bone formation or to promote spinal fusion. The traditional devices for inserting bone graft impair the surgeon's visualization of the operative site, which can lead to imprecise insertion of bone graft and possible harm to the patient. The caulking gun and the collection of large barrel/plunger designs typically present components at the top of their structure which block the view of the surgical site. The surgeon must then resort to applying pressure to the surgical site to approximate the location of the device's delivery area. Such rough maneuvering can result in imprecise placement of bone graft, and in some cases, rupture of the surgical area by penetrating the annulus and entering the abdominal cavity. Also, in some surgical procedures, the devices for inserting bone graft material are applied within a cannula inserted or placed in the surgical area, further limiting the size and/or profile of the bone graft insertion device. When a cannula is involved, some traditional devices such as the large barrel/plunger designs and/or the caulking gun designs simply cannot be used as they cannot be inserted within the cannula.

Traditional devices for inserting bone graft deliver the bone graft material at the bottom of the delivery device along the device's longitudinal axis. Such a delivery method causes the bone grafting material to become impacted at the bottom of the delivery device which jams the device and promotes risk of rupture of the surgical area by penetrating the annulus and entering the abdominal cavity. Further, traditional devices that deliver bone graft material along their longitudinal axis may cause rupture of the surgical area or harm to the patient because of the ensuing pressure imparted by the ejected bone graft material from the longitudinal axis of the device. Furthermore, the graft material is distributed only in the longitudinal axis and does not fill in the peripheral areas of the disk.

Traditional devices for inserting a fusion cage or other medical implants into a patient's spine or other surgical area are distinct and separate from traditional devices that deliver bone graft material to the surgical site. For example, once an implant has been positioned, then bone growth material is packed into the internal cavity of the fusion cage. Also, sometimes the process is reversed, i.e., the bone growth is inserted first, and then the implant. These bone growth inducing substances come into immediate contact with the bone from the vertebral bone structures which project into the internal cavity through the apertures. Two devices are thus traditionally used to insert bone graft material into a patient's spine and to position and insert a fusion cage. These devices thus necessitate a disc space preparation followed by introduction of the biologic materials necessary to induce fusion and, in a separate step, application of a structural interbody fusion cage.

The problems associated with separate administration of the biologic material bone graft material and the insertion of a fusion cage include applying the graft material in the path of the cage, restricting and limiting the biologic material dispersed within the disk space, and requiring that the fusion cage be pushed back into the same place that the fusion material delivery device was, which can lead to additional trauma to the delicate nerve structures.

Fusion cages provide a space for inserting a bone graft between adjacent portions of bone. Such cages are often made of titanium and are hollow, threaded, and porous in order to allow a bone graft contained within the interior of the cage of grow through the cage into adjacent vertebral bodies. Such cages are used to treat a variety of spinal disorders, including degenerative disc diseases such as Grade I or II spondylolistheses of the lumbar spine.

Surgically implantable intervertebral fusion cages are well known in the art and have been actively used to perform spinal fusion procedures for many years. Their use became popularized during the mid-1990's with the introduction of the BAK Device from the Zimmer Inc., a specific intervertebral fusion cage that has been implanted worldwide more than any other intervertebral fusion cage system. The BAK system is a fenestrated, threaded, cylindrical, titanium alloy device that is capable of being implanted into a patient as described above through an anterior or posterior approach, and is indicated for cervical and lumbar spinal surgery. The BAK system typifies a spinal fusion cage in that it is a highly fenestrated, hollow structure that will fit between two vertebrae at the location of the intervertebral disc.

Spinal fusion cages may be placed in front of the spine, a procedure known as anterior lumbar interbody fusion, or ALIF, or placed in back of the spine. The cages are generally inserted through a traditional open operation, though laparoscopic or percutaneous insertion techniques may also be used. Cages may also be placed through a posterior lumbar interbody fusion, or PLIF, technique, involving placement of the cage through a midline incision in the back, or through a direct lateral interbody fusion, or D-LIF, technique, involving placement of the cage through an incision in the side.

A typical procedure for inserting a common threaded and impacted fusion cage is as follows. First, the disc space between two vertebrae of the lumbar spine is opened using a wedge or other device on a first side of the vertebrae. The disk space is then prepared to receive a fusion cage. Conventionally, a threaded cage is inserted into the bore and the wedge is removed. A disk space at the first side of the vertebrae is then prepared, and a second threaded fusion cage inserted into the bore. Alternatively, the disk space between adjacent vertebrae may simply be cleared and a cage inserted therein. Often, only one cage is inserted obliquely into the disk space. Use of a threaded cage may be foregone in favor of a rectangular or pellet-shaped cage that is simply inserted into the disk space. Lastly, bone graft material may be inserted into the surgical area using separate tools and devices.

Traditional fusion cages are available in a variety of designs and composed of a variety of materials. The cages or plugs are commonly made of an inert metal substrate such as stainless steel, cobalt-chromium-molybdenum alloys, titanium or the like having a porous coating of metal particles of similar substrate metal, preferably titanium or the like as disclosed, for example, in the Robert M. Pilliar U.S. Pat. No. 3,855,638 issued Dec. 24, 1974 and U.S. Pat. No. 4,206,516 issued Jun. 10, 1980. These plugs may take the form of flat sided cubical or rectangular slabs, cylindrical rods, cruciform blocks, and the like.

Prior art bone graft delivery devices typically must come pre-loaded with bone graft, or alternatively require constant loading (where permissible) in order to constantly have the desired supply of bone graft available. Moreover, these bone graft delivery devices generally cannot handle particulate bone graft of varying or irregular particulate size. Furthermore, the prior art devices for inserting a fusion cage or other medical implant into a patient's spine or other surgical area are commonly distinct and separate from traditional devices that deliver bone graft material to the surgical site. As such, two devices are traditionally used to insert bone graft material into a patient's spine and to position and insert a fusion cage. The problems associated with separate administration of the biologic material bone graft material and the insertion of a fusion cage include applying the graft material in the path of the cage, restricting and limiting the biologic material dispersed within the disk space, and requiring that the fusion cage be pushed back into the same place that the fusion material delivery device was, which can lead to additional trauma to the delicate nerve structures. These problems can be a great inconvenience, cause avoidable trauma to a patient and make these prior art devices unsuitable in many procedures.

Therefore, there is a long-felt need for an apparatus and method for near-simultaneous and integrated precision delivery of bone graft material during the placement of surgical cages or other medical implants in a patient's spine. The present invention solves these needs. The present invention allows biologic material to flow directly to the fusion cage and be dispersed within the disc space in a single step, and can precisely and simply deliver particulate bone graft of varying or irregular particulate size. Thus, the present invention allows application of bone graft material through a detachable fusion cage, eliminates otherwise restriction of the volume of biologic material that may be dispersed within the disk space, and eliminates the requirement that the fusion cage be pushed back into the same place that the fusion material delivery device was, which can lead to additional trauma to the delicate nerve structures.

SUMMARY OF THE INVENTION

It is one aspect of the present invention to provide a bone graft material delivery system, comprising a hollow tube adapted to receive bone graft material, the hollow tube having a proximal portion; a distal portion with at least one opening therein; a breech area interconnected to at least one of the proximal portion and the distal portion via a breech hinge, and configured to rotate about the breech hinge between an open position and a closed position; and a means for urging bone graft material from the proximal portion through the distal portion and outwardly through the at least one opening of the distal portion, wherein the proximal portion is securely interconnected to the distal portion along a longitudinal axis of the hollow tube, and wherein, when the breech area is in the open position, an interior volume of the proximal portion is exposed to allow for loading of bone graft material therein.

In embodiments, the secure interconnection between the proximal portion and the distal portion may comprise an ultraviolet light-activated adhesive.

In embodiments, the at least one opening may comprise two openings on lateral sides of the hollow tube.

In embodiments, the means for urging may comprise a plunger. The plunger may, but need not, have teeth formed along a longitudinal axis of the plunger. At least a portion of the hollow tube may, but need not, be generally transparent such that the plunger is at least partially visible within the hollow tube. One or more of the hollow tube and the plunger may, but need not, be printed using a three-dimensional printing process, wherein the three-dimensional printing process comprises one or more of fused filament fabrication, plaster-based three-dimensional printing, selective laser sintering, selective heat sintering, and direct ink writing. The bone graft material delivery system may, but need not, further comprise a pivotally mounted trigger configured to engage the teeth of the plunger, wherein the pivotally mounted trigger is operable to advance the plunger toward the distal end of the hollow tube.

In embodiments, the distal end of the hollow tube may comprise a bullet shaped distal tip.

In embodiments, the distal end of the hollow tube may be at least partially closed.

In embodiments, the hollow interior of the hollow tube may have a generally rectangular cross-section.

In embodiments, the hollow tube may be generally linear.

In embodiments, the hollow tube may be flexible.

In embodiments, the bone graft material delivery system may further comprise a funnel configured to be coupled to the proximal end of the hollow tube.

In embodiments, the bone graft material delivery system may further comprise a syringe configured to be coupled to the hollow tube, wherein the bone graft material is mixed within the syringe and subsequently conveyed into the hollow interior of the hollow tube.

In embodiments, the bone graft material delivery system may further comprise a fusion cage detachably coupled to the distal end of the hollow tube.

In embodiments, the bone graft material delivery system may further comprise a breech lock mechanism, configured to selectively lock the breech area in the closed position. The breech lock mechanism may, but need not, be spring-loaded.

In embodiments, the proximal portion of the hollow tube may comprise a vertically extending rail configured to snugly mate with the breech area when the breech area is in the closed position.

In embodiments, the distal portion of the hollow tube may comprise a knuckle and at least one of the proximal portion and the breech area comprises a cavity, wherein the knuckle mates with and snugly fits within the cavity when the breech area is in the closed position.

In an another aspect, a bone graft material delivery system is provided, and includes a hollow tube adapted to receive bone graft material, the hollow tube having a proximal portion, a distal portion with at least one opening therein and a breech area interconnected to at least one of the proximal portion and the distal portion via a breech hinge, and configured to rotate about the breech hinge between an open position and a closed position. The system also includes a plunger configured for urging bone graft material from the proximal portion through the distal portion and outwardly through the at least one opening of the distal portion, wherein the proximal portion is securely interconnected to the distal portion along a longitudinal axis of the hollow tube, and wherein, when the breech area is in the open position, an interior volume of the proximal portion is exposed to allow for loading of bone graft material therein.

In another aspect, a method for delivering a bone graft material to an area within a patient is provided. The method includes the steps of providing a hollow tube having a proximal portion, a distal portion with at least one opening therein, and a breech area interconnected to at least one of the proximal portion and the distal portion via a breech hinge, and configured to rotate about the breech hinge between an open position and a closed position, the hollow tube being adapted to receive bone graft material therein; positioning the distal end within the patient's area; positioning the breech hinge in the open position; loading the bone graft material into the breech area; and urging bone graft material through the hollow tube from the proximal portion to the distal portion and outwardly through the at least one opening of the distal portion, whereby the bone graft material is introduced through the at least one opening into the patient's area.

In another aspect, a bone graft material delivery kit is provided. The kit includes a hollow tube having a proximal portion, a distal portion with at least one opening therein, and a breech area interconnected to at least one of the proximal portion and the distal portion via a breech hinge, and configured to rotate about the breech hinge between an open position and a closed position, the hollow tube being adapted to receive bone graft material therein. The kit also includes a plunger configured for urging bone graft material from the proximal portion through the distal portion and outwardly through the at least one opening of the distal portion. In various embodiments, the kit may include additional elements, such as an implant.

Certain embodiments of the present disclosure relate to an apparatus and method for near-simultaneous and integrated delivery of bone graft material during the placement of surgical cages or other medical implants in a patient's spine. The integrated fusion cage and delivery device (the "device") is comprised generally of a tubular member and a plunger for expelling bone graft from the tubular member, through a surgical fusion cage, and into a bone graft receiving area, then disengaging the fusion cage at the surgical site in a human patient. Thus, the apparatus and method allows the biologic material to flow directly into and through the fusion cage and be dispersed within the disc space in a single step, and leave the detachable fusion cage in the surgical area. In one embodiment, the integrated fusion cage is an expandable integrated fusion cage. Other embodiments and alternatives to this device are described in greater detail below.

By way of providing additional background, context, and to further satisfy the written description requirements of 35 U.S.C. § 112, the following references are incorporated by reference in their entireties for the express purpose of explaining the nature of the surgical procedures in which bone graft is used and to further describe the various tools and other apparatus commonly associated therewith: U.S. Pat. No. 6,309,395 to Smith et al.; U.S. Pat. No. 6,142,998 to Smith et al.; U.S. Pat. No. 7,014,640 to Kemppanien et al.; U.S. Pat. No. 7,406,775 to Funk, et al.; U.S. Pat. No. 7,387,643 to Michelson; U.S. Pat. No. 7,341,590 to Ferree; U.S. Pat. No. 7,288,093 to Michelson; U.S. Pat. No. 7,207,992 to Ritland; U.S. Pat. No. 7,077,864 Byrd III, et al.; U.S. Pat. No. 7,025,769 to Ferree; U.S. Pat. No. 6,719,795 to Cornwall, et al.; U.S. Pat. No. 6,364,880 to Michelson; U.S. Pat. No. 6,328,738 to Suddaby; U.S. Pat. No. 6,290,724 to Marino; U.S. Pat. No. 6,113,602 to Sand; U.S. Pat. No. 6,030,401 to Marino; U.S. Pat. No. 5,865,846 to Bryan, et al.; U.S. Pat. No. 5,569,246 to Ojima, et al.; U.S. Pat. No. 5,527,312 to Ray; and U.S. Pat. Appl. Pub. No. 2008/0255564 to Michelson.

By way of providing additional background, context, and to further satisfy the written description requirements of 35 U.S.C. § 112, the following references are incorporated by reference in their entireties for the express purpose of explaining the nature of the surgical procedures in which fusion cages are used and to further describe the various tools and other apparatus commonly associated therewith: U.S. Pat. No. 6,569,201 to Moumene et al.; U.S. Pat. No. 6,159,211 to Boriani et al.; U.S. Pat. No. 4,743,256 to Brantigan; U.S. Pat. Appl. 2007/0043442 to Abernathie et al.; U.S. Pat. Nos. 3,855,638 and 4,206,516 to Pilliar; U.S. Pat. No. 5,906,616 issued to Pavlov et al.; U.S. Pat. No. 5,702,449 to McKay; U.S. Pat. No. 6,569,201 to Moumene et al.; PCT Appl. No. WO 99/08627 to Gresser; U.S. Pat. Appl. Pub. 2012/0022651 to Akyuz et al.; U.S. Pat. Appl. Pub. 2011/0015748 to Molz et al.; U.S. Pat. Appl. Pub. 2010/0249934 to Melkent; U.S. Pat. Appl. Pub. 2009/0187194 to Hamada; U.S. Pat. No. 7,867,277 issued to Tohmeh; U.S. Pat. No. 7,846,210 to Perez-Cruet et al.; U.S. Pat. No. 7,985,256 issued to Grotz et al.; U.S. Pat. Appl. Pub. 2010/0198140 to Lawson; and U.S. Pat. Appl. Pub. 2010/0262245 to Alfaro et al.

By way of providing additional background and context, the following references are also incorporated by reference in their entireties for the purpose of explaining the nature of spinal fusion and devices and methods commonly associated therewith: U.S. Pat. No. 7,595,043 issued to Hedrick et al.; U.S. Pat. No. 6,890,728 to Dolecek et al.; U.S. Pat. No. 7,364,657 to Mandrusov, and U.S. Pat. No. 8,088,163 to Kleiner.

In addition, by way of providing additional background and context, the following references are also incorporated by reference in their entireties for the purpose of explaining the nature of spinal fusion and devices and methods commonly associated therewith: U.S. Pat. No. D647,202 entitled "Bone Marrow Harvesting Device" to Scifert issued Oct. 18, 2011; U.S. Pat. No. 7,897,164 entitled "Compositions and Methods for Nucleus Pulposus Regeneration" to Seifert issued Mar. 1, 2011; U.S. Pat. Appl. Pub. No. 2010/0112029 entitled "Compositions and Methods for Nucleus Pulposus Regeneration" to Scifert issued May 6, 2010; U.S. Pat. Appl. Pub. No. 2010/0021518 entitled "Foam Carrier for Bone Grafting" to Scifert issued Jan. 28, 2010; U.S. Pat. No. 7,824,703 entitled "Medical Implants with Reservoir(s), and Materials Preparable From Same" to Scifert, et al., issued Nov. 2, 2010; U.S. Pat. Appl. Pub. No. 2006/0247791 entitled "Multi-Purpose Medical Implant Devices" to McKay, et al., issued Nov. 2, 2006; U.S. Pat. Appl. Pub. No. 2007/0225811 entitled "Conformable Orthopedic Implant" to Scifert, et al., issued Sep. 27, 2007; U.S. Pat. No. 6,746,487 entitled "Intramedullary Trial Fixation Device" to Scifert, et al., issued Jun. 9, 2004; U.S. Pat. Appl. Pub. No. 2013/0073041 entitled "Medical Implants With Reservoir(s), and Materials Preparable From Same" to Scifert et al., issued Mar. 21, 2013; U.S. Pat. Appl. Pub. No. 2010/0266689 entitled "Tissue Augmentation With Active Agent For Wound Healing" to Simonton et al., issued Oct. 21, 2010; U.S. Pat. Appl. Pub. No. 2011/0028393 entitled "Flowable Paste And Putty Bone Void Filler" to Vickers et al., issued Feb. 3, 2011; U.S. Pat. Appl. Pub. No. 2009/0099660 entitled "Instrumentation To Facilitate Access Into The Intervertebral Disc Space And Introduction Of Materials Therein" to Scifert issued Apr. 16, 2009; U.S. Pat. Appl. Pub. No. 2011/0014587 entitled "System And Methods Of Preserving An Oral Socket" to Spagnoli et al., issued Jan. 20, 2011; U.S. Pat. No. 8,148,326 entitled "Flowable Carrier Matrix and Methods for Delivering to a Patient" to Beals et al., issued Apr. 3, 2012; U.S. Pat. Appl. Pub. No. 2008/0260598 entitled "Devices, Methods and Systems for Hydrating a Medical Implant Material" to Gross et al., issued Oct. 23, 2008; U.S. Pat. Appl. Pub. No. 2007/0265632 entitled "Bone Cutting Template and Method of Treating Bone Fractures" to Scifert et al., issued Nov. 15, 2007; U.S. Pat. No. 8,293,232 entitled "Flowable Carrier Matrix and Methods for Delivering to a Patient" to Beals et al., issued Oct. 23, 2012; U.S. Pat. No. 8,198,238 entitled "Flowable Carrier Matrix and Methods for Delivering to a Patient" to Beals et al., issued Jun. 12, 2012; U.S. Pat. No. 7,939,092 entitled "Cohesive Osteogenic Putty and Materials Therefor" to McKay et al., issued May 10, 2011; U.S. Pat. Appl. Pub. No. 2007/0264300 entitled "Therapeutic Agent Carrier and Method of Treating Bone Fractures" to Scifert et al., issued Nov. 15, 2007; U.S. Pat. Appl. Pub. No.

2011/0020768 entitled "Implantable Screw and System for Socket Preservation" to Spagnoli et al., issued Jan. 27, 2011; U.S. Pat. Appl. Pub. No. 2012/0065687 entitled "Multi-Radius Vertebral Rod with a Varying Stiffness" to Ballard et al., issued Mar. 15, 2012; U.S. Pat. Appl. Pub. No. 2007/0225219 entitled "Intramedullary Drug Delivery Device and Method of Treating Bone Fractures" to Boden et al., issued Sep. 27, 2007; U.S. Pat. No. 7,723,291 entitled "Release of BMP, Bioactive Agents and/or Cells Via a Pump into a Carrier Matrix" to Beals et al., issued May 25, 2010; U.S. Pat. No. 7,671,014 entitled "Flowable Carrier Matrix And Methods For Delivering To A Patient" to Beals et al., issued Mar. 2, 1010; U.S. Pat. No. 7,897,564 entitled "Flowable Carrier Matrix and Methods for Delivering to a Patient" to Beals et al., issued Mar. 1, 2011; U.S. Pat. Appl. Pub. No. 2011/0160777 entitled "System and Methods of Maintaining Space for Augmentation of the Alveolar Ridge" to Spagnoli et al., issued Jun. 30, 2011; U.S. Pat. Appl. Pub. No. 2009/0246244 entitled "Malleable MultiComponent Implants and Materials Therefor" to McKay et al., issued Oct. 1, 2009; U.S. Pat. Appl. Pub. No. 2009/0246244 entitled "Malleable Multi-Component Implants and Materials Therefor" to McKay et al., issued Oct. 1, 2009; U.S. Pat. Appl. Pub. No. 2013/0110169 entitled "Vertebral Rod System and Methods of Use" to Hynes, et al., issued May 2, 2013; U.S. Pat. Appl. Pub. No. 2011/0184412 entitled "Pre-Assembled Construct With One Or More Non-Rotating Connectors For Insertion Into a Patient" to Scifert, et al., issued Jul. 28, 2011; U.S. Pat. No. 7,964,208 entitled "System and Methods of Maintaining Space For Augmentation of the Alveolar Ridge" to Spagnoli, et al., issued Jun. 21, 2011; U.S. Pat. No. 8,080,521 entitled "Flowable Carrier Matrix and Methods for Delivering to a Patient" to Beals, et al., issued Dec. 20, 2011; U.S. Pat. Appl. Pub. No. 2009/0142385 entitled "Compositions for Treating Bone Defects" to Gross, et al., issued Jun. 4, 2009; U.S. Pat. No. 7,578,820 entitled "Devices and Techniques for a Minimally Invasive Disc Space Preparation and Implant Insertion" to Moore, et al., issued Aug. 25, 2009; U.S. Pat. Appl. Pub. No. 2010/0305575 entitled "Methods and Apparatus for Performing Knee Arthroplasty" to Wilkinson, et al., issued Dec. 2, 2010; U.S. Pat. Appl. Pub. No. 2011/0021427 entitled "Biphasic Calcium Phosphate Cement for Drug Delivery" to Amsden, et al., issued Jan. 27, 2011; U.S. Pat. Appl. Pub. No. 2012/0259335 entitled "Patello-Femoral Joint Implant and Instrumentation" to Scifert, et al., issued Oct. 11, 2012; U.S. Pat. Appl. No. 2011/0106162 entitled "Composite Connecting Elements for Spinal Stabilization Systems" to Ballard, et al., issued May 5, 2011; U.S. Pat. Appl. No. 2004/0073314 entitled "Vertebral Body and Disc Space Replacement Devices" to White, et al., issued Apr. 15, 2004; U.S. Pat. No. 7,513,901 entitled "Graft Syringe Assembly" to Scifert, et al., issued Apr. 7, 2009; U.S. Pat. Appl. No. 2010/0004752 entitled "Vertebral Body and Disc Space Replacement Devices" to White, et al., issued Jan. 7, 2010; U.S. Pat. No. 7,615,078 entitled "Vertebral Body and Disc Space Replacement Devices" to White, et al., issued Nov. 10, 2009; U.S. Pat. No. 6,991,653 entitled "Vertebral Body and Disc Space Replacement Devices" to White, et al., issued Jan. 31, 2006; U.S. Pat. Appl. Pub. No. 2010/0331847 entitled "Methods and Apparatus for Performing Knee Arthroplasty" to Wilkinson, et al., issued Dec. 30, 2010; U.S. Pat. Appl. Pub. No. 2006/0116770 entitled "Vertebral Body and Disc Space Replacement Devices" to White, et al., issued Jun. 1, 2006; and U.S. Pat. No. 8,246,572 entitled "Bone Graft Applicator" to Cantor, et al., issued Aug. 21, 2012.

According to varying embodiments described herein, the present invention is directed to near-simultaneous and integrated delivery of bone graft material during the placement of surgical cages or other medical implants into a patient's spine. The delivery of the bone graft material may be to any area of the body, and in particular, to the intervertebral joints of the spine, for achieving bone graft fusion. The device may be used without the optional near-simultaneous and integrated placement of surgical cages with the delivery of bone graft material. Also, the invention may be used in the repair of a bone joint or in connection with the implantation of prosthetic devices in the body, including, by way of example but not limitation, the hip, knee and a variety of spinal joints. Additionally, the present invention may be used in primary surgery, in which a bone graft is being supplied to promote new bone growth or to reconstruct a joint for the first time, as well as in revision surgery, in which a follow-up procedure is being performed in an area that has previously been subject to one or more surgeries. Further, the invention may be used in any application where material is to be delivered with precision to a confined area where access is restricted, to include surgical procedures, repair of installed or uninstalled mechanical or electrical devices, and arming or disarming of explosive devices.

Although well suited for use in human patients, and although much of the discussion of the present invention is directed toward use in humans, advantages offered by the present invention may be realized in the veterinary and scientific fields for the benefit and study of all types of animals and biological systems. Additionally, although the fusion cages of the present invention are particularly well-suited for implantation into the spinal column between two target vertebrae, and although much of the discussion of the present invention is directed toward their use in spinal applications, advantages offered by embodiments of the present invention may also be realized by implantation at other locations within a patient where the fusion of two or more bony structures may be desired. As one of skill in the art will appreciate, the present invention has applications in the general field of skeletal repair and treatment, with particular application to the treatment of spinal injuries and diseases. It should be appreciated, however that the principles of the present invention can also find application in other areas, specifically where there is a desire to constrain added fluid material to particular regions. For example, the present invention finds application in methods where the objective is to confine added material to predetermined areas of interest and to prohibit the undesired translocation of such material until an operation is complete and/or until a predetermined later time.

One aspect of the present disclosure is a bone graft material delivery system. The system includes, but is not limited to: (1) a hollow tube to receive bone graft material, the hollow tube having: (a) a proximal end; (b) a distal end with at least one opening; (c) a hollow interior from the proximal end to the distal end; and (d) at least one vent port; and (2) a plunger adapted to be inserted into the hollow tube. The plunger includes a distal end with an exterior surface contoured to form a substantially congruent fit with the hollow interior of the hollow tube. The hollow tube and the plunger are configured to deliver bone graft material through the at least one opening in the distal end.

The at least one vent port is positioned between the proximal end and the distal end of the hollow tube. In one embodiment, the at least one vent port has at least one of a size and a shape to prevent passage of the bone graft material through the at least one vent port. Additionally, the at least one vent port is configured to permit air to be released from the hollow interior of the hollow tube. Optionally, the at least one vent port comprises a proximal vent port, a medial vent port, and a distal vent port. In one embodiment, the at least one vent port has a shape that is generally circular or generally linear. Additionally, or alternatively, in one embodiment, the at least one vent port has a width of less than approximately 2 mm.

In one embodiment, the hollow tube comprises a first portion interconnected to a second portion. Optionally, the first portion is sonically welded to the second portion. In another embodiment, the first portion is glued to the second portion. The glue may comprise an adhesive that is activated by ultraviolet light. Other suitable glues and adhesives may be used with the system of the present disclosure.

In one embodiment, the distal end of the hollow tube is configured to engage a fusion cage such that the bone graft material is delivered through an opening of the fusion cage. Additionally, or alternatively, the at least one opening may comprise two openings. Optionally, the two openings may be positioned on lateral sides of the hollow tube.

In one embodiment, the system further comprises a means for advancing the plunger within the hollow interior towards the distal end of the hollow tube. The means for advancing may optionally include notches or teeth formed in the plunger. The teeth may be formed along a longitudinal axis of the plunger.

In one embodiment, the means for advancing includes a ratchet or a gear configured to engage the teeth of the plunger. Optionally, the means for advancing includes a trigger associated with the ratchet, the trigger operable to advance the plunger toward the distal end of the hollow tube. Additionally, or alternatively, the means for advancing may include a knob associated with the gear. In one embodiment, the gear includes teeth such that when the knob is rotated, the gear teeth interact with the plunger teeth to advance the plunger toward the distal end of the hollow tube.

In one embodiment, the means for advancing comprises a manual force applied by an operator. In another embodiment the means for advancing comprises an electric motor. The electric motor can be associated with the gear. In one embodiment, the gear includes teeth such that when the motor rotates the gear, the gear teeth interact with the plunger teeth to advance the plunger toward the distal end of the hollow tube.

The system may further comprise a pivotally mounted trigger configured to engage the teeth of the plunger. The pivotally mounted trigger is operable to advance the plunger toward the distal end of the hollow tube.

In one embodiment, the distal end of the hollow tube comprises a rounded or bullet shape. Optionally, at least a portion of the distal end is closed. In one embodiment, the distal end of the hollow tube is at least partially closed. Additionally, or alternatively, at least a portion of the distal end may include an opening.

In one embodiment, the hollow interior of the hollow tube has a generally rectangular interior cross-section. Alternatively, in another embodiment, the hollow interior of the hollow tube has a generally circular interior cross-section. In one embodiment, the hollow tube is generally linear.

Alternatively, in another embodiment, the distal end may be oriented transverse to the proximal end. Additionally, or alternatively, the hollow tube may be flexible. In one embodiment, at least a portion of the hollow tube is generally transparent or translucent. In this manner, the plunger is at least partially visible within the hollow tube.

The system may further include one or more of an endoscope and a camera associated with the hollow tube. In one embodiment, the endoscope and/or the camera may be positioned outside of the hollow tube. In another embodiment, the endoscope and/or the camera may be positioned within at least a portion of the hollow interior of the hollow tube.

In one embodiment the system further includes a funnel interconnectable to the hollow tube. Accordingly, the proximal end of the hollow tube may be configured to releasably couple to the funnel.

Optionally, the hollow tube is configured to couple to a syringe. Thus, the system may further comprise a syringe interconnectable to the hollow tube. In one embodiment, the bone graft material is mixed within the syringe and subsequently conveyed into the hollow interior of the hollow tube.

The hollow tube and the plunger may be made of a variety of materials including one or more of a metal, polyether ether ketone (PEEK), polyether ketone ether ketone ("PEKEKK"), other plastics, and combinations thereof.

In one embodiment, one or more elements of the system, such as the hollow tube and the plunger, are manufactured by a three-dimensional printing process. A "three-dimensional printing process," as used herein, refers to any of a variety of additive manufacturing processes for making a three-dimensional object based on a three-dimensional model or electronic source input under computer control. Three-dimension printing includes joining material together to make the three-dimensional object. The three-dimensional printing process includes, but is not limited to, fused filament fabrication, plaster based three-dimensional printing, selective laser sintering, selective heat sintering, direct ink writing, and combinations thereof.

Another aspect of the present disclosure is a bone graft material delivery system. The system generally includes, but is not limited to: (1) an elongate tube including a distal end with at least one opening configured to discharge bone graft material; and (2) a means for advancing the bone graft material through the elongate tube. In one embodiment, the means for advancing includes a manual force applied by an operator. Additionally, or alternatively, the means for advancing may include a force applied by a motor.

In one embodiment, the means for advancing includes a plunger with notches. Optionally, the means for advancing further includes a trigger configured to be actuated to the deliver bone graft material through the elongate tube. In one embodiment, the trigger comprises a ratcheting mechanism configured to engage the plunger notches to advance the plunger.

Additionally, or alternatively, the means for advancing may further include a gear to engage the plunger notches. In this manner, a rotational motion of the gear is translated into linear movement of the plunger. Optionally, the motor is interconnected to the gear. In another embodiment, the system further comprises a knob to rotate the gear. In this manner, a user can advance bone graft material through the elongate tube by rotating the knob.

In one embodiment, the means for advancing includes a handle with a trigger configured to be actuated to cause movement of a plunger within the elongate tube. Optionally, the elongate tube is removably coupled to the handle.

In one embodiment, the system further comprises at least two vent ports formed in the elongate tube. The vent ports are configured to release air from the elongate tube. In one embodiment, the at least one opening comprises at least two lateral openings configured to discharge bone graft material.

The elongate tube may be generally linear. In another embodiment, the elongate tube is flexible. The system may optionally include one or more of an endoscope and a camera associated with the elongate tube.

Still another aspect of the present disclosure is method for delivering bone graft material to a surgical location, such as a disc space. The method includes one or more of, but is not limited to: (1) providing a bone graft delivery device comprising a hollow tube with a longitudinal axis, a proximal end and a distal end, and at least one distal opening, the hollow tube adapted to receive bone graft material; (2) loading bone graft material into the hollow tube; (3) inserting a plunger into the hollow tube, the plunger having a distal end with an exterior surface contoured to form a substantially congruent fit with a hollow interior of the hollow tube, wherein the hollow tube and the plunger are configured to deliver the bone graft material through the at least one distal opening; (4) advancing the bone graft material through the hollow tube with a means for advancing; and (5) discharging the bone graft material from the at least one distal opening of the hollow tube, wherein the bone graft material discharged from the at least one distal opening is sufficient to substantially fill a disc space with the bone graft material.

In one embodiment, the distal end of the hollow tube is at least partially closed. Additionally, or alternatively, the distal end of the hollow tube may be at least partially open. Optionally, the hollow interior of the hollow tube has a generally rectangular cross-section. In one embodiment, the hollow tube is generally linear. Additionally, or alternatively, the hollow tube may be flexible. In another embodiment, the distal end of the hollow tube comprises a bullet shaped distal tip. In still another embodiment, the at least one distal opening comprises two openings on lateral sides of the hollow tube.

Optionally, the plunger includes teeth or notches. The teeth may be formed along a longitudinal axis of the plunger. In one embodiment, the means for advancing engages the teeth of the plunger to advance the bone graft material. Additionally, or alternatively, the means for advancing may include a ratcheting mechanism that is actuated to advance the plunger through the hollow tube. In another embodiment, the plunger is pneumatically actuated to advance the bone graft material.

In one embodiment, the means for advancing further comprises a trigger. The trigger is configured to engages the plunger to advance the plunger through the hollow tube. In one embodiment, the trigger is pivotally mounted. Optionally, the trigger may be associated with a handle of the bone grade delivery device.

In one embodiment, the means for advancing includes a gear. The gear includes teeth that engage the plunger to advance the bone graft material. Optionally, the gear teeth engage the teeth of the plunger.

Additionally, or alternatively, the means for advancing includes a motor. The motor is configured to engage the plunger to advance the bone graft material. In one embodiment, the motor is interconnected to the gear.

In one embodiment, the at least one distal opening is formed through a lateral surface of the hollow tube. Optionally, in one embodiment, the hollow tube is configured to facilitate attachment of a funnel. The funnel may serve as a reservoir for application of bone graft material which can then be pushed into the hollow tube and discharged into the disc space. Accordingly, the method may further comprise interconnecting a funnel to the hollow tube.

The method may further include venting air from the hollow tube through at least one vent port positioned between the proximal end and the distal end of the hollow tube as the bone graft material is advanced through the hollow tube.

In one embodiment, the method further includes interconnecting the hollow tube to a handle of the bone graft delivery device, the handle including the means for advancing.

Optionally the method further includes coupling a detachable implant to the distal end of the hollow tube. The implant is adapted to receive bone graft material from the hollow tube. The method may also include expanding the implant in the surgical location. Expanding the implant may comprise rotating a portion of the implant. In one embodiment, the implant is expanded in the surgical location prior to the step of loading bone graft material into the hollow tube.

The step of loading bone graft material may comprise providing a volume of the bone graft material that is at least approximately two times greater than a volume of debrided disc material removed from the disc space. In one embodiment, the step of loading bone graft material comprises providing a volume amount of bone graft material 100% greater than conventionally employed for fusion procedures. In another embodiment, the step of loading bone graft material comprises providing a volume amount of bone graft material 200% greater than conventionally employed for fusion procedures. Additionally, or alternatively, the step of loading bone graft material comprises providing a volume amount of bone graft material 300% greater than conventionally employed for fusion procedures. In still another embodiment, the step of loading bone graft material comprises providing a volume amount of bone graft material 400% greater than conventionally employed for fusion procedures. Optionally, a volume of the bone graft material discharged from the at least one distal opening is at least approximately two times greater than a volume of debrided disc material removed from the disc space.

One aspect of the present disclosure is to provide a bone graft material delivery system. The bone graft material delivery system generally includes, but is not limited to, one or more of: (1) a hollow tube to receive bone graft material, the hollow tube having: (a) a proximal end; (b) a distal end with at least two lateral openings; (c) a hollow interior from the proximal end to the distal end; and (d) at least one vent port; and (2) a plunger adapted for inserting into the proximal end of the hollow tube, the plunger having a distal end with an exterior surface contoured to form a substantially congruent fit with the hollow interior of the hollow tube, wherein the hollow tube and the plunger are configured to deliver bone graft material through the at least two lateral openings in the distal end.

Optionally, the at least one vent port is oriented transverse to an extended axis of the hollow tube. In another embodiment, the at least one vent port is configured to release air from the hollow interior of the hollow tube. Additionally, the at least one vent port can have at least one of a size and a shape to prevent passage of the bone graft material through the at least one vent port. In another embodiment, the at least one vent port comprises a proximal vent port, a medial vent port, and a distal vent port. Additionally, or alternatively, the at least one vent port has a shape that is generally circular or generally linear. In one embodiment, the at least one vent port has a width of less than approximately 2 mm.

In one embodiment, the hollow tube comprises a first portion interconnected to a second portion. Optionally, the first portion is sonically welded to the second portion along a joint.

Additionally, the system may further comprise a grip interconnectable to the proximal end of the hollow tube, the grip operable to advance the plunger into the hollow interior of the hollow tube. In one embodiment, the grip includes a trigger operable to incrementally advance the plunger toward the distal end of the hollow tube.

In one embodiment, the distal end of the hollow tube comprises a closed distal tip. Optionally, the hollow interior of the hollow tube has a generally rectangular interior cross-section. Additionally, the hollow tube may be generally linear. In one embodiment, the distal end is oriented transverse to the proximal end. In another embodiment, the hollow tube is flexible. Accordingly, in one embodiment, the plunger is flexible.

In one embodiment, at least a portion of the hollow tube is generally transparent or translucent such that the plunger is at least partially visible within the hollow tube. In another embodiment, the system further comprises one or more of an endoscope and a camera associated with the distal end of the hollow tube.

Another aspect of the present disclosure is a bone graft material delivery system. The system generally comprises: (1) an elongate tube including a distal end with at least one opening configured to discharge bone graft material; and (2) a handle at a proximal end of the elongate tube configured to be actuated to deliver bone graft material through the elongate tube, the handle comprising a ratcheting mechanism configured to advance a plunger to push bone graft material through the elongate tube. In one embodiment, at least one opening comprises at least two lateral openings configured to discharge bone graft material. Optionally, the handle comprises a trigger configured to be actuated to cause movement of the plunger within the elongate tube. Additionally, or alternatively, the system may further comprise at least two vent ports formed in the elongate tube configured to release air from the elongate tube.

In one embodiment, the elongate tube is removably coupled to the handle. In another embodiment, the elongate tube is generally linear. Optionally, the distal end of the elongate tube is oriented transverse to the proximal end. In another embodiment, the elongate tube is flexible. Additionally, at least a portion of the elongate tube can be generally transparent or translucent such that the plunger is at least partially visible within the elongate tube. In another embodiment, the system further comprises one or more of an endoscope and a camera associated with the distal end of the elongate tube.

Another aspect of the present disclosure is a method for delivering bone graft material to a surgical location, comprising: (1) providing a bone graft delivery device comprising a hollow tube with a lumen; (2) loading bone graft material into the lumen of the hollow tube; (3) advancing the bone graft material through the lumen; and (4) discharging the bone graft material from at least one opening at a distal end of the hollow tube. Optionally, a plunger is advanced through the lumen of the hollow tube to advance the bone graft material. In one embodiment, a ratcheting mechanism is actuated to advance the plunger through the lumen. In another embodiment, the plunger is pneumatically actuated to advance the bone graft material. Optionally, the bone graft material is advanced pneumatically through the lumen.

In one embodiment, advancing the bone graft material further comprises actuating a trigger of a handle of the bone graft delivery device. Optionally, the at least one opening is formed through a lateral surface of the hollow tube. In one embodiment, the method further includes venting air from the hollow tube through at least one vent port as the bone graft material is advanced through the lumen.

In another embodiment, the method includes, after loading the bone graft material into the lumen, interconnecting the hollow tube to a handle of the bone graft delivery device, the handle configured to advance the plunger through the lumen. The method may optionally include one or more of detaching an implant from the distal end of the hollow tube and, after detaching the implant, removing the hollow tube from the surgical location. Optionally, the method includes expanding the implant in the surgical location. In one embodiment, expanding the implant comprises rotating a portion of the implant such that a first plate of the implant moves away from a second plate of the implant. Additionally, the portion of the implant rotates without moving transversely with respect to either the first or the second plate.

According to various embodiments of the present disclosure, one aspect of the invention is to provide an integrated fusion cage and graft delivery device that comprises a tubular member, which is substantially hollow or contains at least one inner lumen and that has a generally rectangular cross-sectional shape. This generally rectangular cross-sectional shape offers a larger amount of surface area through which bone graft material may be inserted and ejected from the hollow tubular member. Furthermore, this generally rectangular shape is more congruent with the size or shape of the annulotomy of most disc spaces, which frequently are accessed by a bone graft delivery device for delivery of bone graft. However, as one skilled in the art would appreciate, the tool cross-section need not be limited to a generally rectangular shape. For example, cross-sections of an oval shape or those with at least one defined angle to include obtuse, acute, and right angles can provide a shape in some situations that is more congruent with the size or shape of the annulotomy of a particular disc space. A substantially round shape may also be employed that provides the surgeon with an indication of directional orientation.

The phrase "removably attached" and/or "detachable" is used herein to indicate an attachment of any sort that is readily releasable.

The phrase "integrated fusion cage", "spinal fusion implant", "biological implant" and/or "fusion cage" is used here to indicate a biological implant.

According to various embodiments of the present disclosure, it is another aspect that the hollow tubular member further comprise at least one opening on a lateral face or surface of the hollow tubular member, at one distal end, for ejecting bone graft material into a bone graft receiving area, such as a disc space, such that the bone graft material is ejected from the hollow tubular member through an additional implant, such as a structural cage implant. In addition, the graft material is dispersed into the area of the debrided disc space surrounding and within the cage. Furthermore, the structural cage implant is removably attached to the hollow tubular member so as to be deposited into the surgical area. Thus, the device may be used in an integrated and near-simultaneous method for depositing bone graft material into a debrided disc space through a structural cage implant and leaving the structural implant.

According to various embodiments of the present disclosure, one aspect of the invention is to provide an integrated fusion cage detachable component of the integrated fusion cage and graft delivery device that comprises a biological implant that fits over the distal end of the substantial hollow tube, and which has a shape that is substantially congruent with the distal end of the hollow tube. However, the shape and configuration of the integrated fusion cage need not be limited to a generally rectangular shape. For example, cross-sections of an oval shape or those with at least one defined angle to include obtuse, acute, and right angles can provide a shape in some situations that is more congruent with the size or shape of the annulotomy of a particular disc space. A substantially round shape may also be employed that provides the surgeon with an indication of directional orientation.

In a preferred embodiment, the fusion cage has a tapered tip, and several open channels along the medial surfaces. In a preferred embodiment, the fusion cage and/or the bone graft delivery portion of the integrated fusion cage and graft delivery device is of oblong or rectangular, or square shape. The integrated fusion cage and graft delivery device is designed to avoid blocking or impacting bone graft material into a surgical disc space, thereby limiting the bone graft material that may be delivered, and not allowing available fusion space to be fully exploited for fusion.

In a preferred embodiment, the fusion cage has a keel-shaped tip to separate disk and prevent annular penetration. Also, the fusion cage has dual portals for bone graft discharge. In one embodiment, the medial openings are larger than the lateral openings. In another embodiment, the medial openings and the lateral openings are of the same size. In another embodiment, the medial and the lateral openings are symmetrical. In another embodiment, the medial openings are smaller than the lateral openings.

Further, the fusion cage may be designed in variable heights and lengths so that it fits snugly into the prepared disk space.

In a preferred embodiment that is ideal for anterior lumbar interbody fusion, the fusion cage has two portals for bone graft discharge positioned on opposite sides of the fusion cage. In a preferred embodiment that is ideal for direct lateral interbody fusion, the fusion cage has six portals for bone graft discharge, with three portals on one side of the fusion cage and three portals on an opposite side of the fusion cage. And, in a preferred embodiment that is ideal for post-vertebrectomy use, two opposing wall portions of the fusion cage are substantially porous to bone graft slurry, while the substantial remainder of the wall of the fusion cage is substantially impervious to bone graft slurry.

In another embodiment of the device, the hollow tube engages with the fusion cage via a break-off collar and the plunger inserts into the interior of the hollow tube. The break-off collar may be severed by any of several means, to include application of torsion and/or rotational force and/or lateral force to the break-off collar, for example by twisting on the hollow tube and/or the plunger. The break-off collar may be formed by any of several means, comprising a thinner and/or reduced cross-sectional, that is thickness, a pre-set fracture-line, one or more notches, a frangible portion defined by a discrete, extended area that is weaker in one or more respects as compared to surrounding and/or adjacent material, and any means known to those skilled in the art to achieve reliable break-off. Preferably a clean break is achieved such that no surgically significant issues arise by such severance of the cage-portion and the hollow for the portion. In other embodiments, other ways devices and features can be employed to achieve separation of a first delivery tube structure and a second structure intended to remain in a patient. For example, electric and/or magnetic disconnecting mechanisms can be used in lieu of a physical breaking/severing of two discrete portions that define the above-referenced first and second structures. A smooth edge preferably remains after such severance of the cage. Moreover, it will be understood as being within the scope of the present invention to use more conventional coupling/decoupling mechanisms to achieve desired separation of the first and second structures, e.g. bayonet mounted features, tongue and groove, male/female interlocking structures, clamping devices, nested arrangements, etc., all of which find support in the various cited references incorporated herein by reference. In one example method of use, the connected hollow tube and fusion cage is inserted into the surgical area, bone graft material is inserted into the hollow tube (or already provided as a pre-packaged material), the plunger is pushed into the hollow tube, so as to deliver bone graft material to the site, then the plunger is reversed or pulled-out so to retreat from the site and move higher or beyond the break-off collar, and then the break-off collar is broken so as to disengage the fusion cage from the hollow tube and therein leave the fusion cage at the surgical site. In another embodiment of the device, the hollow tube engages with a connector conduit which in turn connects with the fusion cage via a break-off collar. One or more connectors connect the hollow tube with the connector conduit. The hollow tube fits over the connector conduit. The one or more connectors fit through the hollow tube and the connector conduit. Alternately, the hollow tube may fit over the connector conduit via a press-fit, aka interference fit, without need of one or more connectors. In one embodiment, the connectors comprise set screws, pins and tabs. The connector conduit allows, for example, various fusion cages designs to be fitted to a common hollow tube/plunger combination. This allows, for example, the common hollow tube/plunger combination to be re-sterilized and thus reused in multiple surgical procedures. In one embodiment, the hollow tube/plunger combination is reusable, and the fusion cage is disposable.

In one embodiment of the connector conduit, the connector conduit is of circular cross-section. In another embodiment, the connector conduit is of conical shape, or any shape that allows a transition in diameter between the fusion cage and the hollow tube.

In one example method of use, the hollow tube is inserted over the connection conduit (which is attached to the fusion cage), then inserted into the surgical area, bone graft material is inserted into the hollow tube (or already provided as a pre-packaged material), the plunger is pushed into the hollow tube (and past the connection conduit), so as to deliver bone graft material to the site, then the plunger is reversed or pulled-out so to retreat from the site and move higher or beyond the break-off collar, and then the break-off collar is broken so as to disengage the fusion cage from the hollow tube (which is still connected to the connection conduit) and therein leave the fusion cage at the surgical site.

The break-off collar may be severed by any of several means, to include application of torsion and/or rotational force and/or lateral force to break-off collar, for example by twisting on the hollow tube and/or the plunger.

In one embodiment of the fusion cage, the fusion cage is of rectangular cross-section, such that one pair of opposite sides, for example a height first pair of sides, has a dimension of approximately 8-14 mm, and a second pair of opposite sides, for example a length dimension, of approximately 22-36 mm. One skilled in the art will appreciate that the exact dimensions of the fusion cage may be adapted to conform to particulars of the surgical site, for example, the relative sizing between the particular vertebrae in which bone graft material and/or a fusion cage is to be inserted. In other embodiments of the fusion cage, the fusion cage is of a substantially cylindrical shape. For example, a preferred embodiment of a fusion cage for use in an ALIF procedure forms a substantially cylindrical shape, with a height of approximately 8-14 mm and a diameter of less than about 36 millimeters. As another example, a preferred embodiment of a fusion cage for use in conjunction with a vertebrectomy has a substantially cylindrical shape with a height equal to or greater than the height of the vertebra (or the collective height of the vertebrae) it is intended to replace and a diameter of less than about 36 millimeters. Preferably, the separation "zone" between the cage and the hollow filling tube is at one end of the cage, preferably the end of the cage (when implanted) closer to the incision site.

A preferred method of using the integrated fusion cage and graft delivery device comprises precisely inserting the integrated fusion cage and graft delivery device, in one or more of the embodiments contained herein, into the surgical area. The integrated fusion cage and graft delivery device is then filled with bone graft material in its one or more substantially hollow tubes, the one or more plungers are inserted into the one or more hollow tubes, and the one or more plunger are pushed into the one or more hollow tubes, guided precisely as enabled by the minimal profile of the device, therein controllably depositing the bone graft material into the surgical area through and into the surgical implant cage. The surgical implant device may then be selectably detached from the integrated fusion cage and graft delivery device so as to remain at the surgical site.

Another method of using the integrated fusion cage and graft delivery device comprises inserting the integrated fusion cage and graft delivery device into a prepared disk space, such that the fusion cage portion fits snugly into the prepared disk space (the fusion cage is designed in variable heights and lengths so as to fit snugly into the prepared disk space), pushing the plunger through the hollow shaft so as to push biological fusion material (e.g. bone graft) through the hollow shaft to flow the biological material through the fusion cage's open lateral and/or medial portals in communication with the hollow tube and plunger, thereby delivering biological material into the prepared disk space, after which the fusion cage is detached from the hollow tube and left in the disk space. Thus, the fusion cage is left in the disk space with a maximum and/or optimal amount of biological material near-simultaneously delivered within the fusion cage and/or surrounding the fusion cage in the disk space.

Using the integrated fusion cage and graft delivery device as described overcomes a problem associated with the traditional separate application of bone graft material and insertion of a fusion cage. Specifically, in the traditional method, the volume of disk space which does not contain bone graft material is limited, which, for example, limits the effectiveness of the surgical procedure. For example, using the traditional two-step procedure, bone graft may be inserted into, for example, a cylindrically shaped area of radius r to a height h of 8 mm, and then a cylindrically shaped fusion cage inserted of height h of 14 mm. Thus, the surgical area is left without a complete volume of bone graft material, i.e. because the volume of a cylinder is Volume=$\pi r^2 h$, the bone graft area is left without $\pi r^2$ (14 mm-8 mm), or $6\pi r^2$ of bone graft material. (Note that this represents a 75% increase in bone graft material delivered to the surgical site for these example dimensions). This effectively dilutes the bone graft material and reduces its effectiveness. The present invention can substantially or completely fill the available disk space with bone graft material because distraction of the disk space is performed substantially simultaneously with application of the fusion cage. Because more biological material is delivered to the prepared disk space, the fusion rate should increase. Also, by directly implanting fusion material, e.g. bone graft material, though a fusion cage positioned for detachment (and then detached) as a single step, time is saved and there is less manipulation of the sensitive nerve tissue at the fusion site (which increases safety).

Furthermore, the integrated fusion cage and graft delivery device may be used without the surgical implant delivery device portion such that the method comprises precisely inserting the integrated fusion cage and graft delivery device, in one or more of the embodiments contained herein, into the surgical area that may already contain one or more additional implants, such as a structural cage implant. The integrated fusion cage and graft delivery device is then filled with bone graft material in its one or more substantially hollow tubes, the one or more plungers are inserted into the one or more hollow tubes, and the one or more plunger are pushed into the one or more hollow tubes, guided precisely as enabled by the minimal profile of the device, therein controllably depositing the bone graft material into the surgical area without depositing bone graft material into the path of any structural cage implant or other implant that may already be present.

According to a still further aspect of the present invention, the integrated fusion cage may be introduced into a spinal target site without the use of the graft delivery device. That is, the integrated fusion cage may be introduced into a spinal target site through use of any of a variety of suitable surgical instruments having the capability to engage the implant. The integrated fusion cage is capable of being used in minimally invasive surgical procedures, needing only a relatively small operative corridor for insertion. The integrated fusion cage may also be used in open procedures. According to a still further aspect of the present invention, the integrated fusion cage of the present invention may be used in a variety of configurations in a fusion procedure, including but not limited to (and by way of example only) unilateral, paired unilateral and bilateral.

Furthermore, the integrated fusion cage and graft delivery device and method of use is applicable to position and deliver fusion cages from the side, directly anterior or in the anterior fusion cages of the cervical spine.

In a preferred embodiment, the integrated fusion cage and graft delivery device comprises a hollow tube or contains at least one inner lumen constructed to receive bone graft, and a plunger adapted for insertion at least partially within the hollow tube and preferably through the full extent of the hollow tube. The plunger of some embodiments is generally of the same geometric configuration as the hollow interior portion of the hollow tube so that the plunger, once fully inserted in to the hollow tube, is substantially congruent with the hollow interior portion of the hollow tube, e.g. both the plunger and the hollow tube are substantially the same shape and/or class. The plunger preferably extends about the same length as the hollow tube, and further comprises an end portion, e.g. at least one knob or handle for grasping and manipulation by a user, or in robotic or automated or semi-automated control or surgeries, by a machine.

Also, according to a preferred embodiment, the hollow interior portion of the hollow tube further comprises a sloped or curved surface at a second end (e.g. positioned near a place for deposit of bone graft material) adjacent and opposite a lateral window or opening in a lateral face of the hollow tube. As the interior of the hollow tube comprises a sloped or curved surface at its second end, the plunger also comprises a sloped or curved surface at a second end of the plunger. The plunger terminates opposite the curved surface at its second end with a laterally faced surface, which corresponds to the lateral window or opening at the second end of the hollow tube. The distal end of the hollow tube is fitted with a substantially conformal fusion cage that covers the exterior surface of the hollow tube, fitted with one or more openings that align with one or more openings of the hollow tube. Thus, in cooperation, the plunger may be inserted into the opening of the hollow tube, and extended the entire length of the hollow tube, at least to a point where the laterally faced surface of plunger is in communication with the lateral window or opening at the second end of the hollow tube. This configuration permits a user to eject substantially all of the bone graft material that is placed into the hollow tube in a lateral direction at the bone graft receiving area, through the substantially conformal and detachable fusion cage that covers the exterior surface of the hollow tube, optionally detach the detachable fusion cage, during a surgical procedure.

In a preferred embodiment, the integrated fusion cage and graft delivery device comprises an integrated fusion cage that comprises a first proximal end and a second distal end, wherein the first proximal end contains an opening adapted to allow fitting and/or engagement to the distal end of the hollow tube. This fitting and/or engagement may be over the external surface of the hollow tube or inside the interior of the hollow tube. Further, the integrated fusion cage may comprise one or more medial openings and one or more lateral openings that align with one or more openings at the distal end of the hollow tube. Further, the integrated fusion cage may contain surfaces, such as belts or striations, along one or more medial surfaces of the integrated fusion cage. The integrated fusion cage is configured such that when a plunger, once fully inserted into the hollow tube, is substantially congruent with the hollow interior portion of the hollow tube, e.g. both the plunger and the hollow tube are substantially the same shape and/or class and bone graft material is delivered through the integrated fusion cage into the surgical area.

In one embodiment, a substantially hollow implant is detachably interconnected to a distal end of the hollow tube, the implant having a proximal end and a tapered distal end, the tapered distal end having an exterior tapered surface and a tapered interior surface, and the plunger adapted for inserting into the proximal end of the hollow tube, the plunger having a tapered distal end being contoured to the tapered interior surface of the distal end of the implant to form a conforming fit between the tapered distal end of the plunger and the tapered interior surface of the distal end of the implant when the plunger is fully inserted into the implant such that bone graft material within the hollow tube is delivered to a graft receiving area through at least one opening of the implant. Further, the distal end of the implant may comprise a closed distal tip, and the tapered distal end of the plunger may be wedge-shaped and the tapered interior surface of the closed distal tip of the distal end of the implant may be wedge-shaped.

The spinal fusion implant of the present invention may be used to provide temporary or permanent fixation along an orthopedic target site.

The spinal fusion implant of the present invention may be provided with any number of additional features for promoting fusion, such as one or more apertures extending between the top and bottom surfaces which allow a boney bridge to form through the spinal fusion implant.

The spinal fusion implant may also be provided with any number of suitable antimigration features to prevent the implant from migrating or moving from the disc space after implantation. Suitable anti-migration features may include, but are not necessarily limited to, angled teeth or ridges formed along the top and bottom surfaces of the implant and/or rod elements disposed within the distal and/or proximal ends.

According to a further aspect of the present invention, the spinal fusion implant may be provided with one or more radiographic markers at the proximal and/or distal ends. These markers allow for a more detailed visualization of the implant after insertion (through radiography) and allow for a more accurate and effective placement of the implant.

According to a still further aspect of the present invention, the distal end of the spinal fusion implant may have a conical (bullet-shaped) shape including a pair of first tapered (angled) surfaces and a pair of second tapered (angled) surfaces. The first tapered surfaces extend between the lateral surfaces and the distal end of the implant, and function to distract the vertebrae adjacent to the target intervertebral space during insertion of the spinal fusion implant. The second tapered surfaces extend between the top and bottom surfaces and the distal end of the spinal fusion implant, and function to maximize contact with the anterior portion of the cortical ring of each adjacent vertebral body. Furthermore, the second tapered surfaces provide for a better fit with the contour of the vertebral body endplates, allowing for a more anterior positioning of the spinal fusion implant and thus advantageous utilization of the cortical rings of the vertebral bodies.

Another embodiment for the integrated fusion cage and graft delivery device comprises a detachable fusion cage that is detachable, or removably attached, by any of several means. As disclosed above, in one embodiment, the fusion cage is substantially conformal with the distal end of the hollow tube in that it covers the exterior surface of the hollow tube, wherein the fusion cage is configured with one or more openings that align with one or more openings of the hollow tube. In one preferred embodiment, the fusion cage of the integrated fusion cage and graft delivery device forms an interference fit with the fusion cage, such that when the integrated fusion cage and graft delivery device is inserted into the surgical area, the integrated fusion cage and graft delivery device presses against bone and/or vertebrates such that when an axial force is applied to the integrated fusion cage and graft delivery device in a rearward direction (toward the proximal end of the integrated fusion cage and graft delivery device), the fusion cage detaches from the integrated fusion cage and graft delivery device and thereby remains in the surgical area.

In another embodiment for the integrated fusion cage and graft delivery device and its method of use, the fusion cage is substantially filled with bone graft material after the fusion cage is implanted. In another embodiment for the integrated fusion cage and graft delivery device and its method of use, the fusion cage is substantially filled with bone graft material simultaneously with the implantation of the fusion cage.

In another embodiment for the integrated fusion cage and graft delivery device and its method of use, the fusion cage and/or the bone graft material associated with the fusion cage may be accessed during subsequent surgical operations.

In another embodiment for the integrated fusion cage and graft delivery device and its method of use, the fusion cage is a separate device, for example a pre-packaged implant device, which may be installed independently from the integrated fusion cage and graft delivery device or installed in coordination with the integrated fusion cage and graft delivery device. In either situation, the device may be used to provide bone graft material in and/or around the prepackaged implant.

In another embodiment for the integrated fusion cage and graft delivery device and its method of use, some or all of the bone graft material is provided as a component of a pre-packaged implant. In another embodiment for the integrated fusion cage and graft delivery device, the detachable fusion cage is detachable by way of an indent-tab that penetrates the interior of the hollow tube, such, when the plunger is substantially inserted into the hollow tube, the indent-tab is pushed out from the interior of the hollow tube so as to no longer be attached to the integrated fusion cage and graft delivery device, thereby remaining in the surgical area.

In another embodiment, the hollow tube is of cylindrical shape and includes one or more locking tabs or indent tabs configured to engage one or more locking slots of the fusion cage. The locking tabs may permanently or not permanently engage the locking slots, and may be of a shape to include rectangular, circular and oblong. In one embodiment of the locking tabs and locking slots, the locking tabs and locking slots engage one another by rotating the hollow tube clockwise and are released by counterclockwise rotation. In another embodiment of the configuration of the locking tabs and locking slots, the locking tabs and locking slots engage one another by rotating the hollow tube counterclockwise and are released by clockwise rotation.

In another embodiment, the fusion cage has internal ramps which assist in directing the bone graft material to one or more openings in the fusion cage.

In another embodiment for the integrated fusion cage and graft delivery device, the detachable fusion cage is detachable by way of receipt of an electrical, mechanical, pneumatic, hydraulic or other communication imparted by the user upon the plunger and/or hollow tube so as to detach the fusion cage and thereby deposit the fusion cage into the surgical area.

In another embodiment for the integrated fusion cage and graft delivery device, the detachable fusion cage is detachable by way of a Luer taper or Luer fitting connection, such as in a Luer-Lok® or Luer-Slip configuration or any other Luer taper or Luer fitting connection configuration. For purposes of illustration, and without wishing to be held to any one embodiment, the following U.S. patent application is incorporated herein by reference in order to provide an illustrative and enabling disclosure and general description of means to selectably detach the fusion cage of the integrated fusion cage and graft delivery device: U.S. Patent Appl. No. 2009/0124980 to Chen.

In another embodiment for the integrated fusion cage and graft delivery device, the detachable fusion cage is detachable by way of a pedicle dart by threadable rotation to achieve attachment, detachment, and axial movement. Other ways include a quick key insertion, an external snap detent, or magnetic attraction or any other structure. For purposes of illustration, and without wishing to be held to any one embodiment, the following U.S. patent application is incorporated herein by reference in order to provide an illustrative and enabling disclosure and general description of means to selectably detach the fusion cage of the integrated fusion cage and graft delivery device: U.S. Patent Appl. No. 2009/0187194 to Hamada.

In another embodiment for the integrated fusion cage and graft delivery device, the detachable fusion cage is detachable by use of magnetism. More specifically, the detachable fusion cage can be made to feature a magnetic field pattern and a resulting force R that are adjustable and may be of different character than the rest of the integrated fusion cage and graft delivery device. With permanent magnets, such adjustments can be made mechanically by orienting various permanent magnet polar geometries and corresponding shapes relative to one another. U.S. Pat. No. 5,595,563 to Moisdon describes further background regarding such adjustment techniques, which is hereby incorporated by reference in its entirety. Alternatively, or additionally, electromagnets could be used in combination with permanent magnets to provide adjustability. In further embodiments, the magnets and corresponding fields and the resultant magnetic field pattern can include both attraction forces from placement of opposite pole types in proximity to one another and repulsion forces from placement of like pole types in proximity to one another. As used herein, "repulsive magnetic force" or "repulsive force" refers to a force resulting from the placement of like magnetic poles in proximity to one another either with or without attractive forces also being present due to opposite magnetic poles being placed in proximity to one another, and further refers to any one of such forces when multiple instances are present. U.S. Pat. No. 6,387,096 is cited as a source of additional information concerning repulsive forces that are provided together with attractive magnetic forces, which is hereby incorporated by reference. In another alternative embodiment example, one or more of surfaces of the fusion cage are roughened or otherwise include bone-engaging structures to secure purchase with vertebral surfaces. In yet other embodiments, the selectable detachable feature between the detachable fusion cage and the integrated fusion cage and graft delivery device can include one or more tethers, cables, braids, wires, cords, bands, filaments, fibers, and/or sheets; a nonfabric tube comprised of an organic polymer, metal, and/or composite; an accordion or bellows tube type that may or may not include a fabric, filamentous, fibrous, and/or woven structure; a combination of these, or such different arrangement as would occur to one skilled in the art. Alternatively or additionally, the selectable detachable feature between the detachable fusion cage and the integrated fusion cage and graft delivery device can be arranged to present one or more openings between members or portions, where such openings extend between end portions of the fusion cage. For purposes of illustration, and without wishing to be held to any one embodiment, the following U.S. patent application is incorporated herein by reference in order to provide an illustrative and enabling disclosure and general description of means to selectably detach the fusion cage of the integrated fusion cage and graft delivery device: U.S. Patent Appl. No. 2011/0015748 to Molz et al.

In another embodiment for the integrated fusion cage and graft delivery device, the detachable fusion cage is detachable by use of plasma treatment. The term "plasma" in this context is an ionized gas containing excited species such as ions, radicals, electrons and photons. (Lunk and Schmid, Contrib. *Plasma Phys.*, 28: 275 (1998)). The term "plasma treatment" refers to a protocol in which a surface is modified using a plasma generated from process gases including, but not limited to, $O_2$, He, $N_2$, Ar and $N_2O$. To excite the plasma, energy is applied to the system through electrodes. This power may be alternating current (AC), direct current (DC), radiofrequency (RF), or microwave frequency (MW). The plasma may be generated in a vacuum or at atmospheric pressure. The plasma can also be used to deposit polymeric, ceramic or metallic thin films onto surfaces (Ratner, Ultrathin Films (by Plasma deposition), 11 *Polymeric Materials Encyclopedia* 8444-8451, (1996)). Plasma treatment is an effective method to uniformly alter the surface properties of substrates having different or unique size, shape and geometry including but not limited to bone and bone composite materials. Plasma Treatment may be employed to effect magnetic properties on elements of the integrated fusion cage and graft delivery device, or to provide selectable detachment of the fusion cage. For purposes of illustration, and without wishing to be held to any one embodiment, the following U.S. patent application is incorporated herein by reference in order to provide an illustrative and enabling disclosure and general description of means to selectably detach the fusion cage of the integrated fusion cage and graft delivery device: U.S. Pat. No. 7,749,555 to Zanella et al.

One having skill in the art will appreciate that the fusion cage may be selectably detachable to the integrated fusion cage and graft delivery device, for example, by means that 30 mechanically grasp the head, means that attach by vacuum, and means that attach by friction, or other means known to those of skill in the art for attaching the head of an apparatus to the shaft of an apparatus.

It is another aspect of the present disclosure that the distal end of the integrated fusion cage and graft delivery device be equipped with various other tools to aid in the procedure. Such tools may include, for example, devices used to assess the condition of the implantation site and surrounding tissue. This may include, for example, a device that transmits or provides an image or signal which carries an image for visual inspection and photography. Such an image capture device may include, for example, a device to illuminate the implant site coupled with an image capture and/or transmission device. Another tool may also include, for example, a device that aids in irrigation or drainage of the surgical site, a tool used to sample or biopsy tissue.

Another embodiment for the integrated fusion cage and graft delivery device comprises a hollow tube constructed to receive bone graft, where the hollow tube has a proximal and distal end, a plunger adapted for insertion at least partially within the hollow tube at the proximal end of the hollow tube, whereby the plunger is constructed and arranged with respect to the hollow tube so as to prevent rotation of the plunger during insertion into the hollow tube, whereby the plunger has a distal end that is contoured to an interior surface of the distal end of the hollow tube such that the contoured distal end of the plunger is nearly congruent with the interior surface of the distal end of the hollow tube for removing substantially all of the bone graft received by the hollow tube and whereby the bone graft is delivered to the graft receiving area. Still another embodiment provides a rifling structure in the hollow tube interior that facilitates rotational movement of the plunder along a lengthwise axis of the hollow tube, therein delivering a substantially steady pressure and/or rate of delivery of the bone graft material as the plunger descends the hollow tube when the plunger is forced through the hollow tube. The rifling or screw-like movement may also translate to a predetermined delivery of material per full rotation, e.g. each 360-degree rotation of the plunger equates to 5 cc of bone graft material delivered to the bone graft site.

Another aspect of the present invention includes providing a hollow tube and plunger assembly, in which the hollow tube and/or the plunger assembly are disposable. The tube may also be at least portions of biocompatible material which can stay in the canal without impairing the final implantation. Alternatively, it may thus be a material that is resorbable, such as a resorbable polymer, in the canal after implantation, so as not to interfere with the growth of the bone or stability of the implant.

A further embodiment of the invention provides pre-packaged inserts for loading into the hollow tube element, or if there are a plurality of hollow tube elements, into one or more of the hollow tube elements. The pre-packaged inserts may be of varying lengths, and/or layered of differing materials or components, to include the patient's own bone graft matter.

Another embodiment of the present invention provides an integrated fusion cage and graft delivery system, by which a hollow tube and/or a hollow tube/plunger assembly can be prepared prior to opening a patient, thus minimizing the overall impact of the grafting aspect of a surgical implantation or other procedure. Moreover, the hollow tube may be made to be stored with bone graft in it for a period of time, whether the tube is made of plastic, metal or any other material. Depending upon the surgical application, it may be desirable to only partially fill the tube for storage, so that a plunger can be at least partially inserted at the time of a surgery.

A further embodiment of the present invention provides a bone graft insertion apparatus comprising a hollow tube constructed to receive bone graft, the hollow tube having a proximal and distal end whereby the hollow tube contains least one opening on a surface of the distal end of the hollow tube. The at least one opening is preferably positioned other than completely along the axial or longitudinal axis of the device. The number and size and shape of such openings can vary but are preferably adapted to deliver bone graft material in a direction substantially transverse to the axial extent of the substantially hollow tube. In one embodiment, two or more apertures are provided. In certain embodiments, apertures are on the same side of the hollow tube, where in others, apertures are on different sides (e.g. opposing sides) of a hollow tube. A plunger, adapted for insertion at least partially within the hollow tube, is constructed and arranged with respect to the hollow tube so as to present at least one substantially flat contour, whereby the plunger has a distal end that is contoured to an interior surface of the distal end of the hollow tube such that the contoured distal end of the plunger is nearly congruent with the interior surface of the distal end of the hollow tube. This facilitates removing substantially all of the bone graft received by the hollow tube whereby the bone graft is delivered to the graft receiving area. It is important to remove substantially all of the bone graft material as it is expensive and/or difficult to obtain.

In another embodiment of the present disclosure the distal end of the plunger is flexible to allow, for example, the user to maneuver the distal end and thereby any bone graft material in the hollow tube to the implantation site. One skilled in the art will appreciate that the flexible aspect of certain embodiments can be both passive and active in nature. Active flexibility and manipulation in the distal end of the plunger may incorporate, for example, the manipulative capabilities of an endoscope, including components for manipulation such as guidewires along the longitudinal axis of the shaft of the plunger.

In another embodiment of the invention, the distal end and the proximal end of the hollow tube are in communication via a conduit to enable electrical, hydraulic, pneumatic, or mechanical transmission, the later such as a wire. Such hydraulic communication allows, for example, a medical or other liquid to be delivered or extracted from the surgical area. Such mechanical communication allows, for example, the distal end to be maneuvered precisely.

In another embodiment of the present disclosure, the hollow tube and/or plunger may be curved and/or may have an angular aspect, in addition to the sloped or curved surface at a second end of the hollow tube/plunger. This shape may, for example, aid the surgeon in more comfortably introducing the delivery device to the implant site, be shaped to better accommodate implantation sites on right or left sides of the body, or be shaped to better accommodate right or left-handed surgeons. One having skill in the art will appreciate that the delivery device may have multiple angles and curved aspects which enable aspects of embodiments of the present disclosure or aid in ergonomics.

In one embodiment of the present disclosure, the device further comprises a footing or shelf at the distal end of the tubular device that is nearest the operating site for preventing or mitigating risk of injury to the patient during surgery. According to this embodiment, the footing may be flexible, semi-flexible, semi-rigid or rigid. The footing serves to protect the anatomy of the patient from being penetrated by the hollow tube of the integrated fusion cage and graft delivery device when the plunger is being inserted or during tamping of the hollow tube or the plunger by the surgeon, which may occur during the surgical procedure for a variety of reasons. In certain embodiments, the distal tip region of the hollow tube comprises a softer, malleable and/or less rigid material than the remainder of the hollow tube. For example, the distal tip could be made of a bioactive collagen.

It is yet another aspect of the present disclosure to provide an integrated fusion cage and graft delivery device that contains one or more detachable elements for use in an operation where bone graft material must be inserted into the integrated fusion cage and graft delivery device and ejected to a bone graft receiving area. According to various embodiments, these detachable devices may include a detachable funnel for gathering and inserting bone graft material at a graspable end of the integrated fusion cage and graft delivery device. The present disclosure may also comprise a plunger that has a detachable handle, which may be selectively removed to avoid blocking the surgeon's view of the operating site. The integrated fusion cage and graft delivery device may further comprise a detachable footing or shelf at one distal end of the hollow tubular member. In one embodiment this footing or shelf is selectively positionable about various points along the hollow tube. For example, a distal portion of the hollow tube has a rotatable portion that can be positioned to deliver bone graft material to areas of a disc space in a manner such that a surgeon has angular directional control as to where bone graft material is directed. Other detachable elements are also contemplated with the present invention, such as a funnel at the proximal end of the hollow tube, or exterior or interior guide wires attached to the hollow tube, or a camera which is positioned near the delivery site of the bone graft material.

In another embodiment of the invention, the device is configured such that the upper or first end of the device (that is, the end in which the plunger is inserted) is not substantially in-line with the second end of the device (that is, the end from which bone graft material is emitted and/or a fusion cage is attached). For example, the body of the hollow tube may be configured with an angle or kink along its length, appearing to be rotated along its length. In this embodiment, the plunger element is flexible and/or conformable so as to flex inside of the tube portion and otherwise traverse through the tube portion. This embodiment of the device is useful, for example, when the user requires entry to the disc space at other than a right angle. Further, the angle or kink along the length of the device may be configured is capable of selectively locking (e.g., by a pin) the upper device portion into a particular position, e.g. so that a desired angle is created between the upper device portion and the remaining portion of the device. The means for communication itself can be locked to alternatively achieve this objective. In one embodiment, when the rotating member is in an unlocked mode, the member is free to rotate in at least one plane. The selective locking mechanism can be remotely accessed by a user of the tool at the upper end of the handle by, for example, an external shaft that communicates with the locking mechanism of the rotating member on the distal end of the body. Yet another aspect of the present disclosure is that the device can be variably angled to allow for a variety of insertion angles. A ratcheting adapter can be fitted to allow for this application.

The present invention can be used in veterinary conditions, in the thoracic spine or can be used for insertion of a laterally based disk replacement.

Thus, according to various embodiments of the present disclosure, a method of introducing bone graft material to a desired operating site ("bone graft receiving area") is provided by use of a hollow tubular member comprising a generally rectangular cross-sectional area, whereby the desired operating area is capable of receiving at least one plunger. The one or more plunger having at least one distal end which is designed to accommodate ejecting bone graft or other material to be inserted into the joint space or between intervertebral members in a generally lateral direction, as opposed to a generally longitudinal direction (in relation to the direction of the primary axis of the device).

One skilled in the art will appreciate that the distal end of the tubular device need not be limited to those specific embodiments described above. Other forms, shapes or designs that enable the foregoing aspects of the present invention are hereby incorporated into this disclosure. Forms, shapes and designs that relate to the provision of an end of a tubular device to perform lateral introduction of bone or bone substitute to an operating site are considered to be within the scope of the present disclosure.

One aspect of the present invention provides an integrated fusion cage and graft delivery device system for delivering bone graft, in a partially formed, fully formed or unformed condition to a bone graft receiving area in a body.

In yet another embodiment the hollow tube of the integrated fusion cage and graft delivery device may further comprise a funnel on the graspable end of the hollow tube, which may be selectively positioned about the graspable end of the hollow tube, for facilitating insertion of new or additional bone graft into the hollow tube. The funnel may take on a variety of shapes and sizes, depending on the nature of the bone graft material being inserted in the hollow tube.

One embodiment of the substantially hollow tube provides that the hollow tube is telescoping, thereby allowing its length to be adapted to the particular desires of the surgeon and/or the surgical area. In this embodiment, the plunger may also be telescoping to substantially conform to the configuration and/or size and/or shape of the substantially hollow tube.

In another embodiment, the size and/or shape of the one or more hollow tubes of the device are sized to fit, and/or not substantially obscure access to the aperture of, the cannula or cannulas that the device is fitted through for delivery of bone graft material to the operating site. In this embodiment, the device's one or more pair of hollow tubes and plungers do not substantially impair access to the operating site nor the surgeon's view of the operating site.

In one embodiment of the invention, a bone graft insertion apparatus comprises: a hollow tube constructed to receive bone graft, the hollow tube having an extended axis and a proximal end and a distal end, the distal end having an interior surface; a plunger adapted for inserting into the proximal end of the hollow tube, the plunger having a distal end being contoured to the interior surface of the distal end of the hollow tube such that bone graft material within the hollow tube is delivered to a graft receiving area through at least one opening near the distal end of the hollow tube; wherein the graft receiving area is configured to accommodate at least one substantially hollow implant.

In another embodiment of the invention, a bone graft insertion apparatus comprises: a hollow tube constructed to receive bone graft, the hollow tube having a proximal and distal end; whereby the hollow tube contains least one opening on a surface of the distal end of the hollow tube; whereby the opening on a surface of the distal end of the hollow tube is positioned other than completely along the axial or longitudinal axis of the device; a plunger adapted for insertion at least partially within the hollow tube at proximal end of the hollow tube; whereby the plunger is constructed and arranged with respect to the hollow tube so as to present at least one substantially flat contour; whereby the plunger has a distal end that is contoured to an interior surface of the distal end of the hollow tube such that the contoured distal end of the plunger is nearly congruent with the interior surface of the distal end of the hollow tube for removing substantially all of the bone graft received by the hollow tube; whereby the bone graft is delivered to a graft receiving area.

In another embodiment of the invention, a method of inserting bone graft comprises: preparing a surgical area to receive bone graft; inserting a tool into the surgical area, the tool consisting essentially of a hollow tube adapted to receive bone graft, a plunger adapted for insertion into the hollow tube, the plunger constructed to prevent rotation during insertion into the hollow tube, the plunger having a distal end contoured to the interior surface of the distal end of the hollow tube; providing bone graft material into the hollow tube of the tool; inserting the plunger into the proximal end of the hollow tube; inserting the distal end of the hollow tube of the tool into surgical area; applying force to the plunger thereby advancing the plunger through the hollow tube wherein the bone graft is inserted into the surgical area.

In another embodiment of the invention, an integrated fusion cage and graft delivery device apparatus comprises: a hollow tube constructed to receive bone graft, the hollow tube having an extended axis and a proximal end and a distal end, the distal end having an interior surface; a plunger adapted for inserting into the proximal end of the hollow tube, the plunger having a distal end being contoured to the interior surface of the distal end of the hollow tube; a selectably detachable fusion cage, the selectably detachable fusion cage having at least one opening that substantially aligns with at least one opening near the distal end of the hollow tube, such that bone graft material within the hollow tube is delivered to a graft receiving area through at least one opening of the selectably detachable fusion cage; and the selectably detachable fusion cage having a means for detachment whereby the fusion cage is delivered to the graft receiving area.

In one embodiment, the device is not a caulking gun style device, that is the bone graft material and/or the fusion cage are not delivered and/or positioned using a hand-pump and/or hand-squeeze mechanism. Instead, the device delivers graft material and/or a fusion cage using a hollow tube and plunger arrangement which is not a caulking gun style device and further, does not appreciably disrupt or block the user's view of the surgical site and/or enable precision delivery of bone graft material and/or a fusion cage to the surgical site. Indeed, the device of one embodiment of the present disclosure is distinctly unlike the caulking gun device of U.S. Pat. Appl. No. 2004/0215201 to Lieberman ("Lieberman"), which requires an L-shaped base member handle, rack teeth to advance a plunger member, and user action on a lever of the L-shaped base member handle to deploy bone graft material.

In one embodiment, the device of this application is not a caulking gun style device and does not comprise rack teeth, a base member handle and at least one component that obscures user viewing of the surgical site. Lieberman is incorporated by reference in its entirety for all purposes.

Similarly, in one embodiment, the device is distinctly unlike the caulking gun device of U.S. Pat. Appl. No. 2002/0049448 to Sand et al ("Sand"), which requires a gun and trigger mechanism in which the user squeezes together a gun-style handle to deploy material into bone. The Sand device obstructs the view of the user of the delivery site. In one embodiment, the device of this application is not a caulking gun style device and does not comprise an opposing-levered, gun-style delivery mechanism and at least one component that obscures user viewing of the surgical site. Sand is incorporated by reference in its entirety for all purposes.

Other caulking gun type devices are described in U.S. Pat. Nos. 8,932,295 and 9,655,748 which are each incorporated herein by reference in their entirety.

In one embodiment, the device is configured to deliver bone graft material substantially laterally from its delivery end, that is substantially not in the axial direction but rather substantially from the side and/or in a radial direction. This is distinctly different than devices that deliver bone graft material along their vertical axis, that is, along or out their bottom end, and/or obstruct the user view of the bone graft and/or fusion cage delivery site, such as that of U.S. Pat. Appl. No. 2010/0087828 to Krueger et al ("Krueger"), U.S. Pat. Appl. No. 2009/0264892 to Beyar et al ("Beyar"), U.S. Pat. Appl. No. 2007/0185496 to Beckman et al ("Beckman"), U.S. Pat. Appl. No. 2009/0275995 to Truckai et al ("Truckai") and U.S. Pat. Appl. No. 2006/0264964 to Scifert et al ("Scifert"). Krueger, Beyar, Beckman, Truckai and Scifert are incorporated by reference in their entireties for all purposes.

In one embodiment, the device is configured to deliver bone graft material so as to completely fill the defined interior of its fusion cage and subsequently deliver bone graft material to the surrounding bone graft site, rather than, for example, to contain the bone material as are the fusion cage designs of U.S. Pat. No. 7,846,210 to Perez-Cruet ("PerezCruet"). Further, the fusion device of this application features a distal tip that functions to precisely position the fusion device and stabilize the device during delivery of bone graft material. Perez-Cruet is incorporated by reference in its entirety for all purposes.

In one embodiment, a bone graft insertion apparatus is disclosed, the bone graft insertion apparatus comprising: a hollow tube constructed to receive bone graft, the hollow tube having an extended axis and a proximal end and a distal end, the distal end having a substantially tapered distal tip interior surface and a distal end interior surface of rectangular cross-section; a plunger adapted for inserting into the proximal end of the hollow tube, the plunger having a distal end exterior surface of rectangular cross-section contoured to the distal end interior surface of the hollow tube, the plunger having a substantially tapered distal tip contoured to the substantially tapered distal tip interior surface of the hollow tube to form a substantially congruent fit, wherein bone graft material within the hollow tube is delivered to a graft receiving area through one or more lateral openings near the distal end of the hollow tube, the one or more lateral openings substantially precluding the delivery of bone graft material directly along the axis of the hollow tube, the plunger precluded from rotating when inserted into the hollow tube.

In another embodiment, a bone graft insertion apparatus is disclosed, the bone graft insertion apparatus comprising: a hollow tube having a length, a proximal end and a distal end, the hollow tube having a rectangular cross-section, the distal end having a tapered tip interior surface and at least one opening; a plunger adapted for insertion within the hollow tube at the proximal end of the hollow tube, the plunger having a rectangular cross-section end portion and a distal tip contoured to conform to the distal end of the hollow tube, the plunger having a length sufficient such that when fully inserted into the hollow tube, the plunger distal end contacts at least one opening.

In another embodiment, a bone graft insertion apparatus is disclosed, the bone graft insertion apparatus comprising: a hollow tube constructed to receive bone graft having an extended axis, a length, a proximal end and a distal end, the hollow tube having a rectangular cross-section, the distal end having a tapered tip interior surface with a terminus and two oval-shaped openings having an upper and a lower end located on opposite lateral sides of the distal end, the tapered tip extending into the hollow tube and the terminus positioned adjacent to the oval-shaped openings; a plunger adapted for insertion within the hollow tube at the proximal end of the hollow tube, the plunger having a rectangular cross-section end portion and a distal lower surface, the plunger having a length sufficient such that when fully inserted into the hollow tube, the plunger distal lower surface contacts the hollow tube terminus at a position adjacent to the oval-shaped openings, the plunger rectangular cross-section end portion forming a continuous surface adjacent each of the oval-shaped openings from a position opposite the terminus to a point extending beyond the upper end of each oval-shaped opening; wherein bone graft material within the hollow tube is delivered to a graft receiving area through the oval-shaped openings of the hollow tube, the oval-shaped openings precluding the delivery of bone graft material directly along the axis of the hollow tube, the plunger precluded from rotating when inserted into the hollow tube; wherein the oval-shaped openings near the distal end of the hollow tube are positioned within a 25% length from the distal end relative to a total length of the hollow tube.

In one embodiment, a combination bone graft insertion and implant insertion apparatus is disclosed, the apparatus comprising: a hollow tube constructed to receive bone graft, the hollow tube having an extended axis and a proximal end and a distal end, the hollow tube having a rectangular interior cross-section from the proximal end to the distal end; a plunger adapted for inserting into the proximal end of the hollow tube along the extended axis, the plunger having a distal end exterior surface of rectangular cross-section contoured to the interior cross-section of the hollow tube, the plunger with a distal exterior tip, the plunger distal end exterior surface of rectangular cross-section forming a substantially congruent fit with the hollow tube rectangular interior cross-section; and an expandable implant comprising a first plate, a second plate, a front block, a rear block and a screw, the expandable implant configured to move the first plate vertically from the second plate by rotation of the screw which rotates without moving transversely with respect to either the first or the second plate, the first plate and second plate moving in parallel upon rotation of the screw, the screw moving the front and the rear blocks so as to move the first and the second plate, the blocks defining an aperture on each lateral side of the expandable implant; wherein the hollow tube and the plunger are configured to deliver bone graft material to the expandable implant and to an adjacent surgical site through at least the apertures on each lateral side of the expandable implant.

In another embodiment, a bone graft material delivery system is disclosed, the system comprising: a hollow tube adapted to receive bone graft material, the hollow tube having a proximal portion, a distal portion with at least one opening therein, and a breech area therebetween, the breech area configured to be opened and closed; a plunger configured for urging bone graft material from the proximal portion through the distal portion and outwardly through the at least one opening of the distal portion, wherein the plunger has at least one engagement feature; and a trigger configured to engage the at least one engagement feature of the plunger and being operable to advance the plunger toward the distal end of the hollow tube. The proximal portion is securely interconnected to the distal portion along a longitudinal axis of the hollow tube. When the breech area is open, an interior volume of the proximal portion is exposed to allow for loading of bone graft material therein.

In another embodiment, a surgical method for bone graft material delivery is disclosed, the method comprising the steps of: (1) providing a bone graft material delivery system including a hollow tube adapted to receive bone graft material, the hollow tube having a proximal portion, a distal portion with at least one opening therein, and a breech area therebetween, the breech area configured to be opened and closed; a plunger configured for urging bone graft material from the proximal portion through the distal portion and outwardly through the at least one opening of the distal portion, wherein the plunger has at least one engagement feature; and a trigger configured to engage the at least one engagement feature of the plunger and being operable to advance the plunger toward the distal end of the hollow tube, wherein the proximal portion is securely interconnected to the distal portion along a longitudinal axis of the hollow tube and wherein, when the breech area is open, an interior volume of the proximal portion is exposed to allow for loading of bone graft material therein; (2) moving the breech area to its open position; (3) inserting bone graft material in the exposed interior volume of the proximal portion; (4) closing the breech area; and (5) advancing the plunger to urge bone graft from the proximal portion through the distal portion and outwardly through the at least one opening of the distal portion.

In addition, by way of providing additional background and context, the following references are also incorporated by reference in their entireties for the purpose of explaining the nature of spinal fusion and devices and methods commonly associated therewith, to include, without limitation, expandable fusion cages: U.S. Pat. No. 4,863,476 to Shepperd; U.S. Pat. No. 6,743,255 to Ferree; U.S. Pat. No. 6,773,460 to Jackson; U.S. Pat. No. 6,835,206 to Jackson; U.S. Pat. No. 6,972,035 to Michelson; U.S. Pat. No. 7,771, 473 to Thramann; U.S. Pat. No. 7,850,733 to Baynham; U.S. Pat. No. 8,506,635 to Palmatier; U.S. Pat. No. 8,556,979 to Glerum; U.S. Pat. No. 8,628,576 to Triplett; U.S. Pat. No. 8,709,086 to Glerum; U.S. Pat. No. 8,715,351 to Pinto; U.S. Pat. No. 8,753,347 to McCormack; U.S. Pat. No. 8,753,377 to McCormack; U.S. Design Pat. No. D708,323 to Reyes; U.S. Pat. No. 8,771,360 to Jimenez; U.S. Pat. No. 8,778,025 to Ragab; U.S. Pat. No. 8,778,027 to Medina; U.S. Pat. No. 8,808,383 to Kwak; U.S. Pat. No. 8,814,940 to Curran; U.S. Pat. No. 8,821,396 to Miles; U.S. Patent Application Publication No. 2006/0142858 to Colleran; U.S. Patent Application Publication No. 2008/0086142 to Kohm; U.S. Patent Application Publication No. 2010/0286779 to Thibodean; U.S. Patent Application Publication No. 2011/0301712 to Palmatier; U.S. Patent Application Publication No. 2012/0022603 to Kirschman; U.S. Patent Application Publication No. 2012/0035729 to Glerum; U.S. Patent Application Publication No. 2012/0089185 to Gabelberger; U.S. Patent Application Publication No. 2012/0123546 to Medina; U.S. Patent Application Publication No. 2012/0197311 to Kirschman; U.S. Patent Application Publication No. 2012/0215316 to Mohr; U.S. Patent Application Publication No. 2013/0158664 to Palmatier; U.S. Patent Application Publication No. 2013/0178940; U.S. Patent Application Publication No. 2014/0012383 to Triplett; U.S. Patent Application Publication No. 2014/0156006; U.S. Patent Application Publication No. 2014/0172103 to O'Neil; U.S. Patent Application Publication No. 014/0172106 to To; U.S. Patent Application Publication No. 2014/0207239 to Barreiro; U.S. Patent Application Publication No. 2014/0228955 to Weiman; U.S. Patent Application Publication No. 2014/0236296 to Wagner; U.S. Patent Application Publication No. 2014/0236297 to Iott; U.S. Patent Application Publication No. 2014/0236298 to Pinto.

Furthermore, by way of providing additional background and context, the following references are also incorporated by reference in their entireties for the purpose of explaining the nature of spinal fusion and devices and methods commonly associated therewith, to include, without limitation, expandable fusion cages: U.S. Pat. No. 7,803,159 to PerezCruet et al.; U.S. Pat. No. 8,852,282 to Farley et al.; U.S. Pat. No. 8,858,598 to Seifert et al.; U.S. Pat. No. D714,933 to Kawamura; U.S. Pat. No. 8,795,366 to Varela; U.S. Pat. No. 8,852,244 to Simonson; U.S. Patent Application Publication No. 2012/0158146 to Glerum et al.; U.S. Pat. No. 8,852,242 to Morgenstern Lopez et al.; U.S. Pat. No. 8,852,281 to Phelps; U.S. Pat. No. 8,840,668 to Donahoe et al.; U.S. Pat. No. 8,840,622 to Vellido et al.; U.S. Patent Application Publication No. 2014/0257405; U.S. Patent Application Publication No. 2014/0257490 to Himmelberger et al.; U.S. Pat. No. 8,828,019 to Raymond et al.; U.S. Patent Application Publication No. 2014/0288652 to Boehm et al.; U.S. Patent Application Publication No. 2014/0287055 to Kunjachan; U.S. Patent Application Publication No. 2014/0276896 to Harper; U.S. Patent Application Publication No. 2014/0277497 to Bennett et al.; U.S. Patent Application Publication No. 2012/0029635 to Schoenhoeffer et al.; U.S. Patent Application Publication No. 2014/0303675 to Mishra; U.S. Patent Application Publication No. 2014/0303731 to Glerum; U.S. Patent Application Publication No. 2014/0303732 to Rhoda et al.; U.S. Pat. No. 8,852,279 to Weiman; PCT Pub. WO 2012/031267 to Weiman; U.S. Pat. No. 8,845,731 to Weiman; U.S. Pat. No. 8,845,732 to Weiman; U.S. Pat. No. 8,845,734 to Weiman; U.S. Patent Application Publication No. 2014/0296985 to Balasubramanian et al.; U.S. Patent Application Publication No. 2014/0309268 to Arnou; U.S. Patent Application Publication No. 2014/0309548 to Merz et al.; U.S. Patent Application Publication No. 2014/0309697 to Iott et al.; U.S. Patent Application Publication No. 2014/0309714 to Mercanzini et al.; U.S. Pat. No. 8,282,683 to McLaughlin et al.; U.S. Pat. No. 8,591,585 to McLaughlin et al; U.S. Pat. No. 8,394,129 to Morgenstern Lopez et al.; U.S. Patent Application Publication No. 2011/0208226 to Fatone et al.; U.S. Patent Application Publication No. 2010/0114147 to Biyani; U.S. Patent Application Publication No. 2011/0144687 to Kleiner; U.S. Pat. No. 8,852,243 to Morgenstern Lopez et al.; U.S. Pat. No. 8,597,333 to Morgenstern Lopez et al.; U.S. Pat. No. 8,518,087 to Lopez et al.; U.S. Patent Application Publication No. 2012/0071981 to Farley et al.; U.S. Patent Application Publication No. 2013/0006366 to Farley et al.; U.S. Patent Application Publication No. 2012/0065613 to Pepper et al.; U.S. Patent Application Publication No. 2013/0006365 to Pepper et al.; U.S. Patent Application Publication No. 2011/0257478 to Kleiner et al.; U.S. Patent Application Publication No. 2009/0182429 to Humphreys et al.; U.S. Patent Application Publication No. 2005/0118550 to Turri; U.S. Patent Application Publication No. 2009/0292361 to Lopez; U.S. Patent Application Publication No. 2011/0054538 to Zehavi et al.; U.S. Patent Application Publication No. 2005/0080443 to Fallin et al.; U.S. Pat. No. 8,778,025 to Ragab et al.; U.S. Pat. No. 8,628,576 to Triplett et al; U.S. Pat. No. 8,808,304 to Weiman, and U.S. Pat. No. 8,828,019 to Raymond.

All of the following U.S. patents are also incorporated herein by reference in their entirety: U.S. Pat. Nos. 6,595,998; 6,997,929; 7,311,713; 7,749,255; 7,753,912; 7,780,734; 7,799,034; 7,875,078; 7,931,688; 7,967,867; 8,075,623; 8,123,755; 8,142,437; 8,162,990; 8,167,887; 8,197,544; 8,202,274; 8,206,395; 8,206,398; 8,317,802; 8,337,531; 8,337,532; 8,337,562; 8,343,193; 8,349,014; 8,372,120; 8,394,108; 8,414,622; 8,430,885; 8,439,929; 8,454,664; 8,475,500; 8,512,383; 8,523,906; 8,529,627; 8,535,353; 8,562,654; 8,574,299; 8,641,739; 8,657,826; 8,663,281; 8,715,351; 8,727,975; 8,828,019; 8,845,640; 8,864,830; 8,900,313; 8,920,507; 8,974,464; 9,039,767; 9,084,686; 9,095,446; 9,095,447; 9,101,488; 9,107,766; 9,113,962; 9,114,026; 9,149,302; 9,174,147; 9,216,094; 9,226,777; 9,295,500; 9,358,134; 9,381,094; 9,439,692; 9,439,783; 9,445,921; 9,456,830; 9,480,578; 9,498,200; 9,498,347; 9,498,351; 9,517,140; 9,517,141; 9,517,142; 9,545,250; 9,545,279; 9,545,313; 9,545,318; 9,610,175; 9,629,668; 9,655,660; 9,655,743; 9,681,889; 9,687,360; 9,707,094; 9,763,700; 9,861,395; 9,980,737; 9,993,353; U.S. Pat. Pub. 2014/0088712; U.S. Pat. Pub. 2014/0276581; U.S. Pat. Pub. 2014/0371721; U.S. Pat. Pub. 2016/0296344; U.S. Pat. Pub. 2017/0367846; U.S. Pat. Pub. 2017/0354514.

One of ordinary skill in the art will appreciate that embodiments of the present disclosure may have various sizes. The sizes of the various elements of embodiments of the present disclosure may be sized based on various factors including, for example, the anatomy of the implant patient, the person or other device operating the apparatus, the implant location, physical features of the implant including, for example, with, length and thickness, and the size of operating site or the size of the surgical tools being used with the device.

One or ordinary skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, rubber, latex, synthetic rubber, and other fiber-encased resinous materials, synthetic materials, polymers, and natural materials. The plunger element could be flexible, semi-rigid, or rigid and made of materials such as stainless steel, titanium alloy, aluminum alloy, chromium alloy, and other metals or metal alloys. Similarly, the tubular element could be flexible, semi-rigid, or rigid and made of materials such as stainless steel, titanium alloy, aluminum alloy, chromium alloy, and other metals or metal alloys. In certain embodiments, the plunger and hollow tube are composed of plastic and are intended for one use only and then discarded. In another embodiment, some or all elements of the device, or portions of some or all of the elements, are luminescent. Also, in another embodiment, some or all elements of the device, or portions of some or all of the elements, include lighting elements. In another embodiment, the hollow tube and/or plunger are made of a substantially transparent material and/or are rigidly opaque.

In one embodiment of the fusion cage, the fusion cage comprises a polymer, such as PEEK, titanium and composite materials.

One of ordinary skill in the art will appreciate that embodiments of the present disclosure may be controlled by means other than manual manipulation. Embodiments of the present disclosure may be designed and shaped such that the apparatus may be controlled, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators.

Embodiments of the present disclosure present several advantages over the prior art including, for example, the speed of the procedure, the minimally invasive aspect of the procedure, the ability to introduce the implant material to the implant site with minimal risk and damage to the surrounding tissue, the lower risk of infection, more optimally placed implant material, a more stable delivery device which is designed to reduce the likelihood of the implant material becoming dislodged prior to fixation, and fewer tools in a surgical site due to the integration of several components required to provide bone graft to a bone graft receiving area. Further, the lower profile of the device allows improved viewing of the area intended for receipt of bone graft material, and use of a reduced set and size of elements therein provided a less expensive device. Also, the device disclosed provides that substantially all of the bone graft material may be ejected from the device and delivered to the surgical site, rather than wasted as irretrievable matter remaining inside the device. The ability to remove substantially all of the bone graft material is of significant benefit because the bone graft material is expensive and/or hard to obtain.

This Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention, and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the Detailed Description of the Invention, the drawing figures, and the exemplary claim set forth herein, taken in conjunction with this Summary of the Invention, define the invention.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

FIG. 1A is a front perspective view of a hollow tubular member of the device for delivering bone graft;

FIG. 1B is a front perspective view of the plunger of the device;

FIG. 1C is a cross sectional view of a portion of the device shown in FIG. 1A;

FIG. 24 is a top plan view of the device shown in FIG. 22;

FIG. 25 is a front elevation view of the device shown in FIG. 22;

FIG. 26 is a right elevation view of the device shown in FIG. 22;

FIG. 27 is a bottom plan view of the device shown in FIG. 22;

FIG. 28 is a cross-sectional view of section A-A of FIG. 25;

FIGS. 46A-H provide scaled views of one embodiment of the hollow tube (aka snap on cannula) of the integrated fusion cage and graft delivery device configured to operate with the fusion cage element of FIGS. 45A-G, plunger of FIGS. 47A-D and ejection tool of FIGS. 48A-E;

FIGS. 47A-D provide scaled views of one embodiment of the plunger (aka snap on plunger) of the integrated fusion cage and graft delivery device configured to operate with the fusion cage element of FIGS. 45A-G, hollow tube of FIGS. 46A-H, and ejection tool of FIGS. 48A-E;

FIGS. 54A-F provide scaled views of the upper plate component of the device shown in FIG. 51;

FIGS. 57A-C provide scaled views of the expansion screw component of the device shown in FIG. 51;

FIG. 75B is a top plan view of the hollow tubular member of FIG. 75A and detachable funnel;

FIG. 75C is a side elevation view of the hollow tubular member of FIG. 75A interconnected to the funnel and including a plunger inserted into a lumen of the hollow tubular member;

FIG. 75D is a front elevation view of the hollow tubular member of FIG. 75A and illustrating an optional opening at the distal end;

FIG. 75E is an expanded cross sectional view of a portion of the hollow tubular member;

FIG. 76A is a cross-sectional view of a surgical site and a bone graft delivery device according to one embodiment of the present disclosure;

FIG. 76B is another cross-sectional view of the surgical site of FIG. 76A after the bone graft delivery device has been removed therefrom;

FIG. 77 is a side perspective view of another embodiment of a device for delivering bone graft;

FIG. 78 is a side perspective view of still another integrated fusion cage and graft delivery device of the present disclosure;

FIG. 79 is a longitudinal cross-sectional view of a graft delivery device of the present disclosure;

FIG. 80 is a perspective view of an exterior of a graft delivery device of the present disclosure;

FIG. 81 is a transverse cross-sectional view of a graft delivery device of the present disclosure;

Figure 82A:
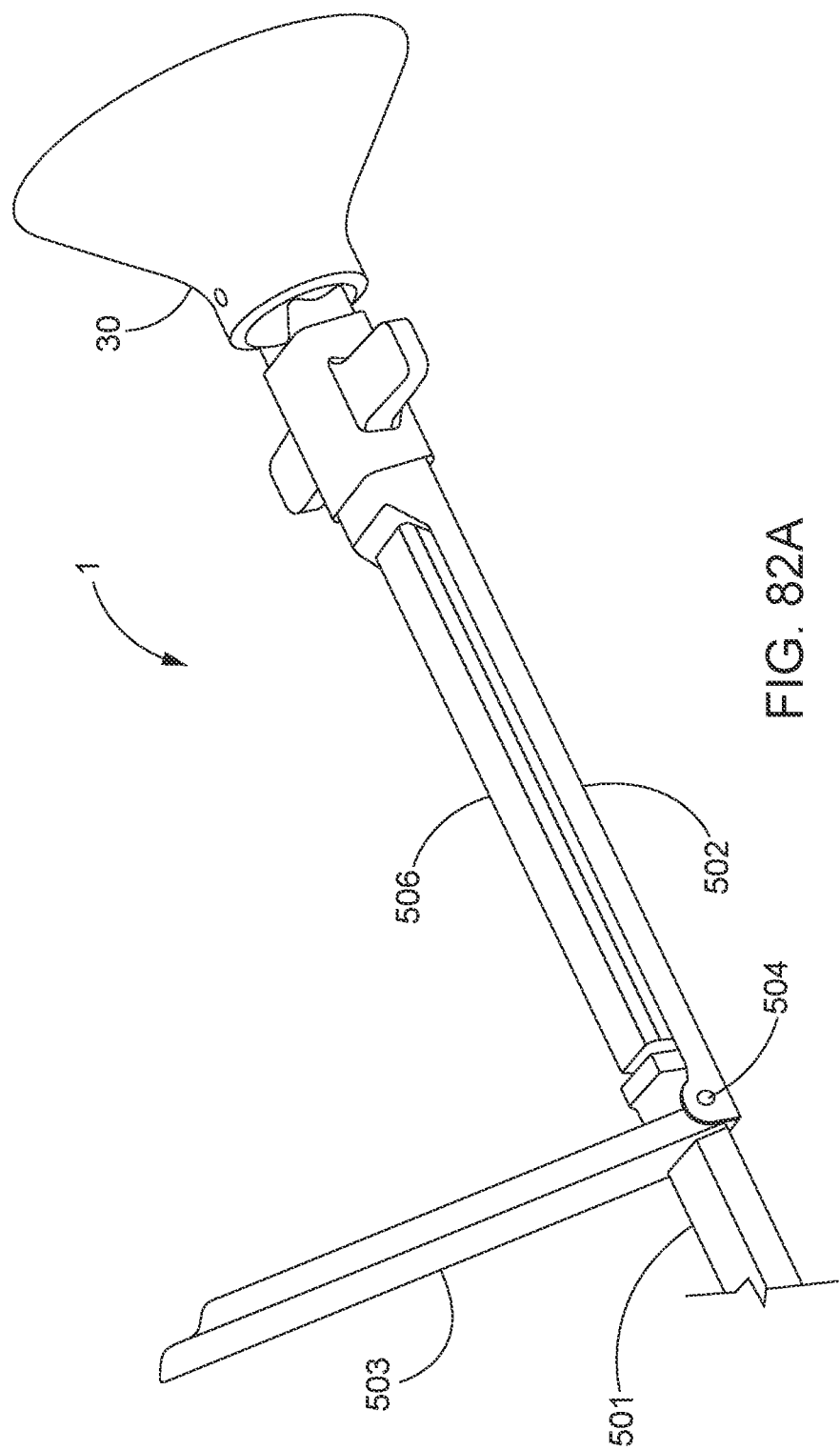
Figure 82B:
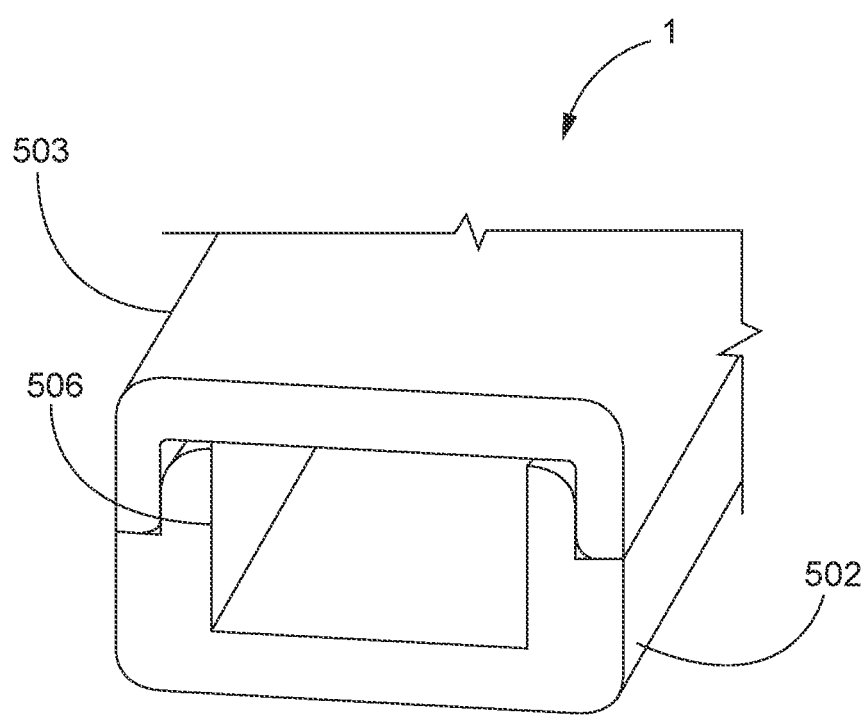
Figure 83A:
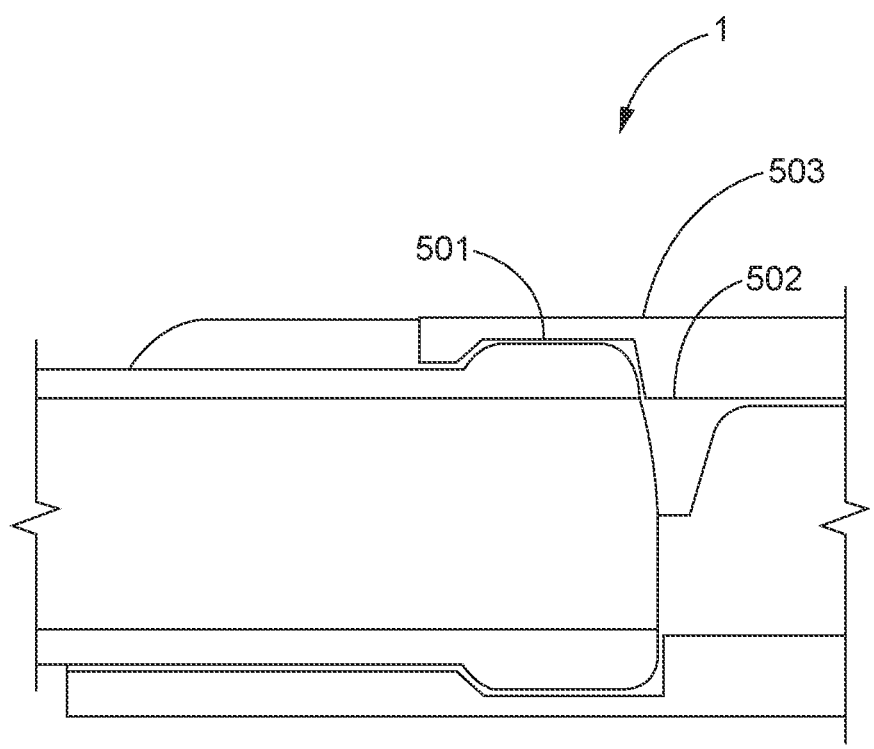
Figure 83B:
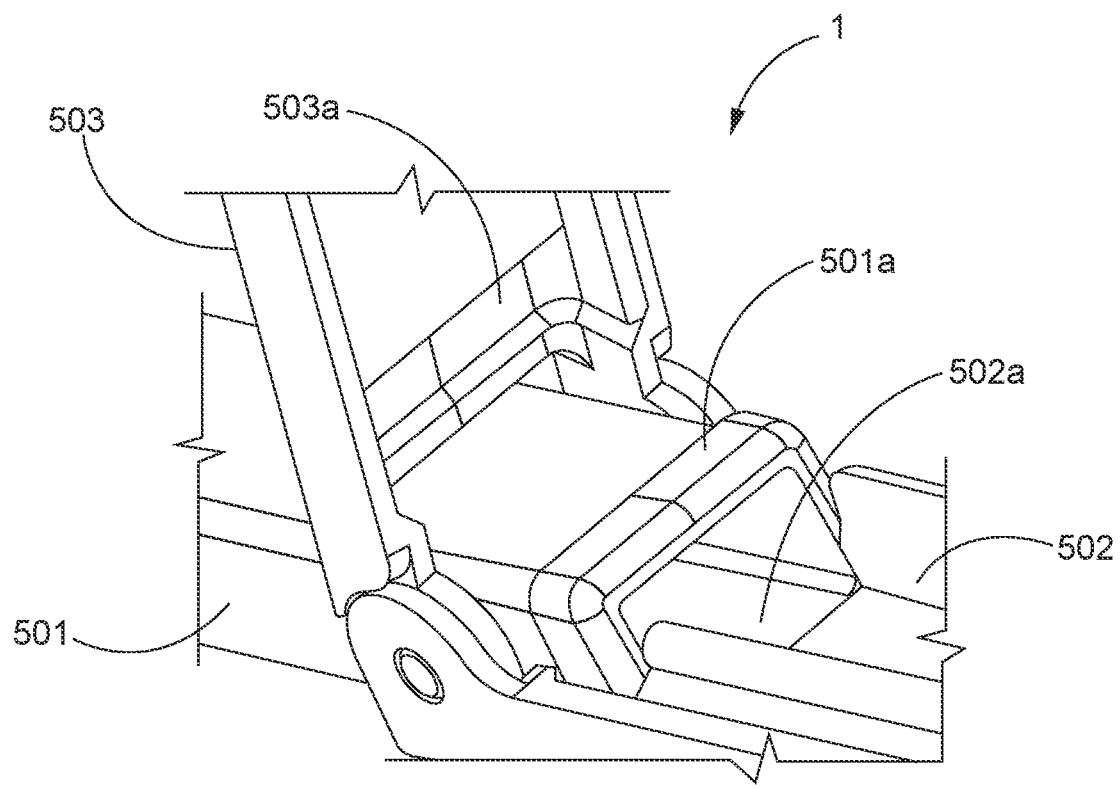

FIGS. 82A and 82B are perspective and transverse cross-sectional views, respectively, of one embodiment of an interconnection between a proximal interior tube and a breech area of a graft delivery device of the present disclosure; and FIGS. 83A and 83B are longitudinal cross-sectional and perspective views, respectively, of a locking mechanism for securely interconnecting a distal tube, a proximal interior tube, and a breech area of a graft delivery device of the present disclosure.

To provide further clarity to the Detailed Description provided herein in the associated drawings, the following list of components and associated numbering are provided as follows:

| Reference No. | Component |
| --- | --- |
| 1 | Integrated fusion cage and graft delivery device |
| 2 | Hollow tube |
| 3 | Hollow tube first (side) exterior surface |
| 4 | Opening (of Hollow tube) |
| 5 | Hollow tube second (top) exterior surface |
| 6 | First (or proximal) end (of Hollow tube) |
| 6A | Knob |
| 6B | Pin |
| 7 | Hollow tube first distal opening |
| 8 | Second (or distal) end (of Hollow tube) |
| 8A | Hollow tube cage clamp |
| 8B | Hollow tube cage clamp radial surface |
| 9 | Hollow tube distal interior ramp |
| 9A | Hollow tube distal interior ramp surface |
| 10 | Curved surface (of Hollow tube) |
| 10A | Curved interior surface (of Hollow tube) |
| 11 | Footing (of Hollow tube) |
| 12 | Plunger |
| 13 | Plunger distal first surface |
| 14 | Plunger distal second surface |
| 15 | Plunger distal third surface |
| 16 | Handle (of Plunger) |
| 16A | Plunger stop |
| 17 | Plunger medial portion |
| 18 | Second (or distal) end (of Plunger) |
| 18A | Pusher |
| 19 | Horizontal surface (of Plunger) |
| 20 | Curved surface (of Plunger) |
| 21 | Vent port |
| 22 | First portion |
| 23 | Second portion |
| 24 | Joint or plane |
| 25 | Peg or pin |
| 26 | Recess |
| 27 | Teeth or notches of plunger |
| 28 | Lumen |
| 29 | Indicia to indicate depth of insertion of distal end |
| 30 | Funnel |
| 32 | Sleeve (of Funnel) |
| 33 | Slot for pin of bayonet mount |
| 34 | Opening (of Funnel) |
| 35 | Vent channel in plunger pusher |
| 36 | Endoscope, camera, or image sensing device |
| 37 | Lighting element |
| 40 | Disc space |
| 42 | Syringe |
| 44 | Bone graft material |
| 46 | Luer lock device |
| 48 | Bore |
| 50 | Wedge-shaped Second end (of Hollow tube) |
| 52 | Wedge-shaped Second end (of Plunger) |
| 60 | Fusion Cage |
| 61 | Fusion cage surface texture |
| 62 | Fusion Cage First (or Proximal) End |
| 64 | Fusion Cage Second (or Distal) End |
| 65 | Fusion Cage First Opening Pair |
| 66 | Fusion Cage First End Opening |
| 67 | Fusion Cage Second Opening Pair |
| 68 | Fusion Cage Medial Opening |
| 69 | Fusion Cage Lateral Opening |
| 70 | Fusion Cage Medial Surfaces |
| 72 | Fusion Cage Internal Ramps |
| 80 | Hollow Tube Locking Tabs |
| 82 | Fusion Cage Locking Slots |
| 90 | Break-off Collar |
| 92 | Fusion Cage Collar |
| 93 | Fusion Cage Collar Face |
| 94 | Fusion Cage Collar Cavity |
| 96 | Fusion Cage Tab Extension |
| 97 | Fusion Cage Tab Extension Latch |
| 100 | Connector Conduit |
| 102 | Connectors |
| 110 | ALIF Fusion Cage |
| 112 | ALIF Fusion Cage Portals |
| 114 | ALIF Fusion Cage Chamber |
| 116 | ALIF Fusion Cage Break-off Collar |
| 120 | D-LIF Fusion Cage |
| 122 | D-LIF Fusion Cage Portals |
| 124 | D-LIF Fusion Cage Chamber |
| 126 | D-LIF Fusion Cage Break-off Collar |
| 130 | Vertebrectomy Fusion Cage |
| 132 | Vertebrectomy Fusion Cage Porous Wall Portion |
| 134 | Vertebrectomy Fusion Cage Chamber |
| 136 | Vertebrectomy Fusion Cage Break-off Collar |
| 138 | Vertebrectomy Fusion Cage Impervious Wall Portion |
| 140 | Ejection Tool |
| 142 | Ejection Tool First (Proximal) End |

-continued

| Reference No. | Component |
| --- | --- |
| 143 | Ejection Tool Stop |
| 144 | Ejection Tool Cover |
| 145 | Ejection Tool Cover Cavity |
| 146 | Spring Cover |
| 147 | Spring Cover Attachment |
| 148 | Spring |
| 149 | Ejection Tool Wings |
| 150 | Ejection Tool Wings Cavity |
| 151 | Ejection Tool L-cut |
| 152 | Ejection Tool Second (Distal) End |
| 160 | Ejection Tool Rod |
| 170 | Bone graft deliver device |
| 171 | Spine |
| 172 | Surgical site |
| 174 | Path for fusion cage |
| 200 | Upper Plate |
| 201 | Upper Plate Front |
| 202 | Upper Plate Rear |
| 203 | Upper Plate Openin |
| 204 | Upper Plate Surface Texture |
| 205 | Upper Plate Track |
| 206 | Upper Plate Slot |
| 209 | Upper Plate Ridge |
| 210 | Lower Plate |
| 211 | Lower Plate Front |
| 212 | Lower Plate Rear |
| 213 | Lower Plate Opening |
| 214 | Lower Plate Surface Texture |
| 215 | Lower Plate Track |
| 216 | Lower Plate Slot |
| 217 | Plate Tab |
| 218 | Plate Nose |
| 219 | Lower Plate Ridge |
| 220 | Front Block |
| 222 | Front Block Upper Rail |
| 224 | Front Block Lower Rail |
| 225 | Front Block Nose |
| 226 | Front Block Ramp |
| 227 | Front Block Aperture |
| 228 | Block Spine |
| 230 | Rear Block |
| 231 | Rear Block Groove |
| 232 | Rear Block Upper Rail |
| 234 | Rear Block Lower Rail |
| 236 | Rear Block Ramp |
| 237 | Rear Block Aperture |
| 238 | Rear Block Aft |
| 239 | Rear Block Detent |
| 240 | Expansion Screw |
| 242 | Expansion Screw Head |
| 244 | Expansion Screw Tip |
| 246 | Expansion Screw Disk |
| 250 | Installer/Impactor |
| 252 | Installer/Impactor Tip |
| 253 | Installer/Impactor Aperture |
| 254 | Installer/Impactor Ridge |
| 255 | Installer/Impactor Channel |
| 256 | Installer/Impactor Ramp |
| 258 | Installer/Impactor Handle |
| 260 | Expansion Driver |
| 268 | Expansion Driver Handle |
| 270 | Removal Pliers |
| 280 | Hollow Tube External Ramp |
| 282 | Hollow Tube Notch |
| 284 | Hollow Tube Slot |
| 285 | Hollow Tube Slot Aperture |
| 290 | Cam |
| 292 | Nose Cone |
| 294 | Ramps |
| 300 | Adaptor |
| 304 | Grip |
| 306 | Trigger |
| 308 | Handle |
| 310 | Knob |
| 312 | Switch or button |
| 314 | Loading port |
| 316 | Capsule or package of bone graft material |
| 318 | Knob of grip |
| 320 | Flange |
| 322 | Slot |
| 324 | Channel |
| 326 | Proximal opening of channel |
| 400 | Prior Art Fusion Cage |
| 400' | Modified Prior Art Fusion Cage |
| 501 | Distal tube |
| 502 | Proximal interior tube |
| 503 | Breech area |
| 504 | Breech hinge |
| 505 | Breech lock |
| 506 | Vertically extending rail |
| α | Vertical Wedge Angle |
| β | Horizontal Wedge Angle |

DETAILED DESCRIPTION

The present invention relates to a device and method for integrated and near-simultaneous delivery of bone graft material and a fusion cage to any portion of a patient which requires bone graft material and/or a fusion cage. Thus, for example, the foregoing description of the various embodiments contemplates delivery to, for example, a window cut in a bone, where access to such window for bone grafting is difficult to obtain because of orientation of such window, presence of muscle tissue, risk of injury or infection, etc. The integrated fusion cage and graft delivery device is formed such that the one or more hollow tubes and/or plungers may be helpful in selectively and controllably placing bone graft material and a fusion cage in or adjacent to such window. The integrated fusion cage and graft delivery device is formed to allow delivery of bone graft material and/or a fusion cage in a direction other than solely along the longitudinal axis of the device, and in some embodiments transverse to the primary axis used by the surgeon or operator of the device when inserting the device into a cannula or other conduit to access the surgical site. This same concept applies to other areas of a patient, whether or not a window has been cut in a bone, for example in a vertebral disc space, and may be used whether this is a first surgery to the area or a follow-up surgery. The present invention also contemplates the delivery of bone graft material and/or a fusion cage with or without the use of a plunger, and with or without the use of various other tools described in greater detail herein.

Referring now to FIGS. 1-33 and 36-45, several embodiments of the present invention are shown.

In regard to FIG. 1A, an integrated fusion cage and graft delivery device portion is shown, which is comprised of a hollow tubular member or hollow tube or contains at least one inner lumen 2, which has a first proximate end 6 (which is referred to elsewhere in this specification as the "graspable end" of hollow tube 2), and a second distal end 8, with a general hollow structure therebetween. Thus, as shown in FIG. 1, the hollow tube 2 allows bone graft material to be inserted into the opening 4 at the graspable end 6 of the hollow tube 2, and ultimately exited from the hollow tube 2 through the second end 8. According to a preferred embodiment, the hollow tube 2 also comprises at least one sloped or curved surface 10 at or near the second end 8 of the hollow tube 2. Although a generally rectangular cross-section is depicted, the cross-section need not be limited to a generally rectangular shape. For example, cross-sections of an oval shape or those with at least one defined angle to include obtuse, acute, and right angles can provide a shape in some situations that is more congruent with the size or shape of the annulotomy of a particular disc space.

Referring now in detail to FIG. 1B, a plunger 12 is shown for use with the hollow tube 2 of FIG. 1A. The plunger 12 is generally of the same geometry as the hollow portion of the hollow tube 2, extending at least the same length of hollow tube 2. The plunger 12 may include, as depicted in FIG. 1B, at least one knob or handle 16 for grasping by a user of the plunger 12. As with the interior of the hollow tube 2 at its second end 8, the plunger 12 also comprises at least one sloped or curved surface 20 at or adjacent to a second end 18 of the plunger 12. The plunger 12 terminates in a generally flat, horizontal surface 19, which corresponds to the opening at the second end 8 of the hollow tube 2 shown in FIG. 1A. Thus, in cooperation, the plunger 12 may be inserted into the opening 4 of the hollow tube 2 shown in FIG. 1A, and extended the entire length of the hollow tube 2, at least to a point where the horizontal surface 19 of plunger 12 is in communication with the second end 8 of the hollow tube 2. This configuration permits a user to eject substantially all of the bone graft material that is placed into the hollow tube 2 during a surgical procedure. One skilled in the art will appreciate that the plunger need not terminate in a generally flat, horizontal surface to affect the substantial removal of all of the bone graft material placed into the hollow tube; more specifically, any shape that allows conformance between the internal contour of the distal end of the hollow tube and the distal end of the plunger will affect the substantial removal of the bone graft material. Further details about the relationship are described below in regard to FIG. 2.

In the embodiment, of FIG. 1A-C, a contoured leading edge is provided on the plunger 12 to correspond with the internal contour of distal end 8 of the hollow tube 2 of the delivery device. This contoured plunger serves several purposes: First, it maintains the plunger in a desirable rotational position with respect to the hollow tube (i.e., prevents the plunger from inadvertently or intentionally being manipulated to rotate about the longitudinal axis of the hollow tube). Second, it ensures that when the plunger is fully inserted, the plunger removes substantially all of the bone graft material from the hollow tube. Also, the contoured plunger, corresponding to the contoured tubular member, allows immediate identification of the orientation of the device, and more specifically the direction of eject of the bone graft material into the surgical area. Alternative positioning means may also be provided to ensure that the plunger remains in the desirable position during delivery of bone graft into the hollow tube, for example by a machined bevel or edge on the outer surface of the plunger, and a corresponding groove in the interior surface of the hollow tube, which must be aligned when inserting the plunger in the hollow tube.

Referring now to FIG. 1C, an elevation view of the hollow tube 2 shown in FIG. 1A is shown in detail. The second end 8 of the hollow tube 2 has an opening with a height A and width B according to the needs of the surgeon, the location of the bone graft receiving area, the nature of the surgical operation to be performed, and the quantity and type of bone graft that is being inserted in (and ultimately ejected from) this integrated fusion cage and graft delivery device. According to a preferred embodiment, the height A of the opening at the second end 8 of the hollow tube 2 is in the range of 4 mm to 9 mm, and in a most preferred embodiment is about 7 mm. According to a preferred embodiment, the width B of the opening at the second end 8 of the hollow tube 2 is in the range of 7 mm to 14 mm, and in a most preferred embodiment is about 10 mm.

Referring to FIGS. 1A-C, it is to be understood that although these particular drawings reflect an embodiment where the second end 8 of the hollow tube 2, and the second end 18 of the plunger 12 comprise a curved or sloped surface which extends at least a certain distance laterally away from the generally longitudinal axis of the hollow tube 2/plunger 12, that in other embodiments, the second end 8 of the hollow tube 2 (and thereby, the second end 18 of the plunger 12) do not extend a lateral distance away, but rather terminate along the longitudinal wall of the hollow tube 2. In this embodiment, the hollow tube 2 may have a second end 8 which has an opening that is carved out of the side of the wall of the hollow tube 2, such that it appears as a window in the tubular body of hollow tube 2. According to this embodiment, the horizontal face 19 of the plunger 12 would also be a face on the outer surface of plunger 12, without extending any lateral distance away from the body of plunger 12. According to this embodiment, the plunger 12 would still retain the curved or sloped surface at the opposite end of the horizontal face 19 (referred to in FIG. 1B as 20) and similarly the hollow tube 2 would still comprise a sloped or curved surface 10 opposite the opening at second end 8. It is to be expressly understood that other variations which deviate from the drawing FIGS. 1A-C are also contemplated with the present invention, so long as that the opening at the second end 8 of hollow tube 2 is oriented to permit bone graft to be exited from the hollow tube 2 in a generally lateral direction (in relation to the longitudinal direction of the axis of the hollow tube 2).

According to another embodiment, the plunger 12 shown in FIG. 1B may further comprise a secondary handle (not shown in FIG. 1B), which includes an opening about at least one end of secondary handle such that it is permitted to couple with handle 16 of plunger 12. In this fashion, the secondary handle may be larger, contain one or more rings or apertures for placing a user's hand and/or fingers, or may simply be of a more ergonomic design, for accommodating use of the plunger 12 during a surgical operation. The secondary handle, according to this embodiment, is selectively removable, which permits a surgeon to use the secondary handle for inserting the plunger 12, and then at a later point remove the secondary handle, for instance, to improve visibility through the incision or through the hollow tube 2, and/or to determine whether substantially all of the bone graft material has been ejected from the hollow tube 2.

Figures 2, 3:
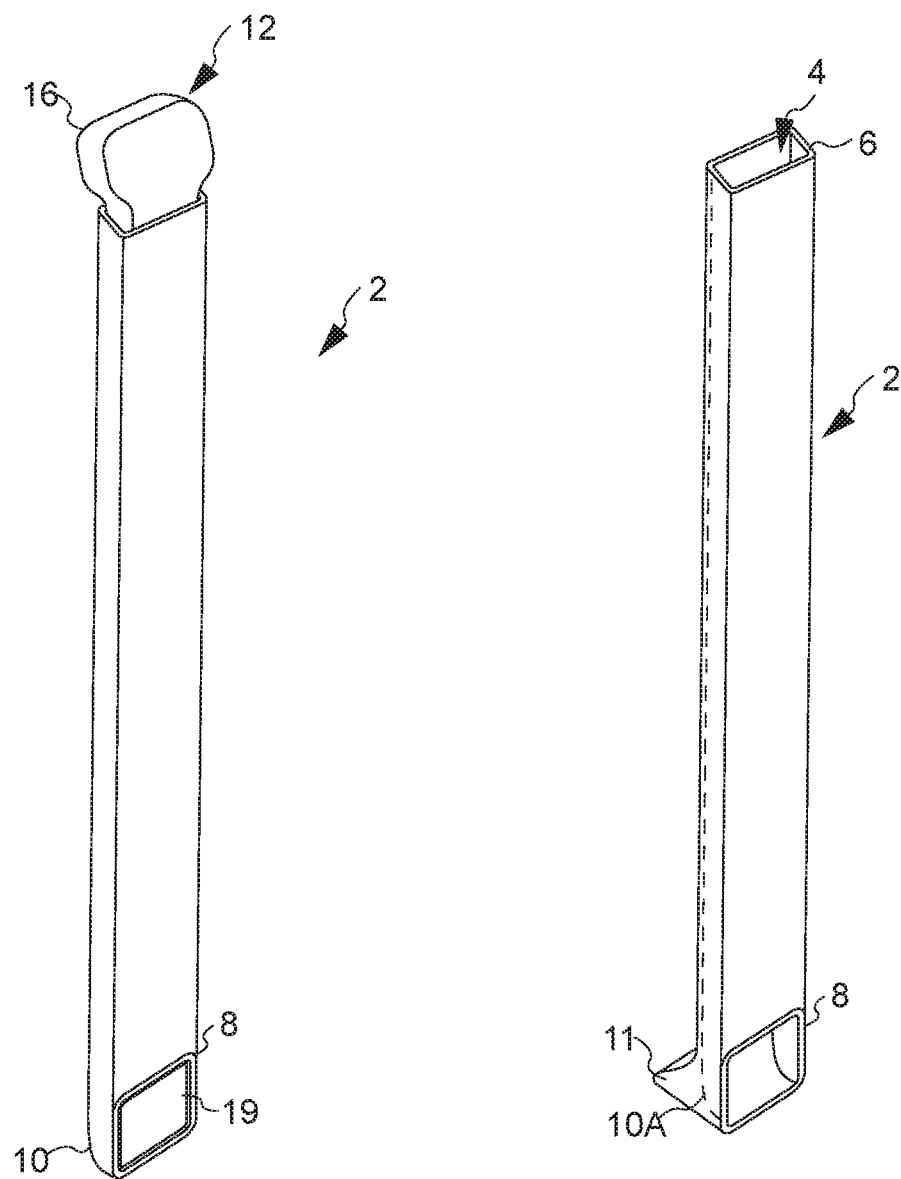
FIG. 2 is another front perspective view of the device of FIGS. 1A and 1B, showing the relationship between the tubular and plunger portions of the device.
FIG. 3 is a front perspective view of the device according to one alternative embodiment where the tubular portion includes a foot section and where the plunger portion has been fully inserted into the tubular portion.

Referring now in detail to FIG. 2, the plunger 12 is shown inserted into the hollow tube 2, such that the horizontal face 19 is substantially planar with the opening at the second end 8 of the hollow tube 2. As described above, the geometry of plunger 12 is such that it fits snuggly or tightly in the interior of the hollow tube 2. This configuration is such that the sloped or curved surface 10 of the hollow tube 2 is substantially congruent to the sloped or curved surface 20 of the plunger (not shown in FIG. 2), thereby allowing the plunger to be inserted into the hollow tube 2 and allowing substantially all of bone graft material which is placed into the hollow tube 2 to be ejected by the user.

Referring now in detail to FIG. 3, an alternate embodiment of the present invention is shown. According to this embodiment, the hollow tube 2 comprises a footing 11 at the second end 8 of the hollow tube 2. This footing 11 extends in a lateral direction, opposite the direction of the opening at the second end 8 of the hollow tube 2. The purpose of this footing 11 is to prevent injury to the annulus of a patient, or other sensitive anatomy adjacent the bone graft receiving area. This footing 11 is helpful when a surgeon or other user of the integrated fusion cage and graft delivery device is using the plunger 12 to drive bone graft through the hollow tube 2, or using another tool, such as a tamp, mallet, or other driving or impacting device to strike the plunger 12 and/or hollow tube 2 during the surgical procedure. Without the footing 11, the hollow tube 2 would have a generally angular second end 8, which may cause damage to the patient during these types of procedures. Thus, the footing 11 prevents the second end 8 of the hollow tube 2 from penetrating the annulus or other sensitive anatomy of the patient.

According to this embodiment, the footing 11 may also operate to ensure a fixed position of the second end 8 of the hollow tube 2 in the surgical site. This in turn allows a user to ensure that bone graft ejecting the second end 8 of the hollow tube 2 is being ejected laterally, and in the desired direction. This may be important, for example, when the integrated fusion cage and graft delivery device is placed within a disc space, and bone graft is being ejected laterally from the second end 8 of the hollow tube 2 in a specific direction. In other embodiments, the footing 11 may also serve as a visual marker for the surgeon, as it extends away from the horizontal wall of the hollow tube 2, and is therefore visible at the second end 8 of the hollow tube 2. As shown in FIG. 3, the presence of the footing 11 does not affect the interior slope or curved surface 10A of the hollow tube 2, so that the plunger 12 of the design shown in FIG. 1B may still be used with the hollow tube 2 of this alternate embodiment.

Figure 4:
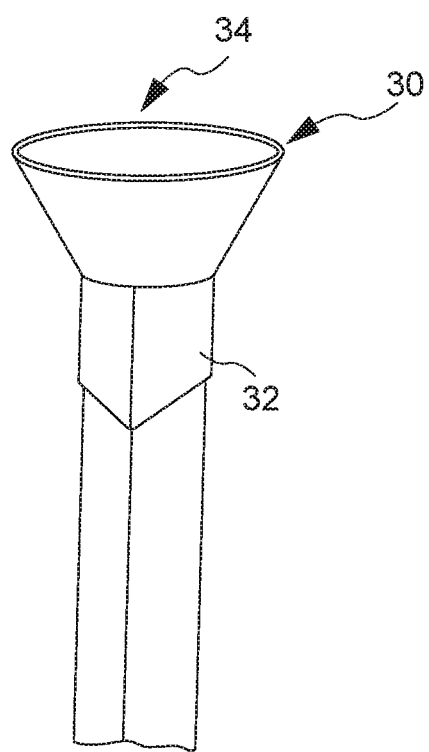
FIG. 4 is a partial front perspective view of another alternative embodiment of the device where the tubular portion includes a funnel at its proximal end designed to receive bone graft.

Referring now in detail to FIG. 4, a removable funnel 30 is shown, which comprises an opening 34 which is generally larger in diameter or dimension when compared to the opening 4 of the hollow tube 2. This removable funnel 30 further comprises a sleeve 32, the sleeve 32 having an internal cross-section which is substantially congruent with the external cross-section of the first end 6 of the hollow tube 2. Thus, according to this embodiment, the funnel 30 is selectively removable from the first end 6 of the hollow tube 2, and may allow a surgeon to more easily place new or additional bone graft into the hollow tube 2 by way of the opening 34 of the funnel 30. This funnel 30 may be used in connection with a hollow tube 2 that has been pre-filled with bone graft, or a hollow tube which is not pre-filled with bone graft. Thus, the funnel may be selectively positioned on the first end 6 of the hollow tube 2 at any point during the surgical operation when the surgeon desires new or additional bone graft be placed in the hollow tube 2 of the integrated fusion cage and graft delivery device.

Figure 5:
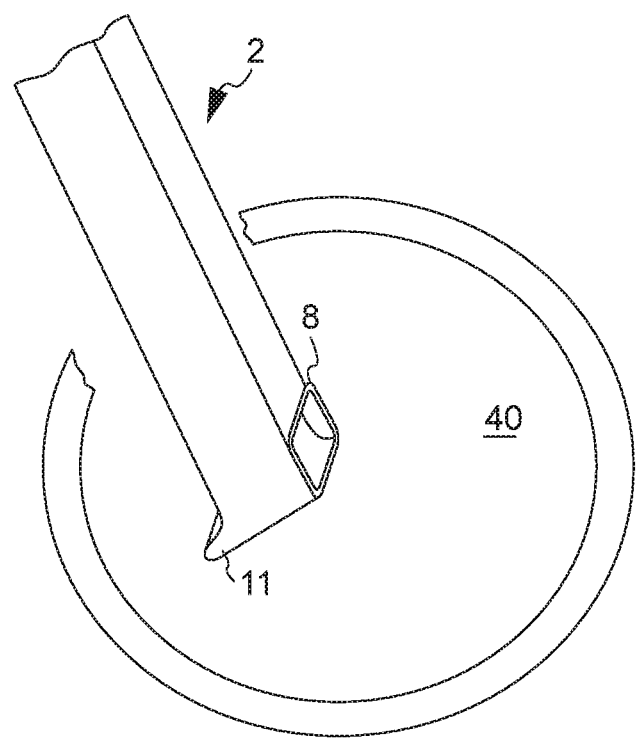
FIG. 5 is a partial front perspective view of the device according to one embodiment where the device is positioned in a disc space during a surgical operation.

Referring now in detail to FIG. 5, one particular application of the integrated fusion cage and graft delivery device is shown in a perspective view. Here, the integrated fusion cage and graft delivery device is shown with the embodiment of the hollow tube 2 further comprising a footing 11, and a second end opening for ejecting bone graft in a generally lateral direction, here in the interior of a disc space 40. The disc is shown with an opening on one end for inserting the second end 8 of the hollow tube 2 of the integrated fusion cage and graft delivery device. As opposed to prior art integrated fusion cage and graft delivery devices which have an opening at a second end that is open to the longitudinal axis of the delivery device, the present invention comprises a lateral opening, which as shown in FIG. 5 allows a surgeon to eject bone graft material into the lateral direction and thereby into the opened areas of the disc space 40. A surgeon has the option to rotate the direction of the opening in the second end 8 of the hollow tube 2 for ejecting additional bone graft to other open areas in the disc space 40.

Once the disc space 40 is substantially full of bone graft, the surgeon may remove the hollow tube 2 without disturbing the disc or anatomy of the patient. The surgeon may also accomplish the delivery of bone graft without displacing any cage or other structural implantable device which may be present in or adjacent the disc space. One skilled in the art will appreciate that the hollow tube 2 further comprising a footing 11, and a second end opening for ejecting bone graft in a generally lateral direction, may affect the delivery of bone graft in a lateral direction simultaneous with delivery in a longitudinal direction.

Figure 6:
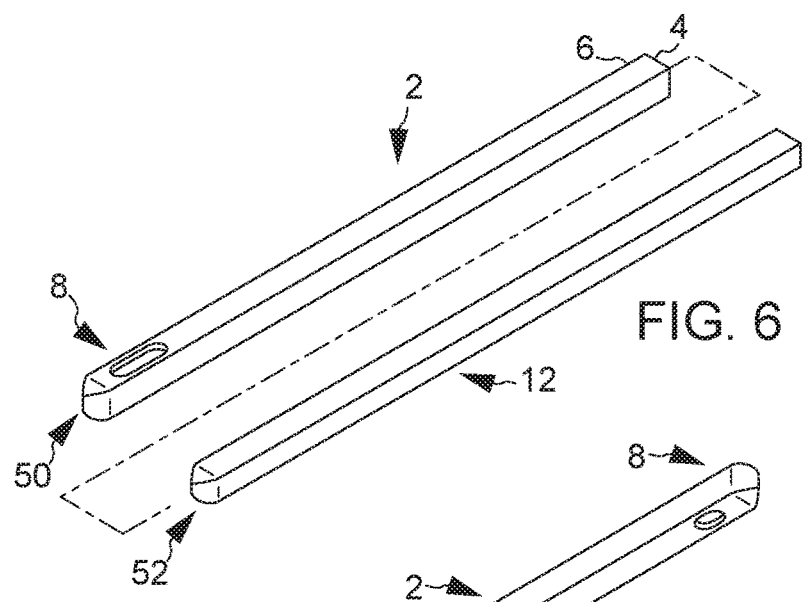
FIG. 6 is a front perspective view of one embodiment of the device, showing the relationship between the tubular and plunger portions where the tubular portion includes two lateral facing openings at the distal end of the tubular portion and a wedge-shaped distal end of the tubular member.

Referring now to FIGS. 6-10, a preferred embodiment of the device is shown. In regard to FIG. 6, an integrated fusion cage and graft delivery device portion is shown, comprised of a hollow tubular member 2, which has a first proximate end 6 and a second distal end 8, with a general hollow structure therebetween. The generally hollow tube 2 is shown with one of two lateral openings at the distal end 8 of the tubular member 2 viewable (the other is viewable in FIG. 7). Also in FIG. 6, the plunger member 12 is shown. The manner of insertion of plunger member 12 into tubular member 2 is also provided. Thus, as shown in FIG. 6, the hollow tube 2 allows bone graft material to be inserted into the opening 4 at the proximal end 6 of the hollow tube 2, and ultimately exited from the hollow tube 2 through the second distal end 8 from the lateral openings at the distal end 8 of the hollow tubular member 2.

Furthermore, regarding FIG. 6, a preferred embodiment of the distal end 8 of the tubular member 2 and the distal end 18 of the plunger member 12 is provided. The configuration provided, a wedge-shaped end 50 of the tubular member 2 and a wedge-shaped end 52 of the plunger 12, allows substantially all of the bone graft material to be removed and thus inserted into the surgical area when the plunger 12 is fully inserted into the tubular member 2. The wedge-shaped feature 50 of the distal end 8 of the tubular member 2 and the wedge-shaped end 52 of the distal end 18 of the plunger member 12 is discussed in additional detail with respect to FIGS. 8 and 9 below. The ability to remove substantially all of the bone graft material is an important feature of the invention because bone graft material is traditionally expensive and may require surgery to obtain.

Figure 7:
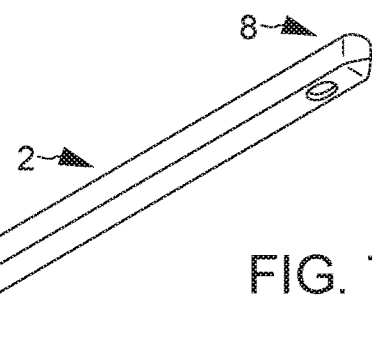
FIG. 7 is another front perspective view of the tubular portion of the device of FIG. 6 showing the second of two lateral openings at the distal end of the tubular portion and a wedge-shaped distal end of the tubular member.

Referring now to FIG. 7, a perspective view of a preferred embodiment of the hollow tubular member 2 is provided. Consistent with FIG. 6, the generally hollow tube 2 is shown with one of two lateral openings at the distal end 8 of the tubular member 2 viewable (the other is viewable in FIG. 6). Thus, in operation the hollow tube 2 allows bone graft material to be inserted into the opening 4 at the proximal end 6 of the hollow tube 2, and ultimately exited from the hollow tube 2 through the second distal end 8 from the lateral openings at the distal end 8 of the hollow tubular member 2. In this configuration, bone graft material is ejected into the surgical area in two lateral directions. One skilled in the art will appreciate that the openings at the distal end 8 of the hollow tubular member 2 need not be positioned exclusively on one or more lateral sides of the distal end 8 of the tubular member to allow bone graft material to be provided to the surgical site in other than a purely axial or longitudinal direction. Further, one skilled in the art will appreciate that the specific absolute and relative geometries and numbers of lateral openings may vary, for example the distal end 8 of the tubular member 2 may have more than two openings that are of different shape (e.g. oval, rectangular).

Figure 8:
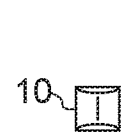
FIG. 8 is a front elevation view of the distal end of the tubular portion of the device of FIG. 6.

Referring now to FIG. 8, an elevation view of the wedge-shaped distal end 50 of the tubular member 2 is provided. In this embodiment, the distal end 52 of the plunger 12 would conform to the same shape, to allow close fitting of the plunger and the hollow tubular member. This contoured plunger, corresponding to the contoured tubular member, serves several purposes: First, it maintains the plunger in a desirable rotational position with respect to the hollow tube (i.e., prevent the plunger from inadvertently or intentionally being manipulated to rotate about the longitudinal axis of the hollow tube); Second, it ensures that when the plunger is fully inserted, the plunger removes substantially all of the bone graft material from the hollow tube. Also, the contoured plunger, corresponding to the contoured tubular member, allows immediate identification of the orientation of the device, and more specifically the direction of eject of the bone graft material into the surgical area. One skilled in the art will appreciate that the plunger 12 need not terminate in a wedge-shape surface 52 to affect the substantial removal of all of the bone graft material placed into the hollow tube 2; more specifically, any shape that allows conformance between the internal contour of the distal end of the hollow tube and the distal end of the plunger will affect the substantial removal of the bone graft material.

Figure 9:
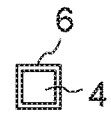
FIG. 9 is a bottom elevation view of the proximal end of the tubular device of FIG. 6.

Referring now to FIG. 9, an elevation view of the opening 4 of the proximal end 6 of the hollow tubular member 2 is provided. As shown in FIG. 9, the opening 4 at the proximal end 6 of the hollow tube 2 allows deposit of bone graft material. In this configuration, the cross-section of the opening 4 at the proximal end 6 of the hollow tube 2 is generally square. Although a generally square cross-section is depicted, the cross-section need not be limited to a generally square shape. For example, cross-sections of an oval shape or those with at least one defined angle to include obtuse, acute, and right angles can provide a shape in some situations that is more congruent with the size or shape of the annulotomy of a particular disc space.

Figure 10A:
FIG. 10A is a top plan view of the device of FIG. 6 with the plunger portion fully inserted into the tubular portion.
Figure 10B:
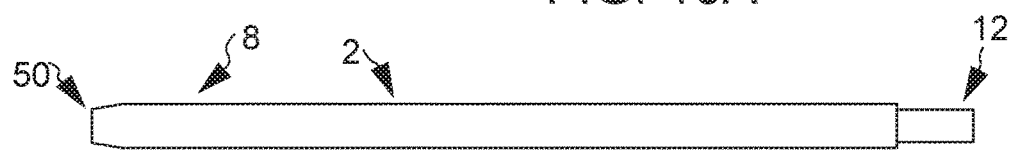
FIG. 10B is a left elevation view of the device of FIG. 6 with the plunger portion fully inserted into the tubular portion.
Figure 10C:
FIG. 10C is a bottom plan view of the device of FIG. 6 with the plunger portion fully inserted into the tubular portion.
Figure 10D:
FIG. 10D is a right elevation view of the device of FIG. 6 with the plunger portion fully inserted into the tubular portion.
Figure 11A:
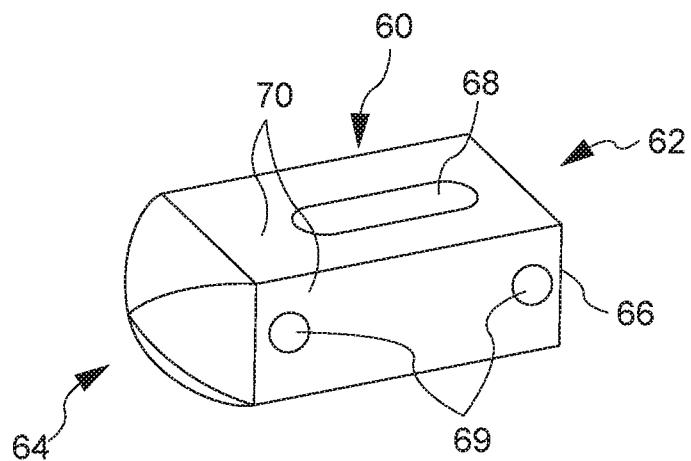
FIG. 11A is a front perspective view of one embodiment of the fusion cage of the device, showing a tapered proximal end and medial openings.
Figure 11B:
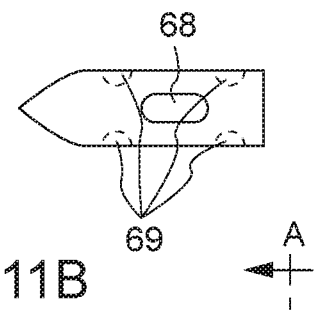
FIG. 11B is a top plan view of the fusion cage of FIG. 11A.
Figure 11C:
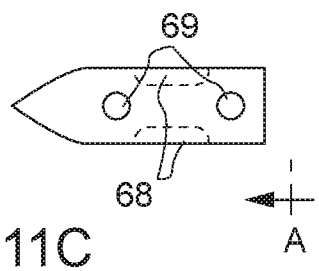
FIG. 11C is a left elevation view of the fusion cage of FIG. 11A.
Figure 11D:
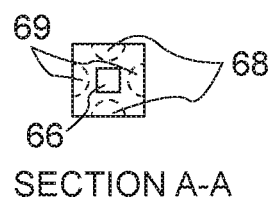
FIG. 11D is a rear elevation view of the fusion cage of FIG. 11A.

Referring to FIGS. 10A-D, sequential elevation views of the square-shaped embodiment of the integrated fusion cage and graft delivery device 1 are provided, depicting the complete insertion of the plunger 12 into the hollow tubular member 2. In each of FIGS. 10A-D, the wedge-shaped distal end 50 of the tubular member 2 is depicted. Also, each of FIGS. 10A-D depict the additional length of the plunger element 12 when inserted into the tubular member 2. FIG. 10A shows one of two lateral openings at the distal end 8 of the hollow tubular member 2. FIG. 10C shows another of the two lateral openings at the distal end 8 of the hollow tubular member 2. One skilled in the art will appreciate that the openings at the distal end 8 of the hollow tubular member 2 need not be positioned exclusively on one or more lateral sides of the distal end 8 of the tubular member to allow bone graft material to be provided to the surgical site in other than a purely axial or longitudinal direction. Further, one skilled in the art will appreciate that the specific absolute and relative geometries and numbers of lateral openings may vary, for example the distal end 8 of the tubular member 2 may have more than two openings that are of different shape (e.g. oval, rectangular).

Referring to FIGS. 11A-D, a fusion cage 60 of an integrated fusion cage and graft delivery device 1 portion is shown, which is comprised of an integrated fusion cage 60 that comprises a first proximal end 62 and a second distal end 64 wherein the first proximal end contains an opening 66 adapted to allow fitting and/or engagement to the distal end 8 of the hollow tube 2. This fitting and/or engagement may be over the external surface of the hollow tube 2 or inside the interior of the hollow tube 2. Further, the integrated fusion cage 60 may comprise one or more medial openings 68 that align with one or more openings at the distal end 8 of the hollow tube 2. Further, the integrated fusion cage 60 may contain non-smooth surfaces, such as belts or striations, along one or more medial surfaces 70 of the integrated fusion cage 60. The integrated fusion cage 60 is configured such that when a plunger 12, once fully inserted in to the hollow tube 2, is substantially congruent with the hollow interior portion of the hollow tube 2, e.g. both the plunger 12 and the hollow tube 2 are substantially the same shape and/or class and bone graft material is delivered through the integrated fusion cage 60 into the surgical area.

In a preferred embodiment, the fusion cage 60 has a tapered tip, and several open channels along the medial and lateral surfaces. In a preferred embodiment, the fusion cage 60 and/or the bone graft delivery portion of the integrated fusion cage and graft delivery device is of oblong or rectangular or square shape. The integrated fusion cage and graft delivery device 1 is designed to avoid blocking or impacting bone graft material into a surgical disc space, thereby limiting the bone graft material that may be delivered, and not allowing available fusion space to be fully exploited for fusion.

In a preferred embodiment, the fusion cage 60 has a keel-shaped tip to separate disk and prevent annular penetration. Also, the fusion cage 60 may have dual portals for bone graft discharge, with the medial openings 68 larger than the lateral openings 69. Further, the fusion cage may be designed in variable heights and lengths so that it fits snugly into the prepared disk space.

Figure 12A:
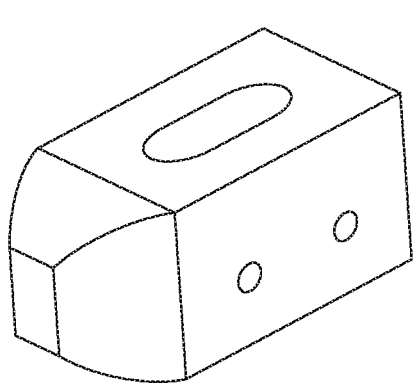
FIG. 12A is a front perspective view of another embodiment of the fusion cage of the device.
Figure 12B:
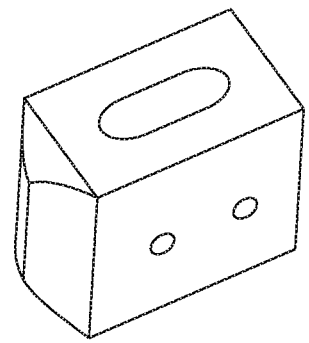
FIG. 12B is a front perspective view of yet another embodiment of the fusion cage of the device.
Figure 12C:
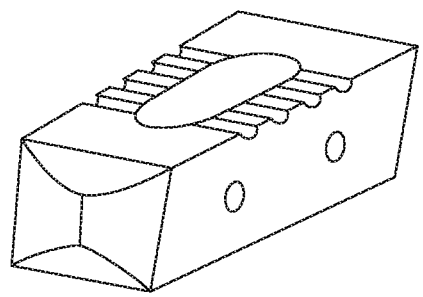
FIG. 12C is a front perspective view of yet another embodiment of the fusion cage of the device.

Referring now to FIGS. 12A-C, two alternate embodiments of the fusion cage 60 are provided. FIG. 12A shows an embodiment of the integrated fusion cage 60 with a second distal end 64 tapered to a flat rectangular shaped end. FIG. 12B shows an embodiment of the integrated fusion cage 60 with a second distal end 64 tapered to a wedged-shaped end. Such a configuration would be, for example, conformal with the wedge-shaped second end 50 of the hollow tube 2, as shown in FIGS. 6-8. FIG. 12C shows an embodiment of the integrated fusion cage 60 with belts of striations imparted to the upper medial surface 70 of the fusion 20 cage 60.

Figure 13:
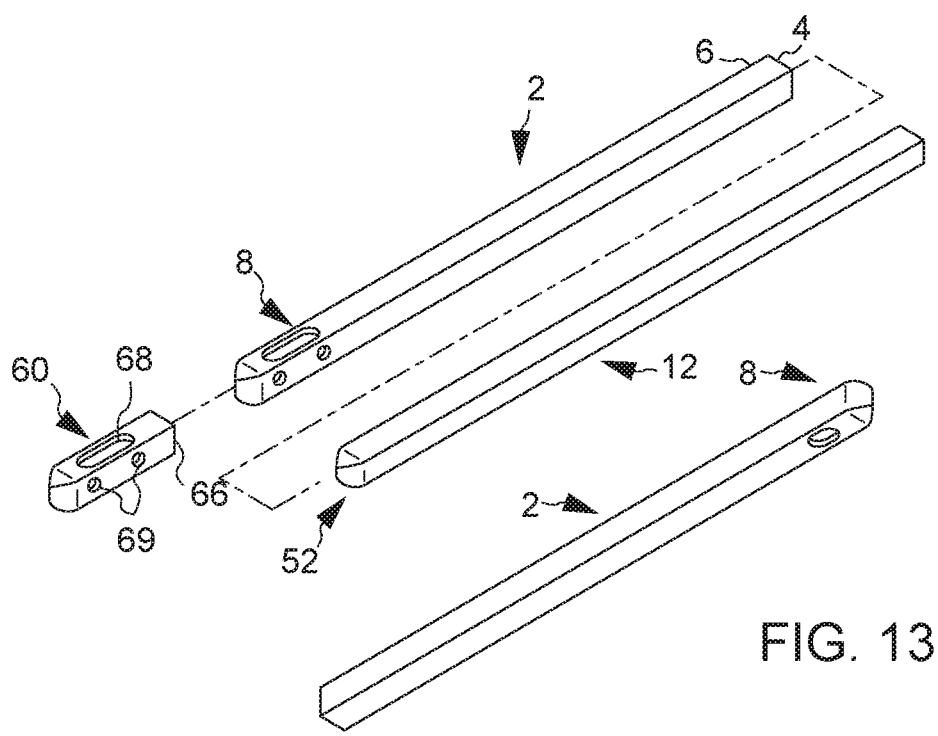
FIG. 13 is a front perspective view of one embodiment of the device, showing the relationship between the tubular and plunger portions where the tubular portion includes two lateral facing openings at the distal end of the tubular portion and a wedge-shaped distal end of the tubular member, and a fusion cage configured for fitting over the exterior distal end of the tubular member.
Figure 14A:
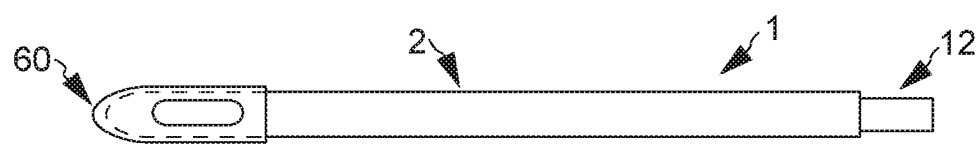
FIG. 14A is a top plan view of the device of FIG. 13 with the plunger portion fully inserted into the tubular portion and the fusion cage fully inserted over the tubular portion.
Figure 14B:
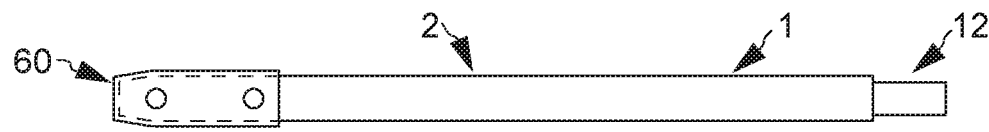
FIG. 14B is a left elevation view of the device of FIG. 13 with the plunger portion fully inserted into the tubular portion and the fusion cage fully inserted over the tubular portion.
Figure 14C:
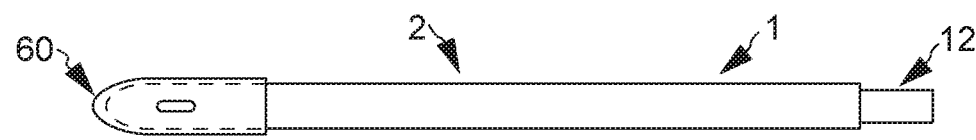
FIG. 14C is a bottom plan view of the device of FIG. 13 with the plunger portion fully inserted into the tubular portion and the fusion cage fully inserted over the tubular portion.
Figure 14D:
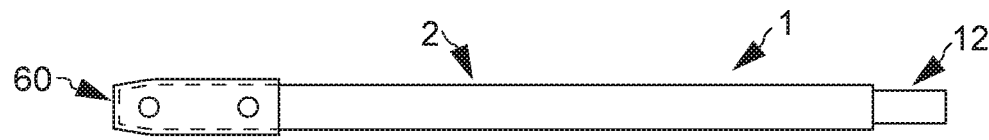
FIG. 14D is a right elevation view of the device of FIG. 13 with the plunger portion fully inserted into the tubular portion and the fusion cage fully inserted over the tubular portion.

In regard to FIG. 13, an integrated fusion cage and graft delivery device 1 is shown, comprised of a hollow tubular member 2, which has a first proximate end 6 and a second distal end 8, with a general hollow structure therebetween. The generally hollow tube 2 is shown with one of two lateral openings at the distal end 8 of the tubular member 2 viewable. Also in FIG. 13, the plunger member 12 is shown and the fusion cage 60. The manner of insertion of plunger member 12 into tubular member 2 is also provided, as is the manner of insertion of fusion cage 60 over tubular member 2 and into the fusion cage first end opening 66. Thus, as shown in FIG. 13, the hollow tube 2 allows bone graft material to be inserted into the opening

4 at the proximal end 6 of the hollow tube 2, and ultimately exited from the hollow tube 2 30 through the second distal end 8 from the lateral openings at the distal end 8 of the hollow tubular member 2 and through the medial openings 68 and/or the lateral openings 69 of the fusion cage 60.

In one embodiment as shown in FIG. 13, the lateral openings at the distal end 8 of the hollow tubular member 2 are preferably disposed within a distance from the distal end 8 not exceeding 25% of the total distance (or length) of the hollow tube member 2, more preferably not exceeding 15% of this identified distance, and most preferably not exceeding 10% of this identified distance. In one embodiment as shown in FIG. 13, the lateral openings at the distal end 8 of the hollow tubular member 2 are preferably disposed within a distance from the distal end 8 not exceeding 10 cm of the total distance (or length) of the hollow tube member 2, more preferably not exceeding 8 cm of this identified distance, and most preferably not exceeding 5 cm of this identified distance.

Referring to FIGS. 14A-D, sequential elevation views of the square-shaped embodiment of the integrated fusion cage and graft delivery device 1 are provided, depicting sequential elevation views of the integrated fusion cage and graft delivery device 1 with the plunger portion 12 fully inserted into the tubular portion 2 and the fusion cage 60 fully inserted over the tubular portion 2. One skilled in the art will appreciate that the openings at the distal end 8 of the hollow tubular member 2 need not be positioned exclusively on one or more lateral sides of the distal end 8 of the tubular member to allow bone graft material to be provided to the surgical site in other than a purely axial or longitudinal direction. Further, one skilled in the art will appreciate that the specific absolute and relative geometries and numbers of lateral and medial openings may vary, for example the distal end 8 of the tubular member 2 may have more than two openings that are of different shape (e.g. oval, rectangular). In one embodiment, the lateral and medial openings 68, 69 of the fusion cage 60 have shapes and sizes that are substantially the same as corresponding openings at the distal end 8 of the tubular member 2. Further, as generally illustrated in FIGS. 14A-D, when the fusion cage 60 is fully inserted over the tubular portion 2, the openings of the fusion cage 60 and the tubular portion substantially align.

Referring to FIGS. 15A-D, a fusion cage 60 of an integrated fusion cage and graft delivery device portion is shown, which is comprised of an integrated fusion cage 60 that comprises a first proximal end 62 and a second distal end 64. The first proximal end contains an opening 66 adapted to allow fitting and/or engagement to the distal end 8 of the hollow tube 2. This fitting and/or engagement may be over the external surface of the hollow tube 2 or inside the interior of the hollow tube 2. Further, the integrated fusion cage 60 may contain non-smooth surfaces, such as belts or striations, along one or more medial surfaces 70 of the integrated fusion cage 60. The integrated fusion cage 60 is configured such that when a plunger 12, once fully inserted in to the hollow tube 2, is substantially congruent with the hollow interior portion of the hollow tube 2, e.g. both the plunger 12 and the hollow tube 2 are substantially the same shape and/or class and bone graft material is delivered through the integrated fusion cage 60 into the surgical area.

In a preferred embodiment, the fusion cage 60 has a tapered tip, and several open channels along the medial and lateral surfaces. In a preferred embodiment, the fusion cage 60 is of a square shape and the bone graft delivery portion of the integrated fusion cage and graft delivery device is of a cylindrical shape. The integrated fusion cage and graft delivery device 1 is designed to avoid blocking or impacting bone graft material into a surgical disc space, thereby limiting the bone graft material that may be delivered, and not allowing available fusion space to be fully exploited for fusion.

Figure 15A:
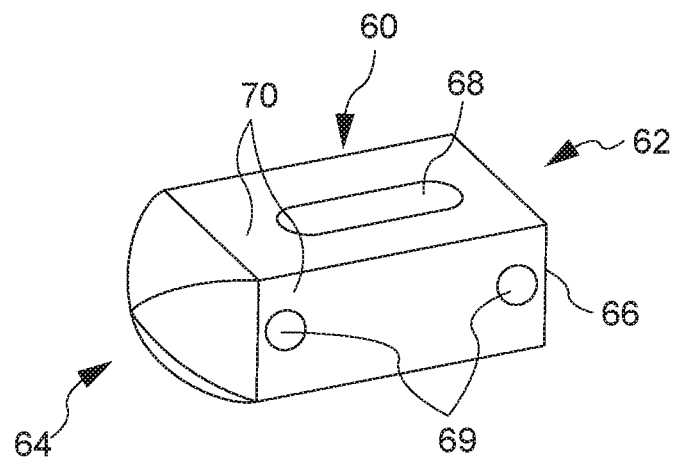
FIG. 15A is a front perspective view of another embodiment of the fusion cage of the device.
Figure 15B:
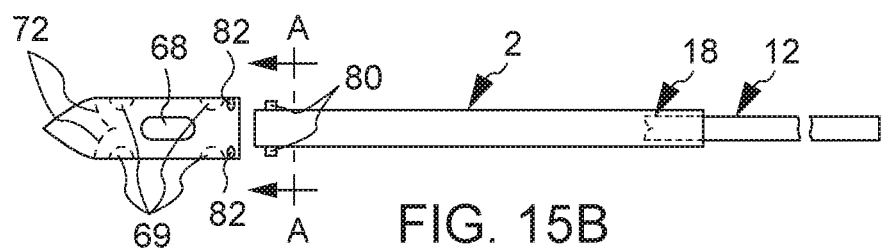
FIG. 15B is a top plan view of another embodiment of the device wherein the fusion cage of the device includes internal ramps and locking slots configured to engage locking tabs of the tubular portion, and the plunger includes a tapered tip.

In a preferred embodiment, the fusion cage 60 has a keel-shaped tip to separate disk and prevent annular penetration and has internal ramps 72 which assist in directing the bone graft material to one or more lateral openings 69. As the plunger 12 is inserted into the hollow tube 2, bone graft material is directed by the fusion cage internal ramps 72 out the lateral openings 69, and bone additionally bone graft material may flow out the one or more medial openings 68. The plunger end 18 may be configured to be conformal with the internal ramps 72 of the fusion cage 60, as depicted in FIG. 15B. Also, the fusion cage 60 may have dual portals for bone graft discharge, with the medial openings 68 larger than the lateral openings 69. Further, the fusion cage may be designed in variable heights and lengths so that it fits snugly into the prepared disk space.

Figure 15C:
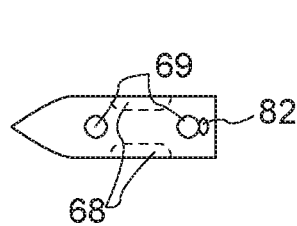
FIG. 15C is a left elevation view of the fusion cage of FIG. 15B.
Figure 15D:
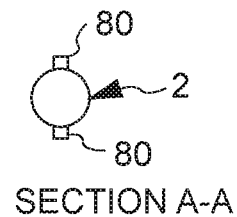
FIG. 15D is a cross sectional view of the tubular portion taken along line A-A of FIG. 15B.

In a preferred embodiment as shown in FIGS. 15B-D, the hollow tube 2 is of cylindrical shape and includes one or more locking tabs 80 configured to engage one or more locking slots 82 of the fusion cage 60. The locking tabs 80 may permanently or not permanently engage the locking slots 82, and may be of shape to include rectangular, circular and oblong. The instruments used with the integrated fusion cage and graft delivery device described above in its varying embodiments may include one or more tamps, preferably having a configuration which at least in part corresponds in shape and contour of the hollow tube portion of the delivery device. The one or more tamps may be adapted to correspond further to the shape and contour of the graspable end of the plunger, for use in driving the plunger through the hollow tube portion of the delivery device to ensure any remaining bone graft located in the hollow tube is delivered to the graft receiving area.

Figure 16:
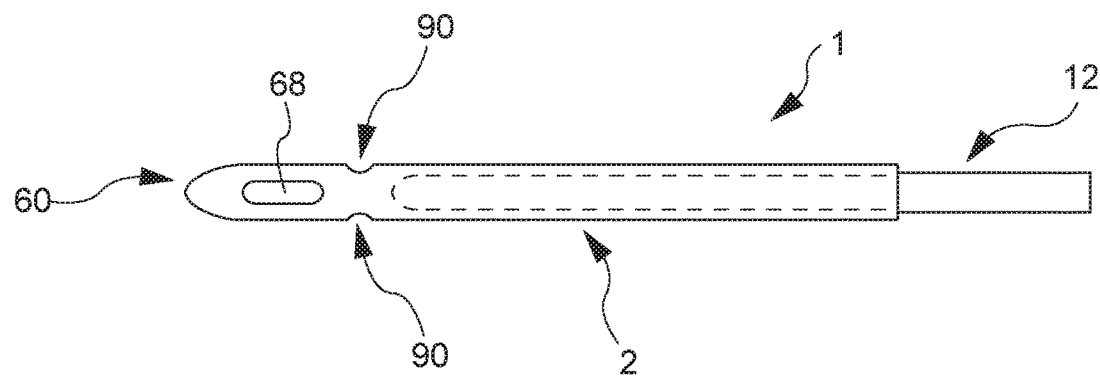
FIG. 16 is a top plan view of another embodiment of the device with the plunger portion partially inserted into the tubular portion and the fusion cage engaged with the tubular portion via a break-off collar.

In the embodiment of the device of FIG. 16, the hollow tube 2 engages with the fusion cage 60 via a break-off collar 90 and the plunger 12 inserts into the interior of the hollow tube 2. The plunger 12 is depicted partially inserted into the hollow tube 2. The break-off collar 90 may be severed by any of several means, to include application of torsion and/or rotational force and/or lateral force to break-off collar 90, for example by twisting on the hollow tube 2 and/or the plunger 12.

Figure 17A:
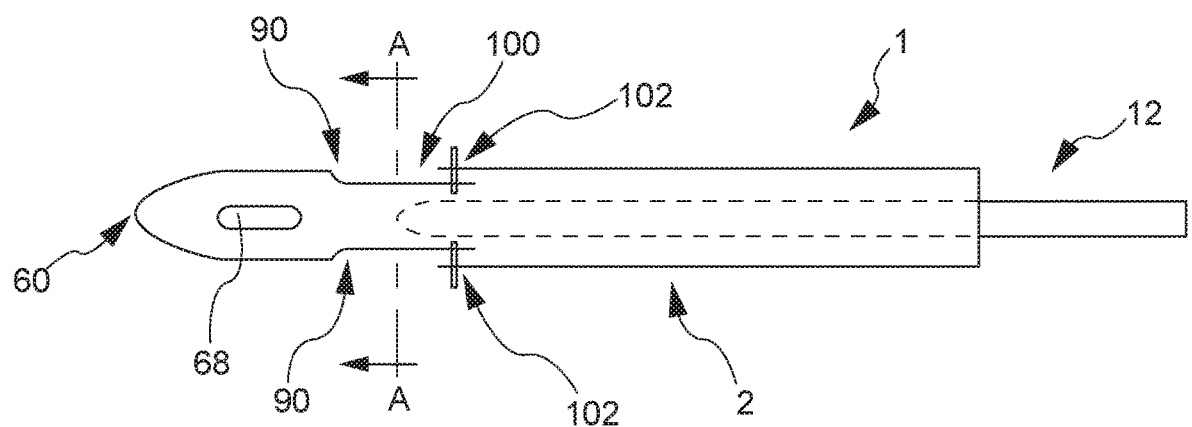
FIG. 17A is a top plan view of another embodiment of the device wherein the fusion cage engages with a connector conduit which in turn engages with the tubular portion.
Figure 17B:
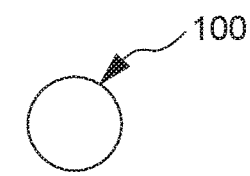
FIG. 17B is a cross-sectional view of section A-A of FIG. 17A.
Figure 18A:
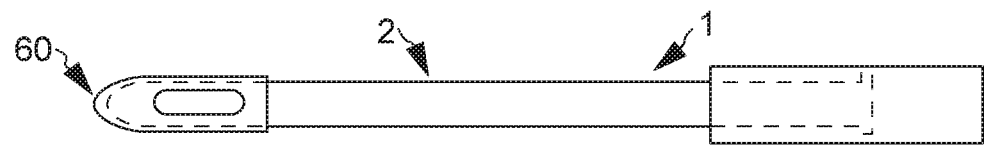
FIG. 18A is a top plan view of another embodiment of the device wherein the tubular portion comprises a telescoping feature.
Figure 18B:
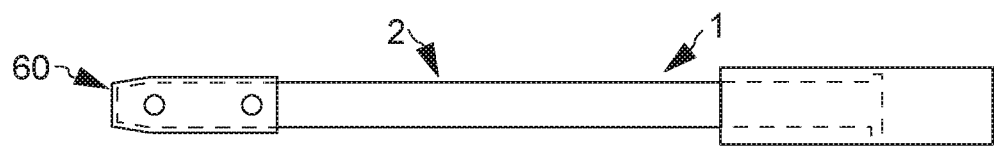
FIG. 18B is a left elevation view of the device of FIG. 18A.
Figure 18C:
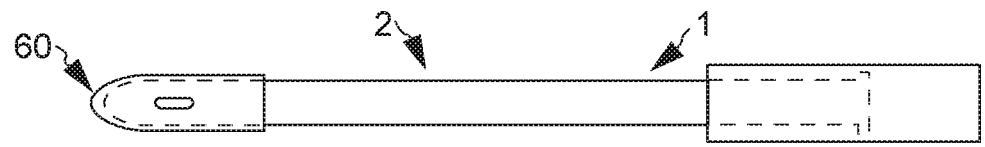
FIG. 18C is a bottom plan view of the device of FIG. 18A.
Figure 18D:
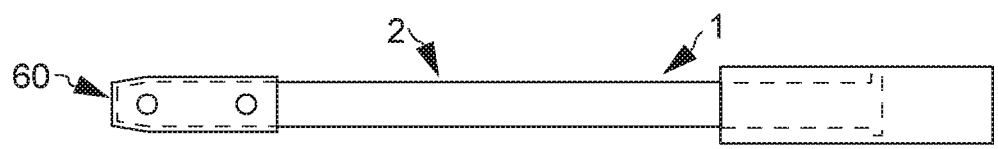
FIG. 18D is a right elevation view of the device of FIG. 18A.
Figure 19A:
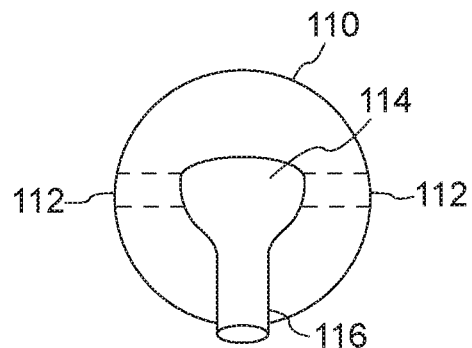
FIG. 19A is a top plan view of a fusion cage of an embodiment of the device particularly adapted for use in anterior lumbar interbody fusion procedures.
Figure 19B:
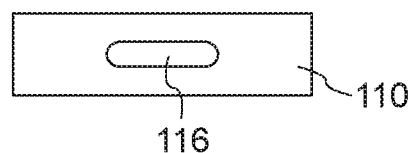
FIG. 19B is a front elevation view of the device of FIG. 19A.
Figure 19C:
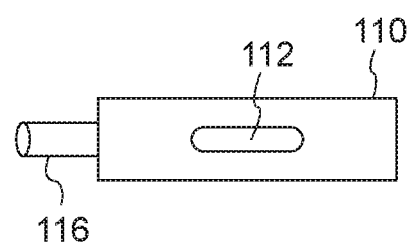
FIG. 19C is a left elevation view of the device of FIG. 19A.
Figure 19D:
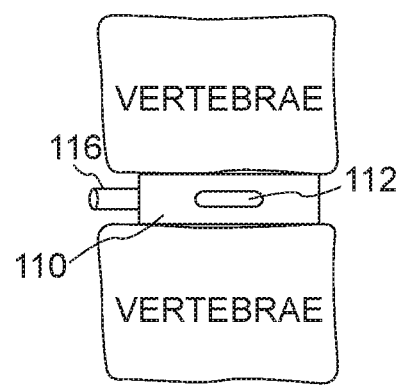
FIG. 19D is a view of the device of FIG. 19A inserted between vertebrae.
Figure 20A:
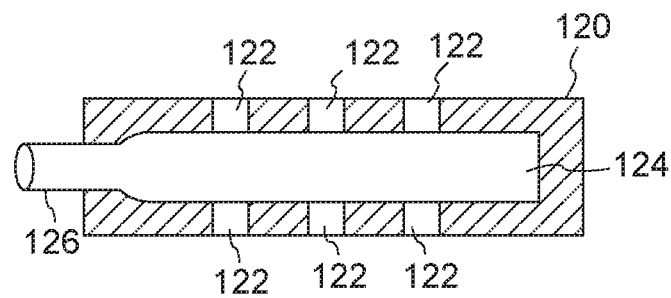
FIG. 20A is a cross-sectional top plan view of a fusion cage of an embodiment of the device particularly adapted for use in direct lateral interbody fusion procedures.
Figure 20B:
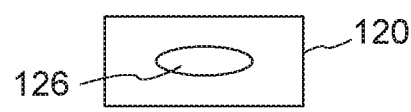
FIG. 20B is a front elevation view of the device of FIG. 20A.
Figure 20C:
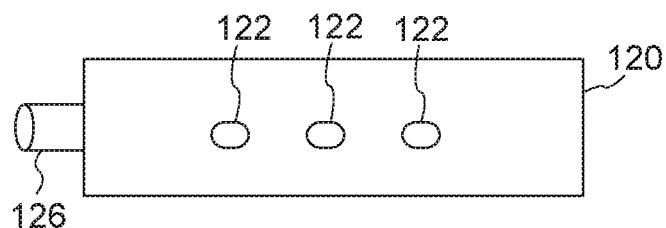
FIG. 20C is a left elevation view of the device of FIG. 20A.
Figure 20D:
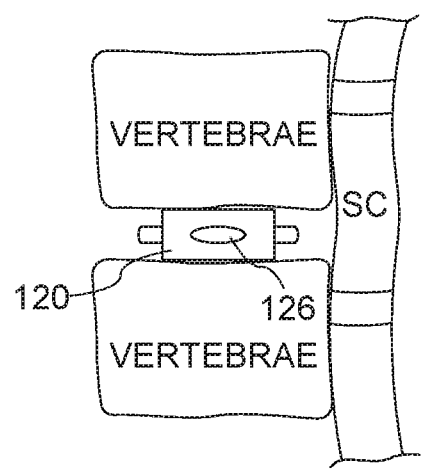
FIG. 20D is a view of the device of FIG. 20A inserted between vertebrae.
Figures 21A, 21B:
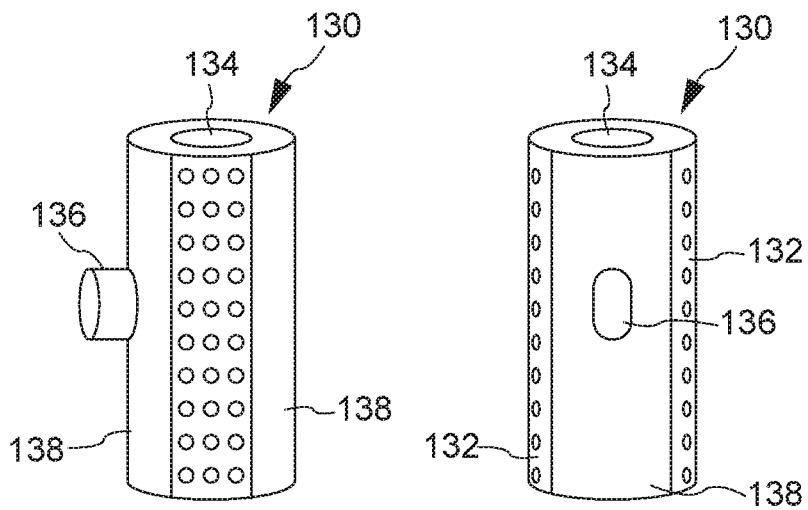
FIG. 21A is a front perspective view of a fusion cage of an embodiment of the device particularly adapted for use in connection with vertebrectomy procedures.
FIG. 21B is a left perspective view of the device of FIG. 21A.
Figures 21C, 21D:
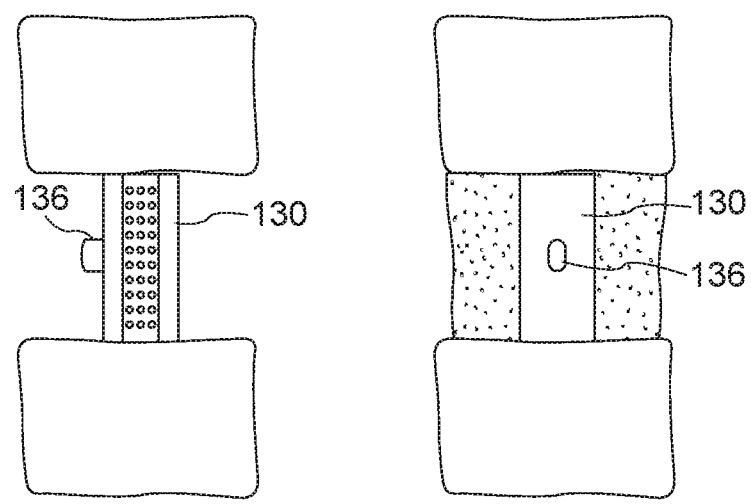
FIG. 21C is a front elevation view of the device of FIG. 21A inserted into a surgical site.
FIG. 21D is a left elevation view of the device of FIG. 21A inserted into a surgical site.

In the embodiment of the device of FIG. 17A-B, the hollow tube 2 engages with a connector conduit 100 which in turn connects with the fusion cage 60 via a break-off collar 90. One or more connectors 102 connect the hollow tube 2 with the connector conduit 100. The hollow tube 2 fits over the connector conduit 100. The one or more connectors 102 fit through the hollow tube 2 and the connector conduit 100. The break-off collar 90 may be severed by any of several means, to include application of torsion and/or rotational force and/or lateral force to break-off collar 90, for example by twisting on the hollow tube 2 and/or the plunger 12. In one embodiment of the connector conduit 100, as shown in FIG. 17B, the connector conduit 100 is of circular cross-section.

Referring to FIGS. 18A-D, sequential elevation views of the square-shaped embodiment of the integrated fusion cage and graft delivery device 1 are provided, depicting sequential elevation views of the integrated fusion cage and graft delivery device 1 with telescoping tubular portion 2 and the fusion cage 60 fully inserted over the tubular portion 2. One skilled in the art will appreciate that the openings at the distal end 8 of the hollow tubular member 2 need not be positioned exclusively on one or more lateral sides of the distal end of the tubular member to allow bone graft material to be provided to the surgical site in other than a purely axial or longitudinal direction.

In an embodiment of the invention particularly suited for ALIF procedures, a fusion cage 110 as shown in FIGS. 19A-D comprises a hollow internal chamber 114 in fluid communication with bone graft discharge portals 112 and a charging portal 116, which comprises a break-off collar in some embodiments such as those depicted in FIGS. 17A-D. The fusion cage 110 has a substantially cylindrical shape, with the discharge portals 112 located opposite each other on the curved lateral portion of the fusion cage 110 and the charging portal 116 located substantially in between the discharge portals 112 on the curved anterior portion of the fusion cage 110. The curved posterior portion of the fusion cage 110 is substantially devoid of portals from the internal chamber 114 to the exterior of the fusion cage 110. The charging portal 116 is adapted to receive a hollow tube such as the hollow tube 2 shown in other embodiments described herein. Bone graft material enters the internal chamber 114 through a hollow tube connected to the charging portal 116, and exits the internal chamber 114 through the discharge portals 112. The discharge portals 112 are positioned so that when the fusion cage 110 is properly positioned in between two vertebrae, bone graft material discharged therethrough fills the space in between the vertebrae on the lateral sides of the spine, but does not discharge into or fill the anterior or posterior space in between the vertebrae. In embodiments of fusion cage 110 comprising a break-off collar, once the fusion cage 110 is properly positioned and the desired amount of bone graft material has been inserted into the chamber 114 and discharged through the discharge portals 112, the break-off collar is severed from the fusion cage 110 (as described with respect to other embodiments herein) and removed from the patient's body.

In embodiments that do not comprise a break-off collar, the charging portal 116 of fusion cage 110 is adapted to removably receive a hollow tube (such as the hollow tube 2 shown in other embodiments described herein). For example, the walls of the charging portal 116 may be threaded so that the hollow tube can be screwed into the charging portal 116.

The fusion cage 110 preferably has a height of from about 8 millimeters to about 14 millimeters, and a diameter of less than about 36 millimeters. The fusion cage 110 is made from polyether ether ketone (PEEK), titanium, a composite material, or any other material suitable for implantation in a human body. The fusion cage 110 comprises, in some embodiments, ramps within internal chamber 114 to guide bone graft material to discharge portals 112.

In an embodiment of the invention particularly suited for D-LIF procedures, a fusion cage 120 as shown in FIGS. 20A-D comprises a hollow internal chamber 124 in fluid communication with bone graft discharge portals 122 and a charging portal 126, which in some embodiments—including the embodiment shown in FIGS. 20A-D—comprises a break-off collar. The fusion cage 120 is substantially shaped as a rectangular prism, with the discharge portals 122 located on opposite sides of the fusion cage 120 and the charging portal 126 located on a lateral face of the fusion cage 120. The opposite lateral face of the fusion cage 120 is devoid of portals from the internal chamber 124 to the exterior of the fusion cage 120. The charging portal 126 is adapted to receive a hollow tube such as the hollow tube 2 shown in other embodiments described herein. Bone graft material enters the chamber 124 through a hollow tube connected to the charging portal 126, and exits the internal chamber 124 through the discharge portals 122. The discharge portals 122 are positioned so that when the fusion cage 120 is properly positioned in between two vertebrae, bone graft material discharged therethrough fills the space in between the vertebrae towards the anterior and posterior of the spine, but does not discharge into or fill the lateral space in between the vertebrae. As with other embodiments described herein, in embodiments that comprise a break-off collar, once the fusion cage 120 is properly positioned and the desired amount of bone graft material has been inserted into the chamber 124 through charging portal 126 and discharged through the discharge portals 122, the break-off collar is severed from the fusion cage 120 (as described with respect to other embodiments herein) and removed from the patient's body.

In embodiments that do not comprise a break-off collar, the charging portal 126 is adapted to removably receive a hollow tube (such as the hollow tube 2 shown in other embodiments described herein). For example, the internal walls of charging portal 126 may be threaded so that the hollow tube can be screwed into the charging portal 126.

The fusion cage 120 preferably has a height of from about 8 millimeters to about 14 millimeters, and a length of from about 22 millimeters to about 36 millimeters. The fusion cage 120 is made from polyether ether ketone (PEEK), titanium, a composite material, or any other material suitable for implantation in a human body. The fusion cage 120 comprises, in some embodiments, ramps within internal chamber 124 to guide bone graft material to discharge portals 122.

Referring now to FIGS. 21A-D, in embodiments of the invention particularly suited for use in connection with a vertebrectomy, a fusion cage 130 comprises a substantially cylindrical wall surrounding an internal chamber 134. Thus, the fusion cage 130 has a substantially cylindrical shape. Internal chamber 134 is open at the top and the bottom of fusion cage 130, and lateral portions 132 of the cylindrical wall of the fusion cage 130 are porous to bone graft material (i.e. bone graft slurry). Anterior and posterior portions 138 of the cylindrical wall of fusion cage 130 in between porous portions 132 are impervious to bone graft material. A charging portal 136—which in some embodiments, including the embodiment shown in FIGS. 21A-D, comprises a break-off collar—is positioned on an impervious portion 138 of fusion cage 130. The charging portal 136 is adapted to receive a hollow tube such as the hollow tube 2 shown in other embodiments described herein. Bone graft material enters the chamber 134 through a hollow tube connected to the charging portal 136, and exits the chamber 134 through porous wall portions 132. The porous wall portions 132 are positioned so that when the fusion cage 130 is properly positioned in between two vertebrae, bone graft material discharged therethrough fills the space in between the vertebrae on either side of the spine, but the impervious wall portions 138 prevent bone graft material from discharging into the anterior or posterior space in between the vertebrae, thus preventing bone graft material from pushing against the spinal cord.

In embodiments of fusion cage 130 comprising a break-off collar, once the fusion cage 130 is properly positioned and the desired amount of bone graft material has been inserted into the chamber 134 through charging portal 136 and discharged through the porous wall portions 132, the break-off collar 136 is severed from the fusion cage 130 (as described with respect to other embodiments herein) and removed from the patient's body. In embodiments that do not comprise a break-off collar, the charging portal 136 is adapted to removably receive a hollow tube (such as the hollow tube 2 shown in other embodiments described herein). For example, the internal walls of the charging portal 136 may be threaded so that the hollow tube can be screwed into the charging portal 136.

The fusion cage 130 preferably has a height equal to or greater than the vertebra or vertebrae it is intended to replace, and a diameter of less than about 36 millimeters. The fusion cage 130 is made of polyether ether ketone, titanium, a composite material, or any other material suitable for implantation in a human body. In some embodiments, ramps in the internal chamber 134 guide the bone graft material to the porous lateral faces 132.

Figure 22:
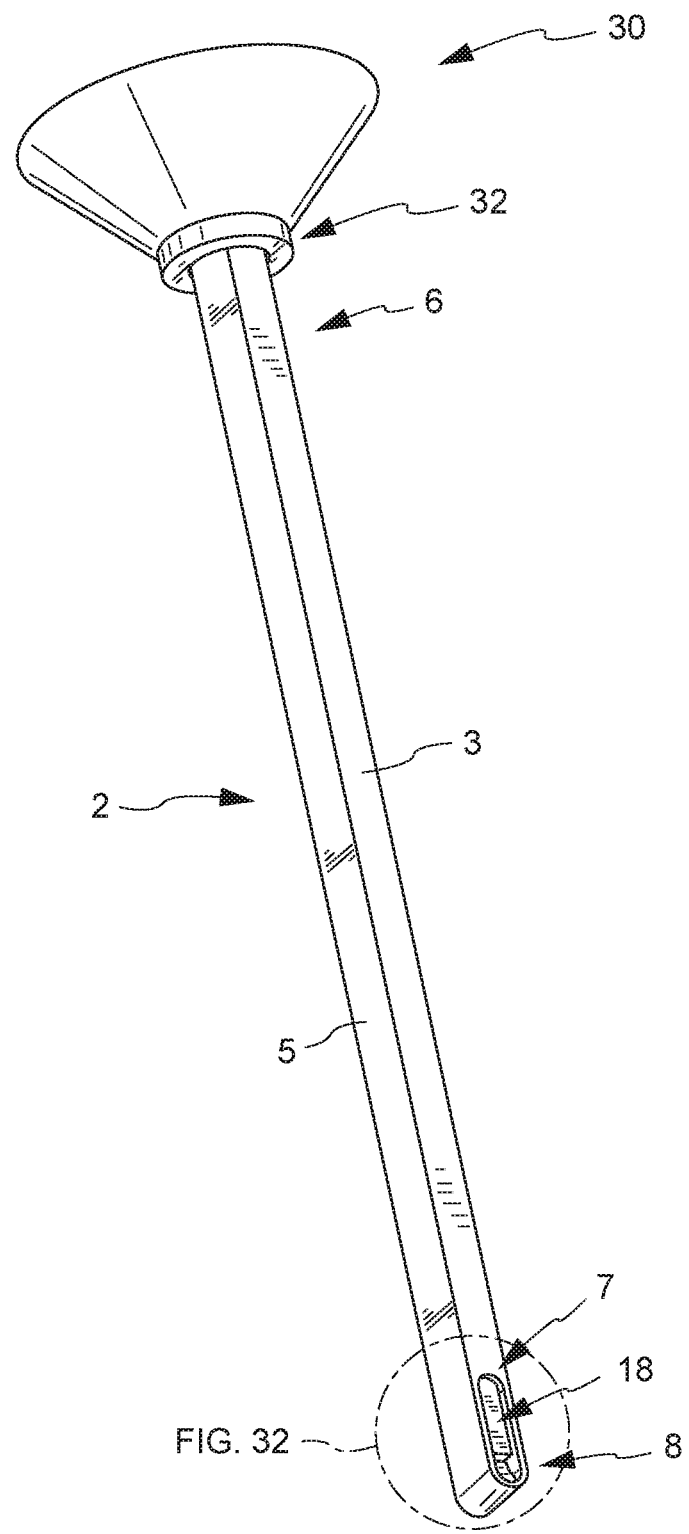
FIG. 22 is a front perspective view of another embodiment of the device for delivering bone graft.

Referring now to FIGS. 22-33, another embodiment of the device for delivering bone graft is provided. In regard to FIGS. 22-28, integrated fusion cage and graft delivery device 1 is shown. FIG. 22 is a perspective view of the device 1, FIG. 23 a perspective exploded view, FIG. 24 a top plan view, FIG. 25 a front elevation view, FIG. 26 a right elevation view, FIG. 27 is a bottom plan view, and FIG. 28 is a cross-sectional view of section A-A of FIG. 25.

Device 1 is comprised of a hollow tubular member or hollow tube 2, a plunger 12 which fits within the hollow tube 2, and a funnel 30. The funnel 30 engages the upper or proximal or first end 6 of the hollow tube, and comprises a sleeve 32 and opening 34. Medical material, such as bone graft material, is inserted into opening 34 of funnel 30, which in turn enters hollow tube 2.

Hollow tube 2 comprises hollow tube first exterior surface 3, hollow tube second exterior surface 5, first end 6, second end 8, and hollow tube first distal opening 7. Hollow tube 2 is generally of symmetrical shape such that first exterior surface 3 comprises two such surfaces opposite or at 180 degrees from one another, and second exterior surface 5 comprises two such surfaces opposite or at 180 degrees from one another. Also, hollow tube first distal opening 7 is positioned on each of two opposite sides of hollow tube 2 at second end 8, each opening from hollow tube first exterior surface 3.

Figure 23:
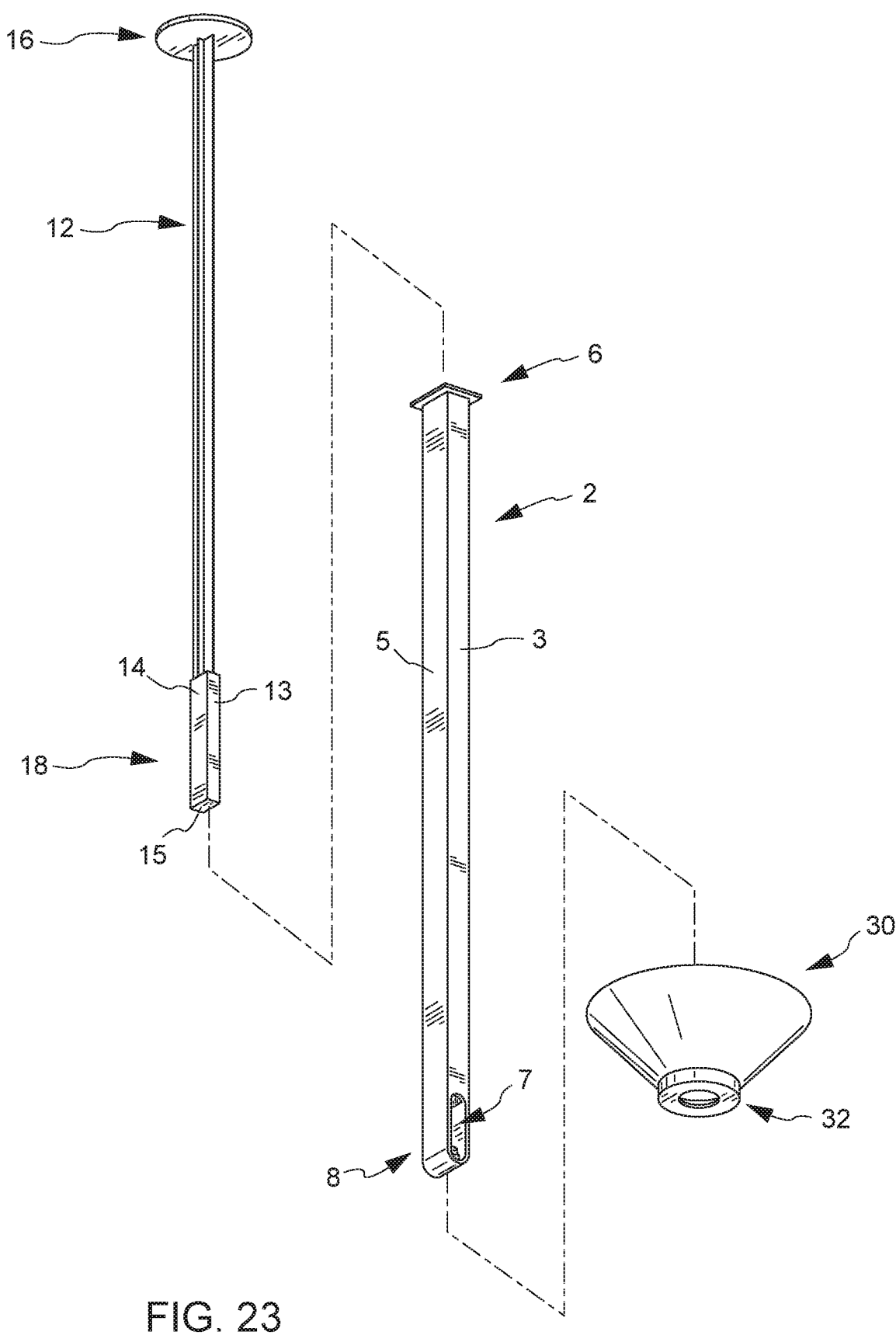
FIG. 23 is a front perspective exploded view of the device shown in FIG. 22.

Funnel 30 is configured with sleeve 32 such that funnel 30 may be positioned at second end 8 of hollow tube 2 such that hollow tube may fit through funnel 30, enabling funnel 30 to move along hollow tube 2 from second end 8 of hollow tube 2 to first end 6 of hollow tube 2 until funnel 30 engages first end 6 of hollow tube, such as at protrusion or shelf depicted in FIG. 23.

Plunger 12 comprises handle 16 at upper or proximal end of plunger 12. Plunger second end 18 comprises distal first surface 13, distal second surface 14 and distal third (or bottom) surface 15. Plunger second end 18 is generally of symmetrical shape such that distal first surface 13 comprises two such surfaces opposite or at 180 degrees from one another, and distal third surface 15 comprises two such surfaces opposite or at 180 degrees from one another. Plunger 12 is configured such that second end 18 forms a congruent or conformal engagement with the interior of the hollow tube 2. Stated another way, the plunger second end 18 fits within the hollow tube 2 so as to slide within the hollow tube with minimal to no effective spacing between the exterior surface of the plunger second end 18 and the interior of the hollow tube 2, thereby forcing bone graft material positioned in the hollow tube 2 through the hollow tube when the plunger 12 (and thus its second end 18) is axially moved from hollow tube first end 6 to hollow tube second end 8.

Figure 29:
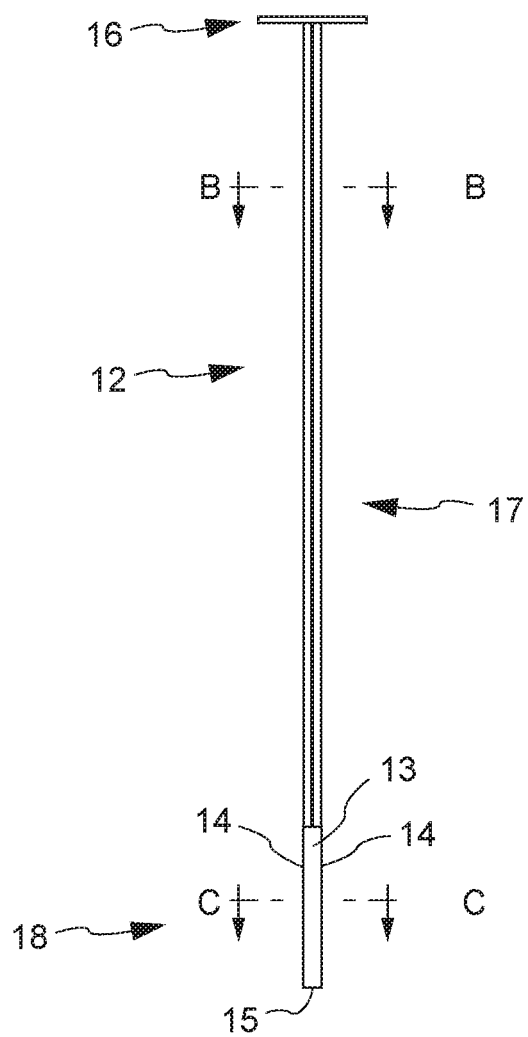
FIG. 29 is a front elevation view of the plunger element of the device shown in FIG. 22.
Figure 30:
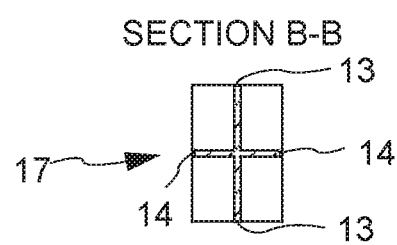
FIG. 30 is a cross-sectional view of section B-B of FIG. 29.
Figure 31:
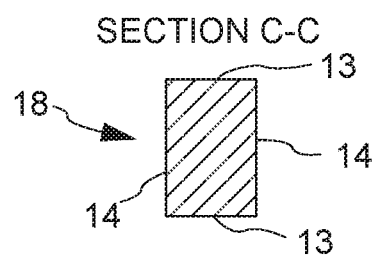
FIG. 31 is a cross-sectional view of section C-C of FIG. 29.

In regard to FIGS. 29-31, further features of the plunger 12 are described. FIG. 29 is a front elevation view of the plunger element of the device shown in FIG. 22, FIG. 30 is a cross-sectional view of section B-B of FIG. 29, and FIG. 31 is a cross-sectional of section C-C of FIG. 29. Plunger 12 comprises handle 16 at upper or proximal end of plunger 12 and plunger distal or second end 18. Plunger second end 18 comprises distal first surface 13, distal second surface 14 and distal third (or bottom) surface 15. Plunger medial portion 17 forms a cross configuration, as depicted in FIG. 30, such that distal first surfaces 13 are of reduced width relative to width at second end 18. Similarly, plunger distal second surfaces 14, at plunger medial portion 17, are of reduced width relative to width at second end 18. At distal end 18 of plunger 12, plunger cross-section is a rectangle, as depicted in FIG. 31.

Figure 32:
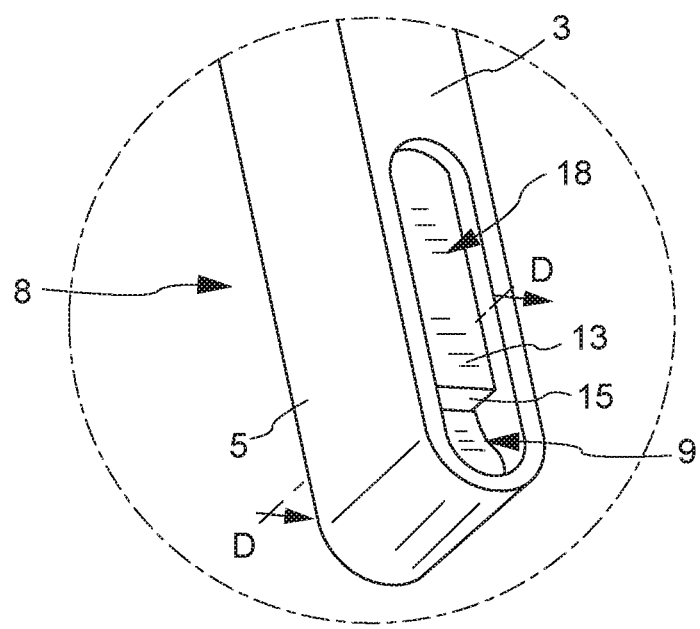
FIG. 32 is a detailed front perspective view of a portion of the device shown in FIG. 22.
Figure 33:
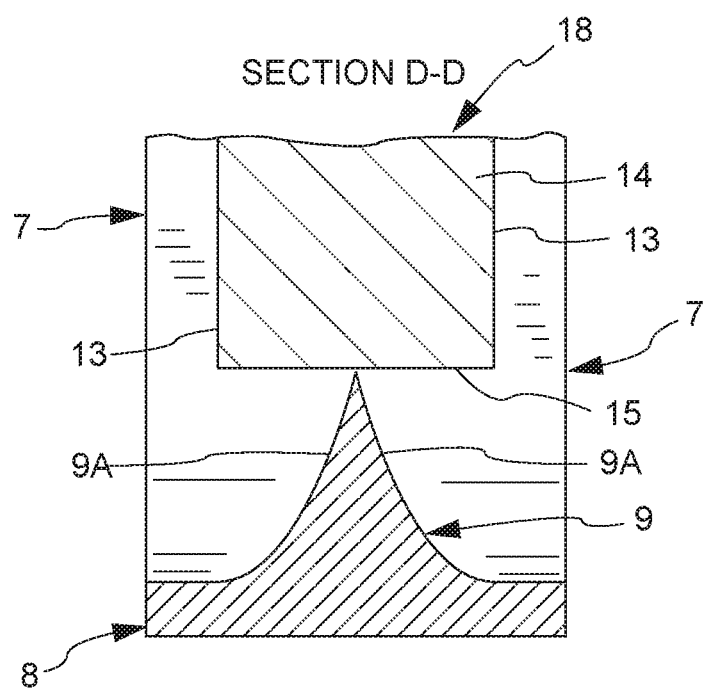
FIG. 33 is a cross-sectional view of section D-D of FIG. 32.

In regard to FIGS. 32 and 33, additional detail of the distal portion of device 1 are provided. FIG. 32 is a detailed view of a portion of the device 1 shown in FIG. 22 and FIG. 33 is a cross-sectional view of section D-D of FIG. 32. Each of FIGS. 32 and 33 depict the device 1 when the plunger 12 is fully inserted into the hollow tube 2, and the plunger distal third surface 15 has engaged and is in contact with the hollow tube distal interior ramp 9. Hollow tube distal interior ramp 9 comprises hollow tube distal interior ramp surfaces 9A, symmetrically positioned about the middle of the hollow tube second end 8. Hollow tube distal interior ramp surfaces 9A are of curvilinear shape forming a terminus, and urge bone graft material, when disposed within the hollow tube 2, to substantially exit the pair of first distal openings 7 of the device 1.

Referring now to FIGS. 36-39 another embodiment of an integrated fusion cage and graft delivery device 1 is provided. With reference to FIGS. 36-39, the integrated fusion cage and graft delivery device 1 comprises plunger 12, hollow tube 2, fusion cage 60 and ejection tool 140. The fusion cage 60 comprises fusion cage second or distal end 64 with tapered end feature and fusion cage first or proximal end 62 comprising fusion cage collar 92, fusion cage collar face 93 and fusion cage collar cavity 94. Hollow tube 2 comprises hollow tube second end 8 which engages fusion cage collar 92 by fitting over fusion cage collar 92 in a press or interference fit. Plunger 12 fits within hollow tube 12, and further may optionally fit within fusion cage collar cavity 94 so as to enter into interior of fusion cage 60 as previously described above.

Ejection tool 140 comprises ejection tool second or distal end 152 and ejection tool first or proximal end 142. Ejection tool second end 152 engages fusion cage collar face 93 to apply force or push fusion cage 60 from engagement with hollow tube 2. Ejection tool second end 152 is configured such that it may not travel past or into the fusion cage. When sufficient axial force is applied to the ejection tool 140 in the direction B of the fusion cage 60, the interference fit that secures the fusion cage 60 (at fusion cage collar 92) to hollow tube 2 (at second end 8 of hollow tube) is overcome and the fusion cage 60 is released or disengaged from the hollow tube 2. Ejection tool 140 further comprises an ejection tool L-cut 151 that engages knobs 6A of hollow tube 2. In one embodiment, knobs 6A of hollow tube 2 are configured to additionally or alternatively engage L-cuts of the funnel 30 at funnel sleeve 32 (See FIG. 23).

Plunger 12 further comprises handle 16 and plunger stop 16A which engages upper portion of hollow tube 2. Plunger stop 16A may be configured to prevent plunger distal most portion from entering fusion cage collar cavity 94 and therefore further prevent entry into interior of fusion cage 60.

Fusion cage 60 further comprises fusion cage internal ramps 72 as described above. The fusion cage internal ramps 72 may be symmetrical about a centerline of the device 1, and may be linear or sloped inwardly. In one embodiment, plunger stop 16A may be configured to prevent plunger distal most portion from striking or contacting fusion cage internal ramps 72 but otherwise allowing entry into fusion cage collar cavity 94 and therefore also allow entry into interior of fusion cage 60.

Fusion cage 60 further comprises fusion cage first opening or port pair 65 and fusion cage second opening or port pair 67. Fusion cage first opening pair 65 are symmetric about a vertical plane intersecting a centerline of the fusion cage 60, and are located such that at least a portion of the openings are adjacent the tip of the fusion cage internal ramps 72. The fusion cage first opening pair 65 are of an oblong racetrack shape, but in other embodiments may be oval, circular and rectangular. The fusion cage second opening pair 67 are of an oval shape, but in other embodiments may be oblong racetrack, circular and rectangular. The fusion cage may have rounded or no square edges, and may have a non-smooth exterior surface on any or all portions. That is, the fusion cage 60 may have ridges, bumps, contours, sawtooth profile edges along or on top of any or all exterior surfaces, such as surfaces adjacent the fusion cage second opening pair 67 and/or fusion cage first opening pair 65.

Figure 40:
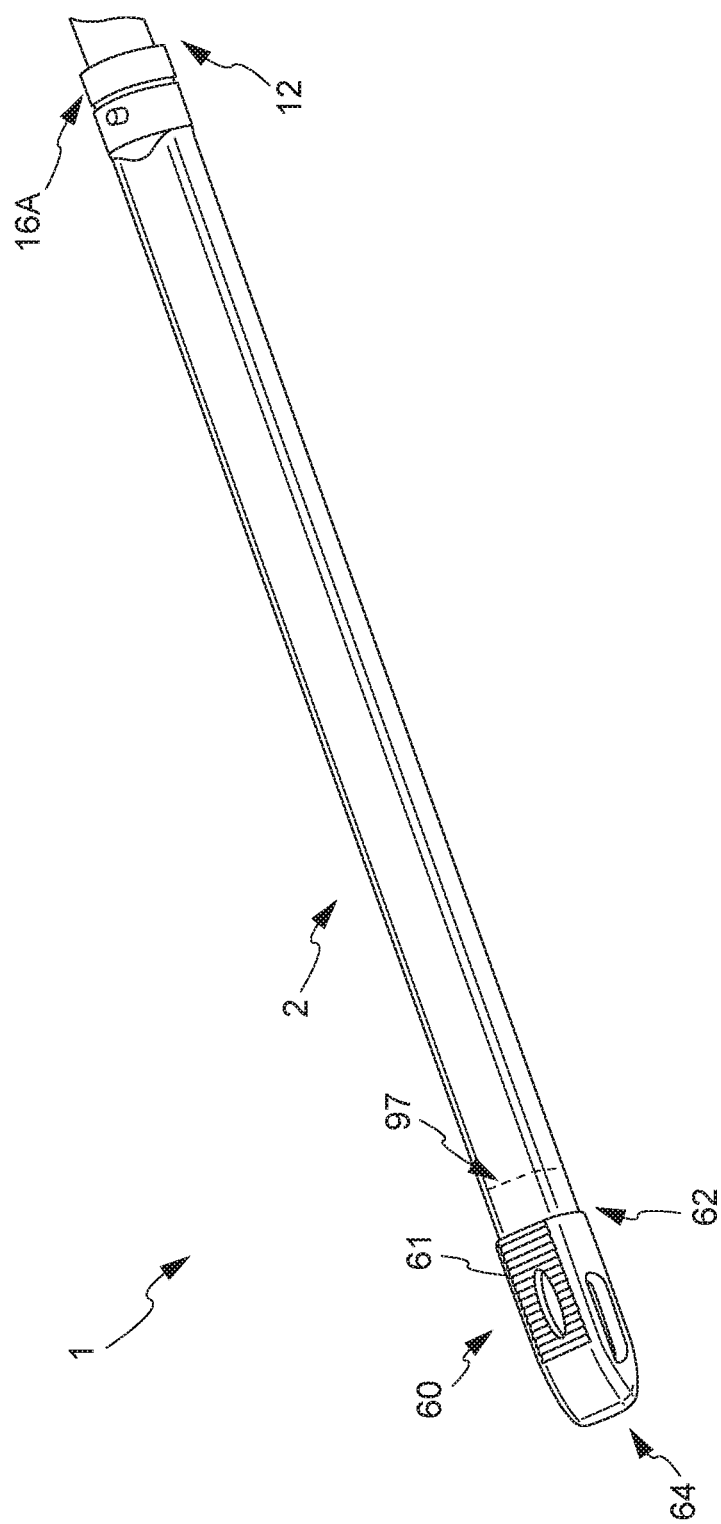
FIG. 40 is a front perspective view of an integrated fusion cage and graft delivery device according to yet another embodiment.
Figure 41:
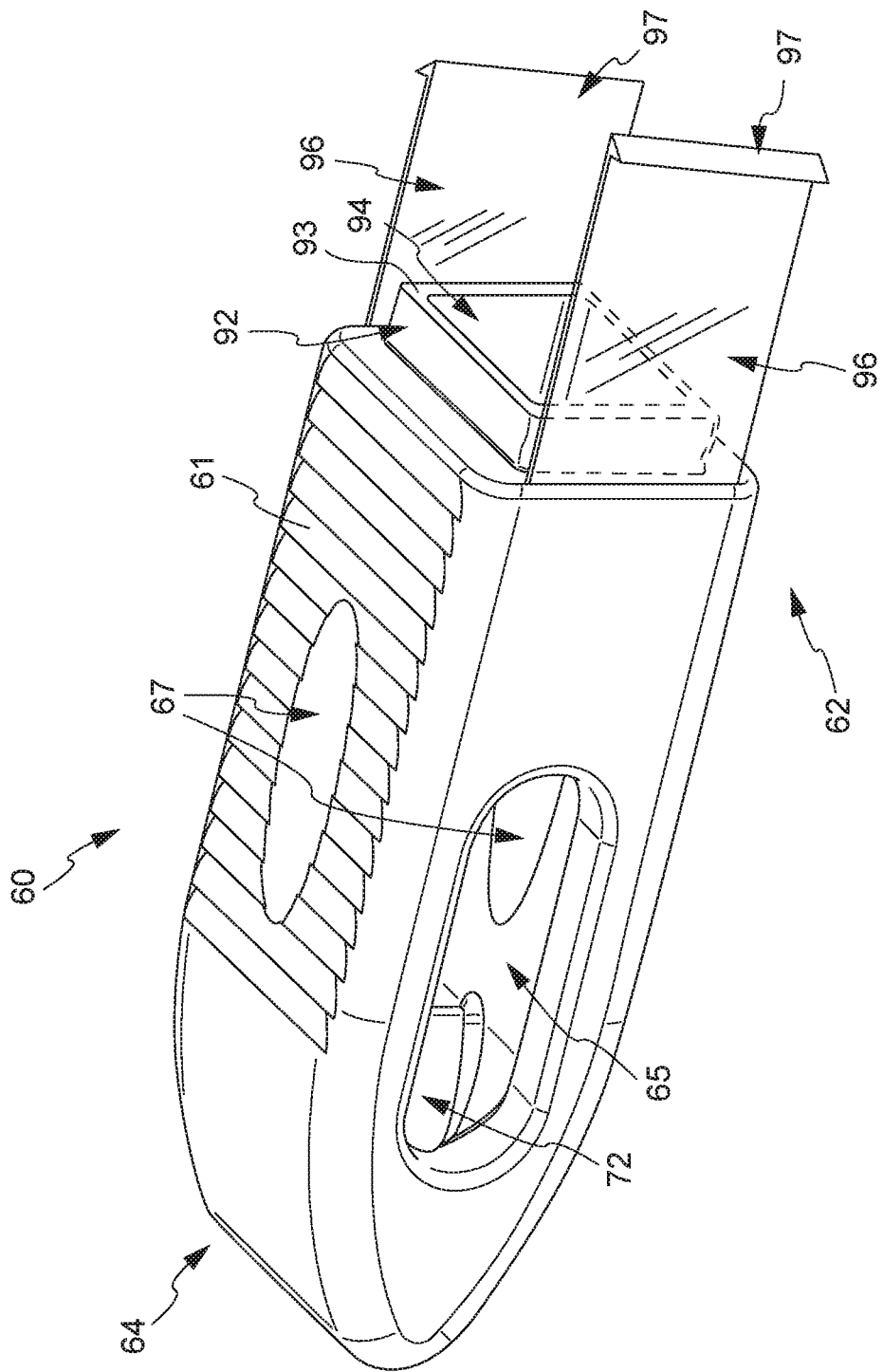
FIG. 41 is a close-up front perspective view of the device of FIG. 40.

Referring now to FIGS. 40-41, another embodiment of an integrated fusion cage and graft delivery device 1 is provided. FIG. 40 is a front perspective view of an integrated fusion cage and graft delivery device 1, and FIG. 41 is a closed-up front perspective view of a portion of the device of FIG. 40. The embodiment of FIGS. 40-41 comprises a pair of fusion cage tab extensions 96, each of which comprises a fusion cage tab extension latch 97. Integrated fusion cage and graft delivery device 1 comprises plunger 12, hollow tube 2 and fusion cage 60. FIG. 40 depicts the integrated fusion cage and graft delivery device 1 with plunger 12 fully inserted into hollow tube 2 such that plunger stop 16A engages upper portion of hollow tube 2. The fusion cage 60 comprises fusion cage second or distal end 64 with tapered end feature and fusion cage first or proximal end 62 comprising fusion cage collar 92, fusion cage collar face 93 and fusion cage collar cavity 94.

Fusion cage 60 further comprises fusion cage internal ramps 72 as described above. The fusion cage internal ramps 72 may be symmetrical about a centerline of the device 1, and may be linear or sloped inwardly. Fusion cage 60 further comprises fusion cage first opening or port pair 65 and fusion cage second opening or port pair 67. Fusion cage first opening pair 65 are symmetric about a vertical plane intersecting a centerline of the fusion cage 60, and are located such that at least a portion of the openings are adjacent the tip of the fusion cage internal ramps 72. The fusion cage first opening pair 65 are of an oblong racetrack shape, but in other embodiments may be oval, circular and rectangular. The fusion cage second opening pair 67 are of an oval shape, but in other embodiments may be oblong racetrack, circular and rectangular. The fusion cage may have rounded or no square edges. Fusion cage 60 has fusion cage surface texture 61, depicted as a series of lateral sawtooth-like ridges.

Fusion cage tab extensions 96, each of which comprises a fusion cage tab extension latch 97, function, among other things, to increase stability of the interface or connection between the distal end of the hollow tube 2 and the fusion cage 60. The fusion cage tab extension latches 97 may be configured to engage corresponding grooves on the interior surface of the hollow tube 2. The fusion cage tab extensions 96 fit inside the end of the hollow tube and, in one embodiment, provide a force directed outwards to or against the interior of the hollow tube. The vertical height and longitudinal (axial) length of the fusion cage tab extensions 96 provide more secure fit between the hollow tube 2 and the fusion cage 60 by restricting rotational movement, for example, of the hollow tube 2 with respect to the fusion cage 60. After bone graft material is provided to the fusion cage 60 by way of the plunger 12 (as described above), the fusion cage tab extensions 96 may be broken-off by application of a tool, such as the ejection tool 140, engaged with the fusion cage tab extension latches 97 so as to fatigue or otherwise severe the fusion cage tab extensions 96.

Figure 42:
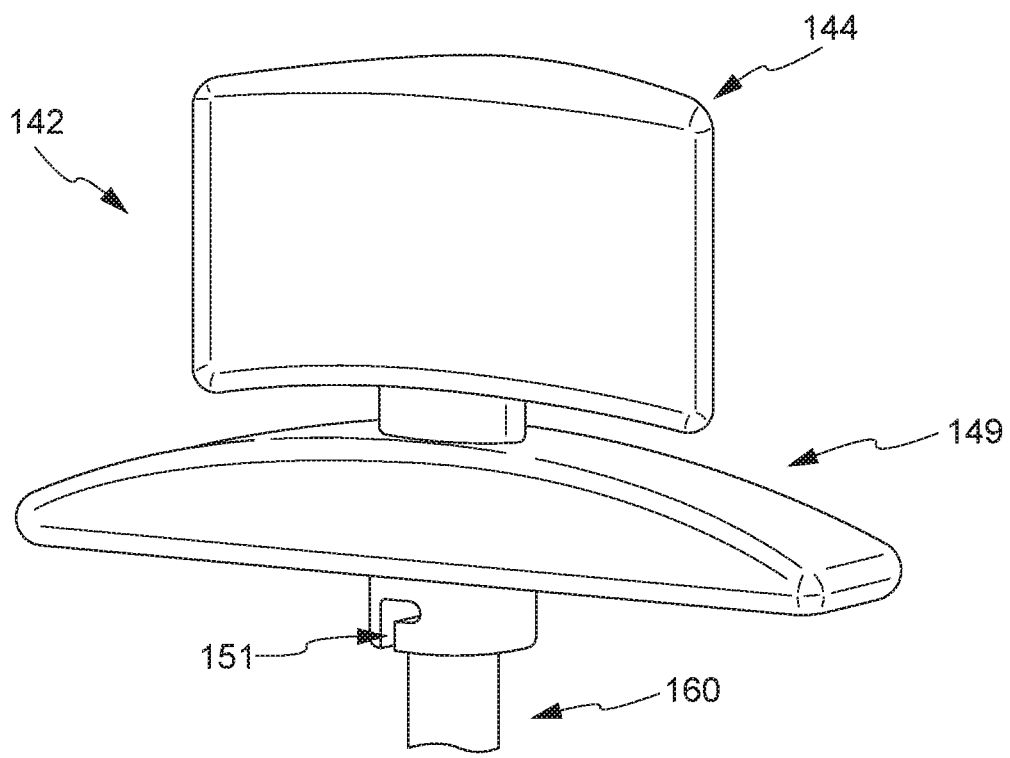
FIG. 42 is a close-up front perspective view of the ejection tool element first end.
Figure 43:
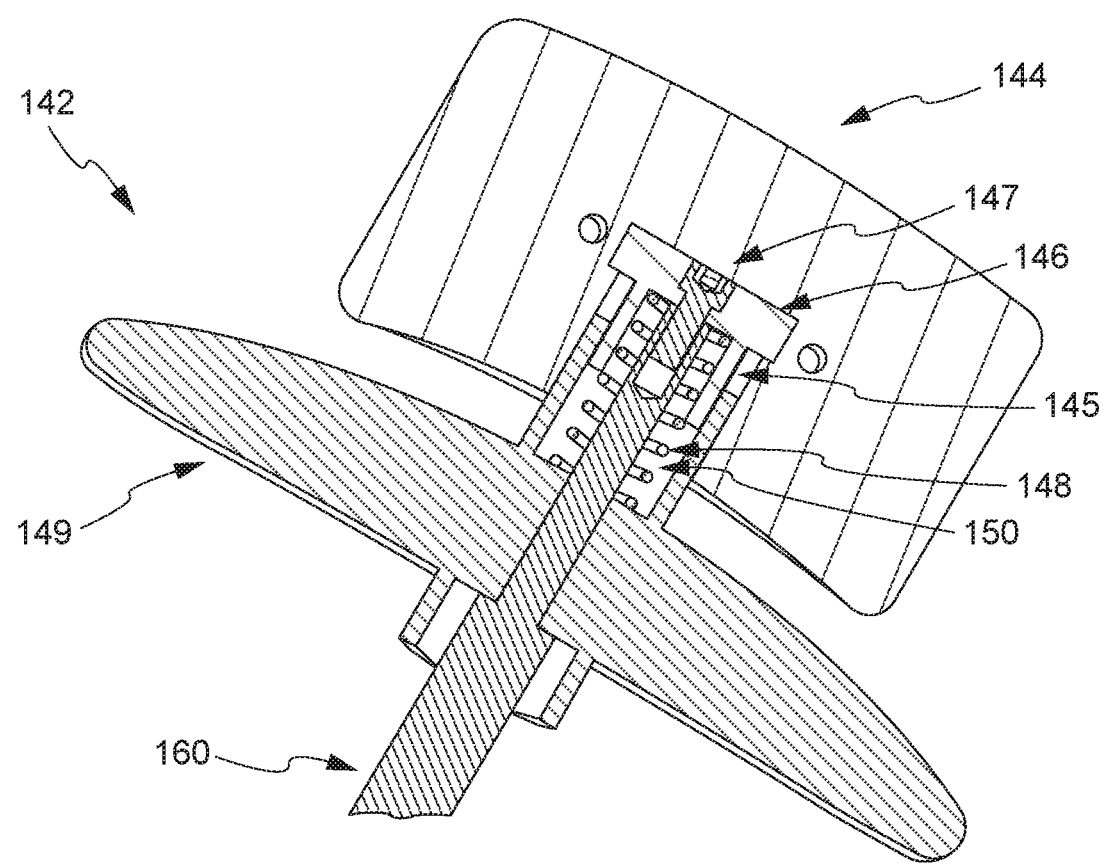
FIG. 43 is a cut-away cross-sectional view of the element of FIG. 42.

Referring now to FIGS. 42-43, another embodiment of the ejection tool 140 of an integrated fusion cage and graft delivery device 1 is provided. FIG. 42 is a close-up front perspective view of the ejection tool first end 142, and FIG. 43 is a cut-away cross-sectional view of FIG. 42. Ejection tool 140 comprises ejection tool cover 144 which engages ejection tool wings 149. Ejection tool 140 engages with hollow tube 2 at hollow tube knobs 6A via ejection tool L-cuts 151. Ejection tool cover 144 comprises cylindrically shaped ejection tool cover cavity 145 which fits over cylindrically-shaped ejection tool wings cavity 150 and over spring cover 146. Spring cover is secured to ejection tool cover 144 by spring cover attachment 147, which may be a pin, a screw or other means known in the art, and further fits around at least a portion of coiled spring 148. When ejection tool cover 144 is pushed downward toward fusion cage 60, the spring 148 compresses and imparts a force in the opposite direction, thereby returning the ejection tool cover 144 to its original (retracted) position. In use, after securing the ejection tool first end 142 to hollow tube 2 as described above, the user (e.g. surgeon) squeezes the ejection tool cover 144 against the ejection tool wings 149, thereby advancing the ejection tool rod 160 downwards inside the hollow tube so as to engage the fusion cage 60 at the fusion cage collar face 93 and release or disengage the fusion cage 60 from the hollow tube 2. The ejection tool 140 and hollow tube 2 may then be removed from the surgical site (e.g. spinal disk space) as one unit, leaving the fusion cage in the surgical site.

Figure 44:
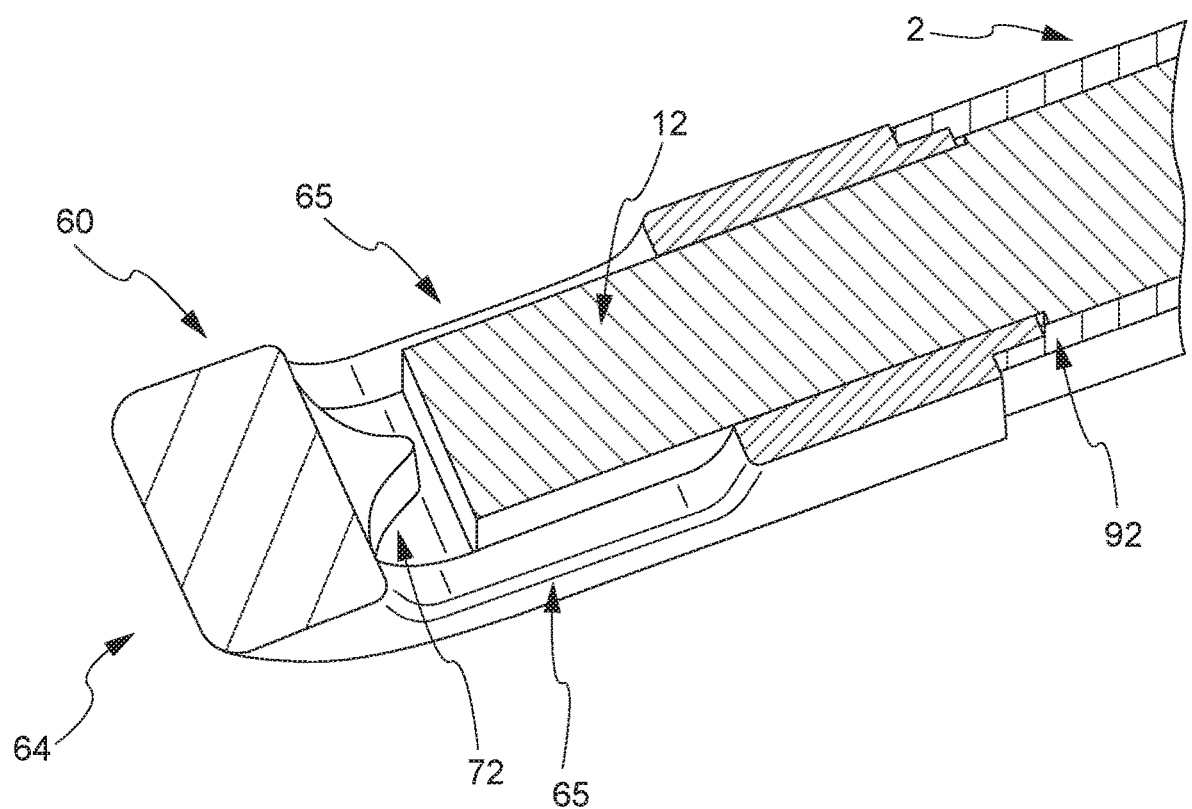
FIG. 44 is a close-up cut-away cross-sectional view of one embodiment of the integrated fusion cage and graft delivery device.
Figure 45A:
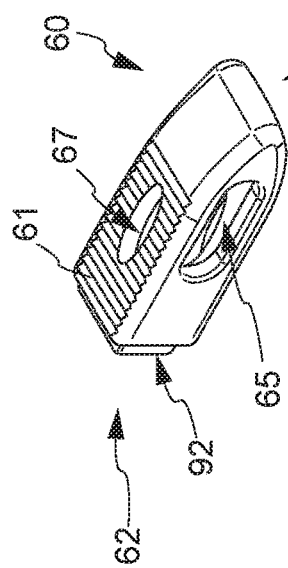
FIGS. 45A-G provide scaled views of one embodiment of the fusion cage element of yet another embodiment of the integrated fusion cage and graft delivery device configured to operate with the hollow tube of FIGS. 46A-H, plunger of FIGS. 47A-D and ejection tool of FIGS. 48A-E.
Figure 45D:
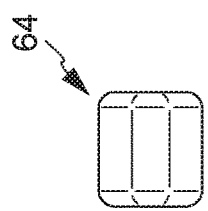
Figure 45F:
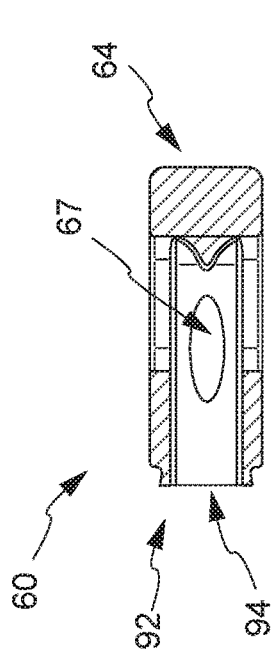
Figure 45C:
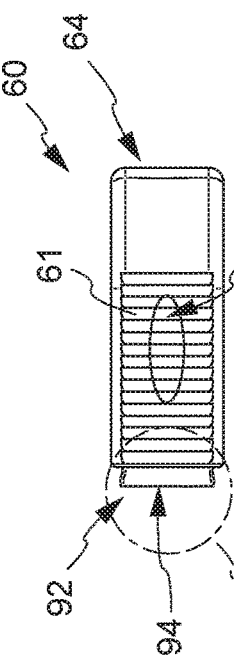
Figure 45B:
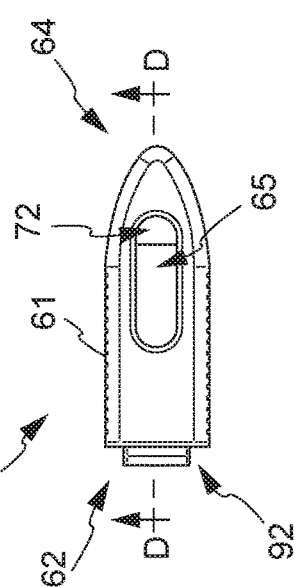
Figure 45G:
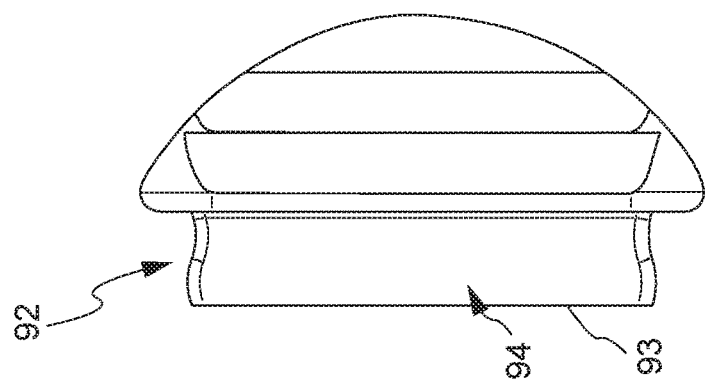
Figure 45E:
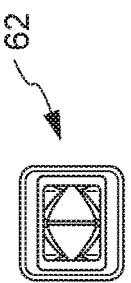
Figure 48A:
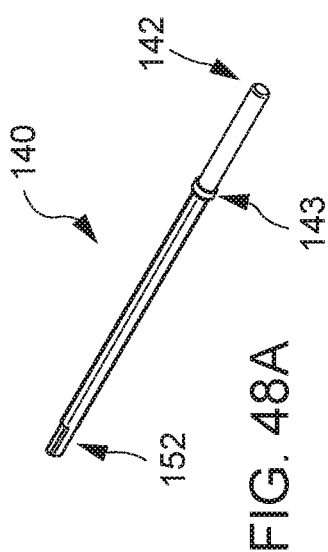
FIGS. 48A-E provide scaled views of one embodiment of the ejection tool (aka cage insertion tool) of the integrated fusion cage and graft delivery device configured to operate with the fusion cage element of FIGS. 45A-G, hollow tube of FIGS. 46A-H and plunger of FIGS. 47A-D.
Figure 48D:
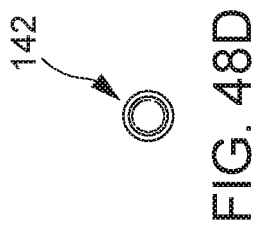
Figure 48C:
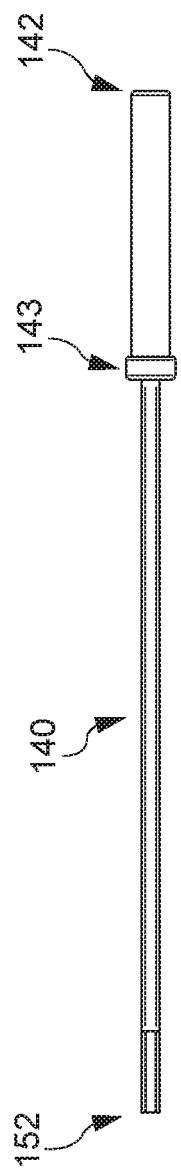
Figure 48B:
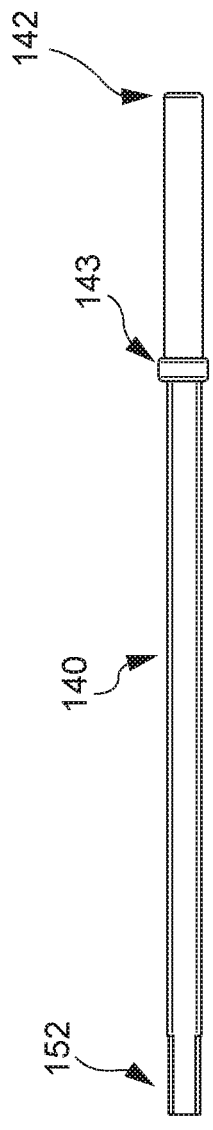
Figure 48E:
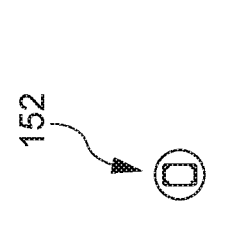

FIG. 44 is a close-up cut-away cross-sectional view of one embodiment of the integrated fusion cage and graft delivery device 1. FIG. 44 depicts a configuration of the integrated fusion cage and graft delivery device 1 wherein the plunger 12 is configured to traverse the length of the hollow tube 2, past the fusion cage collar 92 and into the fusion cage 60, stopping just prior to engaging the tip of the fusion cage internal ramps 72. Fusion cage 60 is depicted with fusion cage first opening pair 65 and fusion cage second end 64.

FIGS. 45-48 are scaled drawings of, respectively, the fusion cage 60, the hollow tube 2, the plunger 12 and the ejection tool 140 of yet another embodiment of the integrated fusion cage and graft delivery device 1, and operate in coordination with one another.

FIGS. 45A-G provide scaled views of one embodiment of the fusion cage element of yet another embodiment of the integrated fusion cage and graft delivery device configured to operate with the hollow tube of FIGS. 46A-H, plunger of FIGS. 47A-D and ejection tool of FIGS. 48A-E. Fusion cage 60 comprises fusion cage second or distal end 64 with tapered end feature and fusion cage first or proximal end 62 comprising fusion cage collar 92, fusion cage collar face 93 and fusion cage collar cavity 94. Fusion cage 60 further comprises fusion cage first opening or port pair 65, fusion cage second opening or port pair 67, fusion cage surface texture 61 and fusion cage internal ramps 72.

FIGS. 46A-H provide scaled views of one embodiment of the hollow tube (aka snap on cannula) of the integrated fusion cage and graft delivery device configured to operate with the fusion cage element of FIGS. 45A-G, plunger of FIGS. 47A-D and ejection tool of FIGS. 48A-E. Hollow tube 2 comprises first end 6 with knobs 6A and second end 8 comprising hollow tube cage clamp 8A and hollow tube cage clamp radial surface 8B. Hollow tube cage clamp radial surface 8B is configured to engage fusion cage collar 92, for example by an interference or friction fit (i.e. to "snap-on").

Other means of connection comprise those known to those skilled in the art, such as a threaded-screw engagement and a tongue and groove engagement.

FIGS. 47A-D provide scaled views of one embodiment of the plunger (aka snap on plunger) of the integrated fusion cage and graft delivery device configured to operate with the fusion cage element of FIGS. 45A-G, hollow tube of FIGS. 46A-H, and ejection tool of FIGS. 48A-E. Plunger 12 comprises handle 16, plunger stop 16A, plunger medial portion 17 and second end 18. Second end 18 may be configured to pass into and/or through fusion cage collar cavity 94.

FIGS. 48A-E provide scaled views of one embodiment of the ejection tool (aka cage insertion tool) of the integrated fusion cage and graft delivery device configured to operate with the fusion cage element of FIGS. 45A-G, hollow tube of FIGS. 46A-H and plunger of FIGS. 47A-D. Ejection tool 140 comprises ejection tool second or distal end 152, ejection tool first or proximal end 142 and ejection tool stop 143. Ejection tool second end 152 engages fusion cage collar face 93 to apply force or push fusion cage 60 from engagement with hollow tube 2. Ejection tool second end 152 is configured such that it may not travel past or into the fusion cage.

A method of use of the integrated fusion cage and graft delivery device 1 as depicted in any of the afore-mentioned embodiments of FIGS. 37-48 would be performed as follows. The fusion cage 60 is attached to the hollow tube 2 by way of the above-discussed interference fit at fusion cage collar 92 and interior surface of distal end of hollow tube 2. Funnel 30 is then attached to upper portion of hollow tube at first or upper or proximal end of hollow tube 2 via knobs 6A. Bone graft or other suitable substance as known to one skilled in the art is inserted at upper or first end 6 of hollow tube 2. Plunger 12 is then inserted into hollow tube 2 at upper or proximal end of hollow tube and pushed or advanced axially down interior of hollow tube, thereby urging or pushing or advancing the bone graft material down the hollow tube 2 toward fusion cage 60. Bone graft then proceeds into the fusion cage 60 whereby it at least substantially fills fusion cage 60 interior and further engages fusion cage internal ramps 72 and emits bone graft material through fusion cage first opening pair 65 and fusion cage second opening pair 67 and thus enters surgical area (e.g. a spinal surgical area). Upon sufficient user (i.e. surgeon) selectable injection of bone graft material into surgical site and fusion cage 60, the plunger 12 is retracted and removed from the hollow tube 2 by opposite axial movement, i.e. by moving the plunger 12 away from the fusion cage 60. The funnel 30 may then be optionally removed.

Next, the ejection tool 140 is inserted into hollow tube 2 at upper or proximal end Ejection tool 140 is advanced until ejection tool second end 152 engages fusion cage collar face 93, whereupon downward force is applied to push fusion cage 60 from engagement with hollow tube 2. As discussed, ejection tool second end 152 is configured such that it may not travel past or into the fusion cage. When sufficient axial force is applied to the ejection tool 140 in the direction of the fusion cage 60, the interference fit that secures the fusion cage 60 (at fusion cage collar 92) to hollow tube 2 (at second end 8 of hollow tube) is overcome and the fusion cage 60 is released or disengaged from the hollow tube 2. The engagement tool 140, and the hollow tube 2 in which it is inserted, are then removed from the surgical site, leaving a fusion cage at least substantially filled with bone graft and a surgical site also at least substantially filled with bone graft.

In one embodiment, all or a portion of fusion cage collar 92 is of a material different than the remainder of the fusion cage 60, e.g. comprising a metal alloy. In one embodiment, a portion of the distal end of the hollow tube 2 is of a material different than the remainder of the hollow tube 2, e.g. comprising a metal alloy. In one embodiment, a portion of the distal end of the ejection tool is comprised of a metal alloy.

In one embodiment of the device, the tip of the hollow tube and/or fusion cage may separate under a threshold pressure as applied axially from the inside of the hollow tube or fusion cage respectively. Such a user-selected threshold would allow bone graft material to enter the surgical site if bone graft material becomes clogged in the hollow tube and/or fusion cage.

Figure 49A:
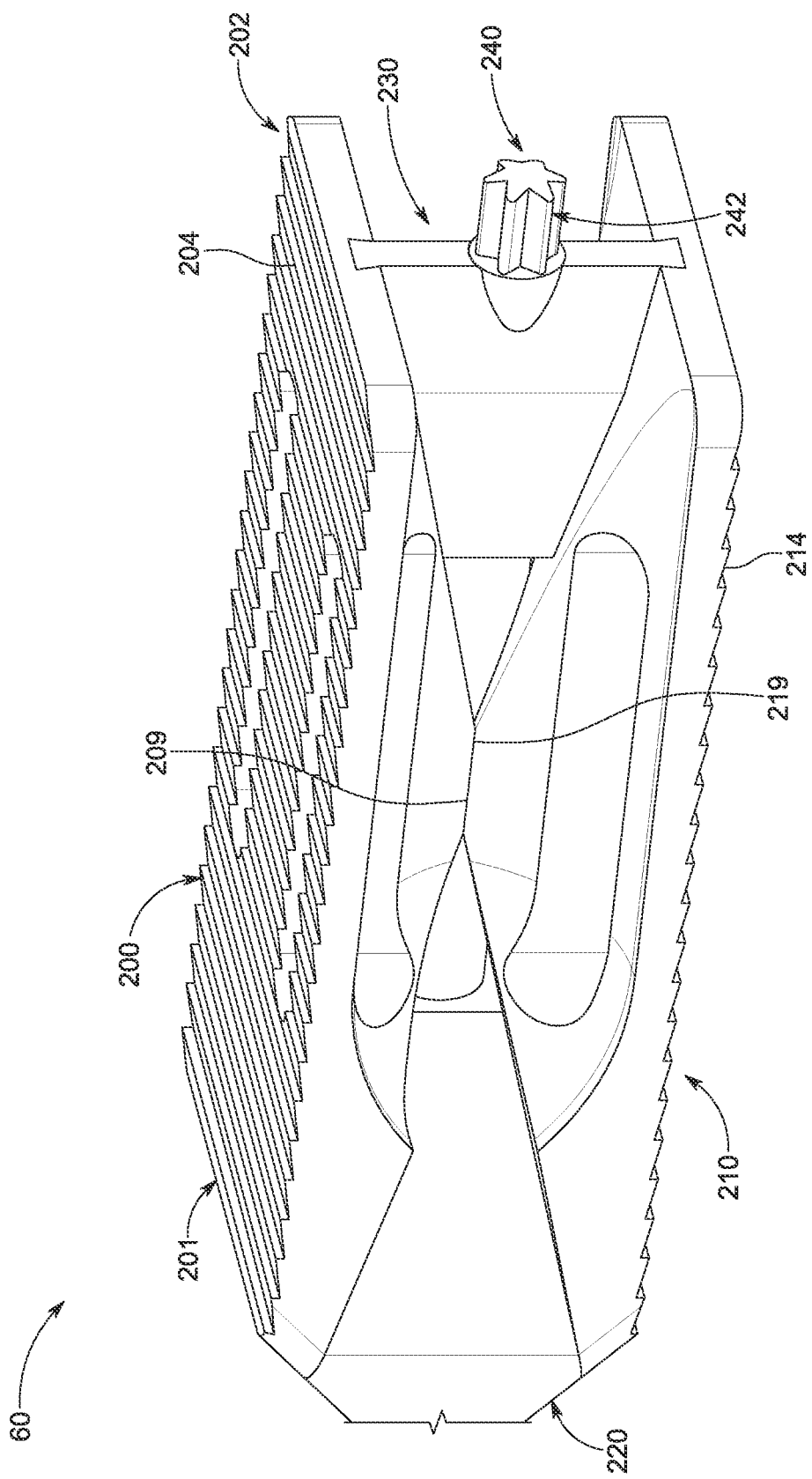
FIG. 49A is a left perspective view of an embodiment of the fusion cage with expandable fusion cage feature, the fusion cage in an unexpanded state.
Figure 49B:
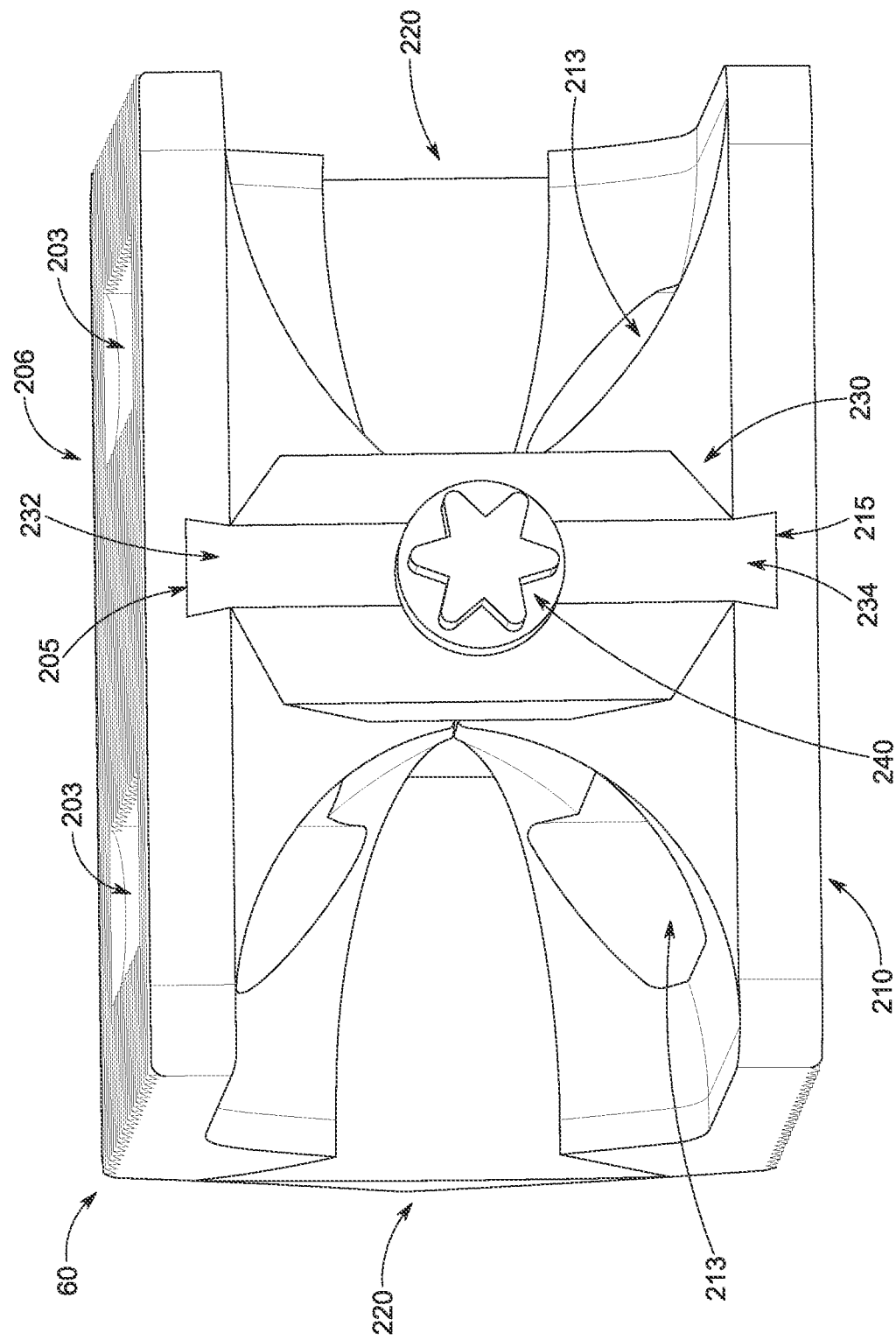
FIG. 49B is a rear perspective view of the device shown in FIG. 49A.
Figure 49C:
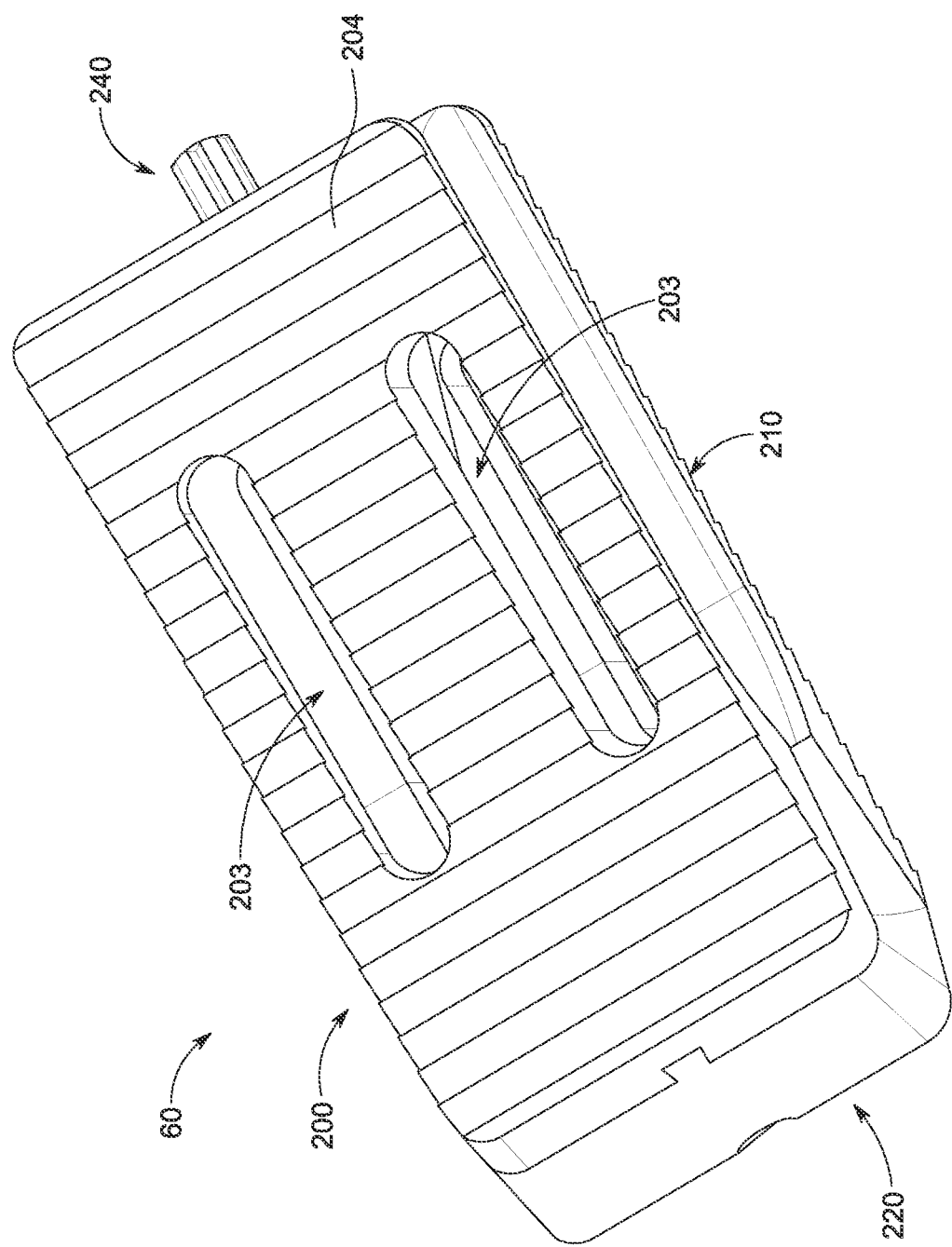
FIG. 49C is a top perspective view of the device shown in FIG. 49A.
Figure 50A:
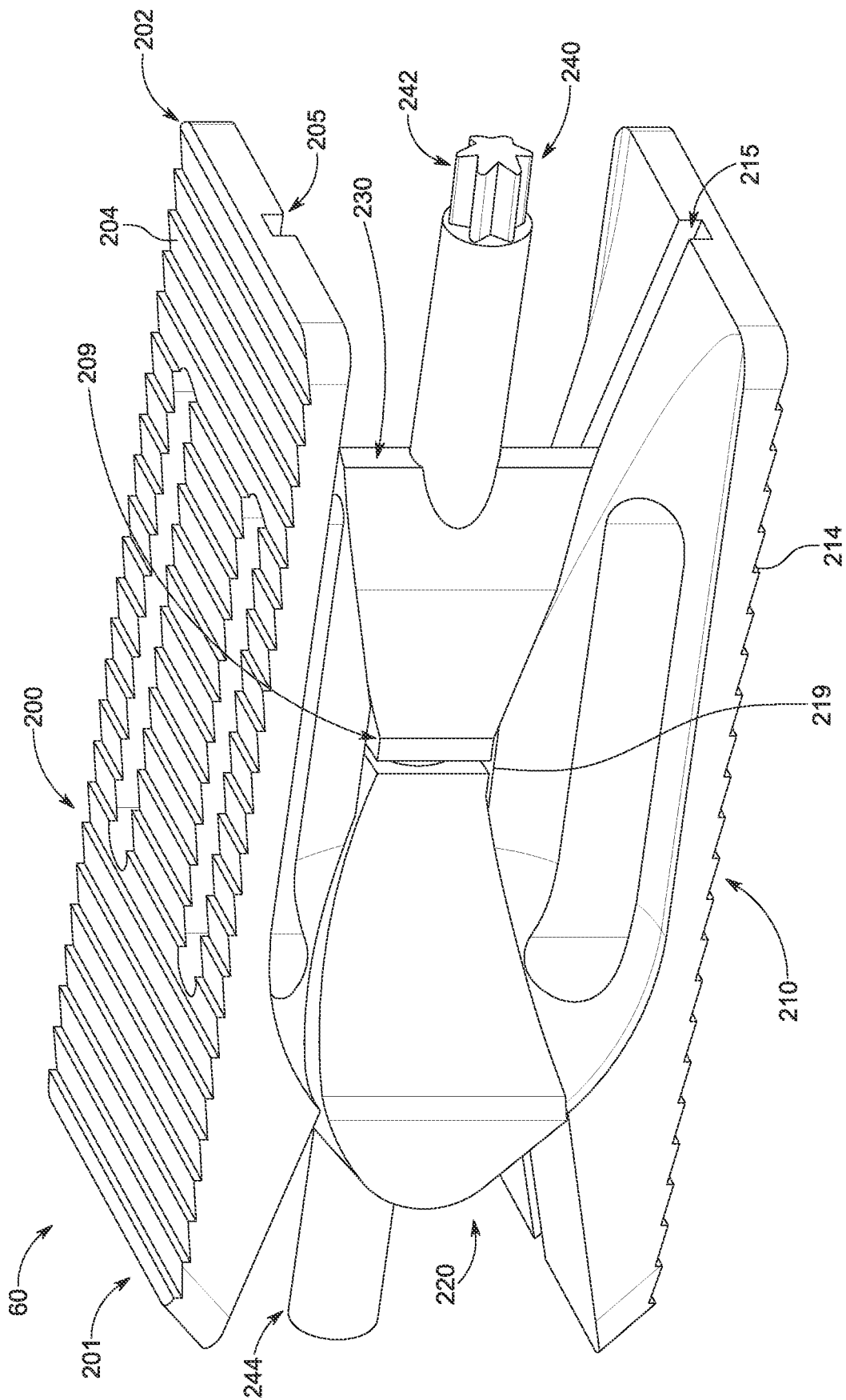
FIG. 50A is a left perspective view of the device shown in FIG. 49A, the fusion cage in an expanded state.
Figure 50B:
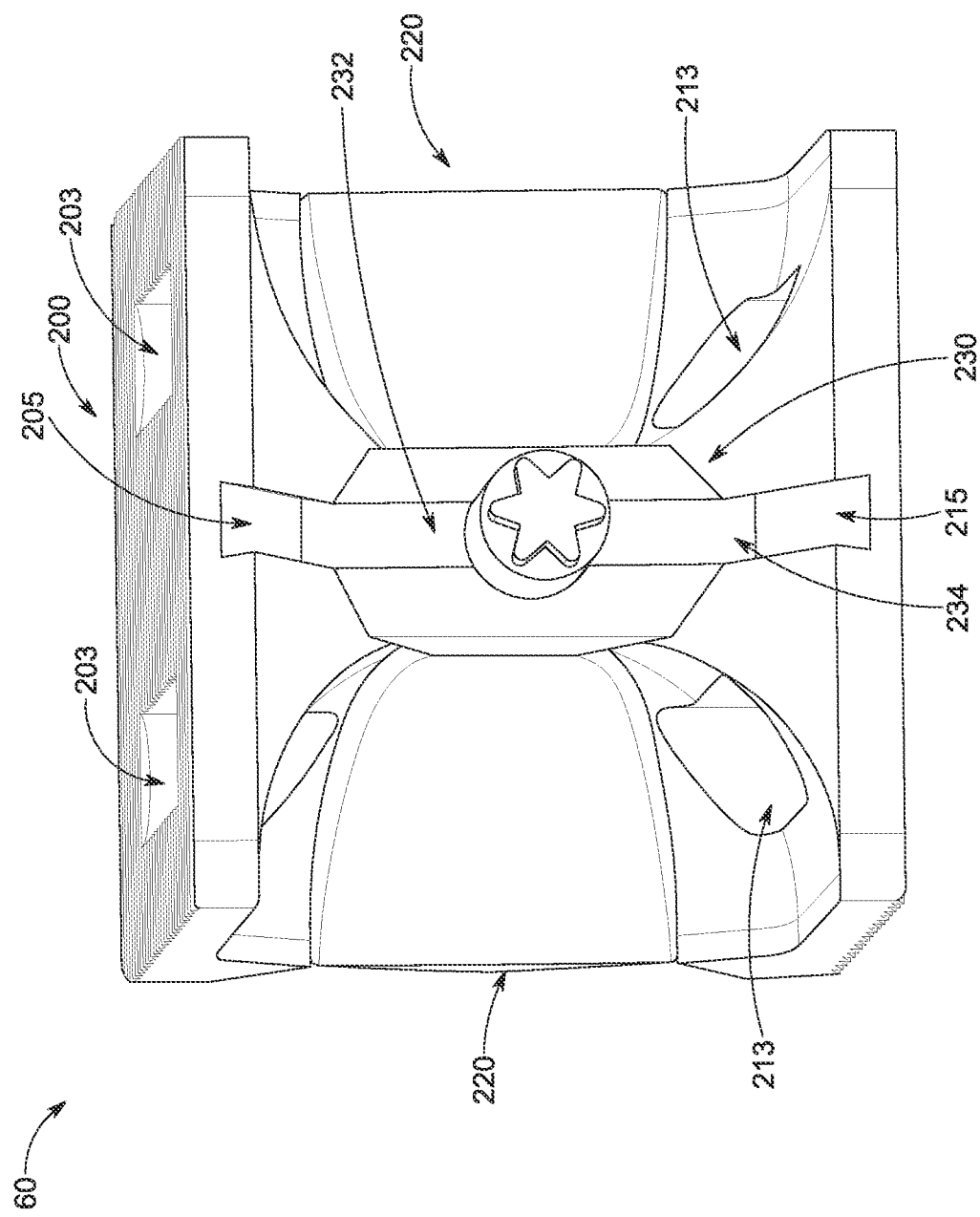
FIG. 50B is a rear perspective view of the device shown in FIG. 50A.
Figure 50C:
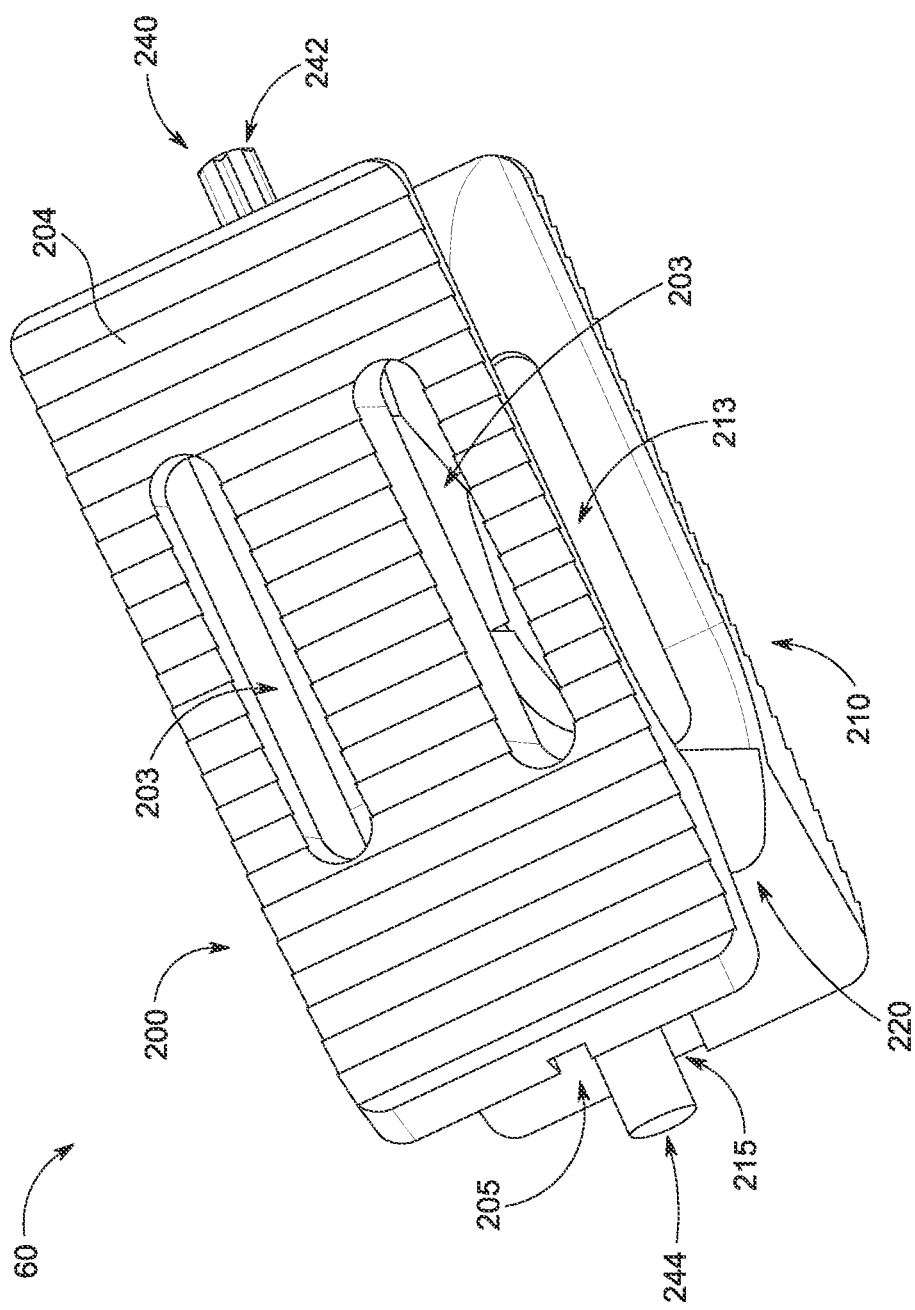
FIG. 50C is a top perspective view of the device shown in FIG. 50A.
Figure 51:
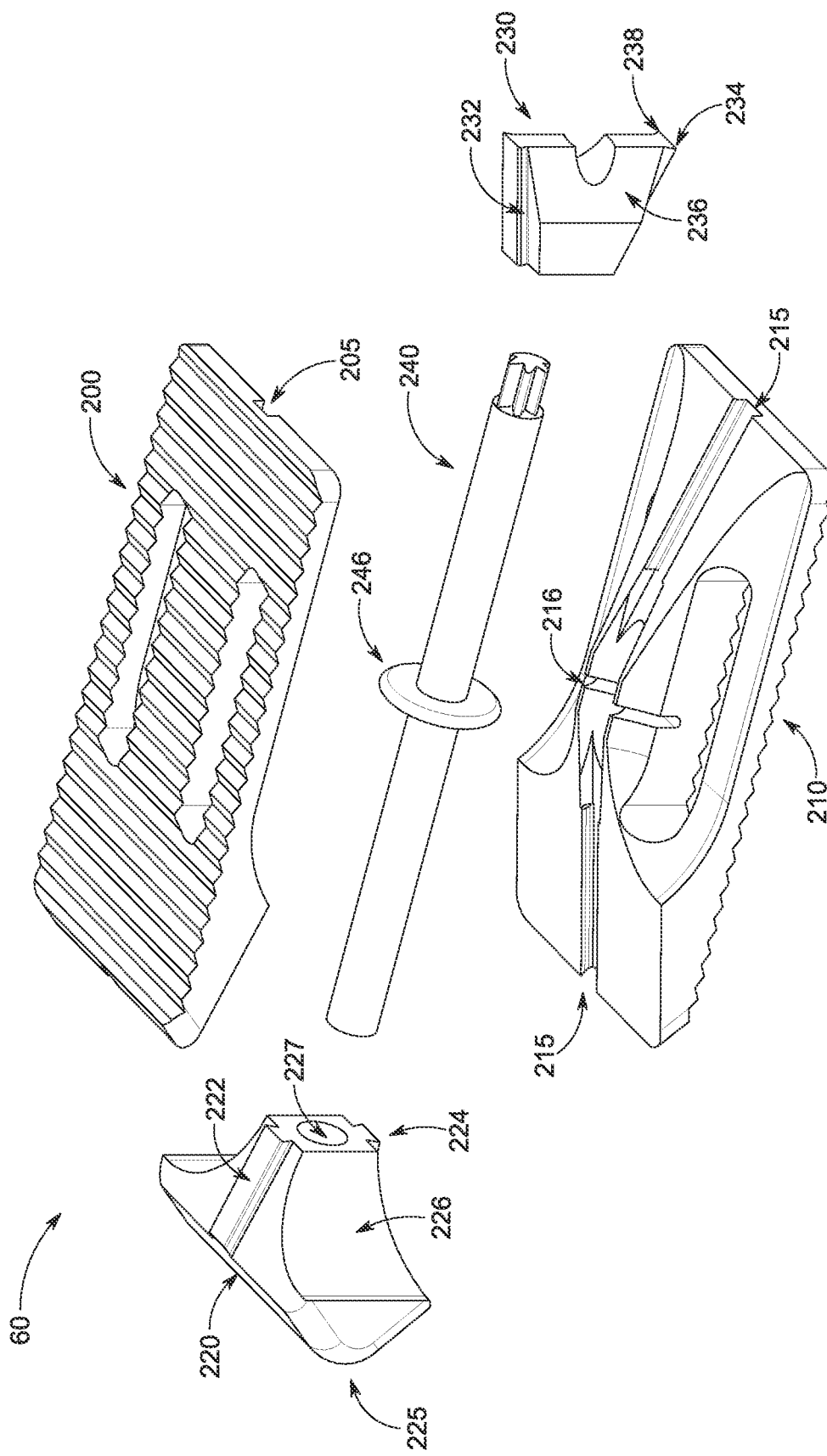
FIG. 51 is a scaled rear perspective exploded view of an embodiment of the fusion cage with expandable fusion cage feature.
Figure 52A:
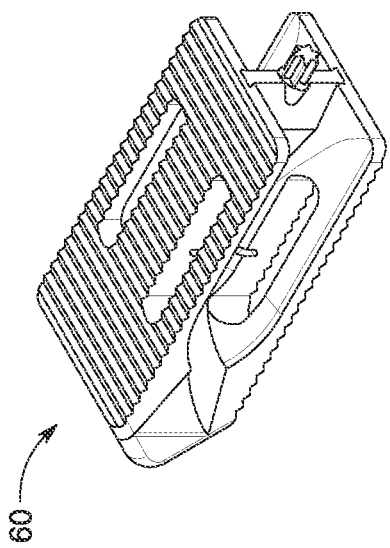
FIGS. 52A-E provide scaled views of the device shown in FIG. 51, the fusion cage in an unexpanded state.
Figure 52E:
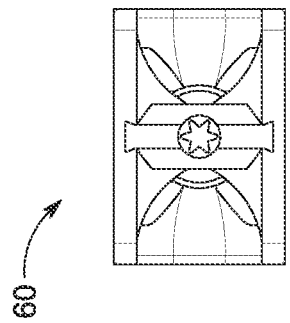
Figure 52C:
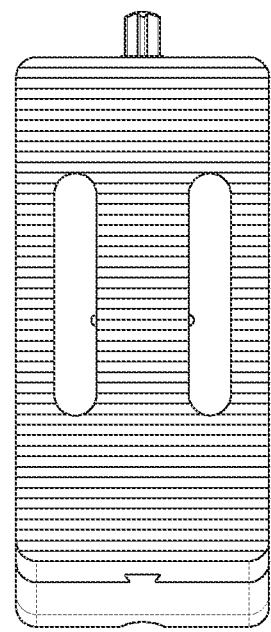
Figure 52B:
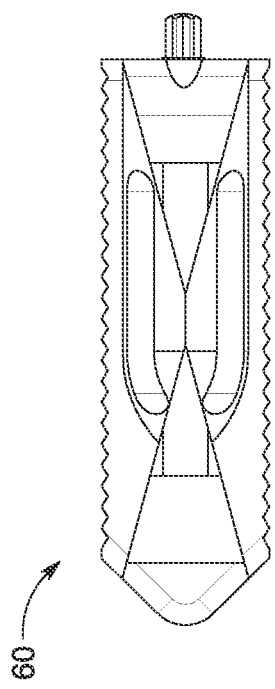
Figure 52D:
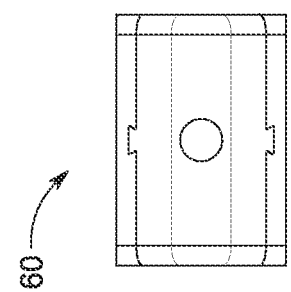
Figure 53A:
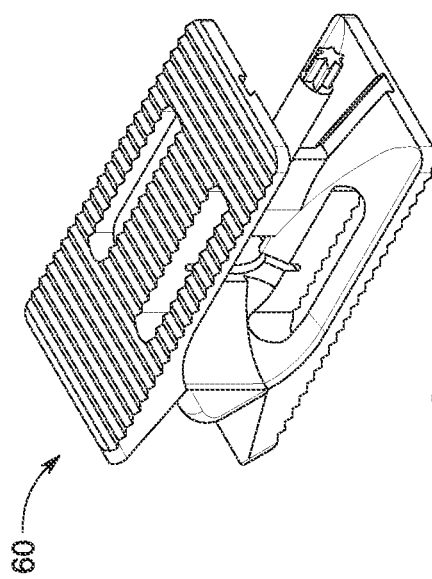
FIGS. 53A-E provide scaled views of the device shown in FIG. 51, the fusion cage in an expanded state.
Figure 53C:
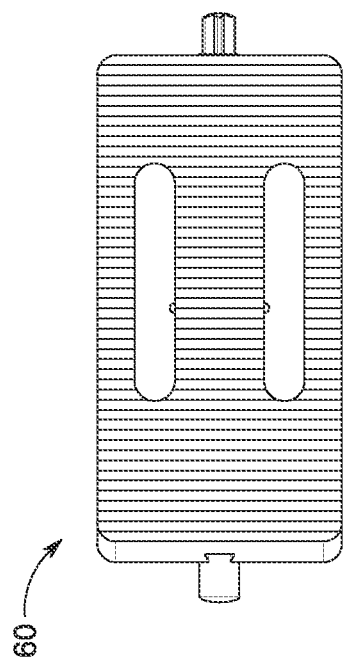
Figure 53E:
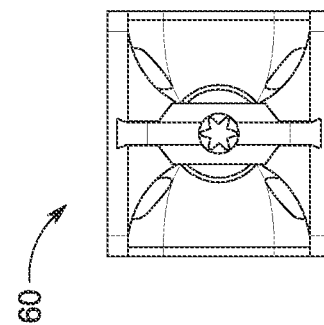
Figure 53B:
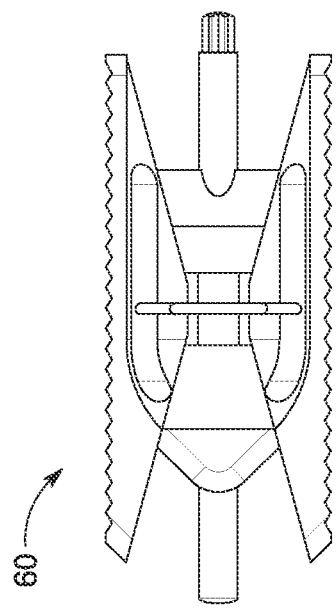
Figure 53D:
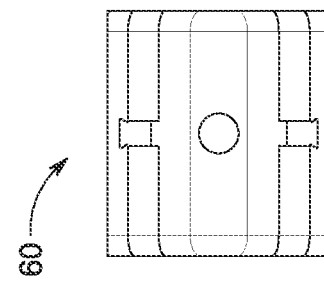
Figure 55A:
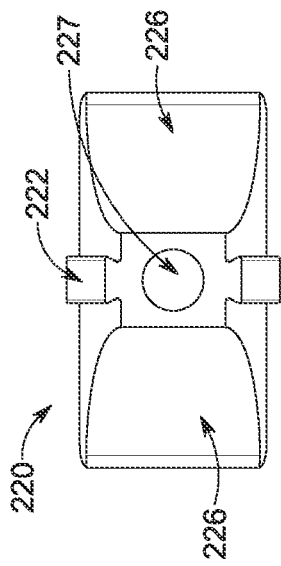
FIGS. 55A-E provide scaled views of the front block component of the device shown in FIG. 51.
Figure 55E:
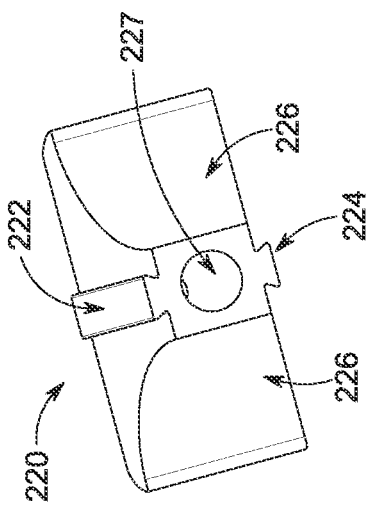
Figure 55C:
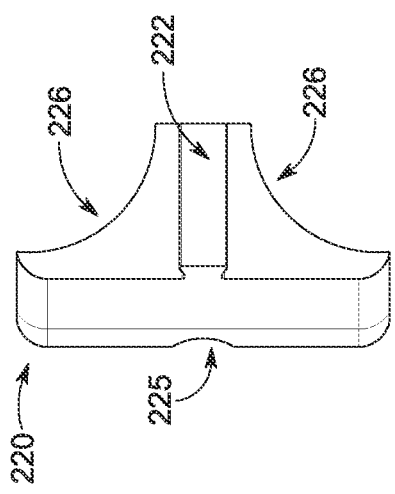
Figure 55B:
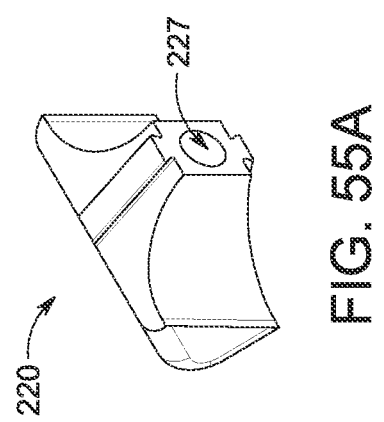
Figure 55D:
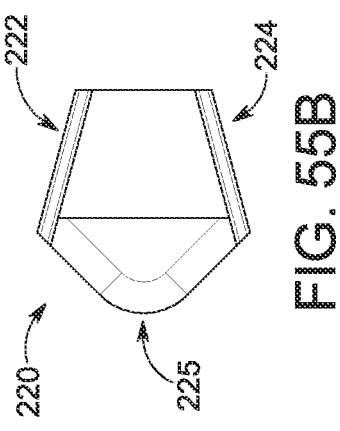
Figure 56F:
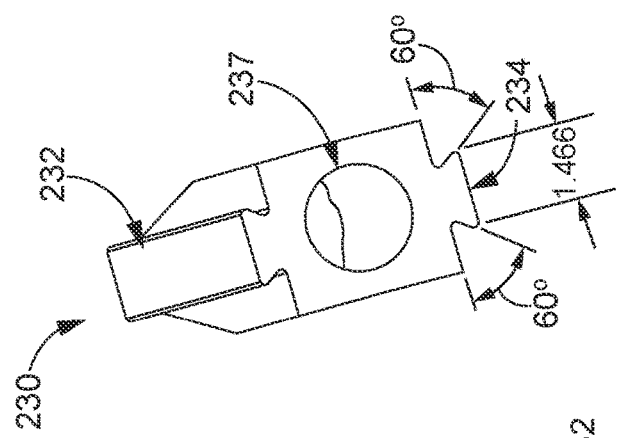
FIGS. 56A-F provide scaled views of the rear block component of the device shown in FIG. 51.
Figure 56E:
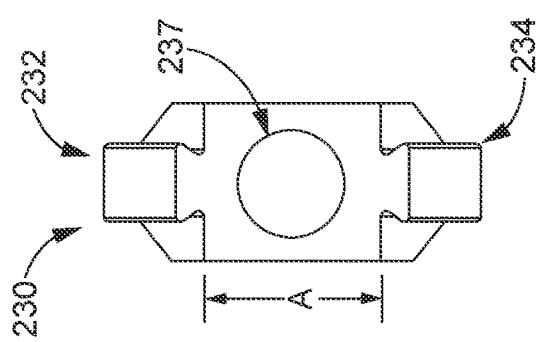
Figure 56C:
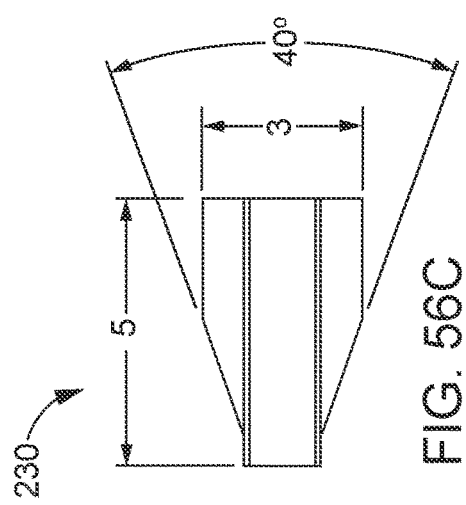
Figure 56B:
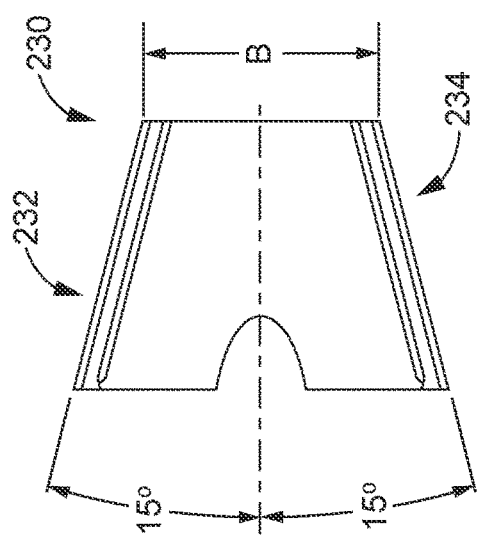
Figure 56A:
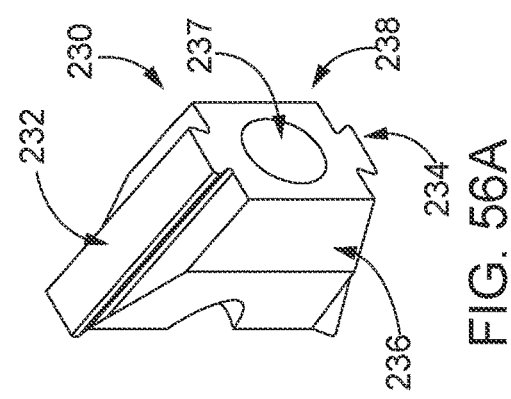
Figure 56D:
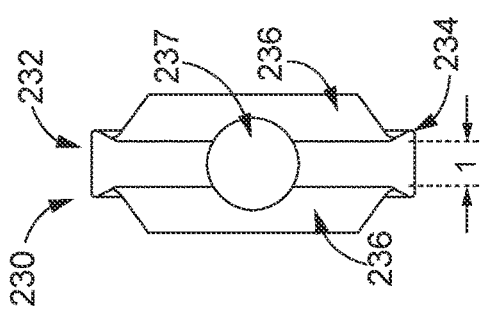
Figure 58:
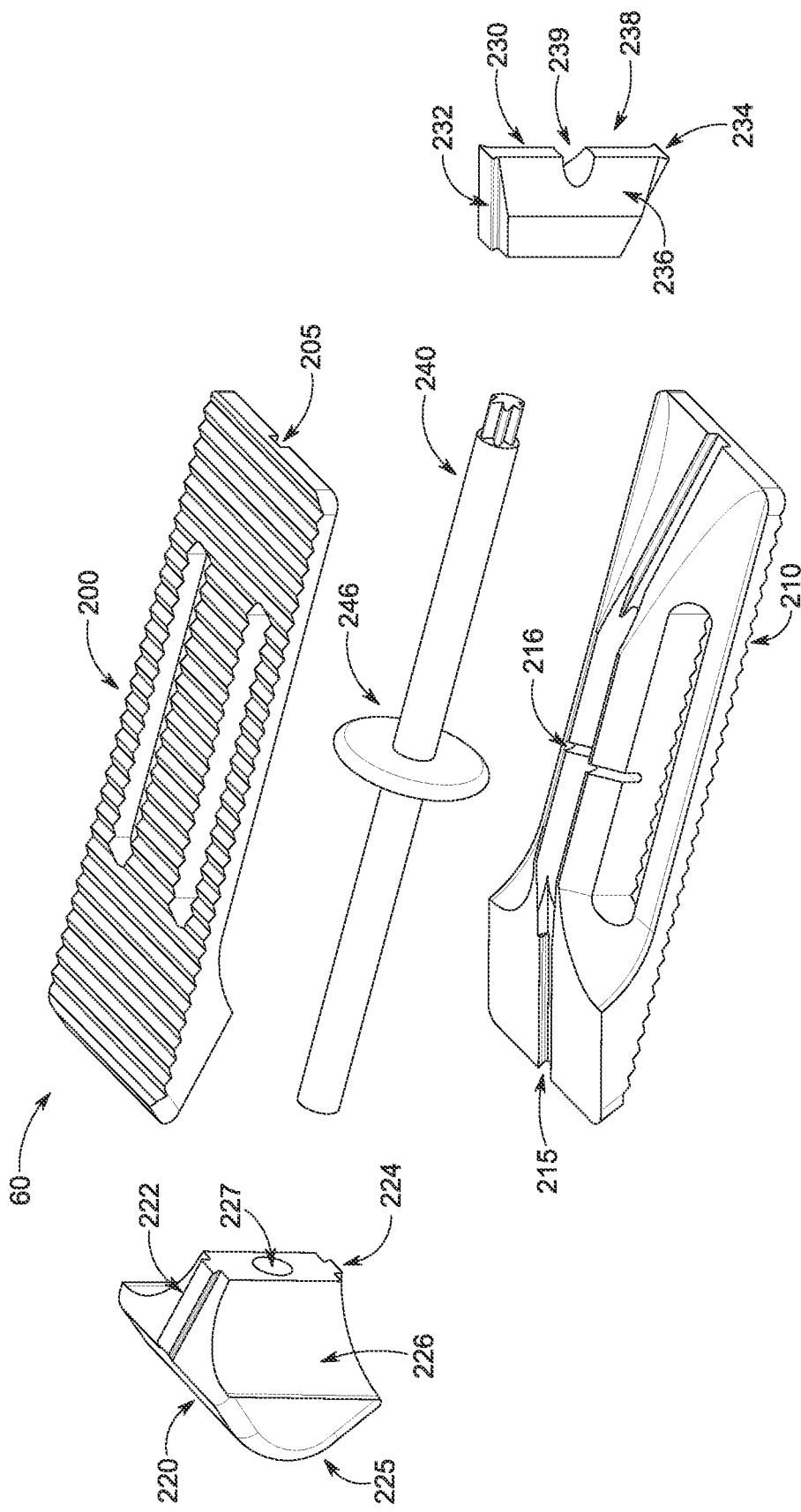
FIG. 58 is a rear perspective exploded view of another embodiment of the fusion cage with expandable fusion cage feature.
Figure 59A:
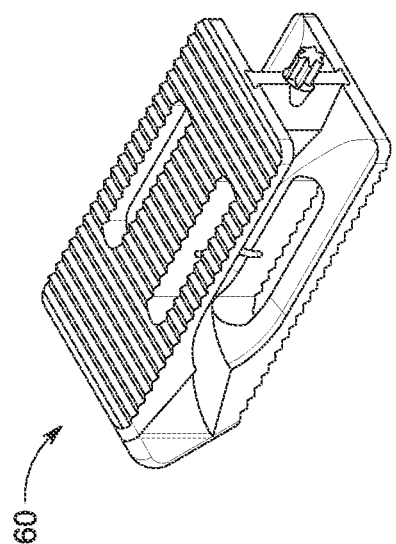
FIGS. 59A-E provide scaled views of the device shown in FIG. 58, the fusion cage in an unexpanded state.
Figure 59C:
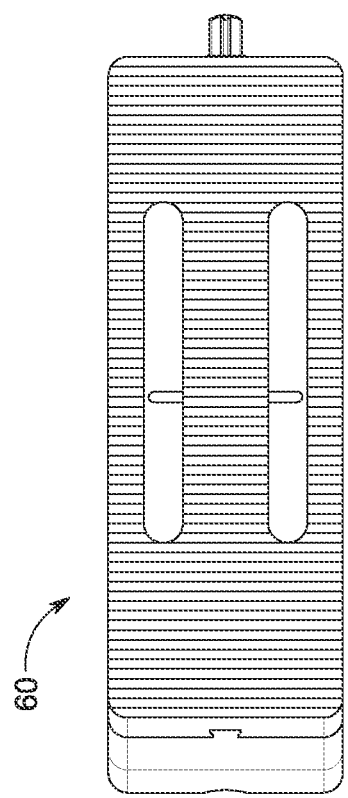
Figure 59E:
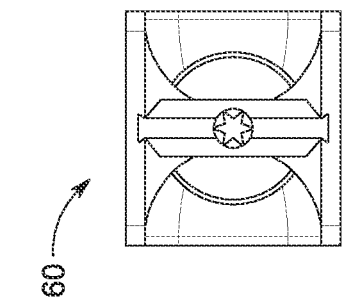
Figure 59B:
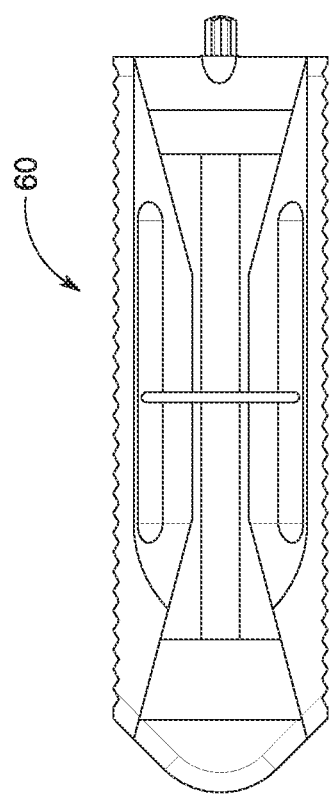
Figure 59D:
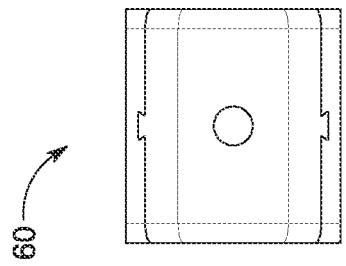
Figure 60A:
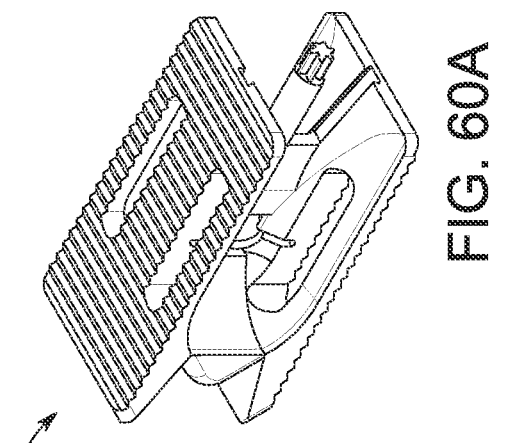
FIGS. 60A-E provide scaled views of the device shown in FIG. 58, the fusion cage in an expanded state.
Figure 60C:
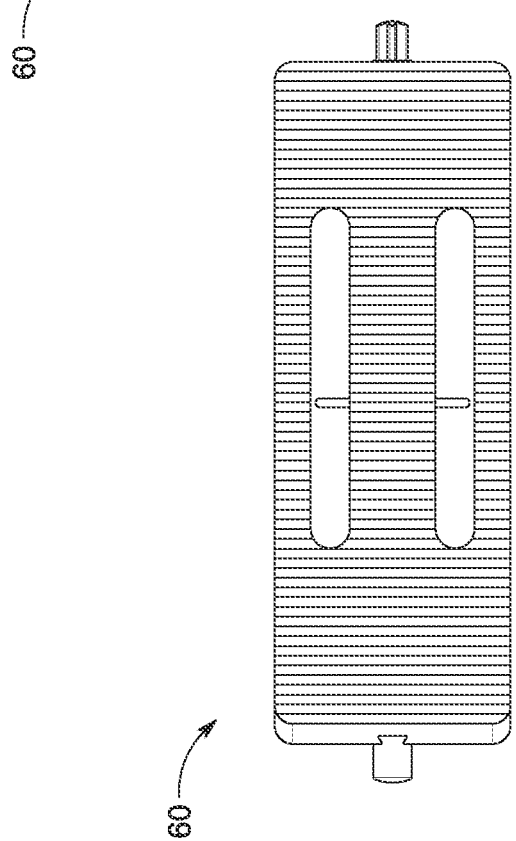
Figure 60E:
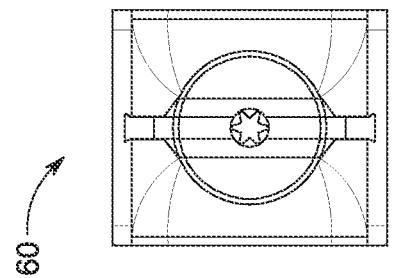
Figure 60B:
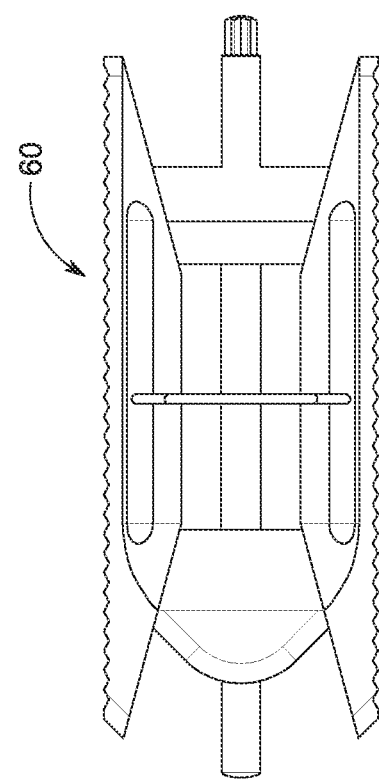
Figure 60D:
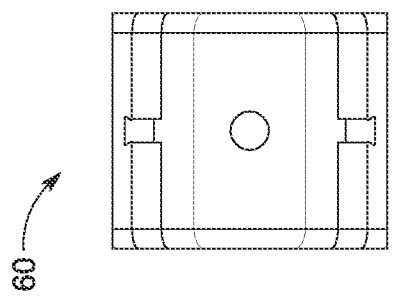
Figure 61A:
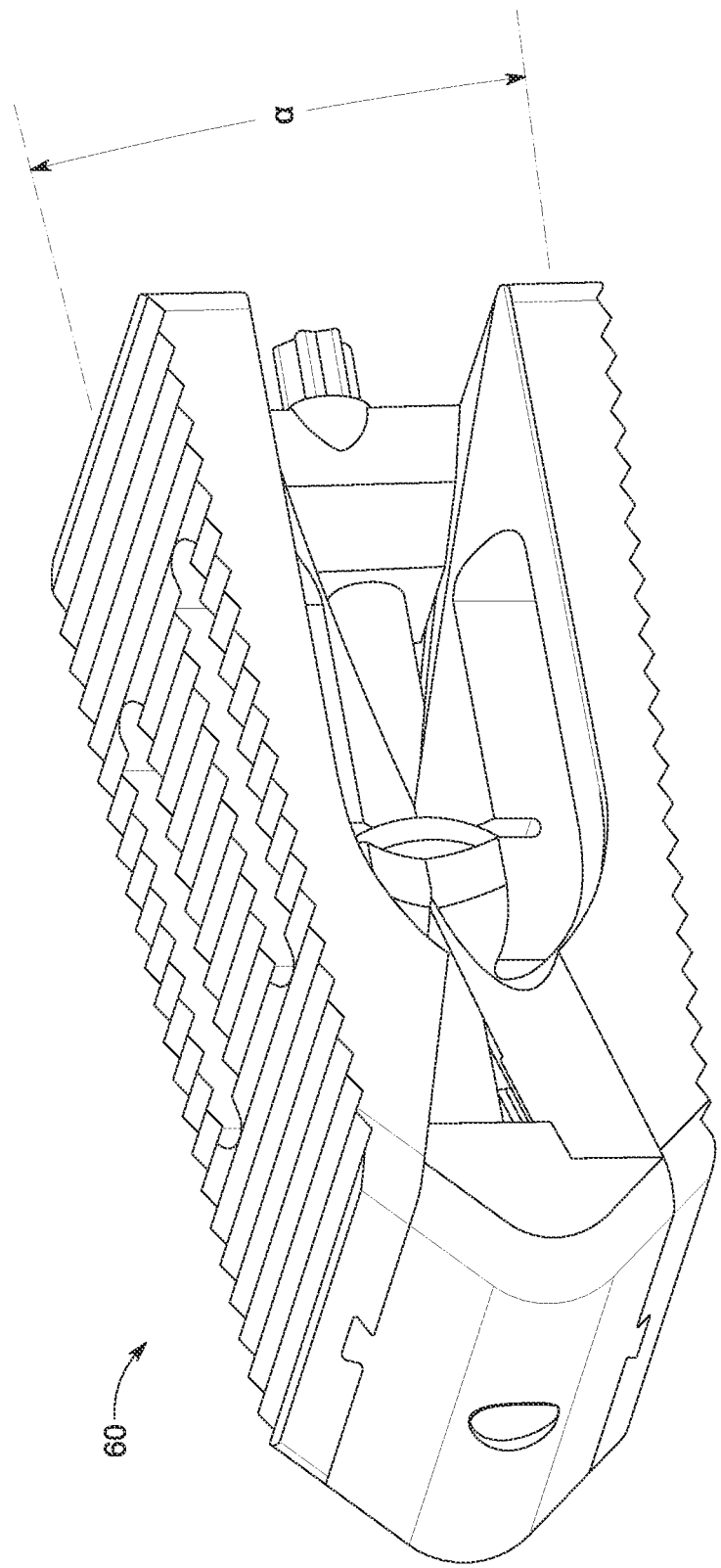
FIG. 61A is a front left perspective view of yet another embodiment of the fusion cage with expandable fusion cage feature, comprising a vertical wedge angle feature.
Figure 61B:
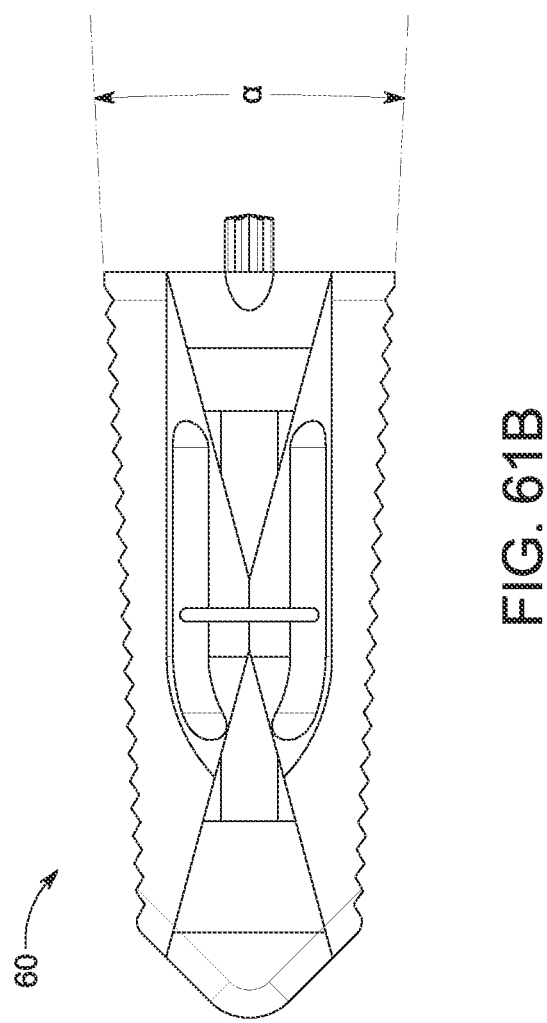
FIG. 61B is a left elevation view of the device of FIG. 61A.
Figure 62A:
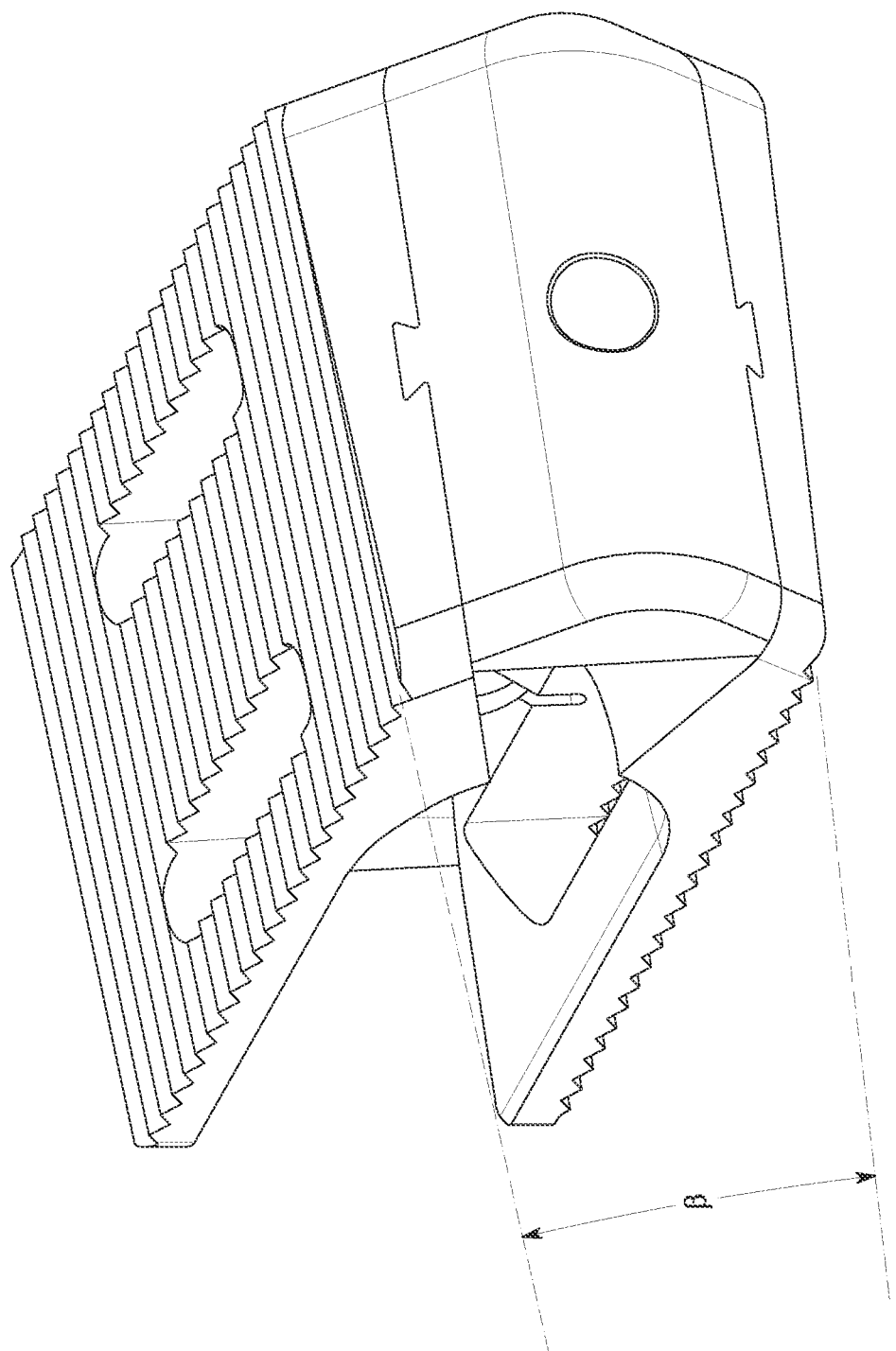
FIG. 62A is a front left perspective view of yet another embodiment of the fusion cage with expandable fusion cage feature, comprising a horizontal wedge angle feature.
Figure 62B:
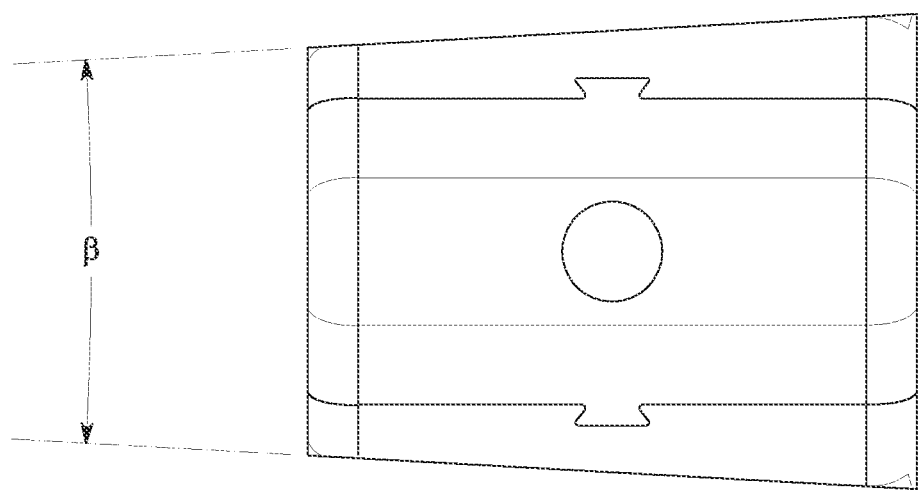
FIG. 62B is a left elevation view of the device of FIG. 62A.
Figure 63A:
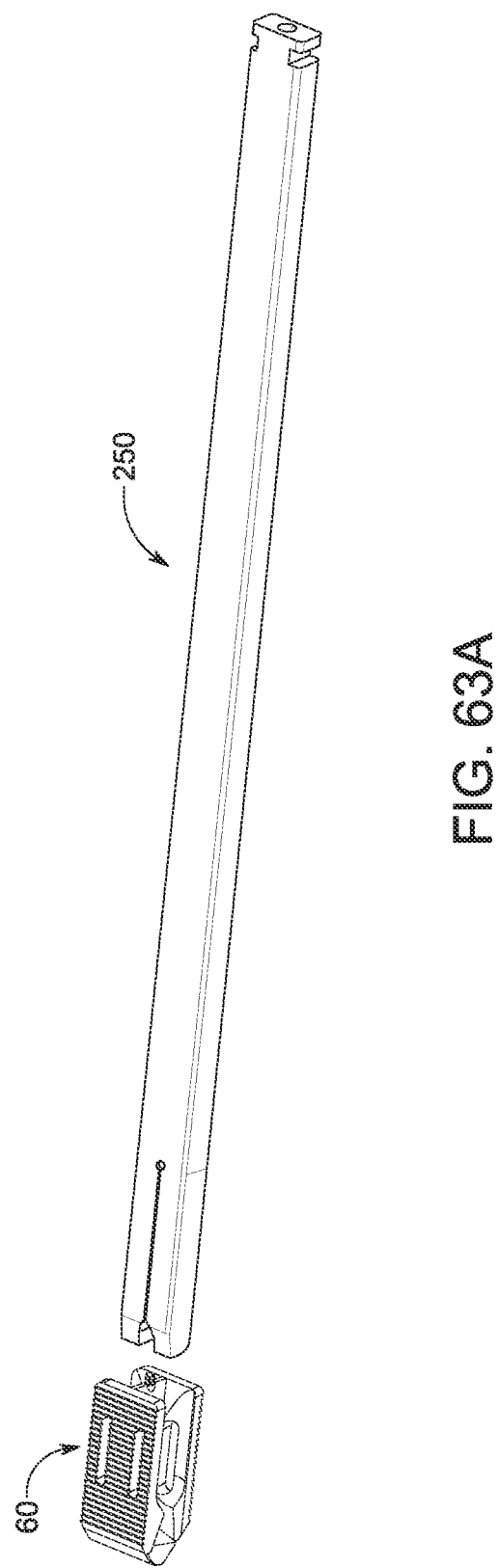
FIG. 63A is a left rear perspective view of a fusion cage with expandable fusion cage feature configured to communicate with an installer/impactor component according to yet another embodiment.
Figure 63B:
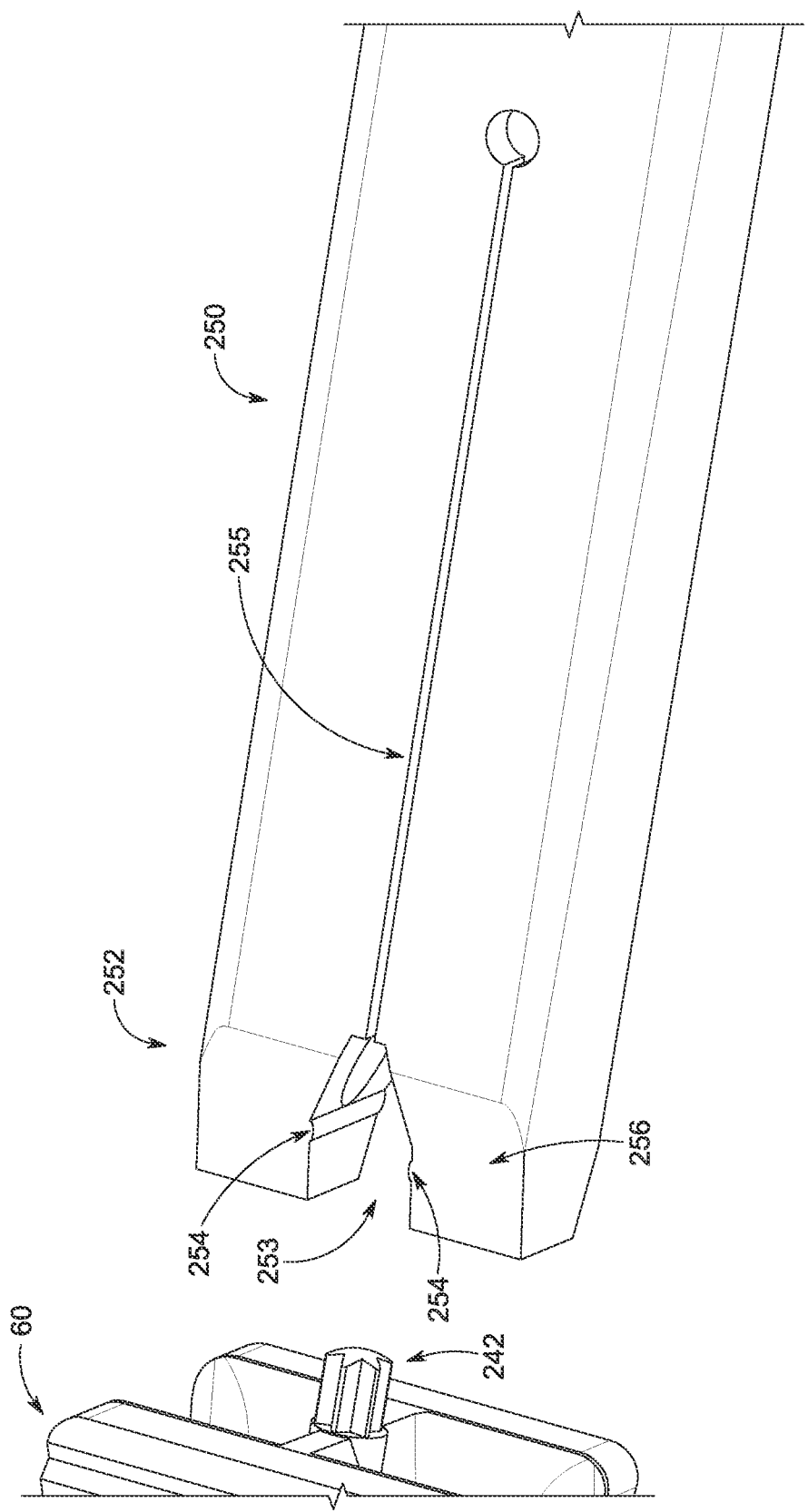
FIG. 63B is a close-up partial left rear perspective view of the devices of FIG. 63A.
Figure 64:
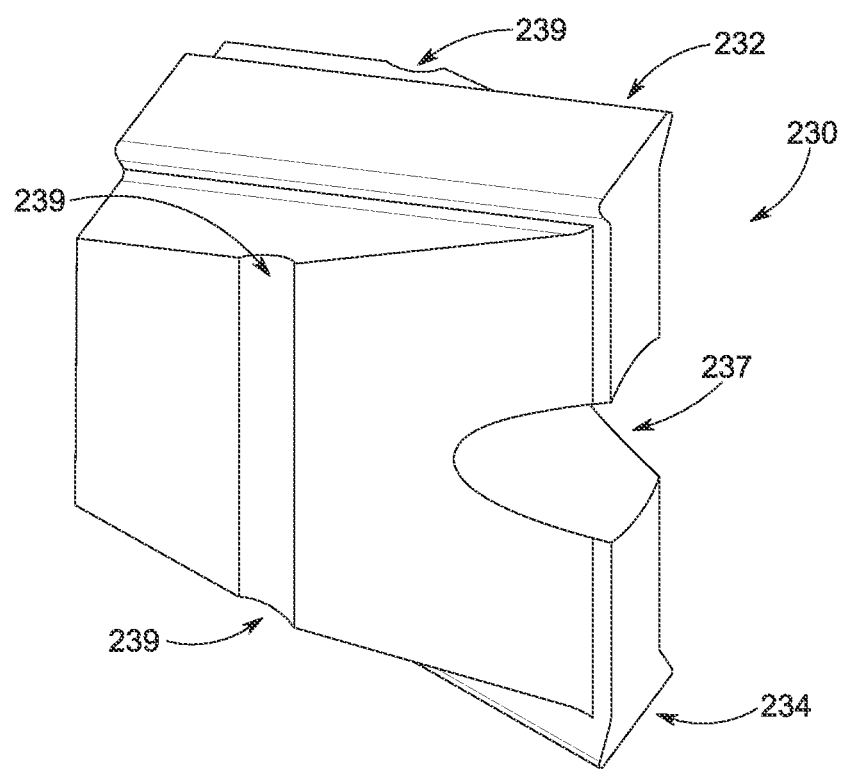
FIG. 64 is a left rear perspective view of the rear block component of the fusion cage of FIG. 63A.

Referring now to FIGS. 49-62, various embodiments and components of a fusion cage 60 with expandable fusion cage feature are depicted. Generally, the fusion cage 60 comprises an upper plate 200, lower plate 210, front block 220, rear block 230, and expansion screw 240. By rotating the expansion screw 240, each of the front block 220 and rear block 230 advance toward the center of the fusion cage 60 while simultaneously advancing each of the lower plate 210 and upper plate 220 away from the center of the fusion cage 60, thereby expanding the overall height of the fusion cage 60. Each of the unexpanded state of the fusion cage 60 and expanded state of the fusion cage 60 are understood most immediately by comparing FIGS. 49A and 50A, respectively. The fusion cage 60 may be expanded in a scalable manner to a maximum threshold height value. At the maximum threshold height value of the fusion cage 60, each of the front block 220 and rear block 230 are unable to continue to advance toward the center of the fusion cage 60 (such a state is shown as FIG. 50A). It is noted that in the embodiments of FIGS. 49-60, the lower plate 210 and upper plate 220 remain substantially parallel in all configurations. Stated another way, the lower plate 210 and upper plate 220 remain substantially parallel in the unexpanded fusion cage 60 state (e.g. FIG. 49A), in the maximum threshold height value expanded state of the fusion cage 60 (e.g. FIG. 50A), and in all states in between. In contrast, in the fusion cage 60 embodiment of FIGS. 61A-B, the lower plate 210 and upper plate 220 maintain a relative vertical wedge angle α, and in the embodiment of FIGS. 62A-B, the lower plate 210 and upper plate 220 maintain a relative horizontal wedge angle β.

Expansion screw 240 comprises expansion screw head 242, expansion screw tip 244 and expansion screw disk 246. The expansion screw 240 rotationally engages each of the front block 220 via front block aperture 227 and rear block 230 via rear block aperture 237. The expansion screw disk 246 engages each of the upper plate 200 via upper plate slot 206 and the lower plate 210 via lower plate slot 216. The expansion screw 240 is configured with opposing screw threads on each side of expansion screw disk 246. Each of the front block aperture 227 and rear block aperture 237 are tapped to accept the expansion screw 240 threads. As such, as the expansion screw 240 is rotated, each of the opposing screw threads engage each of the front block aperture 227 and rear block aperture 237 and advance the respective front block 220 and rear block 230 toward the center of the fusion cage 60. As provided in FIGS. 57A-C, expansion screw 240 comprises left hand threads on a first portion of expansion screw 240 proximal to the expansion screw head 242 and right hand threads on a second portion of expansion screw 240 distal to the expansion screw head 242. Thus, the left hand threads engage the rear block aperture 237 and the right hand threads engage the front block aperture 227. The left hand and right hand threads are symmetrical although in opposite directions such that rotation of the expansion screw 240 results in equal movement of each of the front block 220 and rear block 230. Stated another way, the operation of the expansion screw 240 with respect to the front block 220 and rear block 230 is such that each block advances toward (or retreats from) the center of the fusion cage 60 in equal amounts or distance with rotation of the expansion screw 240.

In an alternate embodiment, the thread configurations (and respective tapped apertures) are reversed. The expansion screw head 242 is fitted with a star terminus so as to engage a star (a.k.a. Torx') screwdriver. In other embodiments, the expansion screw head 242 is fitted with a star screwhead (i.e. female, i.e. receptor, end) so as to engage a star screwdriver (i.e. a male screwdriver). In other embodiments, any means of screw drive known to those skilled in the art may be employed, to include slot or regular, phillips, pozidriv, square, Robertson, hex, hex socket, tri-wing, spanner head, clutch, double-square, triple-square, polydrive, spline drive, double hex, Bristol and pentalobular.

Front block 220 comprises front block upper rail 222, front block lower rail 224, front block nose 225, front block ramp 226 and front block aperture 227. As described above, front block aperture 227 is tapped to engage the threads of expansion screw 240. Each of front block upper rail 222 and front block lower rail 224 engage, respectively, upper plate track 205 and lower plate track 215. Such a configuration or arrangement may be referred to as a dovetail joint slider. As the expansion screw is rotated, front block upper rail 222 moves or slides within upper plate track 205 toward the center of fusion cage and front block lower rail 224 moves or slides within lower plate track 215 toward the fusion cage. Because of the wedged-shaped geometry of each of the front block 220 and rear block 230, such movement toward the center of the fusion cage 60 results in an expansion (in height) of the fusion cage 60. Such movement also causes a reduction in the length of the fusion cage 60, in that the front block nose 225 retreats to the interior of the fusion cage 60, thereby leaving the upper plate front 201 and lower plate front 211, or the expansion screw tip 244, to define the most distal end of the fusion cage 60. Such a change in fusion cage 60 length is apparent by comparing, for example, FIGS. 49A and 50A. In one embodiment, the expansion screw tip 244 is configured such that, when the fusion cage 60 is in a maximum expansion state, the expansion screw tip 244 does not extend beyond a plane between the most distal end of the upper plate front 210 and lower plate front 211. It is noted that in all states of expansion of the fusion cage 60, no aperture is formed at the nose of the fusion cage 60, e.g. between the front block 220 and each of the upper plate 200 and lower plate 210. Stated another way, in all states of expansion of the fusion cage 60, to span unextended state (e.g. FIG. 49a) and maximum extended state (e.g. FIG. 50A), no path for egress of material (e.g. bone graft) is provided from the interior of the fusion cage 60 through the front or nose area (i.e. in a longitudinal direction.) In an alternate embodiment, the front block 220 is configured with one or more apertures, e.g. on one or more of front block ramp 236, so as to allow a path for the egress.

Front block 220 is symmetrical about a vertical plane (i.e. a plane running parallel to each of front block upper rail 222 edge and front block lower rail 224 edge longitudinal axes and bisecting front block aperture 227 at 12 and 6 o'clock positions.) Front block is symmetrical about a horizontal plane (i.e. a plane running parallel to each of front block upper rail 222 surface and front block lower rail 224 surface and bisecting front block aperture 227 at 3 and 9 o'clock positions.)

Rear block 230 comprises rear block groove 231, rear block upper rail 232, rear block lower rail 234, rear block ramp 236, rear block aperture 237, rear block aft 238 and rear block detent 239. As described above, rear block aperture 237 is tapped to engage the threads of expansion screw 240. Each of rear block upper rail 232 and rear block lower rail 234 engage, respectively, upper plate track 205 and lower plate track 215. As the expansion screw is rotated, rear block upper rail 232 moves or slides within upper plate track 205 toward the center of fusion cage and rear block lower rail 234 moves or slides within lower plate track 215 toward the fusion cage. Because of the wedged-shaped geometry of each of the rear block 230 and rear block 230, such movement toward the center of the fusion cage 60 results in an expansion (in height) of the fusion cage 60. The rear block aft 238 is configured such that when the fusion cage 60 is in an unexpended state (e.g. FIG. 49A), the rear block aft 238 is flush with the edges of each of upper plate rear 202 and lower plate rear 212. In one embodiment, the expansion screw head 242 is configured such that, when the fusion cage 60 is in an unexpanded state, the expansion screw head 242 is flush with the edges of each of upper plate rear 202, lower plate rear 212 and rear block aft 238.

Rear block 230 is similarly symmetrical about the same relative axes as front block 220. That is, rear block 230 is symmetrical about a vertical plane (i.e. a plane running parallel to each of rear block upper rail 232 edge and rear block lower rail 234 edge longitudinal axes and bisecting rear block aperture 237 at 12 and 6 o'clock positions.) Rear block is symmetrical about a horizontal plane (i.e. a plane running parallel to each of rear block upper rail 232 surface and rear block lower rail 234 surface and bisecting front block aperture 237 at 3 and 9 o'clock positions.)

Upper plate 200 comprises upper plate front 201, upper plate rear 202, upper plate opening 203, upper plate surface texture 204, upper plate track 205, upper plate slot 206, upper plate ridge 209 and plate tab 217. Upper plate surface texture 204 is formed of consecutive ridges in a lateral orientation, i.e. left-right rather than fore-aft. In alternate embodiments, the upper plate surface texture 204 is formed in a longitudinal direction, i.e. fore-aft rather than left-right. In other alternate embodiments, the upper plate surface texture 204 is of other configurations known to those skilled in the art, to comprise grooves and ridges. Upper plate opening 203 comprises a pair of oval race-track openings. In other embodiments, upper plate opening 203 is a single opening, is of circular shape, is of rectangular shape, or other shapes known to those skilled in the art and/or conventionally used in fusion cages. Upper plate 200 is symmetric about a vertical plane running longitudinally between the two upper plate openings 203 and the upper plate track 205.

Lower plate 210 comprises lower plate front 211, lower plate rear 212, lower plate opening 213, lower plate surface texture 214, lower plate track 215, lower plate slot 216, lower plate ridge 219 and plate tab 217. Lower plate surface texture 214 is formed of consecutive ridges in a lateral orientation, i.e. left-right rather than fore-aft. In alternate embodiments, the lower plate surface texture 214 is formed in a longitudinal direction, i.e. fore-aft rather than left-right. In other alternate embodiments, the lower plate surface texture 214 is of other configurations known to those skilled in the art, to comprise grooves and ridges. Lower plate opening 213 comprises a pair of oval race-track openings. In other embodiments, lower plate opening 213 is a single opening, is of circular shape, is of rectangular shape, or other shapes known to those skilled in the art and/or conventionally used in fusion cages. Lower plate 210 is symmetric about a vertical plane running longitudinally between the two lower plate openings 213 and the lower plate track 215.

When the fusion cage 60 is in the unexpanded state (e.g. FIG. 49A), upper plate ridge 209 and lower plate ridge 219 are in communication, i.e. are touching or substantially touching.

Upper plate 200 and lower plate 210 are identical, and are assembled to form the fusion cage 60 by positioning in opposite orientations. Stated another way, upper plate 200 and lower plate 210 are positioned to mirror one another about a horizontal plane through the center and middle height of the fusion cage 60. Among other things, identical upper plate 200 and lower plate 210 allow fewer unique parts to be used to assemble the fusion cage 60, thereby reducing costs, reducing complexity, and increasing robustness. Also, the fusion cage 60 design is such that the fusion cage remains structural stable and strong while expanded, to include when in the maximum expanded state, as enabled by the type and degree of connections between the wedged blocks and the plates. That is, as enabled by the rail/track connections between the blocks and the plates, and also the adjacent surface connections of the wedged blocks (i.e. the area adjacent the rails of each block) and the plates.

The fusion cage 60 is a modular system in that components may be combined to cover several sizes and configurations. Although each of the upper plate 200 and lower plate 210 are identical, these paired plates may be provided in several sizes. For example, as provided in FIGS. 54A-F, a set of paired (i.e. one upper plate 200 and one lower plate 210) plates may be provided in lengths of 26 mm, 32 mm and 36 mm. Also, the paired wedged blocks (i.e. a front block 220 and a rear block 230) may be provided in assorted sizes, e.g. an 8 mm and an 11 mm size, as depicted in FIGS. 55A-E. Lastly, the expansion screw 240 may be provided in various configurations, as provided in FIGS. 57A-C, to match combinations of paired plates and paired wedged blocks. In one embodiment, the fusion cage 60 may be constructed to range in size from 8×26 mm to 14×36 mm.

In one embodiment, the expansion screw 240 comprises stainless steel and titanium, and the upper plate 200 and lower plate 210 comprise stainless steel, titanium and polyether ether ketone (PEEK.)

Additional components that are configured to engage the fusion cage 60 are provided in FIGS. 63-72. Generally, the additional components comprise those that allow the fusion cage 60 to be positioned at or within a surgical site, to expand and/or contract the fusion cage 60, deliver bone graft material within the fusion cage 60 and to the surrounding surgical site, and detach the fusion cage.

With attention to FIGS. 63-69, a fusion cage 60 with expandable fusion cage feature, as described above, is depicted with an installer/impactor 250 component. The installer/impactor 250 comprises installer/impactor tip 252, installer/impactor aperture 253, installer/impactor ridge 254, installer/impactor channel 255, installer/impactor ramp 256 and installer/impactor handle 258. The installer/impactor aperture 253 is configured to engage the rear block aperture 253 and the installer/impactor ridges 254 are configured to engage the rear block detent 239; once these elements are engaged, the fusion cage 60 may be accurately and reliable positioned at the surgical site. The installer/impactor handle 258, with integrated striking plate, may be used to assist in guiding the fusion cage 60 into place, and further allows a "persuading" with a mallet. The installer/impactor handle 258 attaches in place with, for example, a ball detent or similar feature that secures the installer/impactor handle 250 in place yet allows quick and easy removal.

Figure 65A:
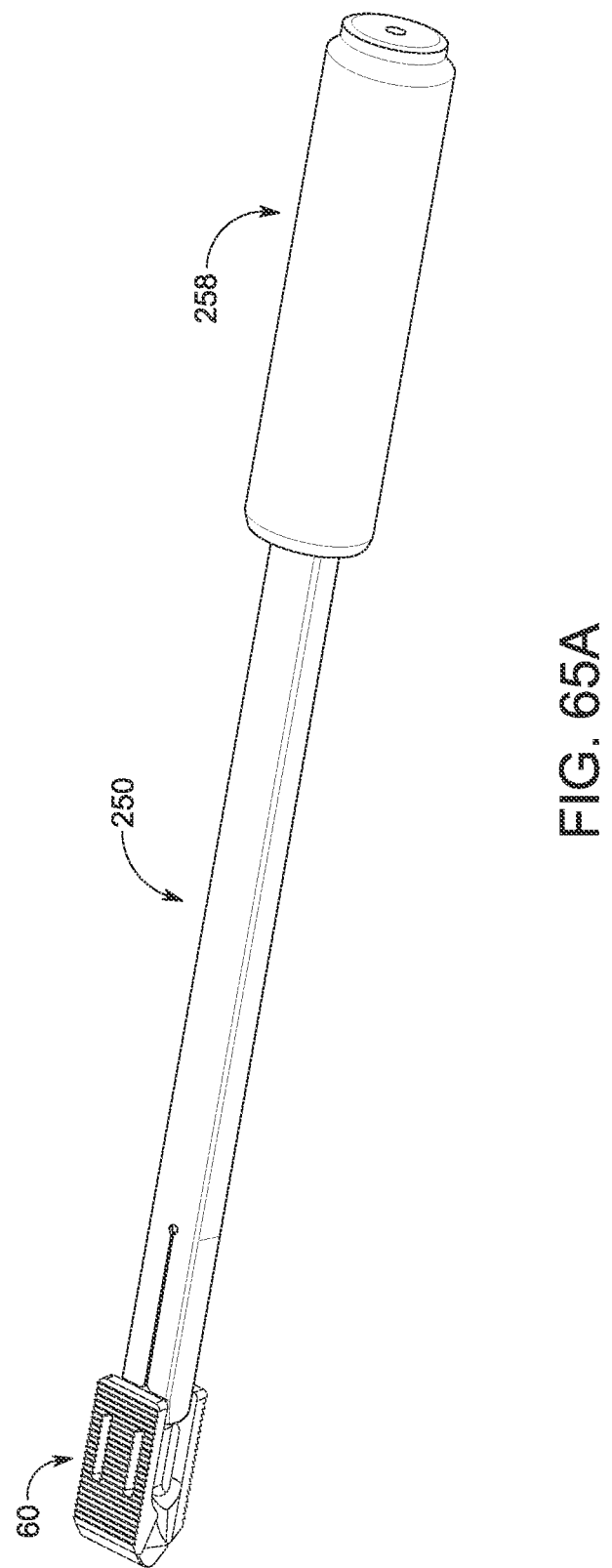
FIG. 65A is a left rear perspective view of the devices of FIG. 63A, shown with the fusion cage and installer/impactor components in an engaged state, and the installer/impactor comprising an installer/impactor handle.
Figure 65B:
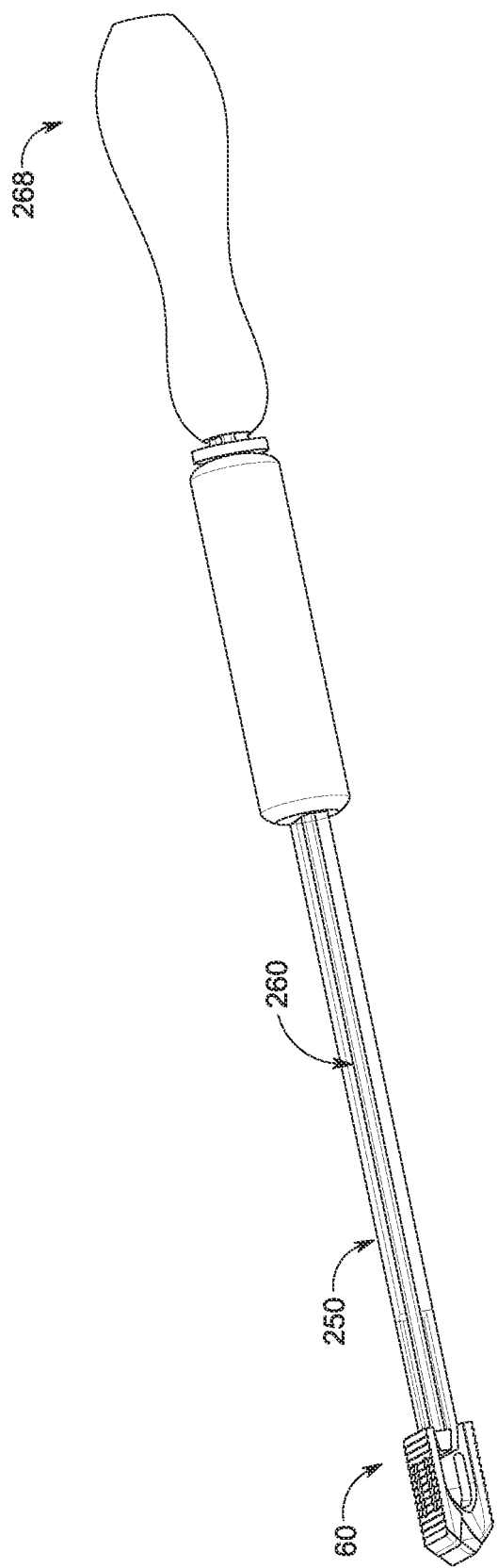
FIG. 65B is a left front perspective partial cross-sectional view of the devices of FIG. 63A in the state of FIG. 65A, shown with the fusion cage and installer/impactor components in an engaged state, the devices engaged with an expansion driver component, the installer/impactor component shown in partial cross-section to partially show the expansion driver fitted within the interior of the installer/impactor.
Figure 66:
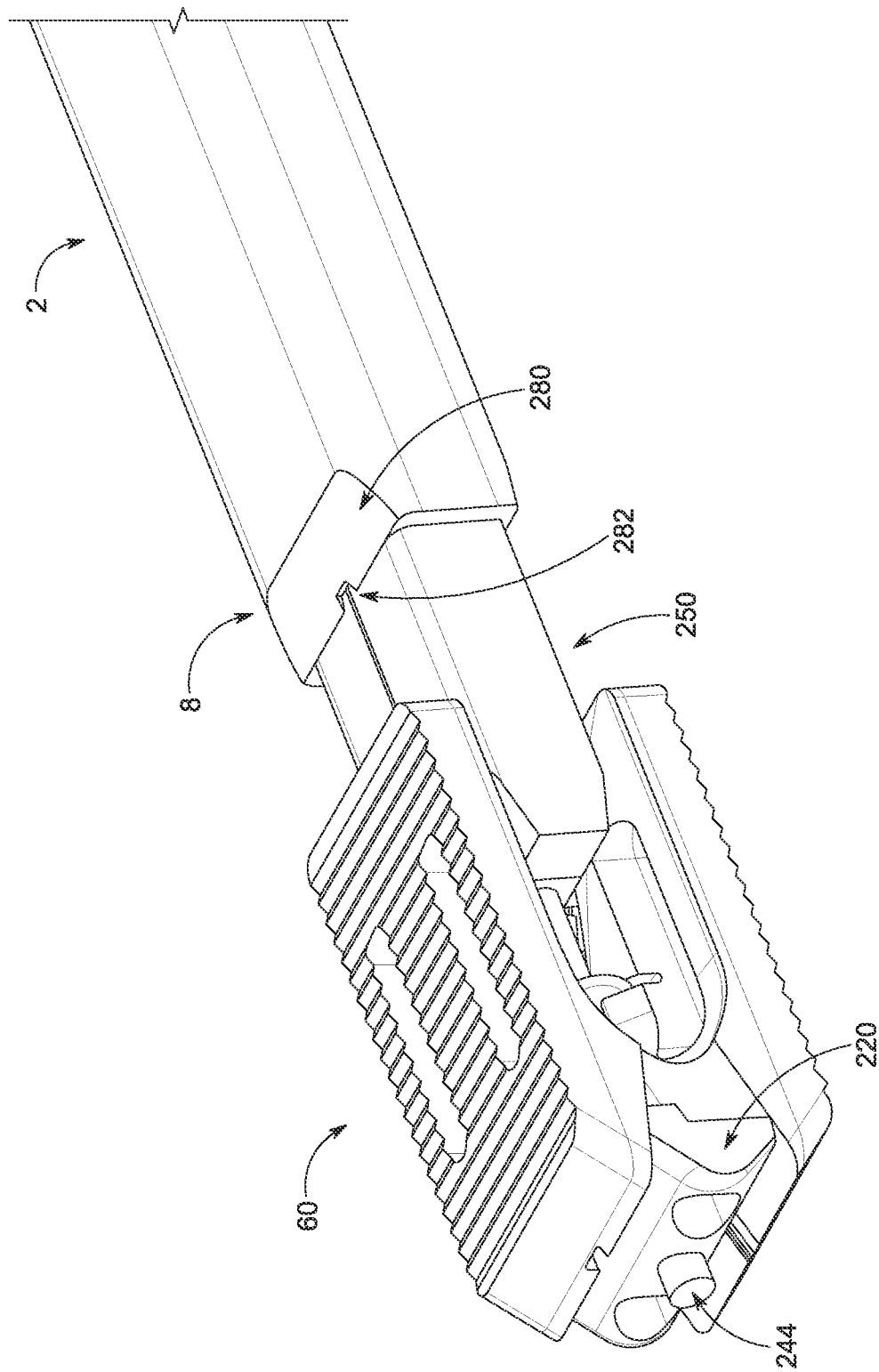
FIG. 66 is a left front perspective view of the devices of FIG. 63A, shown with the fusion cage and installer/impactor components in an engaged state, with the hollow tube component engaged with the installer/impactor component.

FIG. 65A details the installer/impactor 250 engaged with the fusion cage 60, the fusion cage 60 in an unexpanded state. FIG. 65B details the same system and configuration of FIG. 65A, except that the expansion driver 260, with expansion driver handle 268, is engaged with the fusion cage 60. More specifically, the expansion driver 260, which fits within the installer/impactor 250, engages the expansion screw head 242 (e.g. the expansion screw head 242 is a male star or Torx' screw head that engages with the female star or Torx' screwdriver end of the expansion driver 260.) FIG. 66 details the installer/impactor 250 engaged with the fusion cage 60, the fusion cage 60 in an expanded state (as a result of the expansion driver 260 engaging the expansion screw head 242 and, through rotation of the expansion screw head 242, expanding the fusion cage 60), and the hollow tube 2 fitted over the installer/impactor 250.

Figure 67:
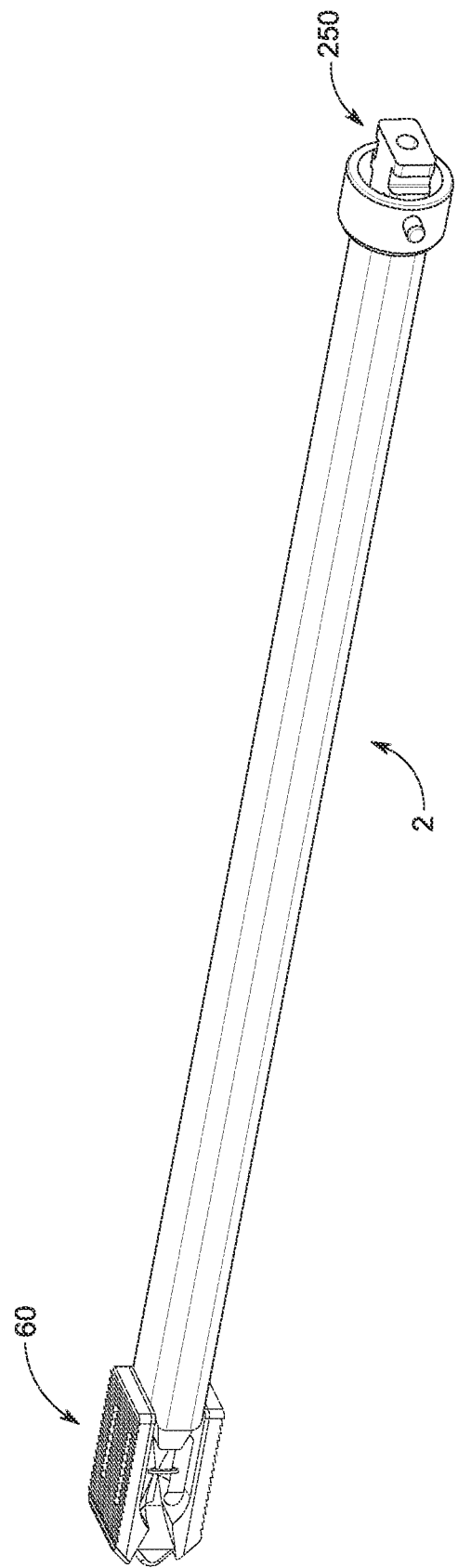
FIG. 67 is a left rear perspective view of the devices of FIG. 63A, shown with the fusion cage and installer/impactor components in an engaged state, and shown with the fusion cage and hollow tube in an engaged state.

After the fusion cage 60 is expanded to the desired degree, i.e. height, the expansion driver 260 disengages from the expansion screw head 242 and is removed. The hollow tube 2 is then slid downward or distally so as to engage the fusion cage 60, and the installer/impactor 250 must be removed (so as to allow bone graft material to be delivered via hollow tube 2 into the fusion cage 60 and the surrounding surgical site.) FIG. 67 details the installer/impactor 250 engaged with the fusion cage 60, the fusion cage 60 in an expanded state, and the hollow tube 2 fitted over the installer/impactor 250 and engaged with the fusion cage 60; this is the configuration of the integrated expandable fusion cage and bone graft delivery device when the installer/impactor 250 must be removed so as to enable bone graft delivery. In an alternate embodiment, the installer/impactor 250 is not used, and instead the hollow tube 2 is used to position the fusion cage 60 by way of the hollow tube external ramp 280 and/or hollow tube notch 282. The hollow tube external ramp 280 may form a press-fit with the fusion cage 60. The hollow tube may also engage the fusion cage 60 via the hollow tube notch 282, the hollow tube notch 282 configured to engage the rear block aft 238 portion above and below the rear block aperture 237.

Figure 68A:
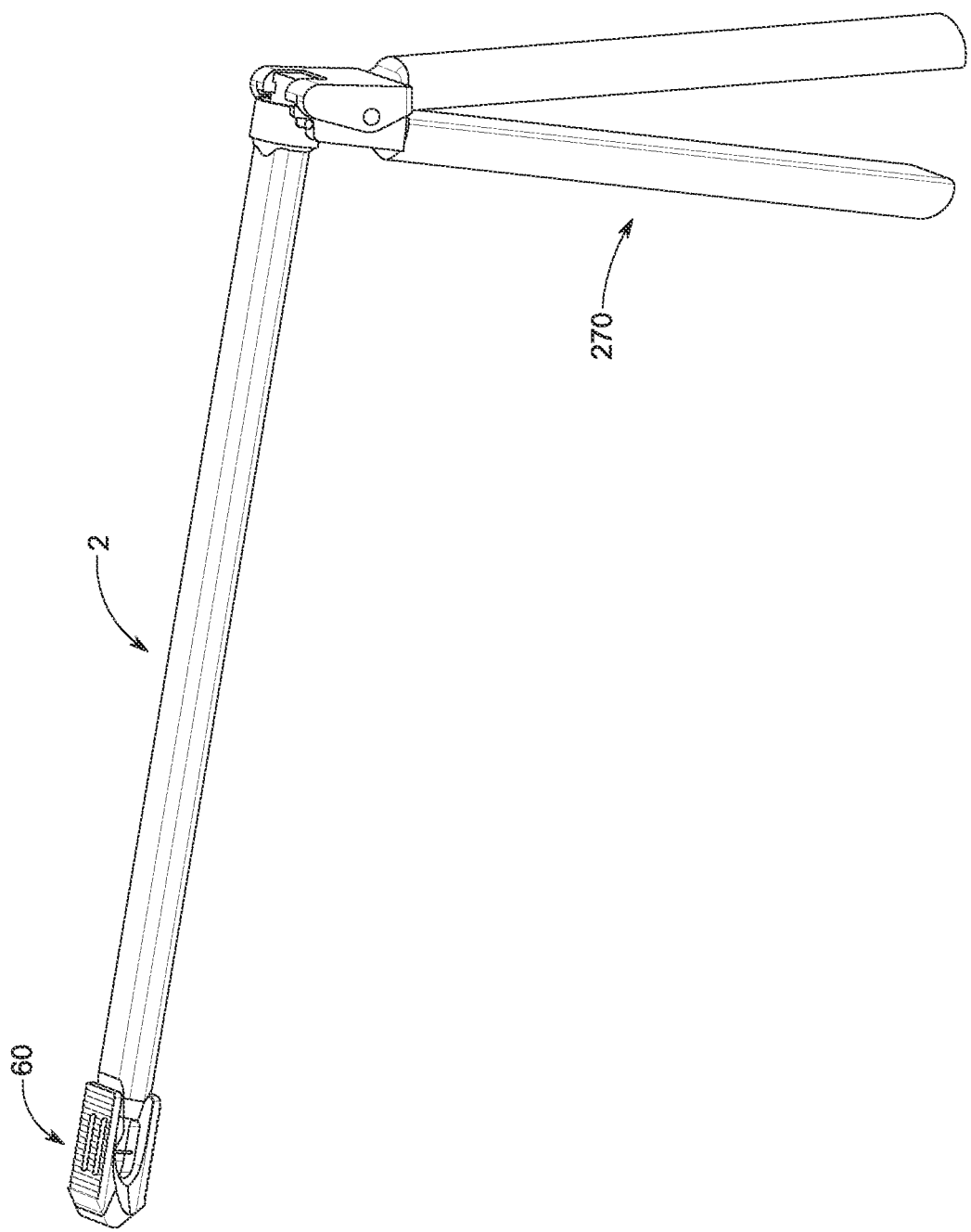
FIG. 68A is a left rear perspective view of the devices of FIG. 63A, shown in the configuration of FIG. 67, with a removal pliers component engaged with the hollow tube component.
Figure 68B:
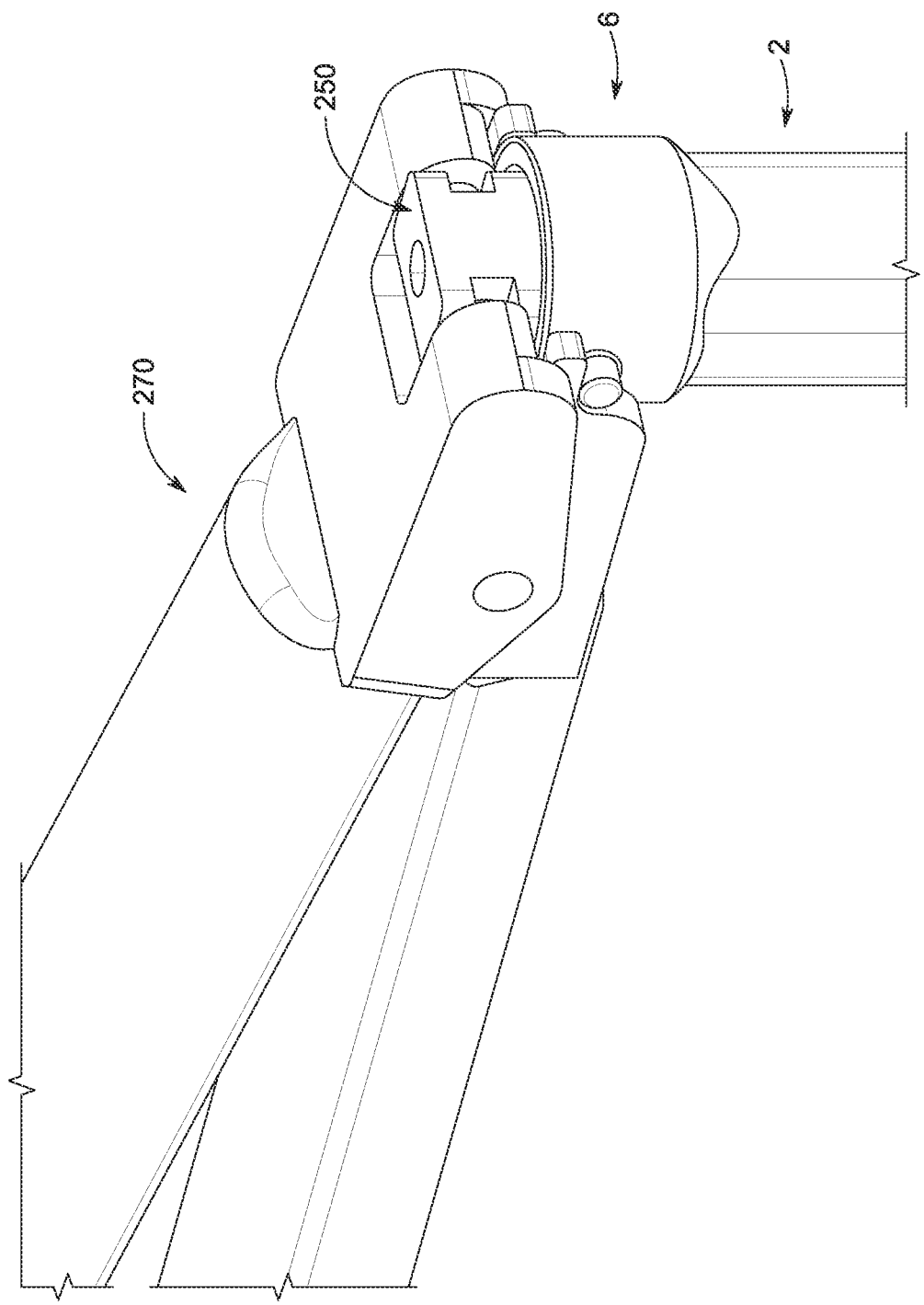
FIG. 68B is a close-up partial perspective view of the devices of FIG. 68A.

FIGS. 68A-B detail a means with which the installer/impactor 250 may be removed by use of removal pliers 270. The removal pliers 270 are configured to engage the first end 6 of hollow tube and the proximal end of the installer/impactor 250, so as to pull the installer/impactor 250 from engagement with the fusion cage 60. Note that the installer/impactor 250 is configured to allow the installer/impactor tip 252 to spread apart over the rear block detent 239 groove, as facilitated by the installer/impactor channel 255.

Figure 69:
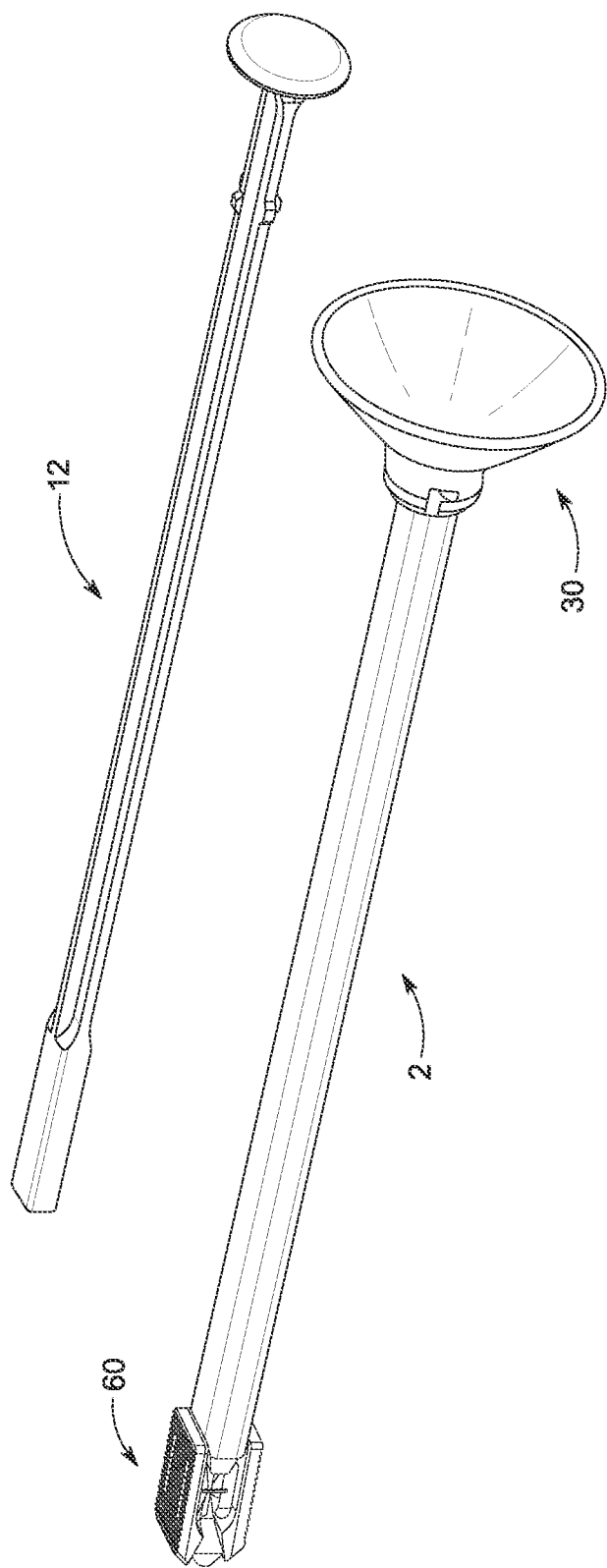
FIG. 69 is a left rear exploded perspective view of a fusion cage with expandable fusion cage feature engaged with a hollow tube component and a funnel component, as configured to engage with a plunger component.

After the fusion cage 60 has been positioned in the surgical site and expanded as required, bone graft material may be inserted into the fusion cage 60 and into the surrounding surgical site. FIG. 69 presents an exploded perspective view of the fusion cage 60 with expandable fusion cage feature engaged with the hollow tube 2 component and funnel 30 component, as configured to engage with the plunger 12 component. As described previously, bone graft material is placed into the funnel 30 and advanced down the hollow tube 2 by the plunger 12, whereby bone graft material flows into the fusion cage 60 and outward into the surgical site via one or more of the upper plate openings 203, lower plate openings 213, and lateral openings distal to the front block 230.

Figure 70:
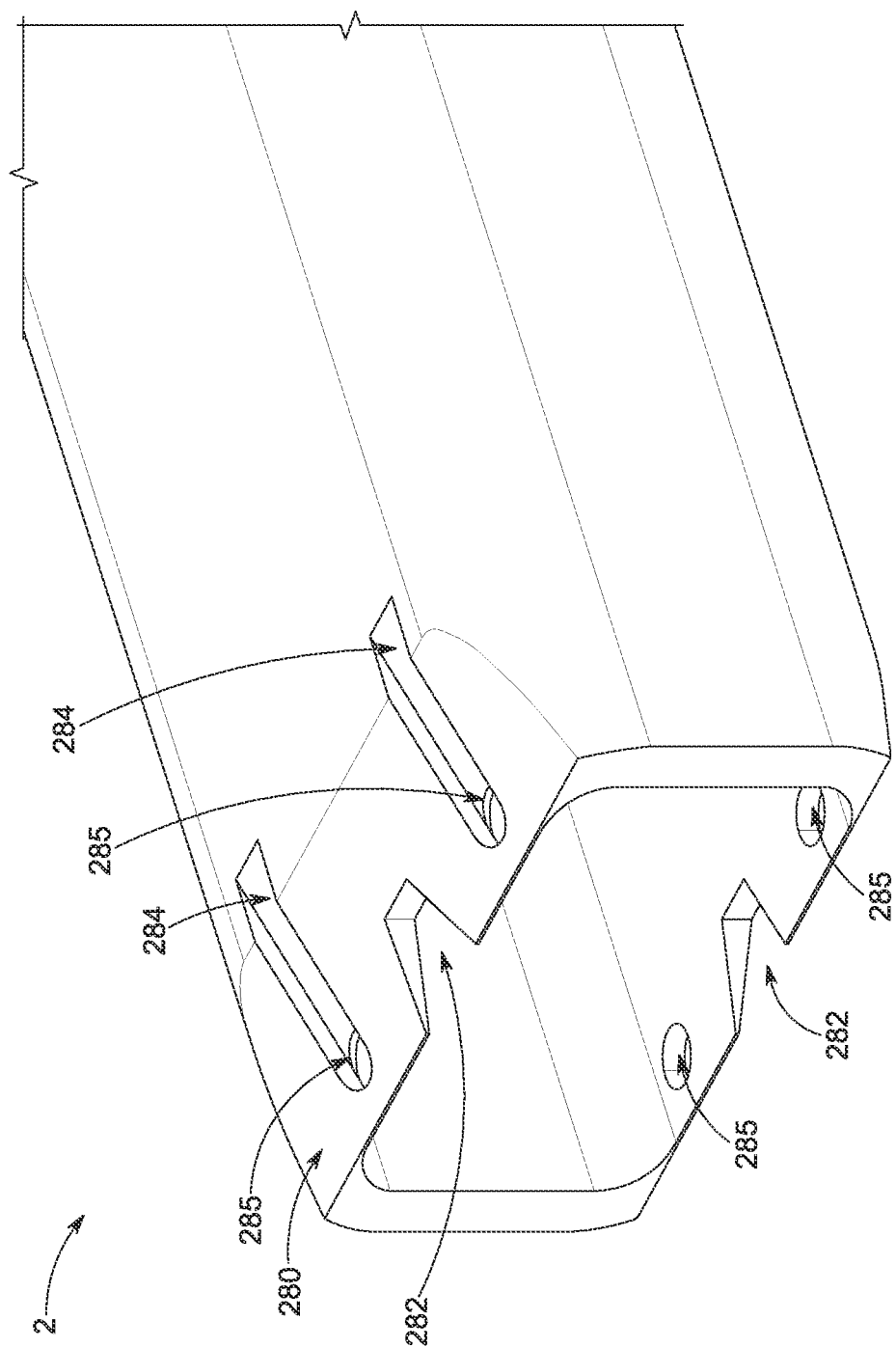
FIG. 70 is a left front partial perspective view of another embodiment of the hollow tube component configured to engage a fusion cage with expandable fusion cage feature, the hollow tube configured with hollow tube slot and hollow tube slot aperture features.
Figure 71:
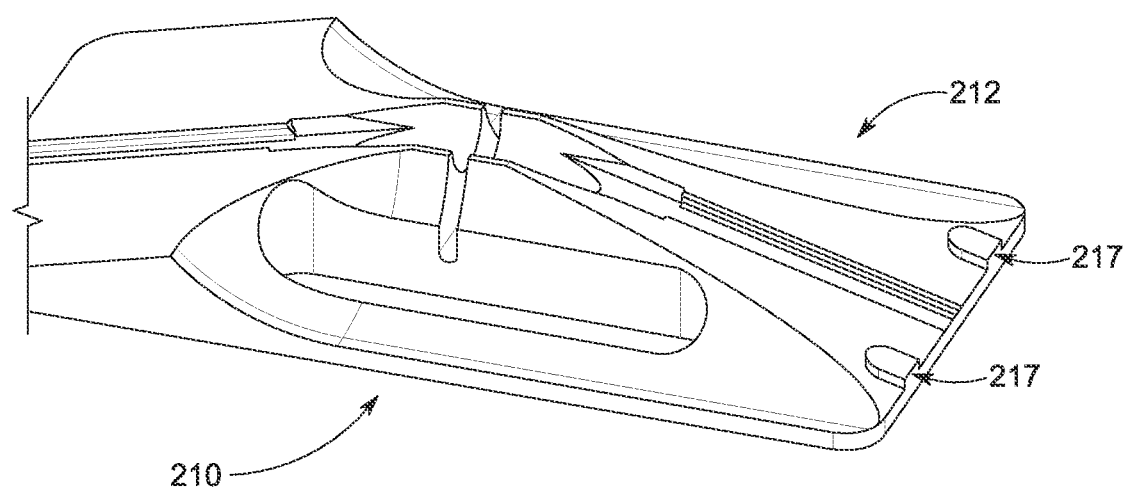
FIG. 71 is a left rear perspective view of another embodiment of the lower plate component of a fusion cage with expandable fusion cage feature, the lower plate configured with a plate tab feature configured to engage the hollow tube slot and hollow tube slot aperture features of FIG. 70.
Figure 72:
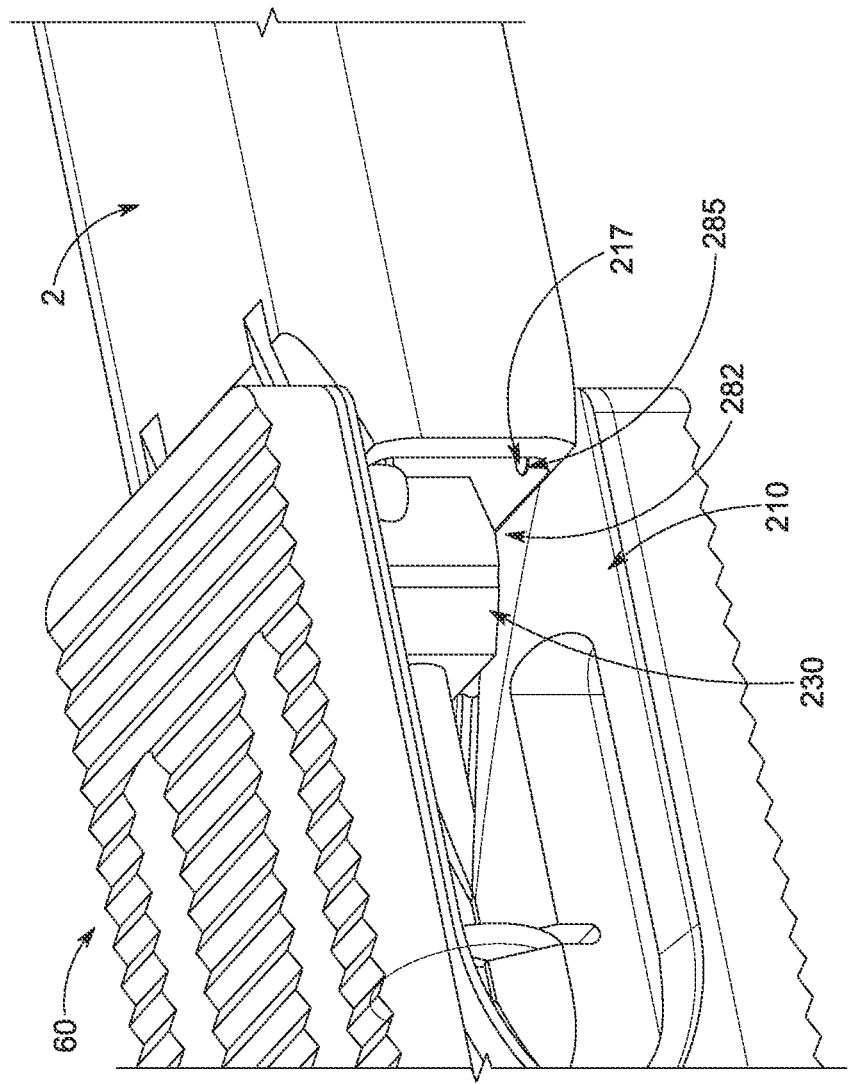
FIG. 72 is a left front partial cross-section perspective view of the devices of FIGS. 70 and 71, shown with the plate tab feature engaged with the hollow tube slot and hollow tube slot aperture features.

FIGS. 70-72 depict an alternate embodiment of hollow tube 2 and fusion cage 60 to enable the fusion cage 60 to be accurately and reliably positioned at a surgical site. The hollow tube 2 comprises two pairs of hollow tube slots 284, each with a hollow tube slot aperture 285 at the distal end. Each hollow tube slot 284 is disposed at least partially on the hollow tube external ramp 280. Each of the upper plate 200 and lower plate 210 comprise a pair of plate tabs 217, each of which engages one of the hollow tube slot apertures 285. When such an engagement occurs, the fusion cage 60 is slightly expanded as the hollow tube 2 is inserted into the fusion cage 60. In this arrangement, as the fusion cage 60 is expanded, the plate tabs 217 retreat or release from the hollow tube slot apertures 285; however, the hollow tube 2 still engages or registers with the fusion cage 60 via the hollow tube notches 282 which remain engaged with the rear block aft 238.

In one embodiment, the expansion screw 240 is configured to lock at defined expansion states of the fusion cage 60, to include at a maximum expansion state (as defined, e.g. as the maximum height dimension of which the fusion cage 60 may expand.)

Figure 73:
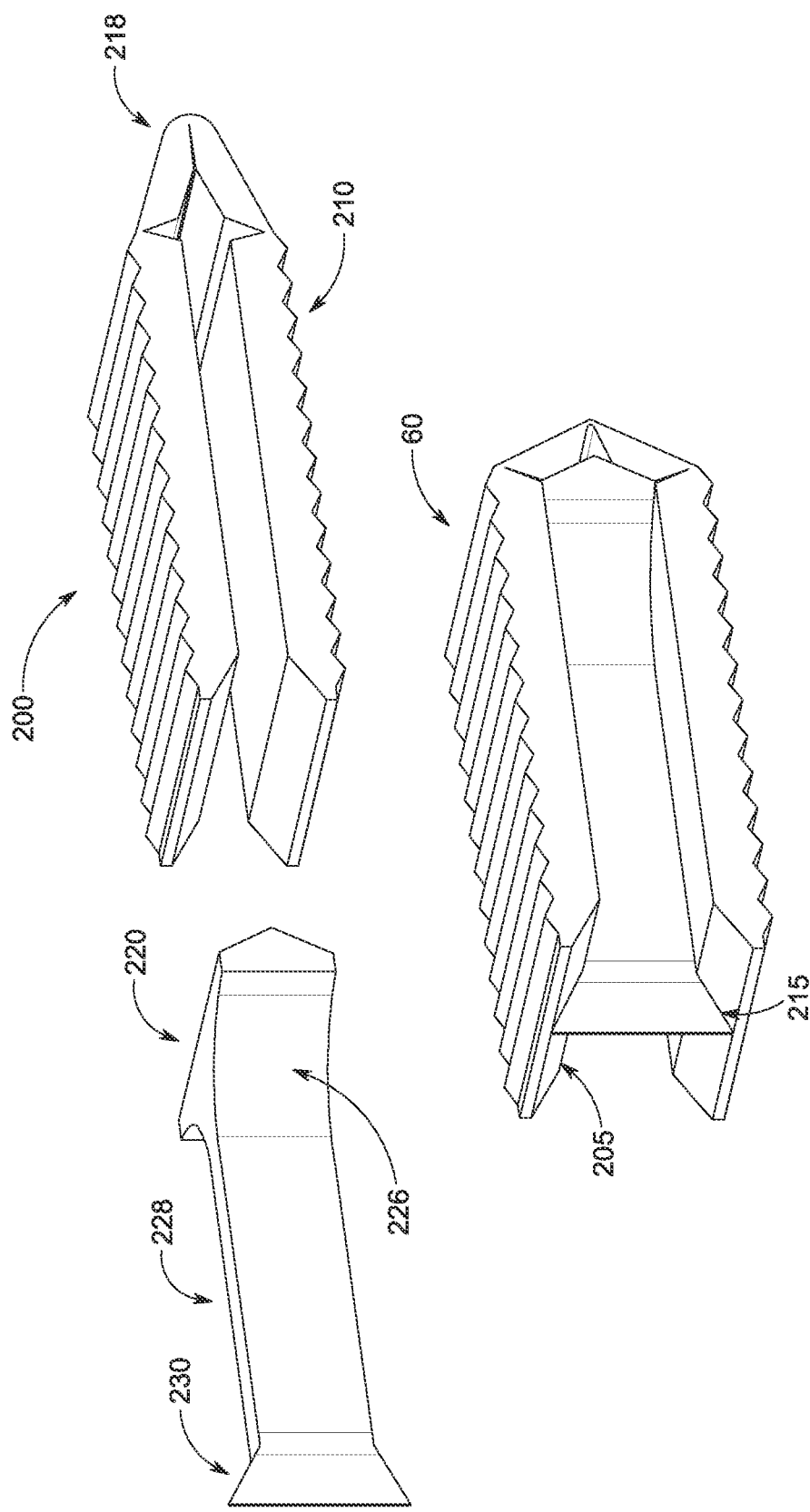
FIG. 73 is a right rear exploded view of another embodiment of the fusion cage with expandable cage feature.

In another embodiment, the fusion cage 60 with expandable cage feature is configured of modified and integrated embodiments of the afore-mentioned components. For example, FIG. 73 depicts a fusion cage 60 with expandable fusion cage feature wherein the upper plate 200 and lower plate 210 are joined through a plate nose element 218 ("plate/nose element"). These combined components are configured to form a first state wherein a minimal vertical height is provided and/or a flat profile is presented. Horizontal notches fitted between the upper plate 200 and plate nose element 218, and between the lower plate element 210 and plate nose element 218, enable the integrated upper plate 200, lower plate 210 and plate nose element to expand upon engagement with an integrated front block 220 and rear block 230 element.

The integrated front block 220 and rear block 230 element comprises a block spine 228 ("block/spine element") such that, when inserted into the afore-mentioned plate/nose element, the fusion cage 60 expands. In one embodiment, each of the afore-mentioned integrated components would be held in a pistol grip type insertion tool (as known to those skilled in the art) which would allow placement of the unexpanded (i.e. the collapsed) plate/nose element into the surgical site (e.g. a disk space) with the block/spine element staged right behind. Upon pulling a lever on the pistol grip tool, the plate/nose element would be inserted into the block/spine element (in one embodiment, this insertion is facilitated by upper plate track 205 and lower plate track 215 engaging respective upper and lower rails of the block/spine element), thereby expanding the plate/nose element and forming an expanded fusion cage 60. In one embodiment, a locking feature is provided such that the plate/nose and block/spine elements are secured or locked together. In one embodiment, the insertion of this fusion cage 60 embodiment is by way of hollow tube 2 (e.g. the embodiment described in FIGS. 70-72). In one embodiment of the fusion cage 60 as provided in FIG. 73, one or more upper plate openings 203 and/or one or more lower plate openings 213 are provided.

In one embodiment, no springs, such as wire springs, are employed to expand the fusion cage 60. In one embodiment, other means, as known to those skilled in the art, are used to expand the fusion cage 60, to include springs, gears, cams, magnetic, electrical, electromechanical, electro-magnetic, and optical.

Figure 74:
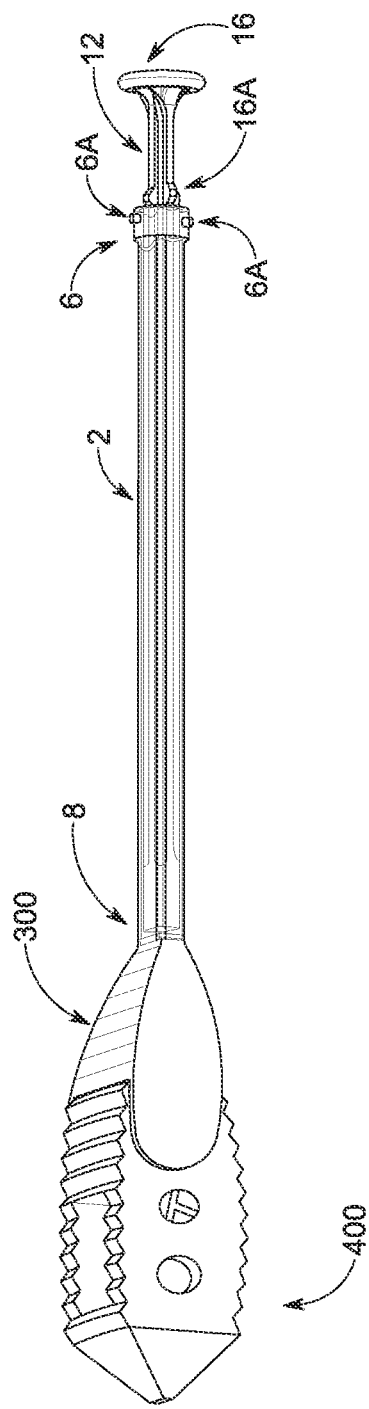
FIG. 74 depicts the fusion cage with expandable cage feature engaged with an angled insertion tool.

The means and components disclosed may engage, integrate and/or communicate with the fusion cage 60 embodiments of the disclosure as well as with traditional and conventional fusion cages. That is, the components of the disclosure may be readily adapted to engage conventional fusion cages, including expandable fusion cages, of the prior art. More specifically, the hollow tube 2, installer/impactor 250, expansion driver 260, and/or plunger 12 may be adapted to engage fusion cages of the prior art. FIG. 74 provides a representative depiction of adaptations of components of the disclosure so as to engage conventional fusion cages, both fixed or static fusion cages and expandable fusion cages.

In one embodiment, the bone graft delivery system of the disclosure may engage with an expandable fusion cage of the prior art. For example, the hollow tube 2 may be configured to engage the prior art (expandable) fusion cage 400 shown by, for example, geometric sizing of the hollow tube first distal opening 8, and/or fitting the hollow tube first distal opening 8 with a malleable portion that may be compressed and/or expanded so as to engage the prior art (expandable) fusion cage 400, and/or fitting to an adaptor 300 portion. Additionally, the installer/impactor 250 may be adapted (e.g. to use the same configuration of expansion end as that of the depicted fusion cage) to communicate with the end portion of the prior art (expandable) fusion cage 400 so as to enable the expansion of the prior art (expandable) fusion cage 400. The prior art (expandable) fusion cage 400 may also be engaged with one or more components of the disclosure, e.g. the hollow tube 2 and/or installer/impactor 250.

In one embodiment of the fusion cage 60, the fusion cage of the prior art is adapted wherein one or more of the upper plate 200 and/or lower plate 210 is adapted to fit on paired opposite sides of the fusion cage.

In another embodiment, the bone graft delivery system of the disclosure may engage with an unexpandable fusion cage of the prior art. The hollow tube 2 is configured to engage the prior art (unexpandable) fusion cage 400 shown by, for example, geometric sizing of the hollow tube first distal opening 8, and/or fitting the hollow tube first distal opening 8 with a malleable portion that may be compressed and/or expanded so as to engage the prior art (expandable) fusion cage 400, and/or fitting to an adaptor portion 300.

FIG. 74 depicts the bone graft delivery system of the disclosure, as engaged with an unexpandable fusion cage of the prior art, specifically an unexpandable fusion cage provided in US2012/0065613 and/or http://thompsonmis-.com/node/23, incorporated herein by reference in entirety. The hollow tube 2 is configured to engage the prior art (unexpandable) fusion cage 400 shown by, for example, geometric sizing of the hollow tube first distal opening 8, and/or fitting the hollow tube first distal opening 8 with a malleable portion that may be compressed and/or expanded so as to engage the prior art (expandable) fusion cage 400, and/or fitting to an adaptor portion 300 (as shown).

In one embodiment, the adaptor 300 comprises at least two forked tines to engage, for example, exterior surfaces of a fusion cage. In one embodiment, the adaptor 300 forms an angled tool, that is, the adaptor 300 and the hollow tube 2 are not aligned or linear. In another embodiment, the adaptor 300 forms an angled tool relative to a fusion cage when engaged with a fusion cage, that is, the adaptor 300 and the hollow tube 2 are aligned or linear but are not in alignment with an engaged fusion cage.

In one embodiment, the fusion cage 60 is actuated, e.g. the expansion screw 240 is operated, remotely, e.g. through electrical means, magnetic means or other means known to those skilled in the art, during surgery or post-operative. The later situation, i.e. post-operative, enables adjustment of the height of the fusion cage 60 after surgery. In one embodiment, the fusion cage (e.g. the expansion screw) is operated or manipulated by way of additional devices to comprise a servo-motor.

In one embodiment, the fusion cage 60 is used in applications comprising L-LIF, ALIF, Corpectomy adaptation, deformity correction and increasing lordosis.

In one embodiment, the expansion screw 240, comprising a left-hand and a right-hand threaded screw portion and a central disk, engages two opposing blocks at a 30-degree ramp angle with a dovetail joint. As the blocks are drawn in, the cage plates are forced outward (in the vertical direction). The narrow disk at the center of the screw registers in the slots of the cage plates to keep the plates from shifting fore/aft, reducing if not eliminating binding of the mechanism.

In one embodiment, at least some of the fusion cage is manufactured using 3-D printing technologies, metal additive manufacturing (AM), subtractive machining and/or direct metal laser sintering (DMLS) and may be provided a porous coating. In one embodiment, the fusion cage 60 comprises one or more surfaces, especially exterior surfaces, with pores so as to, for example, promote osseointegration. The article "EOS Teams with Medical Implant Designer to Advance 3D Printing in Medicine" published Oct. 17, 2012 in Graphic Speak is incorporated by reference in entirety.

In one configuration, the fusion cage of the present disclosure comprises a titanium alloy, such as Ti6AL4V and/or lattice structures, the lattice structures covering all or at least part of one or more apertures of the fusion cage 60.

In one configuration, the hollow tube 2 is configured such that its distal upper and lower interior surfaces have grooves to engage the upper and lower portions of the rear cage actuating wedge. The screw tool, fitting inside the cannula, is still used to expand the cage. Once expanded, the screw tool is removed. Then BG material is inserted using the cannula/plunger scheme. Furthermore, the distal end of the modified cannula may be made of an elastic material so that, if initially engaged with the cage in compression, it expands as the cage expands to provide a sealed fit with the cage as the cage expands, thereby allowing a clean flow of BG material into the cage i.e. no back-flow.

In one embodiment, one or more alignment markers are placed on the funnel, e.g. lines at 0 degree and 180 degree. In one embodiment, one or more clamps are applied to the hollow tube for additional support and/or stability. The clamps may be, e.g. scissor-type clamps. In one embodiment, all or a portion of the plunger, hollow tube, fusion cage and ejection tool comprise a thermoplastic polycarbonate such as Lexan™. In one embodiment, the fusion cage comprises a different material than one or more of the hollow tube, plunger and ejection device. In one embodiment, the plunger comprises an elastic portion and elastic seal which functions, among other things, to restrict wiggle of the plunger when moving through the hollow tube. In one embodiment, one or more portions of the device are manufactured via sonic welding, and/or comprise a sonic weld. For example, the tip of the hollow tube and/or fusion cage may be sonic welded or comprise a sonic weld.

Referring now to FIGS. 75A-75E, an embodiment of an integrated fusion cage and graft delivery device 1 of the present disclosure is illustrated. The graft delivery device generally includes a cannular or hollow tube 2, a plunger 12, and a detachable funnel 30.

The hollow tube 2 is the same as, or similar to, other embodiments of hollow tubes described herein. Accordingly, the hollow tube 2 generally includes an opening 4 at a proximal end 6. At least one discharge opening 7 is associated with a distal end 8 of the hollow tube. In one embodiment, the discharge opening 7 is positioned transverse to a longitudinal axis of the hollow tube 2. Accordingly, in one embodiment, the distal end 8 is at least partially closed opposite to the proximal opening 4. Alternatively, the distal end 8 may be completely closed. Optionally, a discharge opening 7 may be formed through at least a portion of the distal end. Specifically, in one embodiment, the hollow tube 2 can include a discharge opening 7 aligned with a longitudinal axis of the hollow tube.

In one embodiment, the distal end 8 is rounded or smooth with a wedge-shape 50. Specifically, the distal end can have a shape configured to facilitate easy entry into a disc space. In this manner, the shape of the distal end minimizes soft tissue damage or irritation. The wedge-shape 50 enables insertion of the distal end 8 into a collapsed disc space without damaging the endplates or skating off to an unintended location. In contrast, some prior art devices with an open distal end can injure bony end plates of the disc space of a patient.

Optionally, the hollow tube includes two discharge openings 7A, 7B. The two discharge openings 7 can be arranged on opposite sides of the hollow tube to eject graft material. Accordingly, in one embodiment, the hollow tube 2 is operable to dispense bone graft material laterally away from a longitudinal axis of the graft delivery device 1. In one embodiment, the two discharge openings 7 are of substantially the same size and shape. The discharge openings 7 may have a generally oval shape.

In another embodiment, at least one opening 7C (illustrated in FIG. 75D) is formed in the distal end 8. Thus, the graft delivery device 1 may discharge bone graft material through the distal end 8 in line with the longitudinal axis of the graft delivery device 1. The opening 7C may have any predetermined shape. Optionally, the opening 7C has a rectangular, round, or ovoid shape. The distal end 8 may optionally include a taper or wedge shape 50 with an end opening 7C formed therethrough.

The hollow tube 2 is substantial hollow between the proximal end and the distal end. Specifically, a lumen 28 extends through the hollow tube 2. The lumen 28 has a predetermined cross-sectional shape. In one embodiment, the cross-sectional shape of the lumen is one of round, ovoid, square, and rectangular. In another embodiment, the interior of the lumen is not round and is, for example, rectangular. Optionally, the cross-sectional shape of the lumen 28 is substantially uniform along the length of the hollow tube 2. In one embodiment, the lumen 28 has a uniform cross-sectional size along its length. The exterior of the hollow tube 2 may have a shape that is one of round, ovoid, square, and rectangular.

Figure 76B:
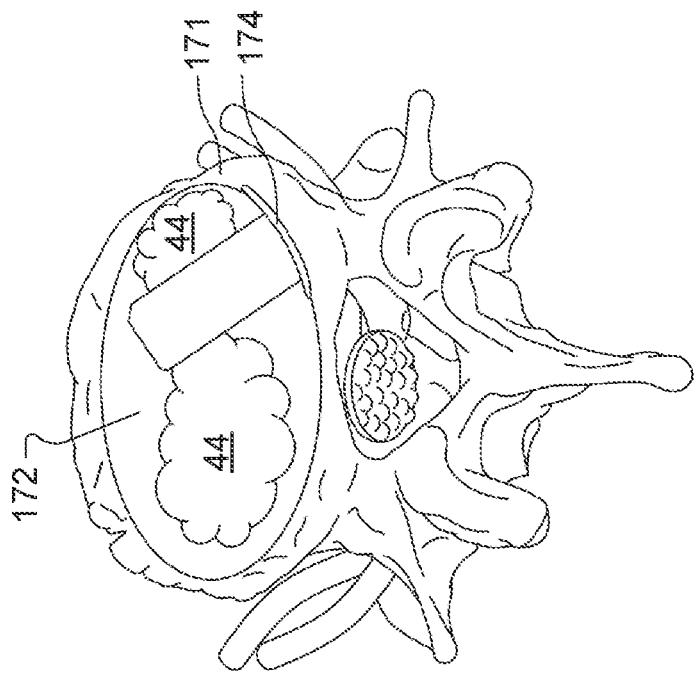
Figure 76A:
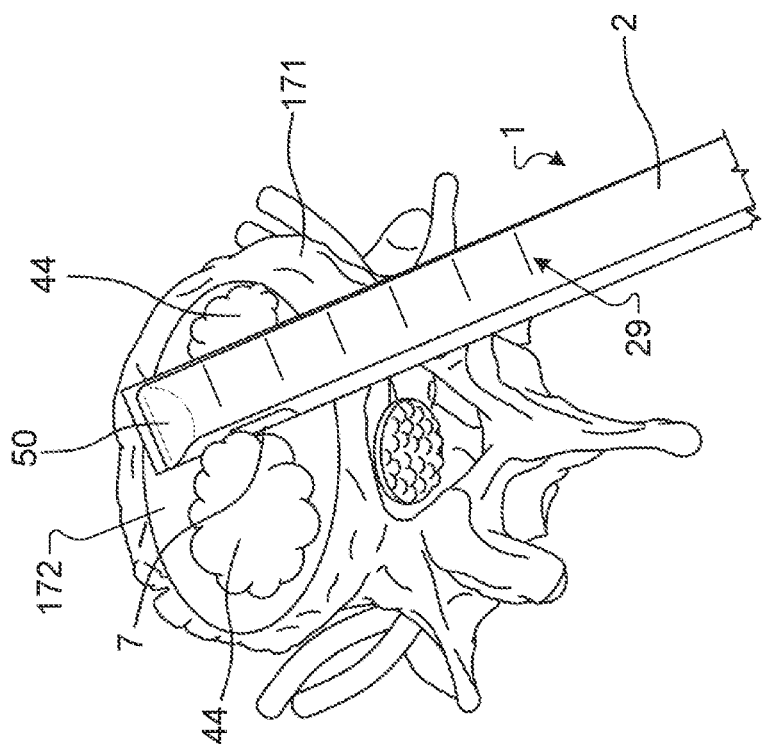

A ramp 9 may be formed within the hollow tube proximate to the opening 7. As described herein, the ramp 9 includes surfaces configured to direct the bone graft material away from the opening 7 into a surgical site, such as a disc space. More specifically, the ramp 9 functions as a reverse funnel to disperse bone graft material ejected from the opening 7 as generally illustrated in FIG. 76A.

In one embodiment, surfaces of the ramp 9 are linear in shape, that is, forming a triangle in cross-section. In another configuration, surfaces of the ramp 9 are of any shape that urges egress of bone graft material contained in the hollow tube to exit the lumen 28 of the hollow tube 2 through the at least one opening 7 of the device 1.

The hollow tube 2 is configured to receive the plunger 12 of the present disclosure within the lumen 28. Any plunger 12 of the present disclosure may be used with the hollow tube 2. The plunger 12 can be used to push bone graft material positioned in the lumen 28 out of the opening 7 at the distal end 8. Optionally, a stop 16A can be formed on the plunger 12 to engage the proximal end 6 of the hollow tube. In this manner, the stop 16A prevents over insertion of the plunger within the lumen.

Optionally, the plunger 12 may include a plurality of teeth separated by notches 27. The notches 27 can be engaged by a means for advancing bone graft material described herein. In one embodiment, the means for advancing comprises a ratchet configured to engage the notches 27. In operation, the ratchet can engage successive notches to advance or withdraw the plunger within the hollow tube.

Additionally, or alternatively, the means for advancing can include a gear with teeth. The gear is aligned with the plunger and operable to convert rotational movement of the rear to linear movement of the plunger. As the gear rotates, the gear teeth engage the plunger notches 27 to move the plunger toward or away from the hollow tube distal end.

In still another embodiment, the means for advancing comprises a worm gear with at least one helical thread. As the worm gear rotates, the helical thread engages the plunger notches 27. In this manner, the worm gear can advance or retract the plunger within the hollow tube.

The plunger 12 includes a distal end 18. The distal end 18 substantially conforms to inner walls of the lumen 28. Specifically, in one embodiment, the distal end 18 has a cross-sectional shape which corresponds to the interior shape of the lumen 28. Optionally, the plunger distal end 18 is round, ovoid, square, or rectangular. In one embodiment, the distal end 18 is not round. In another embodiment, the plunger distal end is configured to contact the inner walls of the lumen 28 about an entire outer periphery of the plunger distal end. Additionally, or alternatively, the plunger 12 (or a portion of the plunger 12) may be made of rubber silicone to improve the seal with interior surfaces of the lumen 28. In some embodiments, at least the distal end 18 is made of a plastic or an elastomeric rubber.

In one embodiment, the plunger has a length sufficient for the distal end 18 of the plunger to extend beyond the opening 7 as generally illustrated in FIG. 75C. In one embodiment, the handle 16 of plunger is a planar disk shape, as depicted in FIG. 75C. In another embodiment, handle 16 is not planar. For example, handle 16 is angled so as to conform to interior of funnel 30 when the plunger 12 is fully inserted into hollow tube 2.

Notably at least one vent port 21 may be formed through the hollow tube 2 to the lumen 28. The vent port 21 is configured to release air from the interior of the hollow tube 2 as bone graft material is delivered to the distal end 8 for discharge out of the opening 7. As one of skill in the art will appreciate, air trapped within the lumen 28 of the hollow tube 2 between the distal end 8 and bone graft material may increase the amount of axial force required by the plunger 12 to move the bone graft material to the discharge opening 7 or may cause the plunger to jam or bind in the lumen. Applying excessive force to the plunger to eject the bone graft material can cause soft tissue inflammation or damage. By allowing air to escape from within the lumen 28 of the hollow tube 2 as the plunger 12 is pressed toward the distal end 8, the vent port 21 may decrease the amount of force required to deliver the bone graft material to the discharge opening 7. The possibility of the plunger 12 jamming within the hollow tube 2 is also reduced. Specifically, the vent port 21 eliminates or reduces the risk of jamming the plunger and also reduces the possibility of trapped air being forced into the disc space and into the patient's vascular system causing an air embolism.

The vent ports 21 also prevent introduction of air or other fluids into the surgical site. For example, air may be introduced into, and trapped within, bone graft material as the bone graft material is loaded into the hollow tube. As the plunger presses against the bone graft material, the air may be released from the bone graft material. The air can escape from the lumen 28 through the vent ports 21.

Vent ports 21 can be formed through the hollow tubes 2 of all embodiments of the present disclosure. Vent ports 21 may be formed at any location of the hollow tube 2 along the length of the hollow tube between to proximal end 6 and the distal end 8. Optionally, a vent port 21 is formed on at least one of the first surface 3 and the second surface 5. In one embodiment, vent ports 21 can be formed on more than one surface 3, 5 of the hollow tube.

The at least one vent port 21 is configured to prevent discharge of bone graft material from the lumen 28. Accordingly, the vent port 21 has one or more of a size and a shape selected to prevent passage of bone graft material therethrough. In one embodiment, a width or a diameter of the vent port is less than approximately 2 mm. Optionally, the vent port 21 includes a mesh or screen with apertures which allow passage of air therethrough.

As illustrated in FIG. 75B, the vent port 21 can optionally have a generally circular shape, such as a bore. Although the vent port 21 illustrated in FIG. 75B is generally circular, other shapes are contemplated. In one embodiment, the vent port is a slit or slot. The slot may be generally linear. In another embodiment, the vent port 21 has a shape that is generally triangular or rectangular. Specifically, the vent port 21 may have any size or shape which allows the passage of air but prevents passage of bone graft material therethrough.

Any number of vent ports 21 may be formed through the hollow tube 2. In one embodiment, the hollow tube 2 includes at least three vent ports 21. A first vent port 21A can be proximate to the proximal end 6 of the hollow tube 2. A second vent port 21B can be proximate to the distal end 8. A third vent port 21C can be formed between the first and second vent ports 21A, 21B.

Figure 75A:
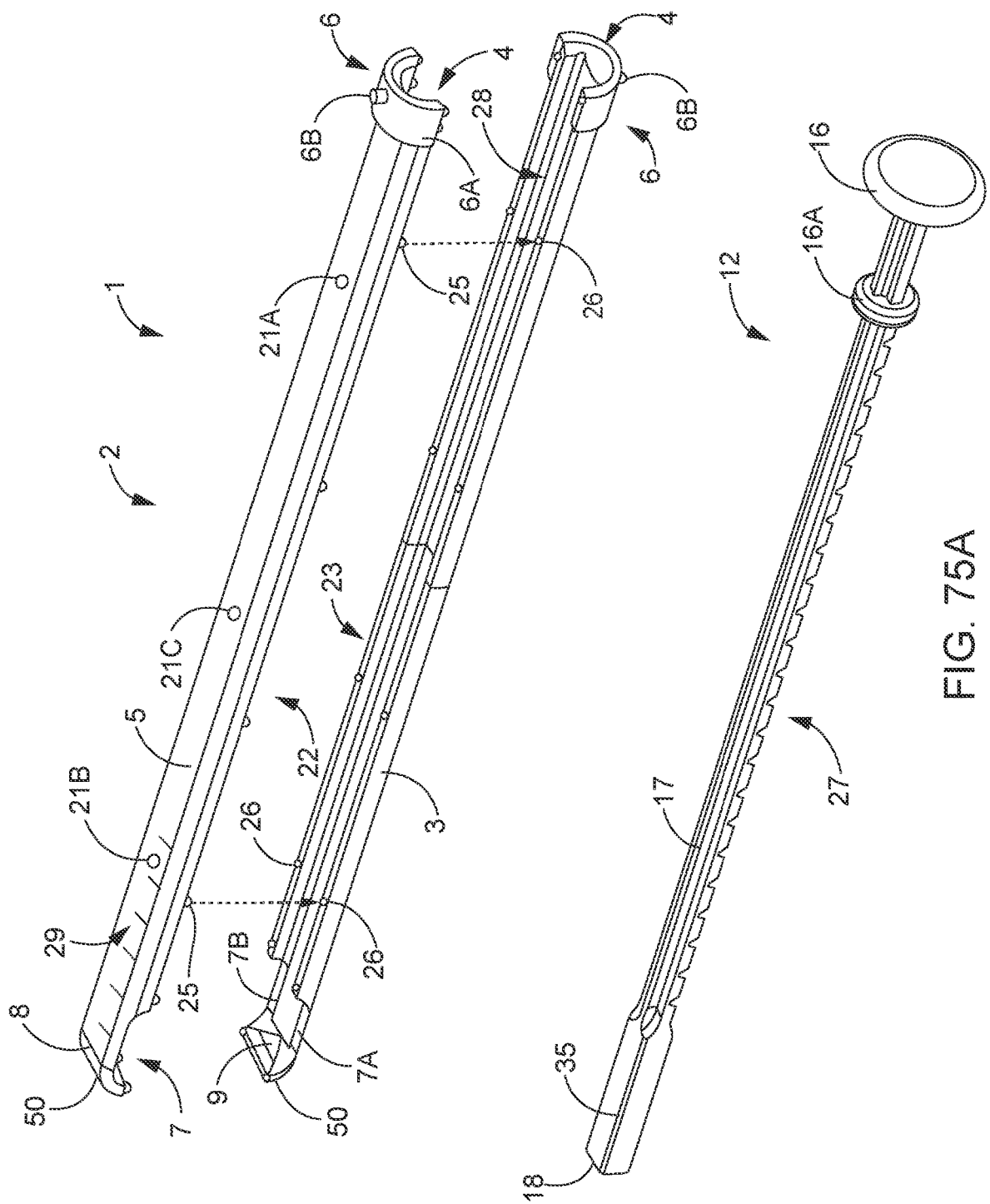
FIG. 75A is a perspective view of a device for delivering bone graft of another embodiment illustrating a hollow tubular member including a plurality of vent ports and a plunger of an embodiment of the present disclosure.

Additionally, or alternatively, in another embodiment, the plunger 17 includes a channel 35 (such as generally illustrated in FIG. 75A) configured to release air from the distal end 8 of the lumen 28 to the proximal end of the lumen. In this manner, as the plunger is advanced to eject bone graft material from the discharge opening 7, air trapped in the bone graft material and/or the lumen distal end 8 (the portion of the lumen distal to the distal end 18 of the plunger 12) can pass through the channel 35 into the proximal portion of the lumen.

Optionally, indicia 29 may be formed on one or more surface of the hollow tube 2. The indicia are configured to indicate a depth of insertion of the distal end 8 of the hollow tube into a surgical site. The indicia 29 can include marking and numerals. Optionally, one or more of the indicia 29 may be radiopaque. The indicia 29 may extend along the length of the hollow tube, or a predetermined portion of the length.

In one embodiment, the hollow tube 2 may comprise a first portion 22 and a second portion 23 which are configured to be interconnected. The hollow tube 2 thus includes a joint 24, illustrated in FIG. 75C, along which the first and second portions 22, 23 are connected. The joint 24 may substantially bisect the hollow tube 2.

The first and second portions 22, 23 can be interconnected by any suitable means. In one preferred embodiment, an ultraviolet activated adhesive is used to interconnect the first and second portions 22, 23. This forms a particularly strong bond in combination with optional alignment features 25, 26 (best seen in FIG. 75E) and the material of the hollow tube 2.

In another embodiment, the first and second portions 22, 23 are sonically welded together. Additionally, or alternatively, other glues or adhesives can be used to join the first and second portions 22, 23.

Optionally, the first and second portions can include the alignment features 25, 26. In addition to ensuring alignment of the first portion 22 with respect to the second portion 23 when the hollow tube 2 is assembled, the alignment features 25, 26 can also provide support to the hollow tube 2. In one embodiment, the alignment features 25, 26 have a shape selected to increase rigidity of the hollow tube 2, such as to prevent unintended or inadvertent bending or movement.

The alignment features 25, 26 may comprise a projection 25 formed on one of the first and second portions 22, 23 that is at least partially received in a bore or aperture 26 of another of the first and second portions 22, 23. In one embodiment, the alignment feature 25 comprises a peg or pin. Optionally, alignment feature 26 comprises a recess configured to receive the peg 25. In one embodiment, one of the alignment features 25, 26 comprises a flange. The flange may extend along some or all of the joint 24. The other one of the alignment features 26, 25 may comprise a groove configured to receive the flange. Similar to the flange, the groove may extend along some or all of the joint 24. Other shapes and features of the alignment features 25, 26 are contemplated.

The alignment features 25, 26 can also be configured to lock the first and second portion 22, 23 together. Specifically, in one embodiment, alignment feature 25 comprises a projection configured to engage a corresponding recess in alignment feature 26. Feature 26 can frictionally engage feature 25.

The hollow tube 2 may be made of a flexible, semi-rigid, or rigid material including one or more of a plastic, a composite, a metal. In one embodiment, the hollow tube 2 is formed of polycarbonate resin thermoplastic. Optionally, at least a portion of the hollow tube 2 is radiopaque. In one embodiment, at least the distal end 8 is radiopaque or includes radiopaque markers, such as indicia 29.

In one embodiment, the hollow tube 2 is substantially rigid. Optionally, at least a portion of the hollow tube 2 may be flexible. For example, in one embodiment, at least about one-half of the hollow tube 2 comprising the distal end 8 is flexible.

In one embodiment, the hollow tube 2 is generally linear. Alternatively, the hollow tube 2 can include a portion that is not linear. More specifically, in one embodiment, the hollow tube 2 can have a permanent (or temporary) curve or bend.

Alternatively, in another embodiment, the proximal end 6 of the hollow tube can extend along a first longitudinal axis. At least the distal end 8 of the hollow tube 2 may extend along a second longitudinal axis that is transverse to the first longitudinal axis of the proximal end. The distal end 8 can extend at a predetermined angle from the proximal end 6. Optionally, the angle can be between about 0° and about 75°. In one embodiment, the distal end 8 intersects the proximal end 6 at a joint. The joint may be adjustable such that a user can alter the angle between the proximal end and the distal end. Alternatively, the joint is not adjustable. The proximal end and the distal end may each extend generally linearly to the joint. Alternatively, the hollow tube 2 may include a transition portion between the proximal end and the distal end. The transition portion can have a shape that is curved, such as an elbow joint.

The hollow tube 2 may be made of a substantially transparent or translucent material. Accordingly, in one embodiment, the hollow tube is not opaque. Optionally, at least a portion of the hollow tube 2 is transparent or translucent. In one embodiment, the hollow tube 2 is comprised of a transparent or translucent material, or includes windows of a transparent or translucent material. Accordingly, in embodiments, the plunger 12 is at least partially visible within the lumen 28.

Also, in another embodiment, the hollow tube 2 can include lighting elements 37. The lighting elements may be associated with the optional endoscope, camera, or image sensor 36. Additionally, or alternatively, one or more lighting elements 37 can be fixed to, or integrally formed with, the hollow tube 2. Suitable lighting elements, cameras, and displays that may be used with the integrated fusion cage and graft delivery device 1 of the present disclosure are described in U.S. Pat. Nos. 8,864,654, 9,717,403, and PCT Pub. WO 2012/145048 which are each incorporated herein by reference in their entirety.

As illustrated in FIGS. 75B, 75C, the funnel 30 can be releasably interconnected to the hollow tube. The funnel facilitates loading of bone graft material into the opening 4 at the proximal end 6 of the hollow tube 2. Once the lumen 28 is loaded with bone graft material, the funnel may be removed to improve visualization of the distal end 8 and opening 7 in a surgical site, such as a disc space. In contrast to prior devices which include a fixed funnel which cannot be removed, the releasable funnel 30 of the present disclosure does not obstruct visualizing the distal end 8 of the hollow tube 2 as it is placed in a disc space or other surgical site. Optionally, if additional bone graft material is required, the funnel 30 may be interconnected to the hollow tube during the surgical procedure without having to remove the hollow tube 2 from the surgical site, resulting in decreased potential trauma to adjacent nerve tissue.

In one embodiment, the funnel 30 is retained on the hollow tube 2 by a friction fit. Alternatively, the funnel can snap onto the hollow tube. Optionally, in one embodiment, the hollow tube 2 include a collar 6A with one or more projection 6B. The funnel 30 has a sleeve 32 that fits over the collar and engages the projection 6B. Optionally, the sleeve 32 includes a slot 33 to engage the projection 6B. The slot 33 and projection 6B form a bayonet mount. In this manner, funnel can be releasably interconnected to the hollow tube.

Optionally, the hollow tube 2 can be configured to receive a fusion cage 60 of one or more of the embodiments described herein. Optionally, the fusion cage 60 may have a fixed height. Alternatively, the fusion cage may be expandable after placement in a disc space.

In one embodiment, the fusion cage includes an opening 65 to discharge bone graft material therethrough. The opening 65 is alignable with the opening 7 of the hollow tube. Optionally, the fusion cage 60 may include two or more openings 65 which each correspond to openings 7A, 7B of the hollow tube. Accordingly, as bone graft material is advanced through the lumen and through the opening 7 of the hollow tube, the bone graft material will be discharged through opening 65 of the fusion cage into a surgical site, such as a disc space.

In one embodiment, a distal end 64 of the fusion cage is closed. The distal end 64 may have a blunt or tapered shape similar to the wedge shaped end 50 of the hollow tube.

In one embodiment of the device 1, the width of the hollow tube second exterior surface 5 is between 9 and 15 mm. In a preferred embodiment, the width of the hollow tube second exterior surface 5 is between 11 and 13 mm. In another embodiment, the width of the hollow tube second exterior surface 5 is between 11.5 mm and 12.5 mm. In yet another embodiment, the width of the hollow tube second exterior surface 5 is 12 mm.

In one embodiment of the device 1, the width of the hollow tube first exterior surface 3 is between 5 and 11 mm. In another embodiment, the width of the hollow tube first exterior surface 3 is between 7 and 9 mm. Optionally, the width of the hollow tube first exterior surface 3 is between 7.5 mm and 8.5 mm. In one embodiment, the width of the hollow tube first exterior surface 3 is 8 mm.

In one embodiment of the device, the ratio of the width of the hollow tube second exterior surface 5 and the width of the hollow tube first exterior surface 3 is between approximately 1.7 and 1.3. In another embodiment, the ratio of the width of the hollow tube second exterior surface 5 and the width of the hollow tube first exterior surface 3 is between 1.6 and 1.4. In still another embodiment, the ratio of the width of the hollow tube second exterior surface 5 and the width of the hollow tube first exterior surface 3 is between 1.55 and 1.45. In one embodiment, the ratio of the width of the hollow tube second exterior surface 5 and the width of the hollow tube first exterior surface 3 is 1.5.

In one embodiment of the device, the width of the interior of the hollow tube major axis (located adjacent the second exterior surface 5) is between 9 and 13 mm. In another embodiment, the width of the interior of the hollow tube major axis is between 10 and 12 mm. Optionally, the width of the interior of the hollow tube major axis is between 10.5 mm and 11.5 mm. In one embodiment, the width of the interior of the hollow tube major axis is 11 mm.

In one embodiment of the device 1, the width of the interior of the hollow tube minor axis (located adjacent the first exterior surface 3) is between 5 and 9 mm. In another embodiment, the width of the interior of the hollow tube minor axis is between 6 and 8 mm. In yet another embodiment, the width of the interior of the hollow tube minor axis is between 6.5 mm and 7.5 mm. In one embodiment, the width of the interior of the hollow tube minor axis is 7 mm.

In one embodiment of the device 1, the ratio of the width of the interior of the hollow tube major axis and the width of the interior of the hollow tube minor axis is between approximately 1.7 and 1.3. In another embodiment, the ratio of the width of the interior of the hollow tube major axis and the width of the interior of the hollow tube minor axis is between 1.6 and 1.4. Optionally, the ratio of the width of the interior of the hollow tube major axis and the width of the interior of the hollow tube minor axis is between 1.55 and 1.45. In one embodiment, the ratio of the width of the interior of the hollow tube major axis and the width of the interior of the hollow tube minor axis is 1.5.

In one embodiment, one or more edges of the device are rounded. For example, the exterior edges of the hollow tube are rounded, and/or the interior edges of the hollow tube are rounded (in which case the edges of the plunger, at least at the plunger distal end, are identically rounded to ensure a congruous or conformal fit between the edges of the plunger and the interior of the hollow tube so as to, among other things, urge the majority of bone graft material to move through the hollow tube).

The device 1 may optionally be printed using a three-dimensional printing process. More specifically, one or more of the hollow tube 2, the plunger 12, the funnel 30, and the fusion cage 60 may be manufactured by one or more three-dimensional printing processes. A variety of materials, including a metal, PEEK, and other plastics may be used in a three-dimensional printer to form the device 1.

The integrated fusion cage and graft deliver device 1 of the present invention provides many benefits over other devices. For example, the rectangular lumen 28 of embodiments of the hollow tube 2 affords several advantages over conventional circular configurations. For a surgical area with a smallest dimension set at a width of 8 mm and a thickness dimension 0.5 mm, a conventional circular device (with resulting interior diameter of 7 mm or a radius of 3.5 mm) would realize a surface area of 38.48 $mm^2$. Applicants' device would carry interior dimension of 7 mm by 11 mm for a surface area of 77 mm, an increased surface area factor of 2.0, thereby resulting in more bone graft material delivery, because, among other things, a given volume of bone graft encounters less surface area of the interior of a particular device which results in, among other things, reduced chance of jamming of bone graft material within the device.

Referring now to FIG. 76A, an integrated fusion cage and graft deliver device 1 according to embodiments of the present disclosure is illustrated delivering bone graft material 44 to a disc space 172 within a patient's spine 171. As shown, the hollow tube 2 of the device 1 is provided with at least one opening 7. Bone graft material 44 is provided to the intervertebral space 172 by ejecting the material from the opening 7. In some embodiments, the hollow tube 2 has two openings such that bone graft material 44 is ejected on opposing sides of the device 1. In this manner, the device 1 provides enhanced distribution of bone graft material 44 and a greater quantity of bone graft material into a surgical site compared to other devices. Further, the larger cross-sectional shape of the hollow tube 2 of the deliver tool 1 of the present invention allows injection of bone graft material in a thicker, more controllable viscous state and with less force than required by other devices.

An additional benefit of some embodiments of devices 1 of the present disclosure is that they avoid injection of bone graft material 44 directly into the path or intended path of a cage, such as is the case with other devices. For example, FIG. 76B provides a top view of the surgical workspace 172 according to FIG. 76A, after the integrated fusion cage and graft deliver device 1 has been removed after insertion or injection of the bone graft material 44. As shown in FIG. 76B, removal of the bone graft delivery tool provides an unobstructed path 174 and void space for subsequent insertion of a fusion cage (not shown in FIG. 76B). In this manner, devices 1 of the present disclosure provide for a sufficient amount of bone graft material within the surgical site 172 and provide an area 174 that is operable to receive a fusion cage.

Figure 77:
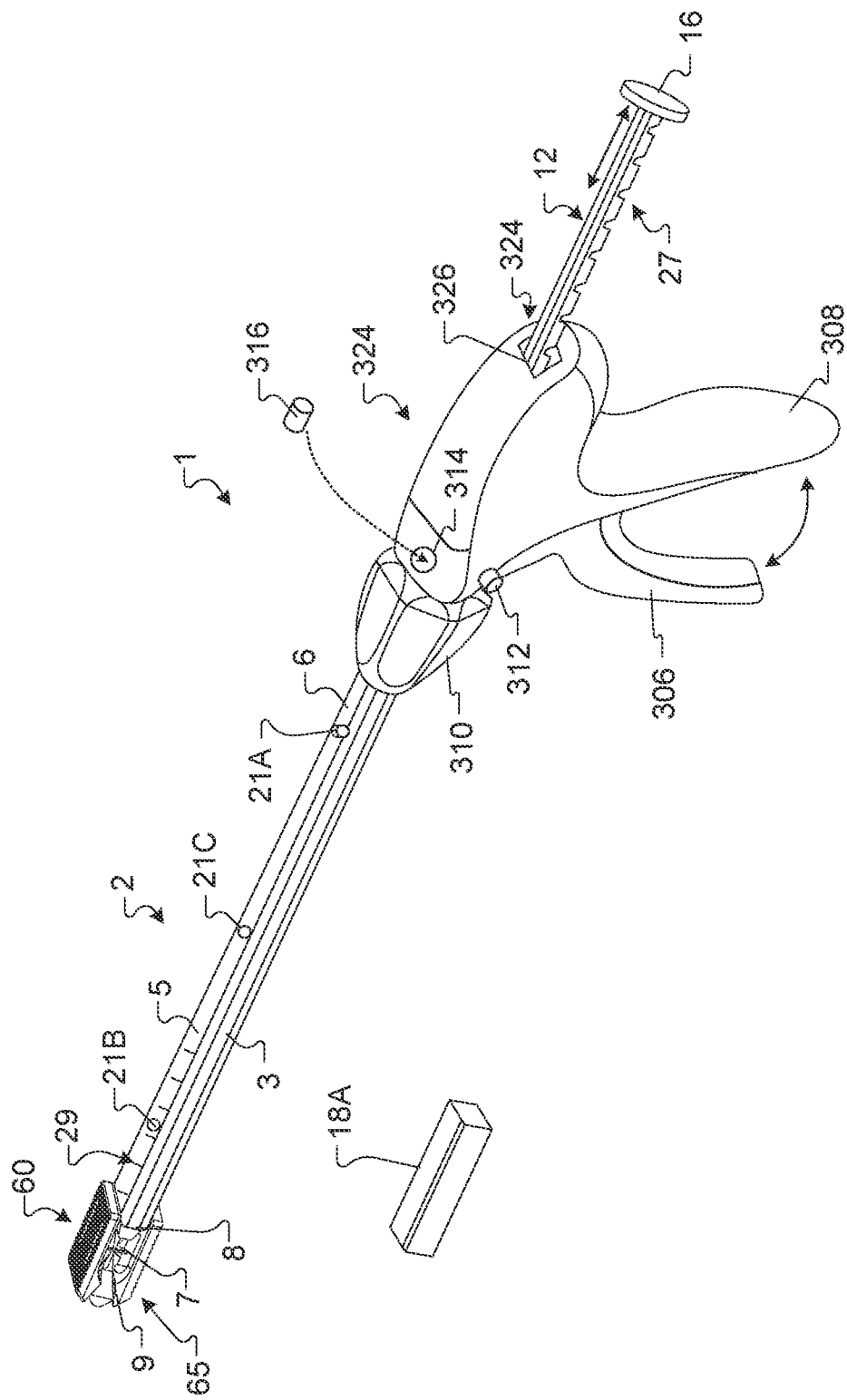

Referring now to FIG. 77, another embodiment of an integrated fusion cage and graft delivery device 1 of the present disclosure is illustrated. The integrated device 1 generally includes a hollow tube 2, a fusion cage 60, and a means for advancing bone graft material through the hollow tube. The means for advancing may use manual force, mechanical force, electric force, pneumatic force, or any other force to advance bone graft material through the hollow tube. In one embodiment, a user can manipulate the integrated device 1 with a single hand. This beneficially frees the user's other hand for other action.

In one embodiment, the means for advancing includes a handle or grip 304. The grip 304 is operable to selectively move bone graft material through the lumen of the hollow tube 2 for discharge from an opening 7 at the tube distal end 8.

The hollow tube 2 includes a proximal end 6 configured to releasably interconnect to the grip 304. Bone graft material can be positioned within the lumen of the hollow tube 2, such as with a funnel 30 (illustrated in FIG. 75B). The funnel 30 may then be removed from the proximal end 6. The proximal end 6 can then be interconnected to the grip 304. Optionally, the hollow tube 2 can be used to eject bone graft material into a surgical site without being affixed to the grip.

The grip 304 can frictionally engage the tube proximal end 6. In one embodiment, the hollow tube 2 or the grip 304 include a lock or a latch to secure the hollow tube 2 to the grip. In another embodiment, a portion of the hollow tube 2 can threadably engage the grip 304. In another embodiment, the proximal end 6 and grip 304 are interconnected with a bayonet mount. Additionally, or alternatively, the grip 304 can optionally include a knob 310 such that the hollow tube 2 can be selectively interconnected to the grip 304. Other means of interconnecting the hollow tube 2 to the grip 304 are contemplated.

A channel 324 is formed through the grip 304. The channel 324 includes a proximal opening 326 and extends through the grip 304 and the knob 310. In one embodiment, the opening 326 is configured to receive a plunger 12. The plunger 12 can extend through the channel 324 into a hollow tube 2 interconnected to the grip 304.

The grip 304 includes a means for advancing bone graft material through the lumen of the hollow tube 2. In one embodiment, the means for advancing comprises a compressed fluid. Specifically, in one embodiment, the grip 304 is configured to advance the bone graft material using the compressed fluid, such as air. Manipulating the grip trigger 306 can release compressed fluid into the proximal end 6 of the lumen. In one embodiment, the hollow tube includes a single vent port 21B at the distal end. When a proximal end of bone graft material within the lumen reaches the vent port 21B, the compressed fluid is released from the lumen. In this manner, the fluid is not introduced into the surgical site.

Optionally, a pusher 18A may be positioned in the lumen of the hollow tube 2 after the lumen is loaded with bone graft material. The pusher 18A may be similar to the distal end 18 of a plunger 12, such as generally illustrated in FIG. 75A. Regardless, the pusher 18A is configured to substantially conform to interior surfaces of the lumen. In this manner, the pusher 18A prevents the fluid from being discharged from the opening 7 into the surgical site.

When a pressurized fluid is introduced into the lumen behind the pusher 18A, the pusher advances toward the distal end 8. The bone graft material is urged toward the distal end 8 and through the opening 7 by the pusher. In one embodiment, when a proximal end of the pusher 18A advances past the vent port 21B, the compressed fluid is released from the lumen and the pusher stops. Alternatively, the pusher may stop advancing by contact with an interior ramp 9 within the hollow tube 2.

In another embodiment, the means for advancing the bone graft material comprises a plunger 12. Accordingly, in one embodiment, the grip 304 is configured to selectively advance a plunger 12 through the lumen to advance the bone graft material. The grip 304 is configured to advance the plunger 12 axially with respect to the lumen of the hollow tube 2. Specifically, the grip can manipulate the plunger 12 such that a distal end of the plunger opposite the plunger handle 16 moves towards the distal end 8 of the hollow tube 2. The grip 304 is configured to manually or automatically apply a force to the plunger 12. The force can be generated by one or more of a user, a motor, a compressed fluid, or any other means of generating a force.

In one embodiment, the plunger 12 includes teeth, notches 27, or depressions which are engageable by the grip 304 to axially adjust the position of the plunger 12. The notches can be substantially evenly spaced along the plunger.

In one embodiment, a motor is positioned within the grip 304 to advance the plunger. Optionally, the motor is operable to rotate a shaft. The shaft may include a gear to translate the rotational movement into a linear movement of the plunger 12. In one embodiment, the gear includes teeth to engage the notches 27 or teeth of the plunger 12. A battery can provide power to the motor. In one embodiment, the battery is housed in the grip 304.

Optionally, the grip includes a gear or a ratchet configured to engage teeth, notches 27, or depressions on the plunger 12. Specifically, in one embodiment, the ratchet of the grip 304 is configured to engage the plurality of notches 27 formed in the plunger. In one embodiment, the channel 324 of the grip 304 includes an aperture or window through which a portion of the gear or ratchet can extend to engage the plunger 12.

In one embodiment, when activated, the ratchet engages a first notch and then a second notch to incrementally advance the plunger distally within the hollow tube 2. Bone graft material within the hollow tube 2 is then pushed by the plunger 12 toward the distal end 8 of the hollow tube. Ratcheting mechanisms that can be used with the grip 304 are known to those of skill in the art. Some examples of ratcheting mechanisms are described in U.S. Pat. App. Pub. 2002/0049448, U.S. Pat. App. Pub. 2004/0215201, U.S. Pat. App. Pub. 2009/0264892, U.S. Pat. Nos. 7,014,640, 8,932, 295, 9,655,748, and 9,668,881 which are each incorporated herein by reference in their entirety.

Optionally, the grip 304 can be configured to discharge a predetermined amount of bone graft material each time the plunger 12 is incrementally advanced within the hollow tube. In one embodiment, between about 0.25 and 1.0 cc of bone graft material is discharged from the distal end 8 of the hollow tube 2 each time the plunger is advanced. In another embodiment, between about 0.25 and 1.0 cc of bone graft material is discharged is discharged each time the trigger 306 is actuated by a user.

The grip 304 can optionally be configured to enable vision of a surgical sight by a user. Specifically, the grip 304 may be substantially even with one or more surfaces 3, 5 of the hollow tube. In this manner, in one embodiment, the grip 304 does not obstruction a line of sight along at least one surface 3, 5. In another embodiment, an exterior surface of the grip is about even with a plane defined by one of the side surfaces 3. Additionally, or alternatively, an upper portion of the grip does not extend beyond a plane defined by a top surface 5 of the hollow tube. Optionally, a window or view port is formed in the grip 304 to allow view of the distal end 8 of the hollow tube 2.

Additionally, or alternatively, a visualization system is associated with the hollow tube. In one embodiment, the visualization system includes (but is not limited to) one or more of a camera, a light, an endoscope, and a display. The visualization system may be permanently or removably affixed to the integrated fusion cage and graft delivery device 1.

In one embodiment, the grip 304 includes a motor or other actuator which can be manipulated by a user to advance or withdraw the plunger in the hollow tube 2. The motor or actuator can operate the ratchet.

Optionally, the grip 304 is manually manipulated by a user to move the plunger 12. In one embodiment, the grip 304 includes a trigger 306. The trigger 306 may be hinged or pivotally interconnected to the grip 304. When the trigger 306 is actuated by a user, the plunger 12 is advanced in the hollow tube 2.

Figure 78:
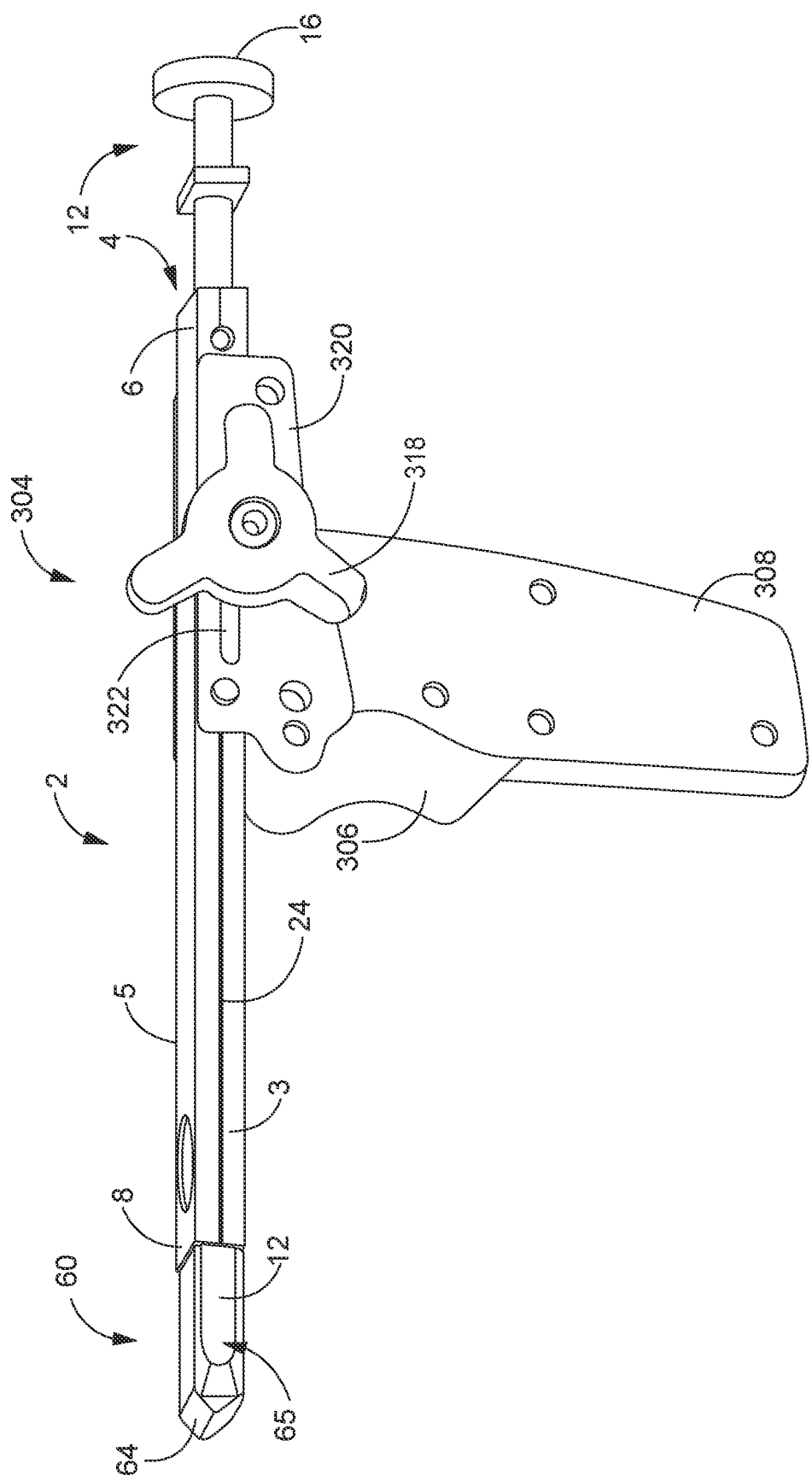

Actuating the trigger 306 may include pulling the trigger toward a handle 308 of the grip. The trigger 306 can be biased away from the handle 308 as generally illustrated in FIG. 78. Pulling the trigger 306 toward the handle 308 causes the ratchet to engage the plunger 12. The ratchet engages a notch 27 of the plunger 12 and moves the plunger toward the distal end 8 of the hollow tube. Successively pulling the trigger 306 incrementally advances the plunger 12 forward in the hollow tube.

In one embodiment, the ratchet is associated with an upper end of the trigger 306. In this embodiment, pulling the trigger 306 causes the ratchet to move toward the hollow tube 2. Optionally, a lock pawl (not illustrated) can be associated with the grip 304. The lock pawl can engage a notch of the plunger 12 to prevent inadvertent movement of the plunger distally.

The grip 304 can be used to advance or withdraw the plunger 12. Optionally, the grip 304 includes a switch 312 operable to change the direction of movement of the plunger 12. By manipulating the switch 312, a user can cause the plunger 12 to advance into the hollow tube 2 or, alternatively, withdraw from the hollow tube. In one embodiment, to withdraw the plunger 12, the plunger handle 16 can be pulled away from the grip 304. The switch 312 may comprise a button.

The grip 304 can optionally include a loading port 314. The loading port 314 provides access to the lumen of the hollow tube 2. In one embodiment, the loading port 314 is in fluid communication with the channel 324 through the grip 304. Accordingly, bone graft material can be added to the hollow tube through the loading port 314. In one embodiment, the loading port 314 is configured to engage a funnel 30 of any embodiment of the present disclosure. Additionally, or alternatively, a syringe 42 may interconnect to the grip 304 to discharge bone graft material 42 into the lumen through the loading port.

Additionally, or alternatively, a capsule or package 316 of bone graft material can be loaded into the lumen through the loading port 314. The package 316 can include any type of bone graft material, including one or more of: autogenous (harvested from the patient's own body), allogeneic (harvested from another person), and synthetic. A predetermined amount of bone graft material can be included in the package 316. In one embodiment, each package includes between about 0.25 and 1.0 cc of bone graft material. One or more packages 316 may be loaded into the lumen to deliver a desired amount of bone graft material to a surgical site.

Referring now to FIG. 78, still another embodiment of an integrated fusion cage and graft delivery device 1 of the present disclosure is illustrated. The device 1 illustrated in FIG. 78 is similar to the device 1 described in conjunction with FIG. 77 and includes many of the same, or similar features. The integrated device 1 generally includes a hollow tube 2 configured to receive a fusion cage 60 and a means for advancing bone graft material through the hollow tube for discharge out of an opening 65 of the fusion cage.

In one embodiment, the means for advancing includes a grip 304. The grip 304 is configured to interconnect to a hollow tube 2 of any embodiment of the present disclosure. The grip 304 is operable to selectively move bone graft material through the lumen of the hollow tube 2 for discharge from the tube distal end 8. Bone graft material can be positioned within the lumen while the hollow tube 2 is interconnected to the grip 304.

The grip 304 can frictionally engage a predetermined portion of the hollow tube 2. In one embodiment, the hollow tube 2 or the grip 304 include a lock or a latch to secure the hollow tube 2 to the grip. Optionally, the grip 304 engages at least the two side surfaces 3 of the hollow tube 2. In one embodiment, the grip 304 includes opposing flanges 320. One or more of the flanges 320 can be moved inwardly toward the hollow tube similar to a clamp. In this manner, the flanges 320 can apply a compressive force to the side surfaces 3 to interconnect the hollow tube 2 to the grip. Other means of interconnecting the hollow tube 2 to the grip 304 are contemplated.

The grip 304 includes a means for advancing bone graft material through the lumen of the hollow tube 2. In one embodiment, the means for advancing comprises a compressed fluid. Specifically, in one embodiment, the grip 304 is configured to advance the bone graft material using the compressed fluid, such as air. Manipulating the grip trigger 306 can release compressed fluid into the proximal end 6 of the lumen. When a pressurized fluid is introduced into the lumen, the plunger advances toward the distal end 8. The bone graft material is urged toward the distal end 8 and through the opening 65 by the plunger 12. In one embodiment, the plunger may stop advancing by contact with an interior ramp within the hollow tube 2.

In another embodiment, the means for advancing the bone graft material is configured to selectively advance the plunger 12 through the lumen to advance the bone graft material. Specifically, the grip 304 is configured to manually or automatically apply a force to the plunger 12. The force can be generated by one or more of a user, a motor, a compressed fluid, or any other means of generating a force.

In one embodiment, a motor is positioned within the grip 304 to advance the plunger. Optionally, the motor is operable to rotate a shaft. The shaft may include a gear to translate the rotational movement of the shaft into a linear movement of the plunger 12. In one embodiment, the plunger includes notches to engage the gear of the shaft. A battery can provide power to the motor. In one embodiment, the battery is housed in the grip 304.

In one embodiment, the plunger 12 includes teeth, notches, or depressions which are engageable by the grip 304 to axially adjust the position of the plunger 12. Optionally, the grip includes a gear or a ratchet configured to engage teeth or notches on the plunger 12. Specifically, in one embodiment, the ratchet of the grip 304 is configured to engage a plurality of notches formed in the plunger. The notches can be substantially evenly spaced along the plunger. The ratchet engages a first notch and then a second notch to incrementally advance the plunger distally within the hollow tube 2. Bone graft material within the hollow tube 2 is then pushed by the plunger 12 toward the distal end 8 of the hollow tube.

The grip 304 is configured to enable vision of a surgical sight by a user. Specifically, in one embodiment, the grip 304 does not extend above a top surface 5 of the hollow tube. In this manner, in one embodiment, the grip 304 does not obstruction a line of sight along at least the top surface 5. In another embodiment, lateral surfaces of the grip are about even with a plane defined by one of the side surfaces 3 of the hollow tube.

In one embodiment, the grip 304 includes a motor or other actuator which can be manipulated by a user to advance or withdraw the plunger in the hollow tube 2. The motor or actuator can operate the ratchet.

Optionally, the grip 304 is manually manipulated by a user to move the plunger 12. In one embodiment, the grip 304 includes a trigger 306. The trigger 306 may be hinged or pivotally interconnected to the grip 304. When the trigger 306 is actuated by a user, the plunger 12 advances in the hollow tube 2. Specifically, in one embodiment, the trigger 306 is functionally interconnected to the plunger 12.

Figure 79:
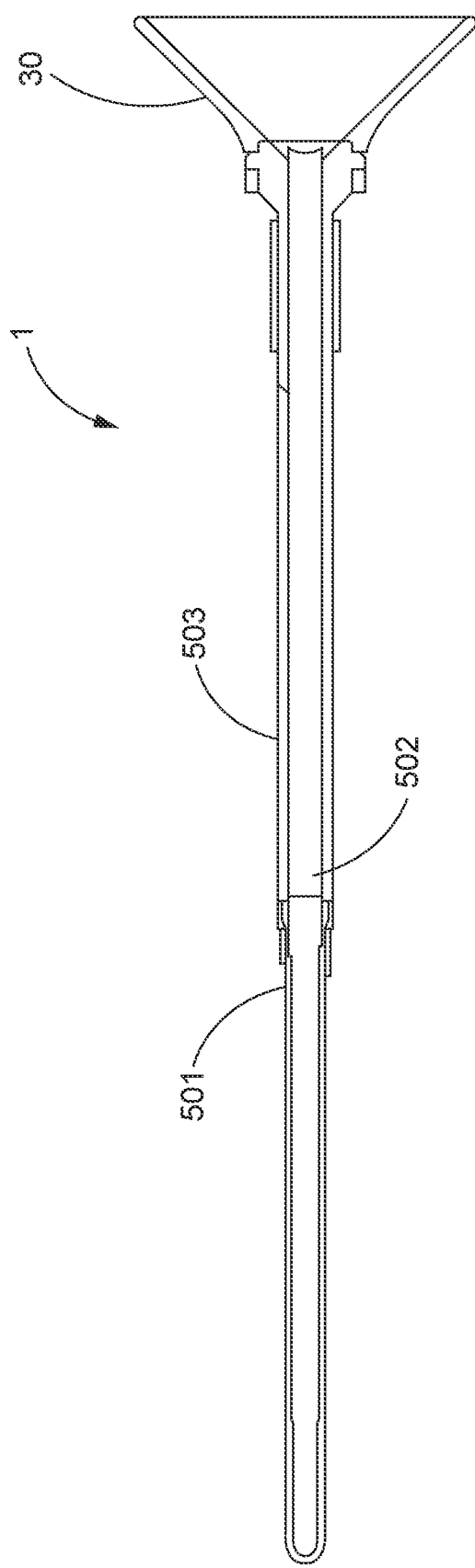

In one embodiment, actuating the trigger 306 includes pulling the trigger toward a handle 308 of the grip. The trigger 306 can be biased away from the handle 308 as generally illustrated in FIG. 79. In one embodiment, pulling the trigger 306 toward the handle 308 causes the ratchet to engage the plunger 12. The ratchet engages a notch of the plunger 12 and moves the plunger toward the distal end 8 of the hollow tube. Successively pulling the trigger 306 incrementally advances the plunger 12 forward in the hollow tube.

In one embodiment, the ratchet is associated with an upper end of the trigger 306. In this embodiment, pulling the trigger 306 causes the ratchet to move toward the distal end of the hollow tube 2. Optionally, a lock pawl (not illustrated) can be associated with the grip 304. The lock pawl can engage a notch of the plunger 12 to prevent the plunger from moving distally.

The grip 304 can be used to advance or withdraw the plunger 12. Optionally, the grip 304 includes a switch operable to change the direction of movement of the plunger 12. By manipulating the switch, a user can cause the plunger 12 to advance into the hollow tube 2 or, alternatively, withdraw from the hollow tube. In one embodiment, to withdraw the plunger 12, the plunger handle 16 can be pulled away from the grip 304.

Additionally, or alternatively, the grip 304 can include a knob 318. In one embodiment, the knob 318 is configured to advance or withdraw the plunger 12 within the hollow tube 2. Specifically, rotating the knob in a first direction causes the plunger 12 to advance toward the distal end 8. Rotating the knob 318 in a second direction causes the plunger 12 to withdraw away from the distal end 8.

In one embodiment, the knob 318 includes a gear, such as a pinion. The gear includes teeth that engage notches or teeth extending linearly along the plunger 12, similar to a rack. Rotational movement of the knob 318 is converted into linear motion of the plunger by interaction between the knob pinion with the plunger rack.

Optionally, the hollow tube 2 may discharge a predetermined amount of bone graft material associated with each rotation, or partial rotation of the knob 318. Specifically, a calibrated amount of bone graft material may be discharged from the hollow tube 2 for each quarter, half, or full rotation of the knob 318. In one embodiment, the hollow tube 2 is configured to discharge approximately 1 cc of bone graft material for each half turn of the knob 318.

In one embodiment, the knob 318 is configured to provide tactile feedback to a user after a predetermined amount of rotation. For example, when the knob is rotated one or more of $\frac{1}{8}$, $\frac{1}{4}$, $\frac{1}{2}$, and 1 turn, the knob and/or the grip 304 may vibrate or provide other tactile feedback to the user.

The grip 304 is also operable to expand the fusion cage 60 and separate the fusion cage 60 from the hollow tube. In one embodiment, the knob 318 can slide within a slot 322 to release the fusion cage 60. In one embodiment, pulling the knob 318 away from the distal end 8 of the hollow tube detaches the fusion cage.

Referring now to FIG. 79, an embodiment of a graft delivery device 1 of the present disclosure is illustrated. In this embodiment, the cannula 2 comprises a distal tube 501, a proximal interior tube 502, and a breech area 503. In the embodiment illustrated in FIG. 79, the distal tube 501 is injection-molded and has an inner cross-section of about 4 mm×7 mm and an outer cross-section of about 6 mm×9 mm, but it is to be expressly understood that the distal tube 501 may be manufactured by any suitable means and may have any suitable size and shape. The proximal interior tube 502 may also be injection-molded, and securely interconnects to the distal tube 501 by mechanisms described in greater detail below. The breech area 503, disposed on a top aspect of the proximal interior tube 502, allows for loading of graft material into the proximal interior tube 502 by mechanisms described in greater detail below.

Figure 80:
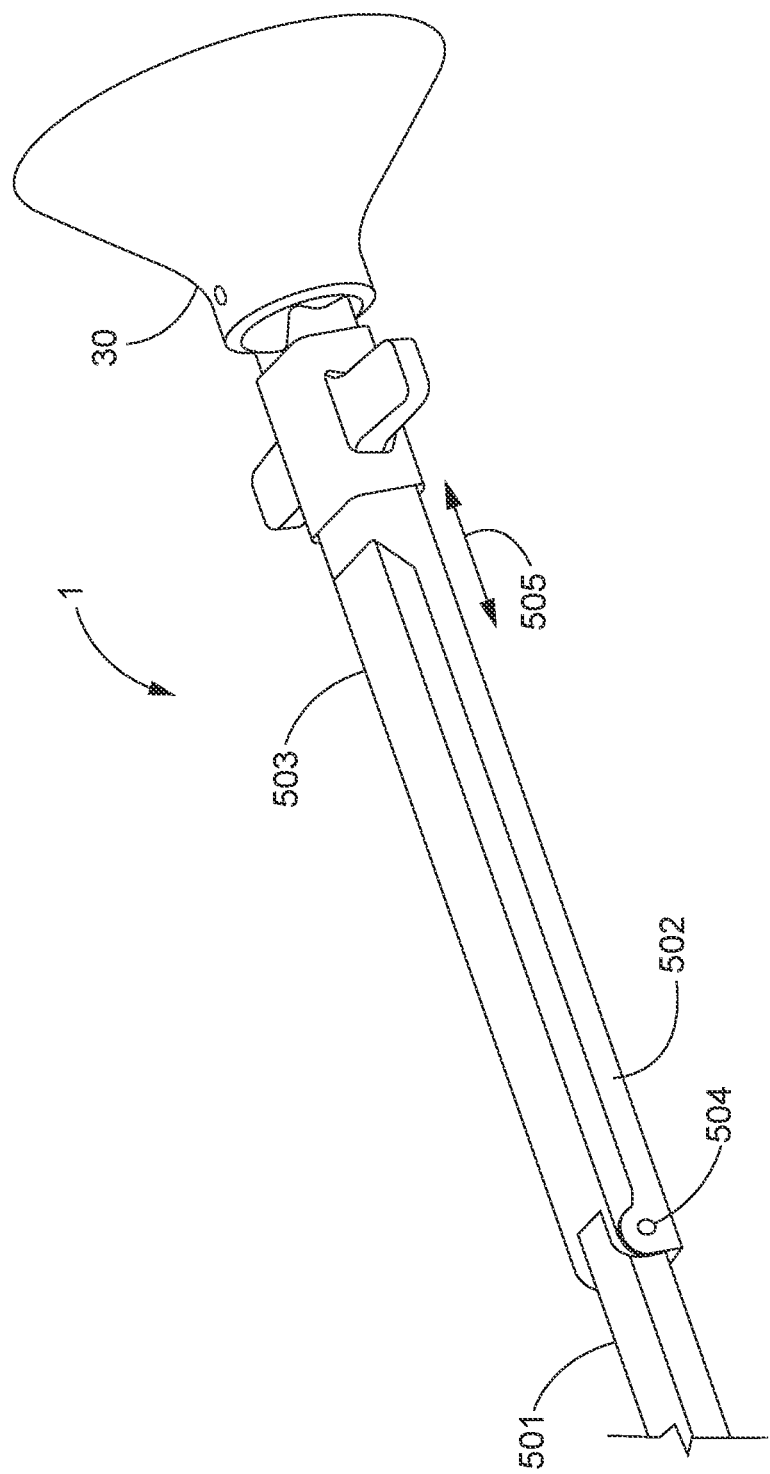

Referring now to FIG. 80, a proximal portion of the graft delivery device 1 depicted in FIG. 79 is illustrated. As illustrated in FIG. 80, the graft delivery device 1 of this embodiment may comprise either or both of two mechanisms for loading graft material into the proximal interior tube 502: a funnel 30, as shown and described elsewhere throughout this description, and the breech area 503. As illustrated in FIG. 80, the breech area 503 may generally take the form of a hinged door or cover, interconnected to lateral walls of the proximal interior tube 502 by a breech hinge 504, which may be adapted to open upwardly in "trap door"-like fashion by rotating about the breech hinge 504 to allow a surgeon or other user to load fibrous or standard graft material into an interior volume of the proximal interior tube 502, and may be further adapted to close downwardly by rotating about the breech hinge 504 to seal the graft material within the proximal interior tube 502 and/or prevent other materials from entering the proximal interior tube 502. The breech hinge 504 may, in addition to providing a secure interconnection between the breech area 503 and walls of the proximal interior tube 502, can be further configured to securely lock, affix, and/or interconnect the proximal interior tube 502 to the distal tube 501. To prevent inadvertent or undesired opening of the breech area 503, the graft delivery device 1 may be further provided with an optional breech lock 505, which may serve to lock the breech area 503 in a closed position by any suitable mechanism, e.g. a spring-loaded mechanism (not shown).

Figure 81:
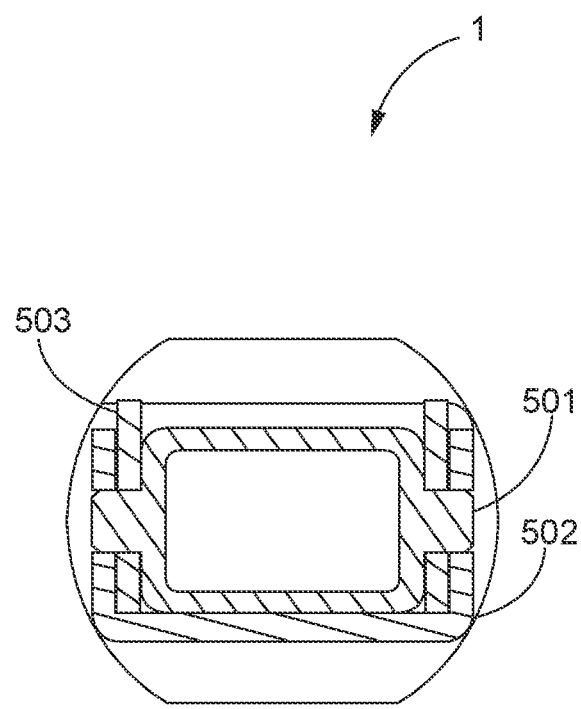

Referring now to FIG. 81, one possible geometry for the secure interconnections between any two or more of the distal tube 501, the proximal interior tube 502, and the breech area 503 is illustrated. As illustrated, the proximal interior tube 502 may, in at least a distal portion, have a larger outer diameter and/or a larger inner diameter than a corresponding outer and/or inner diameter of at least a proximal portion of the distal tube 501, and the distal portion of the proximal interior tube 502 may be adapted to receive therein the proximal portion of the distal tube 501. The distal portion of the proximal interior tube 502 may be adapted to surround the proximal portion of the distal tube 501 about substantially all, or less than substantially all, of a circumference of the proximal portion of the distal tube 501. As illustrated in FIG. 81, in a preferred embodiment, the distal portion of the proximal interior tube 502 may surround the proximal portion of the distal tube 501 about three out of four sides (left, right, and bottom sides) of the rectangular cross-section of the distal tube 501, while the fourth (top) side of the proximal portion of the distal tube 501 is proximate to and enclosed by at least a portion of the breech area 503.

Referring now to FIGS. 82A and 82B, further features of the embodiment of the graft delivery device 1 depicted in FIGS. 79-81 are illustrated. In this embodiment, a vertically extending rail 506 is disposed within an interior volume of the proximal interior tube 502. As illustrated in FIG. 82A, the vertically extending rail 506 provides a greater vertical depth to the interior volume of the proximal interior tube 502 and thereby allows for a greater volume of graft material to be inserted into the proximal interior tube 502, and as illustrated in FIG. 82B, the rail 506 snugly mates with the breech area 503 when the breech area 503 is in the closed position so as to securely enclose the interior volume of the proximal interior tube 502. As further illustrated in FIG. 82A, distally extending portions of the proximal interior tube 502 may "sandwich" the breech area 503 at the breech hinge 504 to ensure that the proximal interior tube 502, breech area 503, and distal tube 501 are all securely affixed at the breech hinge 504.

Referring now to FIGS. 83A and 83B, one embodiment of a mechanism for securely interconnecting the distal tube 501, the proximal interior tube 502, and the breech area 503 is illustrated. As illustrated in FIG. 83A, the distal portion of the proximal interior tube 502 has a generally smooth inner surface, providing for a smooth and contiguous bore and therefore the least resistance to the flow of bone graft material through the graft delivery device 1. The proximal portion of the distal tube 501 is locked into place within the proximal interior tube 502; this is achieved by closing the breech area 503, which causes at least one cavity 502a in the proximal interior tube 502 and at least one cavity 503a in the breech area 503 to interface and interlock with a knuckle 501a of the distal tube 501. This interaction between the cavities 502a, 503a and the knuckle 501a is shown in greater detail in the perspective view of FIG. 83B. As illustrated, the knuckle 501a comprises a vertical rise or protrusion on a top face of an outer surface of the proximal end of distal tube 501. The cavity 503a of the breech area 503, meanwhile, takes the form of a recessed or "cut-out" portion of the breech area 503, i.e. a region where a thickness of the breech area 503 is reduced; the knuckle 501a thus mates with and snugly fits within the cavity 503a, so as to securely interconnect the distal tube 501, the proximal interior tube 502, and the breech area 503 while providing a substantially uniform height of the cannula 2 and a substantially unimpeded flow path for bone graft material within the cannula 2.

Other arrangements of the distal tube 501, the proximal interior tube 502, and the breech area 503 are possible according to the present disclosure. As a non-limiting example, the breech hinge 504 may be placed in another location along the breech area 503, such as closer to a proximal end thereof.

In various embodiments a bone graft tamping device may also be provided, which is adapted to be inserted into the hollow tube 2 after the plunger 12 is removed from the hollow tube. The bone graft tamping device, according to this embodiment, may include one or more longitudinal channels along the outer circumference of the bone graft packer for permitting any trapped air to flow from the bone graft receiving area to the graspable end of the hollow tube during packing of bone graft. The bone graft packer may further include a handle at one end designed ergonomically for improving ease of use. The bone graft packer in this embodiment thereby facilitates packing of bone graft within the hollow tube.

The hollow tube 2 may also be fitted with a passageway wherein a surgical tube or other device may be inserted, such as to deliver a liquid to the surgical area or to extract liquid from the surgical area. In such an embodiment, the plunger 12 is adapted in cross-section to conform to the hollow tube's cross-section.

In another embodiment of the present invention, a kit of surgical instruments comprises a plurality of differently sized and/or shaped hollow tubes 2 and a plurality of differently sized and/or shaped plungers 12. Each of the plungers correspond to at least one of the hollow tubes, whereby a surgeon may select a hollow tube and a plunger which correspond with one another depending upon the size and shape of the graft receiving area and the amount or type of bone graft to be implanted at such area. The corresponding hollow tubes and plungers are constructed and arranged such that bone graft can be placed within the hollow tubes with the plungers, and inserted nearly completely into the hollow tubes for removing substantially all of the bone graft material from the hollow tubes, such as in the preferred embodiments for the plunger described above. The use of more than one hollow tube/plunger combination permits at least two different columns of material to be selectively delivered to the targeted site, e.g. one of bone graft material from the patient and another of Bone Morphogenetic Protein (BMP), or e.g. two different types of bone graft material or one delivering sealant or liquid. Also, one or both hollow tubes could be preloaded with bone graft material.

The kit of surgical instruments may comprise a plurality of differently sized and/or shaped graft retaining structures, each corresponding to at least one hollow tube and at least one plunger.

The bone graft receiving area can be any area of a patient that requires delivery of bone graft. In the preferred embodiment, the bone graft is delivered in a partially formed manner, and in accordance with another aspect of the present invention, requires further formation after initial delivery of the bone graft.

Another embodiment of the present invention provides a method by which a hollow tube and a plunger associated with the hollow tube are provided to facilitate delivery of the bone graft to a bone graft receiving area.

According to one embodiment, the present invention provides a bone graft delivery system, by which a hollow tube and/or plunger assembly may be prepared prior to opening a patient, thus minimizing the overall impact of the grafting aspect of a surgical implantation or other procedure. Moreover, the hollow tube 2 may be made to be stored with bone graft in it for a period of time, whether the tube is made of plastic, metal or any other material. Depending upon the surgical application, it may be desirable to only partially fill the tube for storage, so that a plunger can be at least partially inserted at the time of a surgery.

Thus, the integrated fusion cage and graft delivery device 1 may either come with a pre-filled hollow tube, or a non-filled hollow tube, in which the surgeon will insert bone graft received from the patient (autograft), or from another source (allograft). In either case, the surgeon may first remove any wrapping or seals about the hollow tube, and/or the pre-filled bone graft, and insert the hollow tube into the patient such that the second end of the hollow tube is adjacent the bone graft receiving area. Once the hollow tube is in place, and the opening at the second end of the hollow tube is oriented in the direction of the desired placement of bone graft, the surgeon may then insert the second end of the plunger into the opening at the first end of the hollow tube, and begin pressing the second end of the plunger against the bone graft material in the hollow tube. In this fashion, the plunger 12 and hollow tube 2 cooperate similar to that of a syringe, allowing the surgeon to steadily and controllably release or eject bone graft from the second end of the hollow tube as the plunger is placed farther and farther into the opening in the hollow tube. Once the desired amount of bone graft has been ejected from the hollow tube (for in some instances all of the bone graft has been ejected from the hollow tube) the surgeon may remove the plunger from the hollow tube, and complete the surgery. In certain operations, the surgeon may elect to place additional bone graft into the hollow tube, and repeat the steps described above. Furthermore, the pre-filled bone graft elements may be color-coded to readily identify the type of bone graft material contained therein.

According to the embodiment described in the preceding paragraph, the present invention may be carried out by a method in which access is provided to a graft receiving area in a body, bone graft is placed into a hollow tube having a first end and a second end, the hollow tube, together with the bone graft, is arranged so that the first end of the hollow tube is at least adjacent to the graft receiving area and permits lateral or nearly lateral (in relation to the longitudinal axis of the hollow tube and plunger assembly) introduction of bone graft to the graft receiving area. This method prevents loss of bone graft due to improper or limited orientation of the integrated fusion cage and graft delivery device, and further allows a user to achieve insertion of a desired quantity of bone graft by way of the contoured plunger and hollow tube configuration described according to preferred embodiments herein.

The method of the present invention may also be carried out by providing a hollow tube having a first end and a second end, constructed so that it may receive a measurable quantity of bone graft, and so that the first end may be arranged at least adjacent to a bone graft receiving area, and so that bone graft can be delivered from the first end of the hollow tube through the second end of the hollow tube and eventually to the bone graft receiving area upon movement of the plunger in a generally downward direction through the hollow tube (i.e., in a direction from the first end to the second end). According to this embodiment, a graft retaining structure may also be provided for use in connection with the contoured edge of the plunger, such that the graft retaining structure is positioned between the contoured edge of the plunger and the bone graft, but which is adhered to the bone graft and remains at the graft receiving area following removal from the hollow tube. In one embodiment, the bone graft is provided in discrete packages or containers. Furthermore, this graft retaining structure may also be employed with another tool, such as a graft packer, which is employed either before or after the hollow tube is removed from the graft receiving area.

In another embodiment, the one or more plungers corresponding to the one or more hollow tubes are positioned with distal ends near the proximate end of the horizontal tube before use, the plungers having a detent to retain plunger in ready position without undesired movement before surgeon chooses which one or more plungers to extend through hollow horizontal tube and deliver bone graft material and/or desired material to the surgical area.

According to another embodiment of the present invention, a hollow tube and plunger assembly is provided in which the hollow tube and/or the plunger assembly is disposable. Alternatively, the tube may be made of a biocompatible material which remains at least partially in the patient without impairing the final implantation. Thus, the hollow tube may be formed from a material that is resorbable, such as a resorbable polymer, and remain in the patient after implantation, so as not to interfere with the growth of the bone or stability of any bone graft or implant.

The current design preferably comprises a hollow tubular member comprising a rounded edge rectangular shaft, which may be filled or is pre-filled with grafting material. The loading is carried out by the plunger. The rectangular design is preferable as it allows the largest surface area device to be placed into the annulotomy site of a disc, but in other embodiments may be formed similar to conventional round shafts. The other preferred feature includes a laterally-mounted exit site for the graft material. The combination of this design feature allows direction-oriented dispersion of the graft material. This allows ejection of the graft material into an empty disc space as opposed to below the hollow tube, which would tend to impact the material and not allow its spread through a disc space.

Another feature of this design is that a rectangular design allows the user to readily determine the orientation of the device and thereby the direction of entry of the bone graft material into the surgical area. However, such a feature may be obtained alternatively through exterior markings or grooves on the exterior on the hollow tube. Such exterior grooves or markings would allow use of a range of cross-sections for the device, to include a square, circle, or oval while allowing the user to readily determine the orientation of the device relative to the direction of entry of the bone graft material into the surgical area.

A further feature of this design is that an anti-perforation footing or shelf is paced on the bottom of the hollow tube to prevent annular penetration and/or injury to the patient's abdomen or other anatomy adjacent the bone graft receiving area.

In another embodiment of the invention, all or some of the elements of the device or sections of all or some of the device may be disposable. Disposable medical devices are advantageous as they typically have reduced recurring and initial costs of manufacture.

In another embodiment of the device, the distal tip or end of the plunger device is composed of a different material to the rest of the plunger, so as the material at the distal end of the plunger is sponge-like or softer-than or more malleable than the rest of the plunger so as upon engagement with the interior distal end of the hollow tube, the distal end of the plunger substantially conforms to the interior configuration of the hollow tube. Similarly, the plunger distal end may be made of a material that is adaptable to substantially conform to the interior shape of the distal end of the hollow tube. Such configurations enable substantially all of the material contained within the plunger to be delivered to the targeted site.

Another alterative embodiment to the design described herein includes a navigation aid 29 on one or more surfaces of the hollow tube 2 to permit surgeon to know how far the device 1 has been inserted or to ensure proper alignment relative to a transverse bone graft delivery site (i.e. disc space). Such capability is particularly important when the patient or surgical area is not positioned immediately below the surgeon, or multiple procedures are being performed. A navigation aid allows more immediate and reliable locating of the surgical area for receiving of bone graft material. In one embodiment, the hollow tube 2 is scored or marked 29 or provides some affirmative indication, actively or passively, to the surgeon to indicate degree of delivery of the material, e.g. bone graft material, to the delivery site, and/or position of the plunger 12. For example, the exterior of the hollow tube could be color-coded and/or provided with bars 29. In another embodiment, a computer and/or electromechanical sensor or device is used to provide feedback to the surgeon to indicate degree of delivery of the material, e.g. amount of cc's of bone graft material, to the delivery site, and/or position of the plunger element.

In another alterative embodiment to the design described herein, the plunger 12 could include an activation device, which is often in a liquid or semi-liquid state, and that may be injected once the semi-solid portion of the morphogenic protein has been displaced by the movement of the plunger through the hollow tube 2. That is, the plunger 12 pushes the dry material, and once completed has a bulb or other device on the usable end to insert the liquid portion of the activating agent through the inner lumen 28 within the plunger 12 to evacuate the liquid from the plunger and out an opening at the non-usable end of the plunger so as to contact the dry material already inserted into the disc space).

In one embodiment of the device, all or portions of the device 1 are manufactured using 3-D printing techniques. In another embodiment, all or portions of the device are made by injection molding techniques.

In one embodiment, the ratio of the surface area of the bottom tip of the plunger 12 is approximately half the surface area of the two lateral openings at the distal portion of the hollow tube.

In one embodiment, the device 1 includes a supplemental means of gripping the device, such as a laterally extending cylindrically-shaped handle that engages the hollow tube 2.

In one embodiment, the material inserted into the hollow tube 2 is a non-Newtonian fluid. In one embodiment, the device is adapted to accept and deliver compressible fluids. In another embodiment, the device is adapted to accept and deliver non-compressible fluids. The hollow tube 2 of one embodiment includes a rectangular lumen 28 which provides an increased cross-sectional footprint relative to a round lumen of other bone graft delivery devices. The increased cross-sectional footprint decreases friction of the non-Newtonian fluid material against the interior walls of the lumen, resulting in an improved flow of bone graft material through the lumen and eliminating (or reducing) jamming due compression of the bone graft material. The increased cross-section of hollow tube 2 of the present disclosure improves the flow dynamics of a non-Newtonian fluid by 40% compared to a prior art tool with a diameter equal to the height of the rectangular lumen of embodiments of the present invention.

In one embodiment, the upper portion of plunger is fitted with one or more protrusions, which extends from the surface of the plunger so as to engage the upper surface of the hollow tube, to prevent the plunger from engaging the distal interior portion of the hollow tube. In one embodiment, the upper portion of plunger is fitted with one or more protrusions to prevent the plunger from engaging the apex of the hollow tube distal interior ramp surface.

In one embodiment, the funnel 30 attaches to the hollow tube 2 by a bayonet connection. In one embodiment, the funnel attaches to the hollow tube by an interference fit. In one embodiment, the funnel attaches to the hollow tube by a threaded connection. In one embodiment, the funnel attaches to the hollow tube by a slot/groove connection.

In one embodiment, the distal end 8 of hollow tube has one opening 7. In one embodiment, the hollow tube 8 has two distal openings 7A, 7B located on opposite sides. In one embodiment, the hollow tube has no more than two openings 7, the openings located on opposite sides.

In one embodiment, after bone graft material 44 is delivered to a surgical site 172, a cavity 174 approximately defined by the volume engaged by the device 1 when inserted into the surgical site is left in the surgical site upon removal of the device from the surgical site. In one embodiment, the cavity 174 is then used as the site for insertion of a fusion cage 60.

The integrated fusion cage 60 with expandable cage feature provides a number of unique and innovative features not provided by conventional or traditional integrated fusion cages. For example, the integrated fusion cage with expandable cage feature of the disclosure is intentionally and deliberately designed to receive bone graft material (or any material suitable for use in surgical applications, as known to those skilled in the art) at its proximal end (i.e. the end generally facing the surgeon and/or the end opposite the end initially directed into a surgical site), such that the bone graft material flows into the fusion cage and also flows out from the fusion cage into the surgical site. Such features as the interior ramps of the fusion cage (e.g. located within the interior of the hollow tube, and/or on the front and/or rear blocks of the fusion cage) function to direct received bone graft material into the surgical site. Additionally, the features of the hollow tube and plunger wherein a greater volume of bone graft material may be reliably (e.g. not prone to blockage as is typical with most convention e.g. round hollow tubes or lumen systems) and readily delivered to a surgical site and/or a fusion cage are unique and not found in the prior art. Among other things, such features encourage improved surgical results by delivering more volume and coverage of bone graft material to the surgical site. Also, such features minimize gaps in bone graft coverage to include gaps between the fusion cage area and the surrounding surgical site. Also, the features of the one or more apertures of the fusion cage of the disclosure enable and encourage delivery of bone graft material, as received by the fusion cage, into the surrounding surgical site.

In contrast, conventional fusion cages, to include expandable fusion cages, do not provide such features and/or functions. For example, U.S. Pat. No. 8,852,242 to Morgenstern Lopez ("Lopez"), discloses a dilation introducer for orthopedic surgery for insertion of an intervertebral expandable fusion cage implant. The Lopez device does not allow receipt of bone graft material from its proximal end, or any end, in contrast to the disclosed fusion cage and fusion cage/bone graft delivery system. That is, the Lopez proximal end includes an array of components, all of which do not allow receipt of bone graft material. Furthermore, the Lopez device requires an elaborate array of components, e.g. upper side portion of the upper body portion and lower side portion of the lower body portion, which also block any egress of bone graft from the inside of the Lopez fusion cage once deployed. Also, the Lopez wedges occupy the entire interior of the cage; there are no ramps to direct graft from the interior to the disk space. In short, the Lopez design is not made with bone graft delivery in mind, and indeed, cannot function to accept let alone deliver bone graft. Additionally, suggestions provided in the Lopez disclosure to deliver bone graft to the surgical site would not provide the integrated and complete fusion cage and surgical site bone graft delivery of the invention, e.g. the Lopez slot of the Lopez lumen and funnel assembly at best provides limited delivery of bone graft material only before and after insertion of the Lopez fusion cage, and then only peripheral to the fusion cage. Also, it appears the Lopez device provides wedges and of similar if not identical interior ramp angles. In contrast, in certain embodiments of the present invention the interior wedged surfaces of the invention, i.e. front block ramp 226 and rear block ramp 236, are not of the same configuration and/or shape, e.g. front block ramp 226 is of a curved profile and rear block ramp 236 is of a linear or straight-line profile. Among other things, the curved profile of the front block ramp 226 urges egress of bone graft as received by the fusion cage 60.

In one embodiment of the fusion cage 60, no anti-torque structures or components are employed. In one embodiment of the invention, the lateral sides of the fusion cage 60 are substantially open to, among other things, allow egress of bone graft material as received to the fusion cage. In one embodiment, the expansion screw 240 is configured with a locking mechanism, such that the fusion cage 60 may be locked at a set expansion state. In one embodiment, such a locking mechanism is provided through a toggle device operated at or on the installer/impactor handle 258.

In one embodiment, the front block ramp 226 and rear block ramp 236 are identical and/or symmetrical.

In addition, it is contemplated that some embodiments of the fusion cage 60 can be configured to include side portions that project therefrom and facilitate the alignment, interconnection, and stability of the components of the fusion cage 60.

Furthermore, complementary structures can also include motion limiting portions that prevent expansion of the fusion cage beyond a certain height. This feature can also tend to ensure that the fusion cage is stable and does not disassemble during use.

In some embodiments, the expansion screw 240 can facilitate expansion of the fusion cage 60 through rotation, longitudinal contract of a pin, or other mechanisms. The expansion screw 240 can also facilitate expansion through longitudinal contraction of an actuator shaft as proximal and distal collars disposed on inner and outer sleeves move closer to each other to in turn move the proximal and distal wedged block members closer together. It is contemplated that in other embodiments, at least a portion of the actuator shaft can be axially fixed relative to one of the proximal and distal wedge block members with the actuator shaft being operative to move the other one of the proximal and distal wedge members via rotational movement or longitudinal contraction of the pin.

Further, in embodiments wherein the engagement screw 240 is threaded, it is contemplated that the actuator shaft can be configured to bring the proximal and distal wedged block members closer together at different rates. In such embodiments, the fusion cage 60 could be expanded to a V-configuration or wedged shape. For example, the actuator shaft can comprise a variable pitch thread that causes longitudinal advancement of the distal and proximal wedged block members at different rates. The advancement of one of the wedge members at a faster rate than the other could cause one end of the implant to expand more rapidly and therefore have a different height that the other end. Such a configuration can be advantageous depending on the intervertebral geometry and circumstantial needs.

In other embodiments, an upper plate 200 can be configured to include anti-torque structures. The anti-torque structures can interact with at least a portion of a deployment tool during deployment of the fusion cage 60 implant to ensure that the implant maintains its desired orientation. For example, when the implant is being deployed and a rotational force is exerted on the actuator shaft, the anti-torque structures can be engaged by a non-rotating structure of the deployment tool to maintain the rotational orientation of the implant while the actuator shaft is rotated. The anti-torque structures can comprise one or more inwardly extending holes or indentations on the rear wedged block member. However, the anti-torque structures can also comprise one or more outwardly extending structures.

According to yet other embodiments, the fusion cage 60 can be configured to include one or more additional apertures to facilitate osseointegration of the fusion cage 60 within the intervertebral space. The fusion cage 60 may contain one or more bioactive substances, such as antibiotics, chemotherapeutic substances, angiogenic growth factors, substances for accelerating the healing of the wound, growth hormones, antithrombogenic agents, bone growth accelerators or agents, and the like. Indeed, various biologics can be used with the fusion cage 60 and can be inserted into the disc space or inserted along with the fusion cage 60 The apertures can facilitate circulation and bone growth throughout the intervertebral space and through the implant. In such implementations, the apertures can thereby allow bone growth through the implant and integration of the implant with the surrounding materials.

In one embodiment, the fusion cage 60 comprises an expandable cage configured to move a first surface vertically from a second surface by rotation of at least one screw that rotates without moving transversely with respect to either the first or second surface, the first plate and second plate having perimeters that overlap with each other in a vertical direction and that move along a parallel line upon rotation of the screw.

In one embodiment, the fusion cage 60 is stackable by any means known to those skilled in the art. For example, each upper plate 200 may be fitted with one or more notches on the lateral edges configured to fit with one or more protrusions on each lower plate 210.

Surprisingly, while conventional practice assumed that the amount of material that would be required, let alone desired, to fill a prepared disc space with bone paste (or BMP, etc.) would be roughly equivalent to the amount of material removed from such space prior to inserting a cage, a present inventor discovered that far more bone graft material can be—and should preferably be—inserted into such space to achieve desired fusion results. The reasons why this basic under appreciation for the volume of bone graft necessary to achieve optimal fusion results vary, but the clinical evidence arrived at via practice of the present invention compellingly demonstrates that more than doubling of the amount of bone graft material (and in some cases increasing the amount by 200%, 300% or 400% or more) than traditionally thought necessary or sufficient, is extremely beneficial to achieving desired results from fusion procedures.

The ramifications of this simple yet dramatic discovery (documented in part below) is part of the overall inventive aspect of the present invention, as it has been—to date—simply missed entirely by the practicing spine surgeons in the field. The prospect of reduced return surgeries, the reduction in costs, time, and physical suffering by patients, as well as the volume of legal complaints against surgeons and hospitals due to failed fusion results, is believed to be significant, as the evidence provided via use of the present invention indicates a vast reduction in the overall costs involved in both economic resources, as well as emotional capital, upon acceptance and wide-spread use of the present invention. Insurance costs should thus decrease as the present invention is adopted by the industry. While the costs of infusing increased amount of bone graft materials into the space of a patient's disc may at first appear to increase the costs of an individual operation, the benefits achieved thereby will be considerable, including the reduction of repeat surgeries to fix non-fused spines. Thus, regardless of the actual tools and devices employed to achieve the end result of attaining up to 100% more bone graft material being utilized in fusion operations, (as well as other surgeries where previously under-appreciated bone graft material delivery volumes have occurred) one important aspect of the present invention is directed to the appreciation of a previously unrecognized problem and the solution thereto, which forms part of the inventive aspects of the present invention described and claimed herein.

In one embodiment, at least twice the amount of disc material removed from a surgical site is replaced with bone graft material. In a preferred embodiment, at least three times the amount of disc material removed from a surgical site is replaced with bone graft material. In a most preferred embodiment, at least three and a half times the amount of disc material removed from a surgical site is replaced with bone graft material.

EXPERIMENTAL RESULTS

The following experimental results are with respect to an apparatus and method for near-simultaneous and integrated delivery of bone graft material in a patient's spine. These results are sample results and are not intended to limit the invention.

Materials and Methods

During the time period from July 2010 through December 2012, a set of patients undergoing minimally invasive (MIS) transverse lumbar interbody fusion (T-LIF) at the L4-5 and/or L5-S1 levels were studied for disk material removed and BG delivered at each disk space during the surgical procedure. The diagnosis was spondylosis or spondylolisthesis in all patients. A total of 63 patients with an average age of 56 years were studied. There were 29 male and 34 female patients. Ninety-one disk spaces were analyzed. A single surgeon with the same surgical team performed all surgeries. The operations were carried out through a 22 mm cannula with microscopic control. The midline structures and spinous process attachments were left undisturbed. The disk space was debrided exhaustively using nonmotorized, hand tools to bleeding subchondral bone. The debrided disk material was measured in a volumetric syringe. Bone Graft (BG) material consisting of silicated tricalcium phosphate granules and hyaluronic acid powder were mixed in a 1:1 ratio and local bone graft and bone marrow aspirate concentrate were added together to form a slurry. The slurry was measured volumetrically. Disk space mobilization and distraction was carried out with serial impaction of distractor tools until appropriate disk height was achieved. Distraction ranged from 8 mm to 14 mm, with the 10 mm or 12 mm height being most commonly observed.

The BG delivery tool of this disclosure was used to apply the BG slurry to the disk space. The embodiment had a rectangular cross section with the same footprint as a small fusion cage (8 mm×12 mm). The tapered tip was placed into the debrided disk space under microscopic control to allow for direct visualization, followed by the application of a snap-on funnel for loading the BG. The BG slurry was then placed in the funnel and the slurry was pushed into the disk space with the plunger. The biportal design of the delivery tool directed the slurry into the lateral areas of the prepared disk space, leaving a natural void for the fusion cage once the tool was removed. Once the disk space was filled entirely, the site of insertion was inspected for any BG material, which might have escaped the confines of the disk space. This material was excluded in the final measurement to ensure an accurate calculation of BG delivery. Removal of the delivery tool provided an unobscured path for the fusion cage to be applied.

A polyether ether ketone, hollow interbody fusion cage of the appropriate size was then placed into the disk space. A minimally invasive, bilateral pedicle screw/rod system was applied prior to wound closure. Average blood loss for the procedures was 127 ml±75 ml.

A two-tailed student's t-test was used to determine if any significant difference existed between the volumes of disk material removed at L4-5 versus L5-S1. The null hypothesis was that no significant difference existed between samples. Significance was set at $p<0.05$. The two-tailed t test was also used to determine whether a significant difference existed between volumes of BG delivery and disk material removed. The formula [(BG delivered+graft volume of the fusion cage)/disk material removed] was used to generate the ratio of BG delivery versus disk material removed.

In order to compare the volume of disk material removed during a T-LIF procedure with a complete, surgical discectomy, the volume of disk material removed during L5-S1 anterior lumbar discectomy was measured volumetrically. The L5-S1 disk was harvested and measured for patients undergoing either anterior fusion or total disk replacement. The material removed consisted of anterior and posterior annulus as well as complete nuclectomy, and represented more tissue (in terms of the annuli) than would be typically removed in a T-LIF procedure. There were 29 anterior L5-S1 discectomy patients. The age range, gender distribution and diagnosis were the same as the T-LIF patients.

All study patients were followed up with anterior/posterior radiographs and a physical examination at 4 weeks, 12 weeks, 26 weeks and 52 weeks post-surgery. A visual analog scale (VAS) for pain was obtained at each visit and an Oswestry Disability Index (ODI) was completed preoperatively and at 26 weeks postoperatively.

Results

There were 58 L4-5 disk spaces and 33 L5-S1 disk spaces evaluated. The average volumes of disk material harvested from L4-5 and L5-S1 were 4.1 ml±2.2 ml and 2.8 ml±1.9 ml, respectively. The p-value for the student's two-tailed t-test was equal to 0.01, revealing a significant difference in terms of disk material removed between L4-5 and L5-S1. The range of volume was less than 1 ml to 14.5 ml. The comparison between disk material removed and BG material inserted at L4-5 or at L5-S1 demonstrated a significant difference ($p<<0.001$).

Figure 34A:
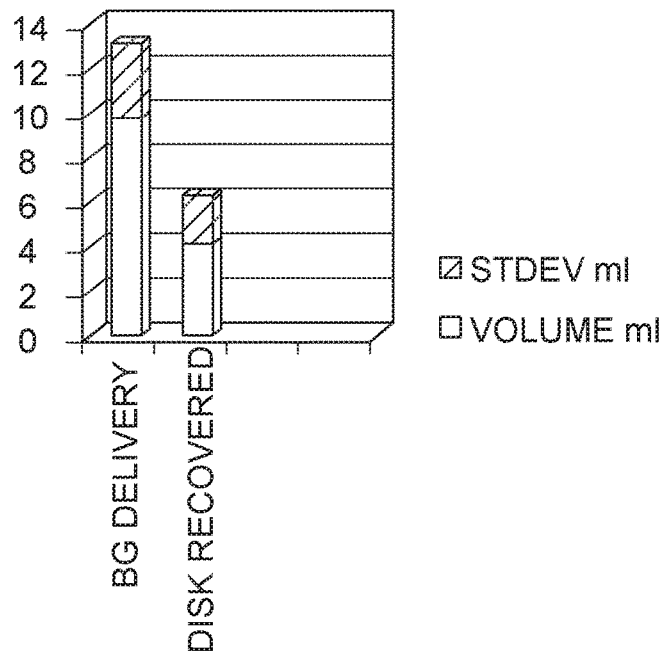
FIG. 34A is a bar graph describing experimental results of bone graft delivery and disk material removed for L4-5.
Figure 34B:
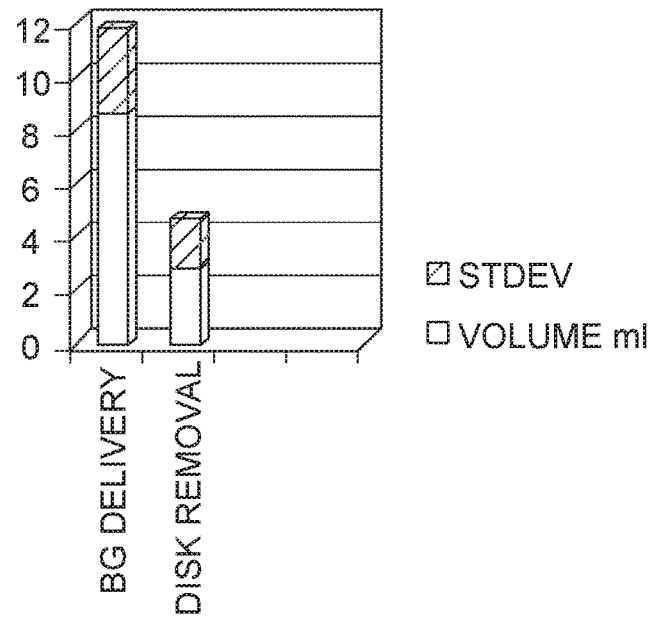
FIG. 34B is a bar graph describing experimental results of bone graft delivery and disk material removed for L5-S1.
Figures 35A, 35B:
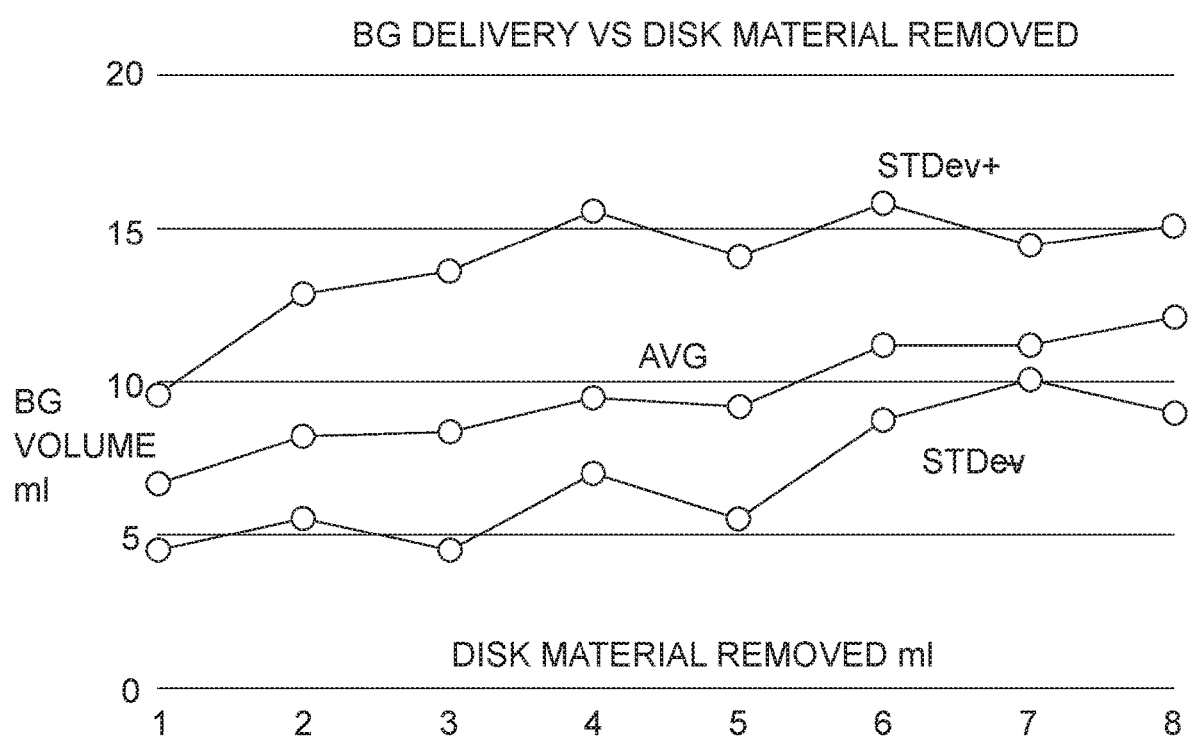
FIG. 35A is a table describing experimental results of bone graft delivery and disk material removed.
FIG. 35B is a graph of the table of FIG. 35A describing experimental results of bone graft delivery and disk material removed.
Figure 36:
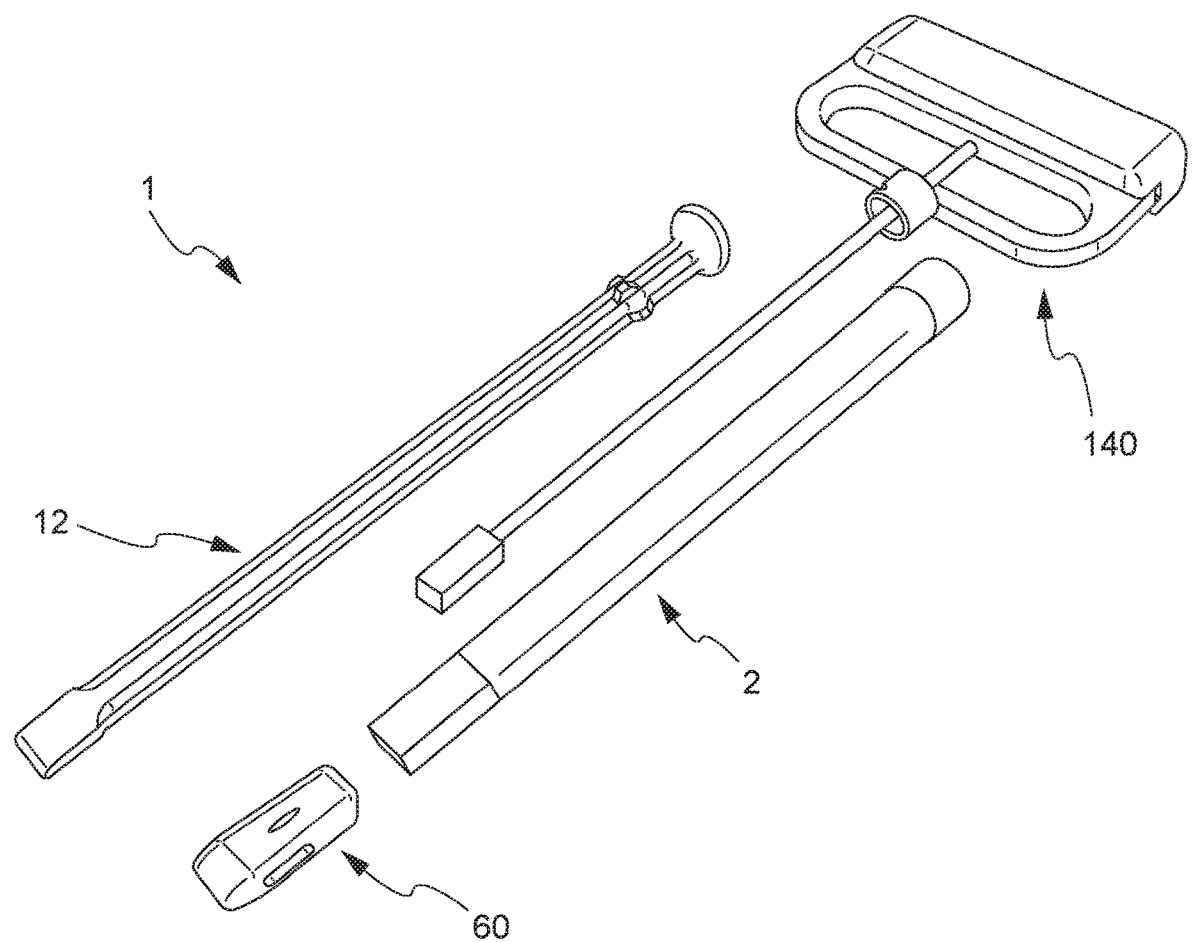
FIG. 36 is a front perspective exploded view of an integrated fusion cage and graft delivery device according to another embodiment.
Figure 37:
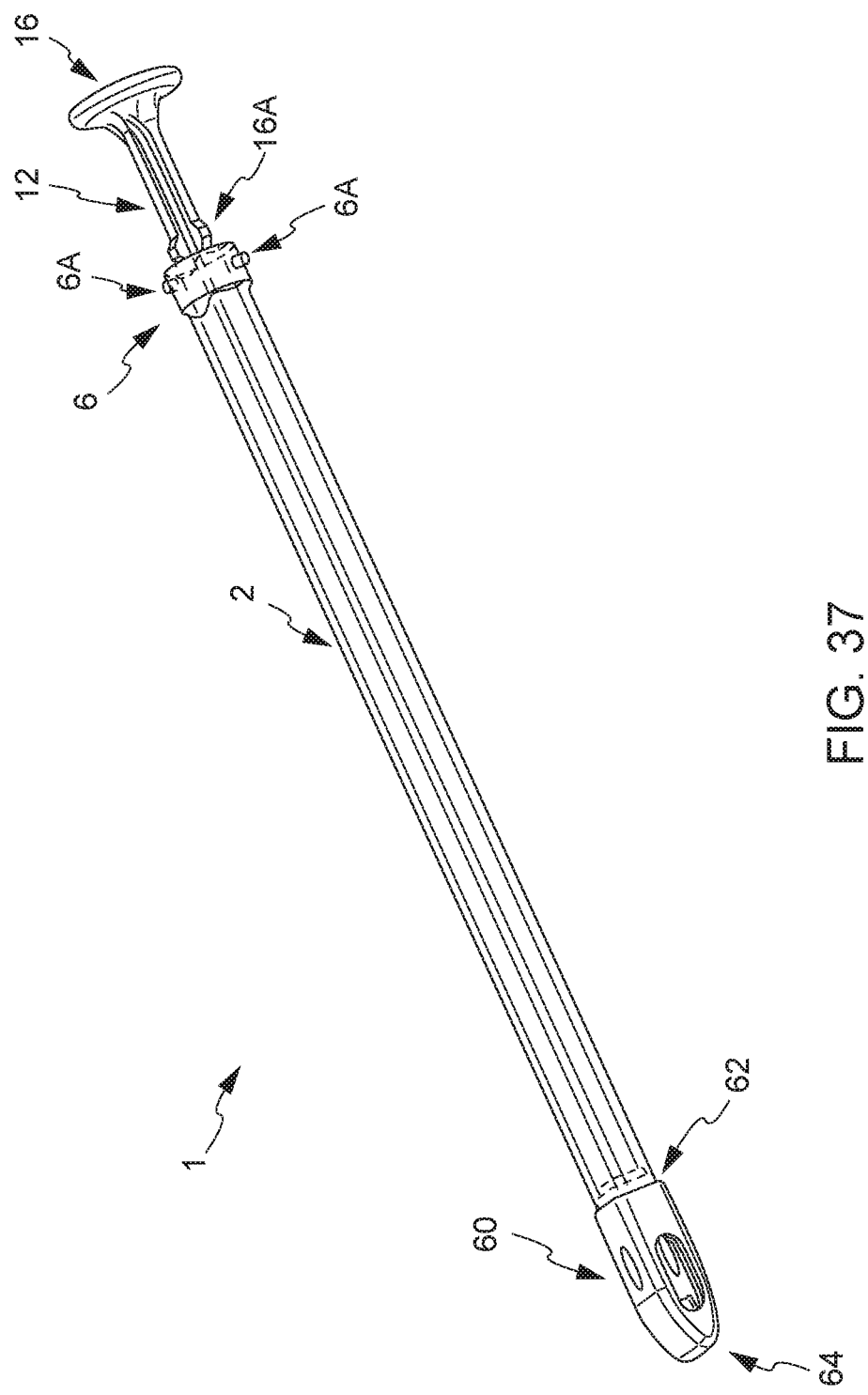
FIG. 37 is a front perspective view of the device of FIG. 36.
Figure 38:
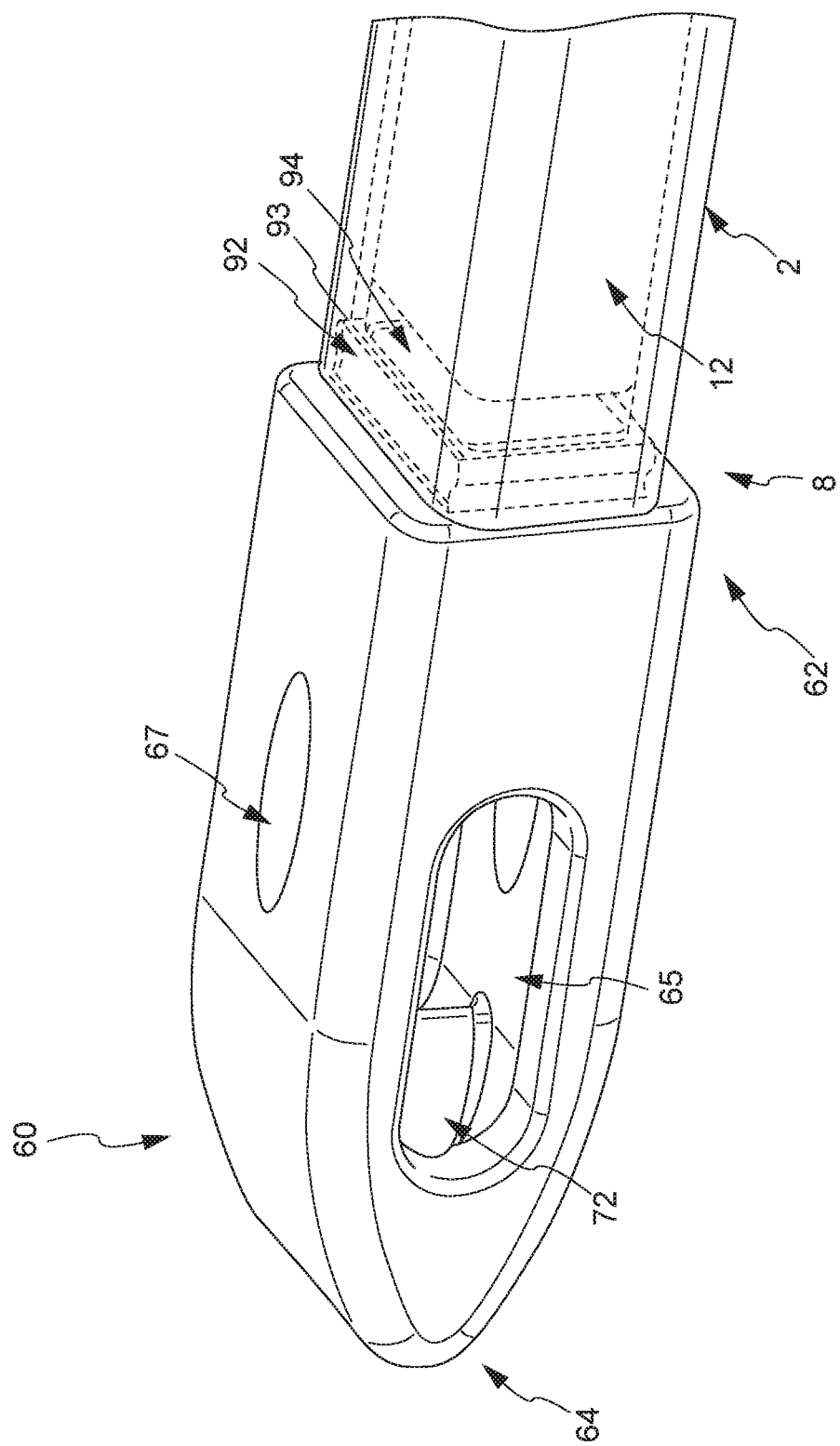
FIG. 38 is a close-up front perspective view of the device of FIG. 36.
Figure 39:
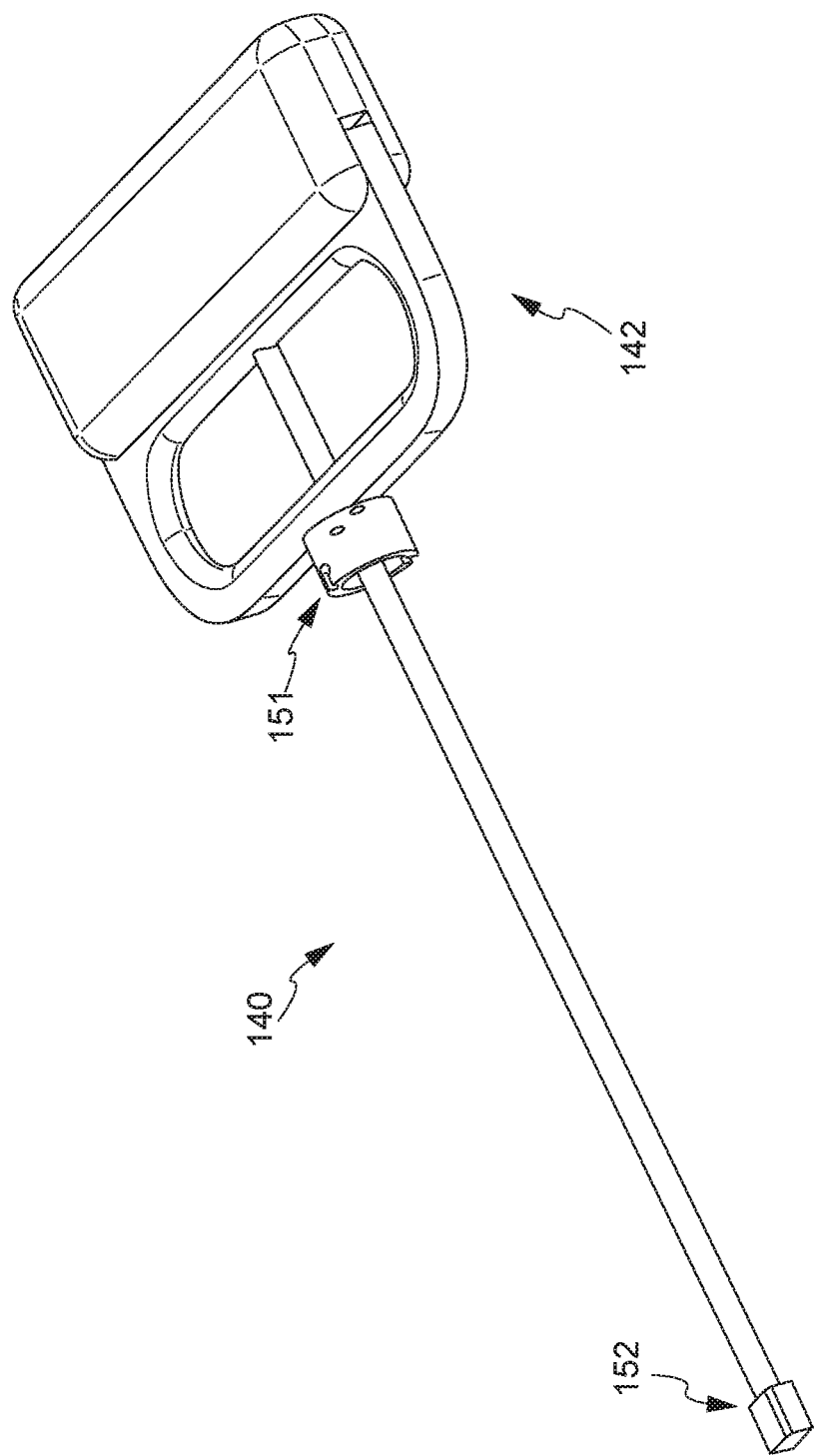
FIG. 39 is a front perspective view of the ejection tool element of the device of FIG. 36.

BG volume applied to L4-5 was 9.8 ml±3.3 ml. At L5-S1 it was 8.6 ml±3.2 ml. The p-value for the student's two-tailed t-test was equal to 0.07, trending to a significant difference in bone graft applied between L4-5 and L5-S1. The combined average was 9.2 ml±3.0 ml. The volume of BG applied ranged from 4.5 ml to 19 ml. The formula of [(BG delivered+graft volume of the fusion cage)/disk material removed] generated a surprising result: The amount of disk material removed compared to the amount of BG placed in the disk space was not a 1:1 ratio, as would have been empirically expected. At L4-5 the ratio was 3.4±2.2 and at L5-S1 it was 4.7±2.7, as shown in FIGS. 34A-B, respectively. This was statistically significant with a p-value of 0.02. With respect to the entire study, the ratio of BG inserted relative to disk material removed revealed that on average 3.7±2.3 times as much BG was inserted into the disk space as disk material removed. This finding was even more dramatic with collapsed disk spaces where 1 ml of disk material harvest led to an average of 6.6 ml±0.9 ml of BG delivery, as shown in FIGS. 35A-B. The volume of BG delivery was asymptotically related to the volume of disk material removed with 12.3 ml of disk material being delivered to a disk where 8.0 ml of disk was removed, as shown in FIGS. 35A-B.

The average volume of disk material removed during a T-LIF discectomy at L5-S1 was 3.2 ml and the average volume of disk material from the anterior L5-S1 discectomy was 8.1 ml. Dividing the average T-LIF volume by the average anterior discectomy (including annuli) volume revealed that on average 34% of the disk material was removed at the time of 25 T-LIF at the L5-S1 disk space.

Because of the tapered tip of the BG delivery tool, it was possible to enter the most collapsed disk space without endplate injury. The delivery device did not jam with the application of the BG slurry. The removable funnel allowed direct visualization of the tool under the microscope without obscuring its tip during insertion. Because the delivery device applied BG out of its side portals, it provided a natural void for fusion cage insertion, and no cage jamming resulted during impaction. BG delivery using the described tool took a fraction of the time (less than 2 minutes) usually devoted to depositing BG to the disk space. There were no complications associated with the use of the BG delivery tool. The average preoperative ODI measured 29±9 and the postoperative value was 21±8. A significant difference was not detected with p=0.06. The VAS similarly improved with 5 pre-operative score measuring 7.5±1.5 and postoperative score 4.0±2.5. The postoperative VAS was statistically significant relative to the corresponding preoperative value with p<0.05. Pseudoarthrosis developed in 7 disks in 4 patients (7.6%). The patients with 2-level pseudoarthrosis had a diagnosis of hypothyroidism. This diagnosis was also present in one of the single level pseudoarthosis patients. The remaining pseudoarthrosis patients did not have discernable risk factors (diabetes, tobacco consumption or obesity).

Discussion

There is substantial variation in fusion rates after T-LIF surgery with pseudoarthrosis rates varying from 23.1% to 2.9%. The reasons for the range of successful arthrodesis vary from surgical technique, including BG preparation and application, to the way in which a pseudoarthrosis is diagnosed—direct surgical exploration or by radiographic means. Reason would dictate that the volume of BG delivered to a prepared disk space would contribute positively to successful arthrodesis with inadequate grafting leading to pseudoarthrosis. Using hand tools and the goal of disk space debridement, a conservative estimate of 34% of disk removal was observed in this study at the L5-S1 level. This substantial difference represents the different goals of the procedures and provides a baseline for general disk space debridement for T-LIF procedures.

The statistically significant difference between the amount of disk material removed from L4-5 versus L5-S1 correlates with the commonly observed radiographic finding of disk height at L4-5 being greater than that of L5-S1. Likewise, BG delivery to L4-5 was greater relative to the L5-81 disk space. Although direct volume of BG insertion was greater in L4-5 relative to L5-S1, the ratio (BG delivered/disk material removed) was higher at L5-S1 (4.7±2.7) than at L4-5 (3.4±2.2). This was a statistically significant difference (p<0.02) and corresponds with the more collapsed disk spaces demonstrating a higher percentage of BG delivery (see FIGS. 34A-B).

On average, 3.7 times as much bone graft was applied to the debrided disk space relative to disk material removed. This is explained by the fact that the disk space was collapsed at the time of discectomy, and then distracted and mobilized during the preparation process to a distracted height. This suggests that relying on an empiric 1:1 ratio of disk removal to BG insertion grossly under-fills the disk space and would be an important contributor to pseudoarthrosis. This is an especially important consideration in the most collapsed disk spaces since distraction to appropriate height in a non-collapsed disk reduces the ratio to 8:12.3 (see FIG. 35A) or a 1:1.4 ratio.

The BG slurry used in this study consisted of a mixture of granular material and liquid. This combination of materials does not behave as a typical, Newtonian (incompressible) fluid. A non-Newtonian fluid will exude its fluid component as it is compressed, and the residual granular BG material occludes a conventional, cylindrical BG delivery device.

The BG delivery tool in this study revealed a number of advantages in that it allowed for BG application in collapsed disc spaces due to its wedged tip, a process which is not possible with round-ended injection cannulas. The increased cross-sectional footprint relative to a round cannula allowed considerably less friction of non-Newtonian fluid material through the cannula, resulting in an increase in the BG flow dynamics, and eliminating jamming due to BG impaction. It is estimated that changing the cross-sectional area from 8 mm×8 mm to 8 mm×12 mm improves the flow dynamics of a non-Newtonian fluid by 40%. The two sites for BG extrusion at the sides of the cannula tip double the exit zone surface area, further decreasing the resistance to flow of the granular mixture. The removable funnel allowed direct visualization of the cannula as it was applied to the disk space without being obscured by the funnel. The biportal expression of the BG material allowed graft inoculation of all prepared areas of the disk space and left a void for the fusion cage. The applied BG delivery tool allowed refilling of the cannula without having to remove the device, resulting in decreased potential trauma to the adjacent nerve tissue.

The fusion rate in this study was 92.4% with three of the pseudoarthrosis patients having a diagnosis of hypothyroidism. This may be related to abnormalities in bone metabolism associated in patients with endocrinopathy. The other pseudoarthrosis patients did not have apparent risk factors. Postoperative pain scores and functional improvement correlated with progression to arthrodesis.

In summary, preparation of the disk spaces at L4-S1 can deliver 34% of the disk volume during debridement. BG delivery was on average 3.7 times the volume of disk removal with a relatively higher ratio of BG being delivered to the more collapsed disk spaces. A novel BG delivery device can be used to dispense a volume of BG to the disk space that is capable of filling the entire debrided area in an efficient and safe fashion. This should allow for maximization of arthrodesis potential, increase patient safety, and decrease operative time.

While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

We claim:

1. A bone graft material delivery system, comprising:
a hollow tube adapted to receive bone graft material, the hollow tube having: a proximal portion;
a distal portion with at least one opening therein; and
a breech area therebetween, the breech area configured to be opened and closed;
a plunger configured for urging bone graft material from the proximal portion through the distal portion and outwardly through the at least one opening of the distal portion, wherein the plunger has at least one engagement feature; and
a trigger configured to engage the at least one engagement feature of the plunger and being operable to advance the plunger toward the distal end of the hollow tube;
wherein the proximal portion is securely interconnected to the distal portion along a longitudinal axis of the hollow tube; and
wherein, when the breech area is open, an interior volume of the proximal portion is exposed to allow for loading of bone graft material therein, a hollow interior of the hollow tube having a generally rectangular cross-section.

2. The system of claim 1, wherein the at least one at least one engagement feature includes teeth formed along a longitudinal axis of the plunger.

3. The system of claim 1, wherein a distal end of the hollow tube is at least partially closed.

4. The system of claim 1, wherein the hollow tube is generally linear.

5. The system of claim 1, further comprising a funnel configured to be coupled to a proximal end of the hollow tube.

6. The system of claim 5, wherein the funnel is configured to receive bone graft material therein and convey bone graft material into the proximal end of the hollow tube.

7. The system of claim 1, further comprising a fusion cage detachably coupled to a distal end of the hollow tube.

8. The system of claim 1, wherein one or more of the hollow tube and the plunger are printed using a three-dimensional printing process, and wherein the three-dimensional printing process comprises one or more of fused filament fabrication, plaster-based three-dimensional printing, selective laser sintering, selective heat sintering, and direct ink writing.

9. The system of claim 1, further comprising a breech lock mechanism, configured to selectively lock the breech area in the closed position.

10. The system of claim 9, wherein the breech lock mechanism is spring-loaded.

11. The system of claim 1, wherein the distal portion comprises a knuckle and at least one of the proximal portion and the breech area comprises a cavity, wherein the knuckle mates with and snugly fits within the cavity when the breech area is in the closed position.

12. The system of claim 1, further comprising a breech hinge interconnecting the breech area and proximal portion, wherein the breech area is adapted to open upwardly by rotating about the breech hinge to allow a user to load graft material into an interior volume of the proximal portion, and is further adapted to close downwardly by rotating about the breech hinge to seal the graft material within the proximal portion.

13. The system of claim 12, wherein the breech hinge is configured to securely interconnect the proximal portion to the distal portion.

14. A bone graft material delivery system, comprising:
a hollow tube adapted to receive bone graft material, the hollow tube having: a proximal portion;
a distal portion with at least one opening therein; and
a breech area therebetween, the breech area configured to be opened and closed;
a plunger configured for urging bone graft material from the proximal portion through the distal portion and outwardly through the at least one opening of the distal portion, wherein the plunger has at least one engagement feature; and
a trigger configured to engage the at least one engagement feature of the plunger and being operable to advance the plunger toward the distal end of the hollow tube;
wherein the proximal portion is securely interconnected to the distal portion along a longitudinal axis of the hollow tube; and
wherein, when the breech area is open, an interior volume of the proximal portion is exposed to allow for loading of bone graft material therein, the proximal portion of the hollow tube comprising a vertically extending rail configured to snugly mate with the breech area when the breech area is in a closed position.

15. A surgical method for bone graft material delivery, comprising the steps of:
providing a bone graft material delivery system including
a hollow tube adapted to receive bone graft material, the hollow tube having: a proximal portion;
a distal portion with at least one opening therein; and
a breech area therebetween, the breech area configured to be opened and closed;
a plunger configured for urging bone graft material from the proximal portion through the distal portion and outwardly through the at least one opening of the distal portion, wherein the plunger has at least one engagement feature; and a trigger configured to engage the at least one engagement feature of the plunger and being operable to advance the plunger toward the distal end of the hollow tube;
wherein the proximal portion is securely interconnected to the distal portion along a longitudinal axis of the hollow tube; and
wherein, when the breech area is open, an interior volume of the proximal portion is exposed to allow for loading of bone graft material therein moving the breech area to its open position;
inserting bone graft material in the exposed interior volume of the proximal portion;
closing the breech area; and
advancing the plunger to urge bone graft from the proximal portion through the distal portion and outwardly through the at least one opening of the distal portion the proximal portion of the bone graft material delivery system comprising a vertically extending rail configured to snugly mate with the breech area when the breech area is closed, and wherein the surgical method further comprises the step of snugly mating the vertically extending rail with the breech area when the breech area is closed.

16. The surgical method of claim 15, wherein the bone graft material delivery system further comprises a funnel configured to be coupled to the proximal end of the hollow tube and to receive bone graft material therein, and wherein the surgical method further comprises the step of conveying bone graft material into the proximal end of the hollow tube using the funnel.

17. The surgical method of claim 15, wherein the bone graft material delivery system further comprises a spring-loaded breech lock mechanism configured to selectively lock the breech area in the closed position, and wherein the surgical method further comprises the step of locking the breech area in a closed position using the spring-loaded breech lock mechanism.

18. The surgical method of claim 15, wherein the distal portion of the bone graft material delivery system comprises a knuckle and at least one of the proximal portion and the breech area comprises a cavity, wherein the knuckle mates with and snugly fits within the cavity when the breech area is closed; and wherein the surgical method further comprises the step of mating and snugly fitting the knuckle within the cavity when the breech area is closed.

* * * * *